US012622431B2

(12) United States Patent
Oren-Benaroya et al.

(10) Patent No.: US 12,622,431 B2
(45) Date of Patent: May 12, 2026

(54) INSECT CONTROL NANOBODIES AND USES THEREOF

(71) Applicant: IBI-Ag Innovative Bio Insecticides Ltd., Doar-Na Misgav (IL)

(72) Inventors: Rony Oren-Benaroya, Givat Brenner (IL); Amir Ayali, Sde Warburg (IL); Jessica Monserrate, Chapel Hill, NC (US); Jeroen Van Rie, Merelbeke (BE)

(73) Assignee: IBI-Ag Innovative Bio Insecticides Ltd., Ness Ziona (IL)

( * ) Notice: Subject to any disclaimer, the term of this patent is extended or adjusted under 35 U.S.C. 154(b) by 1037 days.

(21) Appl. No.: 17/775,898

(22) PCT Filed: Nov. 11, 2020

(86) PCT No.: PCT/IL2020/051170
§ 371 (c)(1),
(2) Date: May 11, 2022

(87) PCT Pub. No.: WO2021/095031
PCT Pub. Date: May 20, 2021

(65) Prior Publication Data
US 2022/0386594 A1 Dec. 8, 2022

Related U.S. Application Data

(60) Provisional application No. 62/933,533, filed on Nov. 11, 2019.

(51) Int. Cl.
| | |
|---|---|
| *A01N 25/28* | (2006.01) |
| *A01N 63/50* | (2020.01) |
| *C07K 16/18* | (2006.01) |
| *C07K 16/40* | (2006.01) |

(52) U.S. Cl.
CPC ............. *A01N 25/28* (2013.01); *A01N 63/50* (2020.01); *C07K 16/18* (2013.01); *C07K 16/40* (2013.01); *C07K 2317/22* (2013.01)

(58) Field of Classification Search
None
See application file for complete search history.

(56) References Cited

U.S. PATENT DOCUMENTS

| | | | |
|---|---|---|---|
| 5,686,600 | A | 11/1997 | Carozzi et al. |
| 6,187,558 | B1 | 2/2001 | Granados |
| 9,516,879 | B2 | 12/2016 | Verheesen et al. |
| 9,803,003 | B2 | 10/2017 | Verheesen et al. |
| 12,011,000 | B2 | 6/2024 | Abdelgaffar et al. |
| 2012/0164205 | A1 | 6/2012 | Baum et al. |
| 2013/0164307 | A1 | 6/2013 | Markham |
| 2016/0145352 | A1 | 5/2016 | Mirey et al. |
| 2019/0300595 | A1 | 10/2019 | Mahr et al. |

FOREIGN PATENT DOCUMENTS

| | | |
|---|---|---|
| CN | 101745111 | 6/2010 |
| CN | 109734808 | 5/2019 |
| CN | 110198734 | 9/2019 |
| CN | 104630247 | 5/2020 |
| EP | 3415010 | 12/2018 |
| JP | 9-124489 | 5/1997 |
| JP | 2012-157315 | 8/2012 |
| WO | WO 94/25591 | 11/1994 |
| WO | WO 95/04827 | 2/1995 |
| WO | WO 96/00783 | 1/1996 |
| WO | WO 02/070712 | 9/2002 |
| WO | WO 2010/066740 | 6/2010 |
| WO | WO 2012/002560 | 1/2012 |
| WO | WO 2014/020218 | 2/2014 |
| WO | WO 2014/191146 | 12/2014 |
| WO | WO 2012/025602 | 12/2019 |
| WO | WO 2021/095031 | 5/2021 |

OTHER PUBLICATIONS

Schroeder et al. (J Allergy Clin Immunol 2010, 125:S41-S52).*
Lloyd et al. (Protein Engineering, Design & Selection 2009, 22:159-168).*
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Padlan et al. (PNAS 1989, 86:5938-5942).*
Lamminmaki et al. (JBC 2001, 276:36687-36694).*
Piche-Nicholas et al. MABS 2018, 10:81-94.*
Yang et al. (Comparative Biochemistry and Physiology, Part B 219-220 (2018) 10-16).*
Examination and Search Report Dated Oct. 30, 2024 From the Republica de Colombia, Superintendencia de Industria y Comercio Re. Application No. NC2022/0006986 and its Transaltion into English. (29 Pages).
Office Action Dated Nov. 28, 2024 From the Israel Patent Office Re. Application No. 292879. (4 Pages).
Oliveira et al. "A Peritrophin Mediates the Peritrophic Matrix Permeability in the Workers of the Bees Melipona Quadrifasciata and Apis Mellifera", Arthropod Structure & Development, XP055771455, 53: 100885, Published Online Oct. 12, 2019.

(Continued)

*Primary Examiner* — Sharon X Wen

(57) ABSTRACT

Insect control nanobodies are provided. Accordingly there is provided a nanobody which specifically binds to an insect polypeptide selected from the group consisting of: a polypeptide comprising a chitin binding domain (CBD), V-AT-Pase subunit c, trehalase, cytochrome p450 monooxygenase, chitin deacetylase, chitin synthase and NPC1 sterol transporter, wherein binding of the nanobody to the insect polypeptide confers an insect control activity to the nanobody. Also provided are polynucleotides encoding the nanobody, host cells expressing the nanobody and methods of using it.

21 Claims, 19 Drawing Sheets

Specification includes a Sequence Listing.

(56) References Cited

OTHER PUBLICATIONS

Trembley et al. Camelid Single Domain Antibodies (VHHs) as Neuronal Cell Intrabody Binding Agents and Inhibitors of Clostridium Botulinum Neurotoxin (BoNT) Proteases. Toxicon: Official Journal of the International Society on Toxinoloov, 56(6), 990-998, Nov. 2010.

Vance et al. High-Resolution Epitope Positioning of a Large Collection of Neutralizing and Nonneutralizing Single-Domain Antibodies on the Enzymatic and Binding Subunits of Ricin Toxin. Clinical and Vaccine Immunology, 56(6): 990-998, Nov. 2010.

Wang et al. "An Intestinal Mucin is the Target Substrate for a Baculovirus Enhancin", Proceedings of the National Academy of Sciences of the United States of America, 94(13), 6977-6982, Jun. 24, 1997.

International Preliminary Report on Patentability Dated May 27, 2022 From the International Bureau of WIPO Re. Application No. PCT/IL2020/050742. (14 Pages).

International Search Report and the Written Opinion Dated May 17, 2021 From the International Searching Authority Re. Application No. PCT/IL2020/050742. (23 Pages).

Invitation to Pay Additional Fees, Communication Relating to the Results of the Partial International Search and the Provisional Opinion Dated Feb. 15, 2021 From the International Searching Authority Re. Application No. PCT/IL2020/051170. (13 Pages).

Adhav et al. "Functional Characterization of Helicoverpa Armigera Trehalase and Investigation of Physiological Effects Caused Due to Its Inhibition by Validamycin A Formulation", International Journal of Biological Macromolecules, 112: 638-647, Available Online Feb. 26, 2018.

Agrawal et al. "Two Essential Peritrophic Matrix Proteins Mediate Matrix Barrier Functions in the Insect Midgut", Insect Biochemistry and Molecular Biology, 49:24-34, Published Online Mar. 26, 2014.

Arakane et al. "Analysis of Functions of the Chitin Deacetylase Gene Family in Tribolium Castaneu", Insect Biochemistry and Molecular Biology, XP026158850, 39(5-6):355-365, May 1, 2009.

Arakane et al. "The Tribolium Chitin Synthase Genes TcCHS1 and TcCHS2 Are Specialized for Synthesis of Epidermal Cuticle and Midgut Peritrophic Matrix", Insect Molecular Biology, 14(5): 453-463, Oct. 2005.

Asokan et al. "Response of Various Target Genes to Diet-Delivered DsRNA Mediated RNA Interference in the Cotton Bollworm, *Helicoverpa armigera*", Journal of Pest Science, 87(1): 163-172, Published Online Dec. 5, 2013.

Baum et al. "Control of Coleopteran Insect Pests Through RNA Interference", Nature Biotechnology, 25(11): 1322-1326, Published Online Nov. 4, 2007.

Casu et al. "Antibody-Mediated Inhibition of the Growth of Larvae From an Insect Causing Cutaneous Myiasis in a Mammalian Host", Proc. Natl. Acad. Sci. USA, 94(17): 8939-8944, Aug. 19, 1997.

Chartier et al. "Prevention of Oculopharyngeal Muscular Dystrophy by Muscular Expression of Llama Single-Chain Intrabodies In Vivo", Human Molecular Genetics, XP055770523, 18(10): 1849-1859, Advance Access Publication Mar. 3, 2009.

Chen et al. "Different Functions of the Insect Soluble and Membrane-Bound Trehalase Genes in Chitin Biosynthesis Revealed by RNA Interference", PLoS One, 5(4): e10133-1-e10133-13, Published Online Apr. 12, 2010.

Chikate et al. "RNAi of Selected Candidate Genes Interrupts Growth and Development of Helicoverpa Armigera", Pesticide Biochemistry and Physiology, 133: 44-51, Available Online Mar. 22, 2016.

Han et al. "Cloning and Tissue-Specific Expression of a Chitin Oeacetylase Gene from Helicoverpa armigera (Lepidoptera: Noctuidae) and Its Response to Bacillus Thuringiensis", Journal of Insect Science, 15(1):1-7,Jul. 10, 2015.

Henrique Oliveira et al. "A Peritrophin Mediates the Peritrophic Matrix Permeability in the Workers of the Bees Melipona Quadrifasciata and Apis Mellifera", Arthropod Structure & Development, XP055771455, 53: 100885, Published Online Oct. 12, 2019.

Jasrapuria et al. "Genes Encoding Proteins With Peritrophin A-Type Chitin-Binding Domains in Tribolium Castaneum Are Grouped Into Three Distinct Families Based on Phylogeny, Expression and Function", Insects Biochemistry and Molecular Biology, XP055770882, 40(3): 214-227, Published Online Feb. 6, 2010.

Jin et al. "Engineered Chloroplast DsRNA Silences Cytochrome p450 Monooxygenase, V-ATPase and Chitin Synthase Genes in the Insect Gut and Disrupts Helicoverpa Armigera Larval Development and Pupation", Plant Biotechnology Journal, 13(3): 435-446, Published Online Mar. 17, 2015.

Kariu et al. A Chitin Deacetylase-Like Protein Is a Predominant Constituent of Tick Peritrophic Membrane That Influences the Persistence of Lyme Disease Pathogens within the Vector, PLoS One, XP055801137, 8(10) e78376: 1-10, Oct. 17, 2013.

Macedo et al. "Knocking Down Chitin Synthase 2 by RNAi Is Lethal to the Cotton Boll Weevil", Biotechnology Research and Innovation, 1(1): 72-86, Jan. 2017.

Mao et al. "Co-Silence of the Coatomer Beta and V-ATPase A Genes by SiRNA Feeding Reduces Larval Survival Rate and Weight Gain of Cotton Bollworm, *Helicoverpa armigera*", Pesticide Biochemistry and Physiology, 118: 71-76, Available Online Dec. 10, 2014.

Mohammed "RNAi-Based Silencing of Genes Encoding the Vacuolar-ATPase Subunits A and C in Pink Bollworm (*Pectinophora gossypiella*)", African Journal of Biotechnology, 15(45): 2547-2557, Nov. 9, 2016.

Scott "Insect Cytochrome P450s: Thinking Beyond Detoxification", Recent Advances in Insect Physiology, Toxicology and Molecular Biology, 1: 117-124, 2008.

Shukla et al. "Insect Trehalase: Physiological Significance and Potential Applications", Glycobiology, 25(4): 357-367, Advance Access Publication Nov. 26, 2014.

Silver et al. "The Tribolium Castaneum Cell line TcA: A New Tool Kit for Cell Biology", Scientific Report, XP055793669, 4( 6840):1-8, Oct. 30, 2014.

Tellam et al. "Role of Oligosaccharides in the Immune Response of Sheep Vaccinated With Lucilia Cuprina Larval Glycoprotein, Peritrophin-95", International Journal of Parasitology, XP055771458, 31(8): 798-809, Jun. 1, 2001.

UniParc "Uncharacterized Protein LOC110370350 [Helicoverpa Armigera]", Database UniParc [Online], XP055771770, NCBI Reference Sequence: XP_021181774.1, Database Accession No. XP_021181774, Jun. 1, 2017.

Voght et al. "*Drosophila* NPC1b Promotes an Early Step in Sterol Absorption From the Midgut Epithelium", Cell Metabolism, 5(3): 195-205, Mar. 2007.

Wang et al. "Calcofluor Disrupts the Midgut Defense System in Insects", Insect Biochemistry and Molecular Biology, 30(2): 135-143, Feb. 2000.

Wang et al. "Insect Intestinal Mucin IIM14 {ECO:0000313/ EMBL:AAC47556.1}", Database UniProtKB/TrEMBL [Online], XP055771629, UniProtKb/TrEMBL Accession No. O18510_ TRINI, Database Accession No. O18510, Jan. 1, 1998.

Wang et al. "Insect Intestinal Mucin IIM22 {ECO:0000313/ EMBL:AAC47557.1}", Database UniProtKB/TrEMBL [Online], XP055771627, UniProtKb/TrEMBL Accession No. O18511_ TRINI, Database Accession No. O18511, Jan. 7, 1998.

Wang et al. "Localization of Midgut-Specific Protein Antigens From Aedes Aegypti (Diptera: Culicidae) Using Monoclonal Antibodies", Journal of Medical Entomology, XP055771467, 38(2): 223-230, Mar. 1, 2001.

Wu et al. "Silencing Chitin Deacetylase 2 Impairs Larval-Pupal and Pupal-Adult Molts in Leptinotarsa Decemlineata", Insect Molecular Biology, 28(1): 52-64, Published Online Oct. 5, 2018.

Yu et al. "Effects of Toxic Beta-Glucosides on Carbohydrate Metabolism in Cotton Bollworm, *Helicoverpa armigera* (Hübner)", Archives of Insect Biochemistry and Physiology, 100(4): e21526-1-e21526-11, Published Online Jan. 19, 2019.

Zhang et al. "Silencing of Cytochrome P450 CYP6B6 Gene of Cotton Bollworm (*Helicoverpa armigera*) by RNAi", Bulletin of Entomological Research, 103(5):584-591, Published Online Apr. 16, 2013.

(56)                    References Cited

OTHER PUBLICATIONS

Zhong et al. "Identification and Molecular Characterization of a Chitin Oeacetylase from Bombyx mori Peritrophic Membrane", International Journal of Molecular Science, XP055801130, 15(2): 1946-1961, Jan. 27, 2014.

Zhuo et al. "Chitin Synthase A: A Novel Epidermal Development Regulation Gene in the Larvae of Bombyx Mori", Molecular Biology Reports, 41(7): 4177-4186, Published Online Feb. 28, 2014.

Zhuo et al. "Chitin Synthase B: A Midgut-Specific Gene Induced by Insect Hormones and Involved in Food Intake in Bombyx Mori Larvae", Archives of Insect Biochemistry and Physiology, 85(1): 36-47, Published Online Dec. 13, 2013.

Li et al. "Research Progress on Heterologous Expression of Nanobodies", Chinese Journal of Bioengineering, 37(8): 84-95, 2017.

Decision of Rejection Dated Mar. 25, 2025 From the National Intellectual Property Administration of the People's Republic of China Re. Application No. 202080091545.1 together with its Translation and Summary in English. (12 Pages).

Examination Report Dated Apr. 7, 2025 From the Republica de Colombia, Superintendencia de Industria y Comercio Re. Application No. NC2022/0006986 and Its Translation Into English. (37 Pages).

Notice of Reason(s) for Rejection Dated May 7, 2025 From the Japan Patent Office Re. Application No. 2022-553234 and Its Translation Into English. (19 Pages).

International Preliminary Report on Patentability Dated May 27, 2022 From the International Bureau of WIPO Re. Application No. PCT/IL2020/051170. (14 Pages).

International Search Report and the Written Opinion Dated May 17, 2021 From the International Searching Authority Re. Application No. PCT/IL2020/051170. (23 Pages).

Notification of Office Action and Search Report Dated Dec. 23, 2024 From the National Intellectual Property Administration of the People's Republic of China Re. Application No. 202080091545.1 together with English Summary and Machine Translation of Office Action into English. (17 Pages).

Joshi et al. "In-Vitro Detection of Phytopathogenic Fungal Cell Wall by Polyclonal Sera Raised Against Trimethyl Chitosan Nanoparticles", International Journal of Nanomedicine, 14: 10023-10033, Published Online Dec. 20, 2019.

English Summary and Machine Translation Dated Jul. 31, 2024 of Notification of Office Action and Search Report Dated Jul. 19, 2024 From the National Intellectual Property Administration of the People's Republic of China Re. Application No. 202080091545.1. (12 Pages).

Notification of Office Action and Search Report Dated Jul. 19, 2024 From the National Intellectual Property Administration of the People's Republic of China Re. Application No. 202080091545.1. (9 Pages).

Notice of Reason(s) for Rejection Dated Jan. 7, 2025 From the Japan Patent Office Re. Application No. 2022-553234 and Its Translation Into English. (11 Pages).

Notice of Reason(s) for Rejection Dated Sep. 9, 2025 From the Japan Patent Office Re. Application No. 2022-553234 and Its Translation Into English. (16 Pages).

* cited by examiner

|----------------Artificial food with the addition of----------------|
|-------PBS-------||---------------With Cys3-labeled NB-CB12901-------------|
|------------------------48hrs---------------------------||-------6 days ------|

|--------------------------1x---------------------------|  |---------2x---------|  |---------1x---------|

|----------------------Signal for Cy3 labeled NB-CB12901 in live larvae--------------------|
|----------Larvae pictured after feeding 48hrs ---------||-----------Larvae pictured after feeding 36hrs----------|
              on Cy3-NB                          on food with Cy3-NB followed by 12hrs without NB

|-----------1.4x----------|  |-----------4x-----------|  |----------1.4x----------|  |-----------4x-----------|

■ Day 4    ▨ Day 7    ▧ Day 10

SEQUENCE LISTING

```
<160> NUMBER OF SEQ ID NOS: 596

<210> SEQ ID NO 1
<211> LENGTH: 526
<212> TYPE: PRT
<213> ORGANISM: Artificial sequence
<220> FEATURE:
<223> OTHER INFORMATION: A polypeptide comprising Chitin binding domain
      CBD - HaPMP5B1

<400> SEQUENCE: 1

Met Gly Ser Ser His His His His His His Ser Ser Gly Leu Val Pro
1               5                   10                  15

Arg Gly Ser His Met Gly Asp Arg Gly Ile Ser Glu Pro Gly Asn Asp
            20                  25                  30

Gln Gly Asn Asp Asn Asp Ser Asn Asp Asn Asn Ser Ser Asn Glu Gln
        35                  40                  45

Gly Gly Val Cys Asn Cys Asn Pro Glu Glu Ala Pro Ala Ile Cys Ala
    50                  55                  60

Ser Pro Gly Ser Glu Gly Val Leu Val Ala His Glu Asn Cys Glu Lys
65                  70                  75                  80

Tyr Tyr Ile Cys Asn His Gly Arg Pro Val Val Ala Ser Cys Ser Gly
                85                  90                  95

Asn Leu Leu Phe Asn Pro Tyr Thr Asn Glu Cys Gly Trp Pro Arg Asp
            100                 105                 110

Val Asp Cys Gly Asp Arg Ile Glu Pro Gly Cys Thr Gly Cys Asn Asp
        115                 120                 125

Asn Asn Asn Asn Asp Asp Asp Asp Ser Asp Cys Asp Gly Asp Asp Pro
    130                 135                 140

Val Pro Pro Pro Ala Asp Asn Asp Asp Ser Glu Ser Ala Asp Ile Asp
145                 150                 155                 160

Asp Leu Pro Pro Pro Gly Asp Asp Ala Ser Val Arg Pro Pro Val Asp
                165                 170                 175

Glu Gly Thr Cys Asn Cys Asn Pro Glu Gln Ala Pro Ser Ile Cys Ala
                180                 185                 190

Glu Asp Asp Ser Asp Gly Val Leu Val Ala His Glu Asp Cys Asn Lys
        195                 200                 205

Phe Tyr Lys Cys His Asn Gly Lys Pro Val Ala Leu Tyr Cys Pro Gly
```

-continued

```
        210              215              220

Asn Leu Leu Tyr Asn Pro Asn Thr Glu Gln Cys Asp Trp Pro Glu Lys
225              230              235              240

Val Asp Cys Gly Asp Arg Val Ile Pro Asp Pro Glu Asp Asn Thr Val
                 245              250              255

Gly Gly Asn Asn Asp Gly Glu Asp Asp Ser Glu Gly Val Leu Val Ala
                 260              265              270

His Glu Asn Cys Asn Gln Phe Tyr Lys Cys Ser Gly Gly Lys Pro Val
                 275              280              285

Ala Leu Leu Cys Pro Gly Asn Leu Leu Phe Asn Pro Asn Thr Asp Gln
                 290              295              300

Cys Asp Trp Pro Trp Glu Val Asp Cys Gly Asp Arg Ile Ile Pro Asp
305              310              315              320

Pro Asp Arg Thr His Cys Gly Ser His Cys Ser Thr His Cys Ser Thr
                 325              330              335

His Cys Gly Ser Leu Leu Arg Leu Pro Leu Arg Leu His Cys Gly Ser
                 340              345              350

His Cys Gly Ser His Cys Cys Thr Asn Thr Ala Thr Asn Arg Arg Arg
                 355              360              365

Asn Met Gln Leu Gln Ser Trp Ser Thr Phe His Leu Cys Ser Arg Arg
                 370              375              380

Leu Leu Ile Ala His Glu Asp Cys Asn Lys Phe Tyr Ile Cys Asp His
385              390              395              400

Gly Lys Pro Val Ala Leu Ser Cys Pro Gly Asn Leu Leu Tyr Asn Pro
                 405              410              415

Tyr Thr Glu Lys Cys Asp Trp Pro Glu Asn Val Glu Cys Gly Asp Arg
                 420              425              430

Ala Pro Asp Pro Asp Ala Ser Gln Ala Pro Ala Ile Cys Ala Asp Ser
                 435              440              445

Gly Ser Glu Gly Val Leu Val Ala His Glu Asn Cys Asp Gln Tyr Tyr
                 450              455              460

Ile Cys Asp Gly Gly Arg Pro Val Ala Arg Pro Cys Gln Gly Gly Leu
465              470              475              480

Leu Tyr Asn Pro Leu Thr Gln Tyr Cys Asp Gly Gln Glu Met Ser Thr
                 485              490              495

Ala Val Thr Gly Leu Ser Leu Met Thr Ala Pro Val Ile Pro Glu Met
                 500              505              510

Arg Pro Asp Cys Ala Val Ser Gln Thr Pro Lys Glu Ala Trp
                 515              520              525
```

<210> SEQ ID NO 2
<211> LENGTH: 220
<212> TYPE: PRT
<213> ORGANISM: Artificial sequence
<220> FEATURE:
<223> OTHER INFORMATION: A polypeptide comprising Chitin binding domain
      CBD - HaPMP5B1

<400> SEQUENCE: 2

```
Met Gly Ser Ser His His His His His His Ser Ser Gly Leu Val Pro
1               5               10              15

Arg Gly Ser His Met Asp Arg Val Ile Pro Asp Pro Glu Asp Asn Thr
                20              25              30

Val Gly Gly Asn Asn Asp Gly Glu Asp Asp Ser Glu Gly Val Leu Val
        35              40              45
```

-continued

```
Ala His Glu Asn Cys Asn Gln Phe Tyr Lys Cys Ser Gly Gly Lys Pro
    50              55              60

Val Ala Leu Leu Cys Pro Gly Asn Leu Leu Phe Asn Pro Asn Thr Asp
65              70              75              80

Gln Cys Asp Trp Pro Trp Glu Val Asp Cys Gly Asp Arg Ile Ile Pro
                85              90              95

Asp Pro Asp Arg Thr His Cys Gly Ser His Cys Ser Thr His Cys Ser
            100             105             110

Thr His Cys Gly Ser Leu Leu Arg Leu Pro Leu Arg Leu His Cys Gly
            115             120             125

Ser His Cys Gly Ser His Cys Cys Thr Asn Thr Ala Thr Asn Arg Arg
        130             135             140

Arg Asn Met Gln Leu Gln Ser Trp Ser Thr Phe His Leu Cys Ser Arg
145             150             155             160

Arg Leu Leu Ile Ala His Glu Asp Cys Asn Lys Phe Tyr Ile Cys Asp
                165             170             175

His Gly Lys Pro Val Ala Leu Ser Cys Pro Gly Asn Leu Leu Tyr Asn
            180             185             190

Pro Tyr Thr Glu Lys Cys Asp Trp Pro Glu Asn Val Glu Cys Gly Asp
            195             200             205

Arg Ala Pro Asp Pro Asp Ala Ser Gln Ala Pro Ala
    210             215             220
```

```
<210> SEQ ID NO 3
<211> LENGTH: 45
<212> TYPE: PRT
<213> ORGANISM: Artificial sequence
<220> FEATURE:
<223> OTHER INFORMATION: Chitin binding domain (CBD)

<400> SEQUENCE: 3

Ser Glu Gly Val Leu Val Ala His Glu Asn Cys Glu Lys Tyr Tyr Ile
1               5               10              15

Cys Asn His Gly Arg Pro Val Val Ala Ser Cys Ser Gly Asn Leu Leu
            20              25              30

Phe Asn Pro Tyr Thr Asn Glu Cys Gly Trp Pro Arg Asp
        35              40              45
```

```
<210> SEQ ID NO 4
<211> LENGTH: 33
<212> TYPE: PRT
<213> ORGANISM: Artificial sequence
<220> FEATURE:
<223> OTHER INFORMATION: Chitin binding domain (CBD)

<400> SEQUENCE: 4

Cys Asn Lys Phe Tyr Lys Cys His Asn Gly Lys Pro Val Ala Leu Tyr
1               5               10              15

Cys Pro Gly Asn Leu Leu Tyr Asn Pro Asn Thr Glu Gln Cys Asp Trp
            20              25              30

Pro
```

```
<210> SEQ ID NO 5
<211> LENGTH: 45
<212> TYPE: PRT
<213> ORGANISM: Artificial sequence
<220> FEATURE:
<223> OTHER INFORMATION: Chitin binding domain (CBD)

<400> SEQUENCE: 5
```

Ser Glu Gly Val Leu Val Ala His Glu Asn Cys Asn Gln Phe Tyr Lys
1                   5                   10                  15

Cys Ser Gly Gly Lys Pro Val Ala Leu Leu Cys Pro Gly Asn Leu Leu
                20                  25                  30

Phe Asn Pro Asn Thr Asp Gln Cys Asp Trp Pro Trp Glu
        35                  40                  45

<210> SEQ ID NO 6
<211> LENGTH: 37
<212> TYPE: PRT
<213> ORGANISM: Artificial sequence
<220> FEATURE:
<223> OTHER INFORMATION: Chitin binding domain (CBD)

<400> SEQUENCE: 6

Glu Asp Cys Asn Lys Phe Tyr Ile Cys Asp His Gly Lys Pro Val Ala
1                   5                   10                  15

Leu Ser Cys Pro Gly Asn Leu Leu Tyr Asn Pro Tyr Thr Glu Lys Cys
                20                  25                  30

Asp Trp Pro Glu Asn
        35

<210> SEQ ID NO 7
<211> LENGTH: 41
<212> TYPE: PRT
<213> ORGANISM: Artificial sequence
<220> FEATURE:
<223> OTHER INFORMATION: Chitin binding domain (CBD)

<400> SEQUENCE: 7

Ser Glu Gly Val Leu Val Ala His Glu Asn Cys Asp Gln Tyr Tyr Ile
1                   5                   10                  15

Cys Asp Gly Gly Arg Pro Val Ala Arg Pro Cys Gln Gly Gly Leu Leu
                20                  25                  30

Tyr Asn Pro Leu Thr Gln Tyr Cys Asp
        35                  40

<210> SEQ ID NO 8
<211> LENGTH: 400
<212> TYPE: PRT
<213> ORGANISM: Artificial sequence
<220> FEATURE:
<223> OTHER INFORMATION: V-ATPase sub unit c

<400> SEQUENCE: 8

Met His His His His His His Met Ser Glu Tyr Trp Val Ile Ser Ala
1                   5                   10                  15

Pro Gly Asp Lys Thr Cys Gln Gln Thr Trp Asp Thr Leu Asn Asn Ala
                20                  25                  30

Thr Lys Ser Gly Asn Leu Ser Ala Asn Tyr Lys Phe Pro Ile Pro Asp
        35                  40                  45

Leu Lys Val Gly Thr Leu Asp Gln Leu Val Gly Leu Ser Asp Asp Leu
    50                  55                  60

Gly Lys Leu Asp Thr Phe Val Glu Ser Val Thr Arg Lys Val Ala Gln
65                  70                  75                  80

Tyr Leu Gly Glu Val Leu Glu Asp Gln Arg Asp Lys Leu His Glu Asn
                85                  90                  95

Leu Met Ala Asn Asn Ser Asp Met Pro Ser Tyr Leu Thr Arg Phe Gln
            100                 105                 110

-continued

```
Trp Asp Met Ala Lys Tyr Pro Ile Lys Gln Ser Leu Arg Asn Ile Ala
        115                 120                 125

Asp Ile Ile Ser Lys Gln Val Gly Gln Ile Asp Ser Asp Leu Lys Gln
        130                 135                 140

Lys Ser Ala Ala Tyr Asn Ala Leu Lys Gly Asn Leu Gln Asn Leu Glu
145                 150                 155                 160

Lys Lys Gln Thr Gly Ser Leu Leu Thr Arg Asn Leu Ala Asp Leu Val
                165                 170                 175

Lys Arg Glu His Phe Ile Leu Asp Ser Glu Tyr Leu Thr Thr Leu Leu
                180                 185                 190

Val Ile Val Pro Lys Ser Met Phe Asn Asp Trp Thr Ala Asn Tyr Glu
                195                 200                 205

Lys Ile Thr Asp Met Ile Val Pro Arg Ser Ser Gln Leu Ile His Gln
        210                 215                 220

Asp Asn Asp Tyr Gly Leu Phe Asn Val Thr Leu Phe Lys Lys Val Val
225                 230                 235                 240

Glu Glu Phe Lys His His Ala Arg Glu Arg Lys Phe Val Val Arg Glu
                245                 250                 255

Phe Ser Tyr Asn Glu Ala Asp Met Ala Ala Ala Arg Thr Arg Ser Pro
                260                 265                 270

Ser Ser Ser Pro Thr Arg Arg Ser Ser Ser Ile Leu Arg Lys Phe Ile
                275                 280                 285

Asn Phe Leu Gly Pro Leu Val Arg Trp Leu Lys Val Asn Phe Ser Glu
        290                 295                 300

Cys Phe Cys Ala Trp Ile His Val Lys Ala Leu Arg Val Phe Val Glu
305                 310                 315                 320

Ser Val Leu Arg Tyr Gly Leu Pro Val Asn Phe Gln Ala Val Val Met
                325                 330                 335

Val Pro Ser Arg Lys Asn Thr Lys Lys Leu Arg Glu Val Leu Gln Thr
                340                 345                 350

Leu Tyr Ala His Leu Asp His Ser Ala His Gln His Thr Ser Ser Ala
                355                 360                 365

Gln Asp Asn Ala Glu Leu Ala Gly Leu Gly Phe Gly Ser Ser Glu Tyr
        370                 375                 380

Phe Pro Tyr Val Phe Tyr Lys Ile Asn Val Asp Met Leu Asp Lys Asn
385                 390                 395                 400
```

```
<210> SEQ ID NO 9
<211> LENGTH: 516
<212> TYPE: PRT
<213> ORGANISM: Artificial sequence
<220> FEATURE:
<223> OTHER INFORMATION: Chitin deacetylase

<400> SEQUENCE: 9
```

```
Met Glu Thr Arg Val Lys Arg Gln Glu Glu Asp Gly Gly Asp Glu Val
1               5                   10                  15

Asn Ala Glu Gln Leu Cys Asp Gly Arg Pro Ala Asp Glu Tyr Phe Arg
                20                  25                  30

Leu Thr Thr Glu Gly Asp Cys Arg Asp Val Val Arg Cys Thr Arg Ser
        35                  40                  45

Gly Leu Lys Gln Ile Thr Cys Pro Ser Gly Leu Ala Phe Asp Leu Asp
        50                  55                  60

Lys Gln Thr Cys Asp Trp Lys Gly Lys Val Thr Asn Cys Asp Lys Leu
65                  70                  75                  80
```

-continued

```
Glu Lys Pro Arg Lys Val Leu Pro Ile Leu Lys Thr Asp Glu Pro Ile
                85                90                95

Cys Pro Glu Gly Lys Leu Ala Cys Gly Ser Gly Asp Cys Ile Glu Lys
            100               105               110

Glu Leu Phe Cys Asn Gly Lys Pro Asp Cys Lys Asp Glu Ser Asp Glu
        115               120               125

Asn Ala Cys Thr Val Asp Val Asp Pro Asn Arg Ala Pro Asp Cys Asp
    130               135               140

Pro Asn Gln Cys Ala Leu Pro Asp Cys Phe Cys Ser Ala Asp Gly Thr
145               150               155               160

Arg Ile Pro Gly Gly Ile Glu Val Asn Gln Val Pro Gln Met Ile Thr
                165               170               175

Ile Thr Phe Asn Gly Ala Val Asn Val Asp Asn Ile Asp Leu Tyr Glu
                180               185               190

Gln Ile Phe Asn Gly Asn Arg His Asn Pro Asn Gly Cys Gln Ile Arg
        195               200               205

Gly Thr Phe Phe Val Ser His Lys Tyr Thr Asn Tyr Ala Ala Val Gln
    210               215               220

Glu Leu His Arg Lys Gly His Glu Ile Ser Val Phe Ser Ile Thr His
225               230               235               240

Lys Asp Asp Pro Gln Tyr Trp Ser Ser Gly Ser Tyr Asp Asp Trp Leu
                245               250               255

Ala Glu Met Ala Gly Ala Arg Leu Ile Val Glu Arg Phe Ala Asn Ile
            260               265               270

Thr Asp Ser Ser Ile Ile Gly Val Arg Ala Pro Tyr Leu Arg Val Gly
            275               280               285

Gly Asn Lys Gln Phe Glu Met Met Ala Asp Gln Tyr Phe Val Tyr Asp
    290               295               300

Ala Ser Ile Thr Ala Pro Leu Gly Arg Val Pro Ile Trp Pro Tyr Thr
305               310               315               320

Leu Tyr Phe Arg Met Pro His Lys Cys Asn Gly Asn Ala His Asn Cys
                325               330               335

Pro Ser Arg Ser His Pro Val Trp Glu Met Val Met Asn Glu Leu Asp
            340               345               350

Arg Arg Asp Asp Pro Thr Phe Asp Glu Ser Leu Pro Gly Cys His Val
        355               360               365

Val Asp Ser Cys Ser Asn Ile Gln Thr Gly Glu Gln Phe Ala Arg Leu
    370               375               380

Leu Arg His Asn Ser Asn Arg His Tyr Ser Thr Asn Arg Ala Pro Leu
385               390               395               400

Gly Phe His Phe His Ala Ser Trp Leu Lys Ser Lys Lys Glu Phe Arg
            405               410               415

Asp Glu Leu Ile Lys Phe Ile Glu Glu Met Leu Glu Lys Asn Asp Val
            420               425               430

Tyr Phe Thr Ser Leu Ile Gln Val Ile Gln Trp Met Gln Asn Pro Thr
            435               440               445

Glu Leu Thr Ser Leu Arg Asp Phe Gln Glu Trp Lys Gln Asp Lys Cys
    450               455               460

Asp Val Lys Gly Gln Pro Phe Cys Ser Leu Pro Asn Ala Cys Pro Leu
465               470               475               480

Thr Thr Arg Glu Leu Pro Gly Glu Thr Leu Arg Leu Phe Thr Cys Met
                485               490               495

Glu Cys Pro Asn Asn Tyr Pro Trp Ile Leu Asp Pro Thr Gly Glu Gly
```

-continued

```
                500                 505                 510

Phe Asn Val Lys
        515

<210> SEQ ID NO 10
<211> LENGTH: 548
<212> TYPE: PRT
<213> ORGANISM: Artificial sequence
<220> FEATURE:
<223> OTHER INFORMATION: Trehalase

<400> SEQUENCE: 10

Met Asp Leu Pro Leu Thr Cys Thr Lys Pro Val Tyr Cys Asn Ser Asn
1                5                  10                  15

Leu Leu His Gln Ile Gln Met Ala Arg Leu Tyr Asn Asp Ser Lys Thr
            20                  25                  30

Phe Val Asp Leu Gln Met Asn Phe Asp Glu Asn Lys Thr Leu Thr Asp
        35                  40                  45

Phe Glu Thr Phe Phe Asn Leu His Asn Lys Asn Pro Thr Lys Glu Gln
    50                  55                  60

Leu Met Glu Phe Val Asn Glu Tyr Phe Ser Asn Asp Asn Glu Leu Glu
65                  70                  75                  80

Pro Trp Gln Pro Lys Asp Phe Ser Asp Asn Pro Ala Phe Leu Ala Lys
                85                  90                  95

Ile Lys Asp Asp Ala Leu Arg Glu Phe Gly Lys Gly Ile Asn Asn Ile
            100                 105                 110

Trp Pro Leu Leu Ala Arg Lys Val Lys Ala Glu Val Phe Gln Lys Pro
            115                 120                 125

Asp Gln Phe Ser Leu Val Pro Leu Thr His Gly Phe Ile Ile Pro Gly
        130                 135                 140

Gly Arg Phe Lys Glu Ile Tyr Tyr Trp Asp Thr Phe Trp Ile Ile Glu
145                 150                 155                 160

Gly Leu Leu Ile Ser Gly Met Gln Glu Thr Ala Lys Gly Met Ile Glu
                165                 170                 175

Asn Leu Ile Glu Leu Leu Asn Leu Phe Gly His Ile Pro Asn Gly Ser
            180                 185                 190

Arg Gly Tyr Tyr Gln Gln Arg Ser Gln Pro Pro Met Leu Asn Ala Met
        195                 200                 205

Val Ala Thr Tyr Tyr Met Tyr Thr Lys Asp Leu Glu Phe Leu Arg Asn
        210                 215                 220

Asn Ile Ala Tyr Leu Glu Lys Glu Leu Asp Phe Trp Met Asp Asn Arg
225                 230                 235                 240

Val Val Ser Val Asn Arg Gly Gly Lys Asn Tyr Thr Leu Leu Arg Tyr
                245                 250                 255

Tyr Ala Pro Ser Lys Gly Pro Arg Pro Glu Ser Tyr Tyr Glu Asp Tyr
                260                 265                 270

Ser Asn Thr Glu Gly Phe Ser Glu Glu Asp Ser Thr Asn Phe Cys Ile
        275                 280                 285

Asp Ile Lys Ser Ala Ala Glu Ser Gly Trp Asp Phe Ser Thr Arg Trp
        290                 295                 300

Phe Leu Met Pro Asp Gly Ser Asn Asn Gly Thr Leu Thr Asp Leu His
305                 310                 315                 320

Thr Arg Tyr Ile Ile Pro Val Asp Leu Asn Ala Ile Phe Ala Gly Ala
            325                 330                 335

Ala Gln Tyr Val Ser Asn Phe His Ala Leu Leu Lys Asn Pro Gln Lys
```

```
                340             345             350

Ala Ala Arg Tyr Gly Gln Leu Ala Gln Thr Trp Arg Asp Asn Ile Gln
        355             360             365

Ala Val Leu Trp Asn Asp Gln Asp Ala Met Trp Tyr Asp Phe Asn Ile
    370             375             380

Arg Asp Asn Leu His Arg Arg Tyr Tyr Tyr Ser Ser Asn Ala Ala Pro
385             390             395             400

Leu Trp Gln Asn Ala Val Asn Pro Asp Phe Leu Lys Leu Asn Ala Asp
            405             410             415

Arg Ile Leu Lys Ala Ile Thr Glu Ser Gly Gly Val Asp Phe Pro Gly
        420             425             430

Gly Val Pro Thr Ser Leu Ile Arg Ser Gly Glu Gln Trp Asp Phe Pro
        435             440             445

Asn Val Trp Pro Pro Glu Val Ser Ile Glu Val Ala Ala Ile Glu Asn
    450             455             460

Ile Gly Thr Pro Glu Ala Ile Thr Leu Ala Gln Glu Val Ala Gln Thr
465             470             475             480

Phe Val Arg Ser Cys His Trp Gly Phe Gln Lys Tyr Lys Gln Met Phe
            485             490             495

Glu Lys Tyr Asp Ala Glu Thr Pro Gly Arg Phe Gly Gly Gly Gly Glu
            500             505             510

Tyr Asn Val Gln Phe Gly Phe Gly Trp Ser Asn Gly Val Val Leu Glu
        515             520             525

Phe Leu Asn Lys Tyr Gly Ser Gln Leu Thr Ala Asp Asp Ser Asn Asn
    530             535             540

Thr Asn Asn Ser
545

<210> SEQ ID NO 11
<211> LENGTH: 483
<212> TYPE: PRT
<213> ORGANISM: Artificial sequence
<220> FEATURE:
<223> OTHER INFORMATION: cytochrome p450 monooxygenase

<400> SEQUENCE: 11

Met Arg Thr Phe Asn Tyr Trp Lys Lys Arg Asn Val Arg Gly Pro Glu
1               5               10              15

Pro Val Val Phe Phe Gly Asn Leu Lys Asp Ser Ala Leu Arg Lys Lys
            20              25              30

Asn Met Gly Val Val Met Glu Glu Leu Tyr Asn Met Phe Pro Glu Glu
        35              40              45

Lys Val Ile Gly Ile Tyr Arg Met Thr Ser Pro Cys Leu Leu Val Arg
    50              55              60

Asp Leu Asp Val Ile Lys His Ile Met Ile Lys Asp Phe Glu Val Phe
65              70              75              80

Ser Asp Arg Gly Val Glu Phe Ser Lys Glu Gly Leu Gly Ser Asn Leu
            85              90              95

Phe His Ala Asp Gly Glu Thr Trp Arg Ala Leu Gly Asn Arg Phe Thr
            100             105             110

Pro Ile Phe Thr Ser Gly Lys Leu Lys Asn Met Phe Tyr Leu Met His
        115             120             125

Glu Gly Ala Asp Asn Phe Ile Asp His Val Ser Ala Glu Cys Glu Lys
        130             135             140

Asn Gln Glu Phe Glu Val His Ser Leu Leu Gln Thr Tyr Thr Met Ser
```

```
145              150              155              160

Thr Ile Ala Ala Cys Ala Phe Gly Ile Ser Tyr Asp Ser Ile Gly Asp
             165              170              175

Lys Val Lys Ala Leu Asp Ile Val Asp Lys Ile Ile Ser Glu Pro Ser
             180              185              190

Tyr Ala Ile Glu Leu Asp Met Met Tyr Pro Gly Leu Leu Ser Lys Leu
             195              200              205

Asn Leu Ser Ile Phe Pro Thr Val Val Lys Asn Phe Phe Lys Ser Leu
     210              215              220

Val Asp Asn Ile Val Ala Gln Arg Asn Gly Lys Pro Ser Gly Arg Asn
225              230              235              240

Asp Phe Met Asp Leu Ile Leu Glu Leu Arg Gln Leu Gly Glu Val Thr
             245              250              255

Ser Asn Lys Tyr Gly Ser Ser Ala Ser Ser Leu Glu Ile Thr Asp Glu
             260              265              270

Val Ile Cys Ala Gln Ala Phe Val Phe Tyr Ile Ala Gly Tyr Glu Thr
             275              280              285

Ser Ala Thr Thr Met Ala Tyr Met Ile Tyr Gln Leu Ala Leu Asn Pro
     290              295              300

Asp Ile Gln Asn Lys Leu Ile Ala Glu Val Asp Glu Val Leu Lys Ala
305              310              315              320

Asn Asp Gly Lys Val Thr Tyr Asp Thr Val Lys Glu Met Lys Tyr Leu
             325              330              335

Asn Lys Ala Phe Asp Glu Thr Leu Arg Met Tyr Ser Ile Val Glu Pro
             340              345              350

Leu Gln Arg Lys Ala Thr Arg Asp Tyr Lys Ile Pro Gly Thr Asp Val
             355              360              365

Val Ile Glu Lys Asp Thr Ile Val Leu Ile Ser Pro Arg Gly Ile His
     370              375              380

Tyr Asp Pro Lys Tyr Tyr Asp Asn Pro Lys Gln Phe Asn Pro Asp Arg
385              390              395              400

Phe Asp Ala Glu Glu Val Gly Lys Arg His Pro Cys Ala Tyr Leu Pro
             405              410              415

Phe Gly Leu Gly Gln Arg Asn Cys Ile Gly Met Arg Phe Gly Arg Leu
             420              425              430

Gln Ser Leu Leu Cys Ile Thr Lys Ile Leu Ser Lys Phe Arg Ile Glu
             435              440              445

Pro Ser Lys Asn Thr Asp Arg Asn Leu Gln Val Glu Pro His Arg Gly
     450              455              460

Leu Ile Gly Pro Lys Gly Gly Ile Arg Val Asn Ala Ile Pro Arg Lys
465              470              475              480

Leu Val Ser
```

```
<210> SEQ ID NO 12
<211> LENGTH: 415
<212> TYPE: PRT
<213> ORGANISM: Artificial sequence
<220> FEATURE:
<223> OTHER INFORMATION: Chitin synthase

<400> SEQUENCE: 12

Asn Cys Tyr Phe His Gly Thr Val Pro Asp Tyr Leu Tyr Phe Glu Ser
1               5               10              15

Pro Pro Val Phe Thr Leu Ser Asp Phe Ile Ser Arg Gln Met Ala Trp
             20              25              30
```

-continued

```
Ile Cys Arg Thr Phe Gly Leu Asn Glu Lys Leu Phe Val Met Pro Met
        35              40              45

Tyr Asn Gly Leu Leu Ile Asp Gln Ser Met Ala Leu Asn Arg Lys Arg
        50              55              60

Asn Asp Gln Arg Asp Val Lys Thr Glu Asp Leu Ala Glu Ile Glu Lys
65              70              75              80

Glu Lys Gly Asp Glu Tyr Tyr Glu Thr Ile Ser Val His Thr Asp Asn
                85              90              95

Thr Gly Ser Ser Pro Lys Ala Ile Lys Ser Ser Asp Gln Ile Thr Arg
                100             105             110

Ile Tyr Ala Cys Ala Thr Met Trp His Glu Thr Lys Asp Glu Met Met
        115             120             125

Glu Phe Leu Lys Ser Ile Leu Arg Leu Asp Glu Asp Gln Cys Ala Arg
        130             135             140

Arg Val Ala Gln Lys Tyr Leu Arg Val Val Asp Pro Asp Tyr Tyr Glu
145             150             155             160

Phe Glu Thr His Ile Phe Leu Asp Asp Ala Phe Glu Ile Ser Asp His
                165             170             175

Ser Asp Asp Asp Ser Gln Val Asn Arg Phe Val Lys Leu Leu Val Asp
                180             185             190

Thr Ile Asp Glu Ala Ala Ser Glu Val His Gln Thr Asn Ile Arg Asp
        195             200             205

Val His Val Leu Pro Ser Arg Ser Ser Phe Asn Gly Thr Ala Asp Ile
        210             215             220

Leu Asp Arg Lys Glu Val Met Ala Glu Asn Thr Tyr Leu Leu Thr Leu
225             230             235             240

Asp Gly Asp Ile Asp Phe Gln Pro His Ala Val Arg Leu Leu Ile Asp
                245             250             255

Leu Met Lys Lys Asn Lys Asn Leu Gly Ala Ala Cys Gly Arg Ile His
                260             265             270

Pro Val Gly Ser Gly Pro Met Val Trp Tyr Gln Met Phe Glu Tyr Ala
        275             280             285

Ile Gly His Trp Leu Gln Lys Ala Thr Glu His Met Ile Gly Cys Val
        290             295             300

Leu Cys Ser Pro Gly Cys Phe Ser Leu Phe Arg Gly Lys Ala Leu Met
305             310             315             320

Asp Asp Asn Val Met Lys Lys Tyr Thr Leu Arg Ser Asp Glu Ala Arg
                325             330             335

His Tyr Val His Thr Ile Arg Gly Arg Ser Met Val Met Tyr Ala Ile
                340             345             350

Thr Ala Thr Trp Leu Ser Cys Arg Ile Leu Ser Cys Leu Arg Cys Tyr
        355             360             365

Thr His Cys Pro Glu Gly Phe Asn Glu Phe Tyr Asn Arg Arg Arg Trp
        370             375             380

Val Pro Ser Thr Ile Ala Asn Ile Met Asp Leu Leu Ala Asp Cys Lys
385             390             395             400

His Thr Ile Lys Ile Asn Asp Asn Ile Ser Ser Pro Tyr Ile Ala
                405             410             415
```

<210> SEQ ID NO 13
<211> LENGTH: 240
<212> TYPE: PRT
<213> ORGANISM: Artificial sequence
<220> FEATURE:

<223> OTHER INFORMATION: 13 NPC1-sterol transporter

<400> SEQUENCE: 13

```
Asp Ser Phe Gln Thr Lys Tyr Phe Gln Tyr Leu Asn Arg Tyr Leu Asn
1               5                   10                  15

Ile Gly Pro Pro Val Tyr Phe Val Val Thr Glu Gly Leu Asn Tyr Ser
            20                  25                  30

Asp Met Asp Thr Gln Asn Met Ile Cys Gly Thr Arg Phe Cys Arg Pro
        35                  40                  45

Asp Ser Leu Ser Met Gln Leu Tyr Ala Ala Tyr Arg Asn Pro Asn Glu
    50                  55                  60

Thr Tyr Ile Ala Gln Pro Pro Asn Ser Trp Leu Asp Asp Tyr Phe Asp
65                  70                  75                  80

Trp Ser Ala Leu Pro Asn Cys Cys Lys Tyr Phe Pro Ser Asn Ser Ser
            85                  90                  95

Phe Cys Pro Asn Asp Arg Gly Ala Pro Cys Lys Ala Cys Gly Ile Ala
            100                 105                 110

Leu Glu Gly Asp Glu Gln Arg Pro Asn Ser Thr Glu Phe Glu Arg Tyr
        115                 120                 125

Val Pro Phe Phe Leu Gln Asp Ile Pro Asp Thr Ser Gly Ser Gly Cys
    130                 135                 140

Val Lys Gly Gly His Ala Ala Tyr Gly Gln Ala Val Asn Tyr Lys Met
145                 150                 155                 160

Phe Asn Lys Thr Gln Ala His Val Gly Ala Thr Tyr Tyr Gln Gly Tyr
                165                 170                 175

His Thr Val Leu Lys Thr Ser Leu Asp Tyr Tyr Ser Ala Leu Lys Gly
            180                 185                 190

Ala Arg Glu Val Ala Ala Asn Leu Thr Glu Thr Leu Asn Arg Asn Leu
        195                 200                 205

Lys His Gln Leu Asn Gly Thr Thr Ile Asn Val Phe Pro Tyr Ser Val
    210                 215                 220

Phe Tyr Val Phe Tyr Glu Gln Tyr Leu Thr Met Trp Pro Asp Thr Leu
225                 230                 235                 240
```

<210> SEQ ID NO 14
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 14

```
Met Gln Val Gln Leu Gln Glu Ser Gly Gly Gly Leu Val Gln Ala Gly
1               5                   10                  15

Asp Ser Leu Arg Leu Ser Cys Ala Ala Ser Gly Arg Ser Phe Ser Ile
            20                  25                  30

Tyr Thr Met Gly Trp Phe Arg Gln Ala Pro Gly Asn Glu Arg Glu Phe
        35                  40                  45

Val Thr Ala Ile Ser Pro Ser Gly Gly Ser Thr His Tyr Ala Asp Phe
    50                  55                  60

Val Lys Gly Arg Phe Thr Ile Ser Arg Asp Asn Thr Lys Asn Thr Met
65                  70                  75                  80

Tyr Leu Gln Met Asn Ser Leu Lys Pro Glu Asp Thr Ala Val Tyr Phe
            85                  90                  95

Cys Ala Ser Thr Ser Ser Gln His Tyr Glu Asp Thr Glu Glu Ser Tyr
            100                 105                 110
```

-continued

```
Lys Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
        130                 135                 140
```

<210> SEQ ID NO 15
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 15

```
Gly Arg Ser Phe Ser Ile Tyr Thr
1               5
```

<210> SEQ ID NO 16
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 16

```
Ile Ser Pro Ser Gly Gly Ser Thr
1               5
```

<210> SEQ ID NO 17
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 17

```
Ala Ser Thr Ser Ser Gln His Tyr Glu Asp Thr Glu Glu Ser Tyr Lys
1               5                   10                  15

Tyr
```

<210> SEQ ID NO 18
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 18

```
Met Gln Val Gln Leu Gln Glu Ser Gly Gly Gly Leu Val Glu Ala Ala
1               5                   10                  15

Gly Ser Leu Arg Leu Ser Cys Ala Ala Leu Gly Ser Asn Leu Arg Ile
            20                  25                  30

Asn Thr Met Gly Trp Tyr Arg Gln Ala Pro Gly Lys Gln Arg Glu Leu
            35                  40                  45

Val Ala Thr Ile Thr Asn Gly Gly Arg Lys Asn Tyr Ala Asp Ser Val
        50                  55                  60

Lys Gly Arg Phe Thr Ile Phe Arg Gly Asn Ala Asn Thr Val Tyr Leu
65                  70                  75                  80

Gln Met Asn Ser Leu Lys Pro Glu Asp Thr Ala Val Tyr Tyr Cys Asn
                85                  90                  95
```

```
Ala Gly Leu Leu Asp Pro Pro Tyr Ser Ala Pro Gly Asp Tyr Trp Gly
            100                 105                 110

Glu Gly Thr Gln Val Thr Val Ser Ser Ala Ala Ala Tyr Pro Tyr Asp
        115                 120                 125

Val Pro Asp Tyr Gly Ser His His His His His His
    130                 135                 140

<210> SEQ ID NO 19
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 19

Leu Gly Ser Asn Leu Arg Ile Asn Thr
1               5

<210> SEQ ID NO 20
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 20

Thr Ile Thr Asn Gly Gly Arg Lys Asn Tyr
1               5                   10

<210> SEQ ID NO 21
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 21

Asn Ala Gly Leu Leu Asp Pro Pro Tyr Ser Ala Pro Gly Asp Tyr
1               5                   10                  15

<210> SEQ ID NO 22
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 22

Met Gln Val Gln Leu Gln Glu Ser Gly Gly Gly Leu Val Gln Ala Gly
1               5                   10                  15

Gly Ser Leu Thr Leu Ser Cys Ala Ala Ser Gly Arg Ser Phe Ser Thr
            20                  25                  30

Tyr Ala Met Gly Trp Ser Arg Gln Ala Pro Gly Lys Glu Arg Glu Phe
        35                  40                  45

Leu Ala Gly Ile Ser Arg Gly Gly Gly Thr Thr Val Tyr Ala Asp Ser
    50                  55                  60

Val Lys Gly Arg Phe Thr Ile Ser Arg Asp Asn Val Lys Asn Thr Val
65                  70                  75                  80

Tyr Leu Gln Met Asn Ser Leu Lys Pro Glu Asp Ala Ala Val Tyr Tyr
                85                  90                  95
```

```
Cys Ala Ala Ala Leu Arg Pro Phe Asp Gly Ser Gly Glu Arg Arg Tyr
            100                 105                 110

Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140
```

```
<210> SEQ ID NO 23
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 23

Gly Arg Ser Phe Ser Thr Tyr Ala
1               5
```

```
<210> SEQ ID NO 24
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 24

Gly Ile Ser Arg Gly Gly Gly Thr Thr
1               5
```

```
<210> SEQ ID NO 25
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 25

Ala Ala Leu Arg Pro Phe Asp Gly Ser Gly Glu Arg Arg Tyr Asp Tyr
1               5                   10                  15
```

```
<210> SEQ ID NO 26
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 26

Met Gln Val Gln Leu Gln Glu Ser Gly Gly Gly Leu Val Gln Ala Gly
1               5                   10                  15

Asp Ser Leu Arg Leu Ser Cys Ala Ala Ser Gly Arg Ser Phe Ser Ile
            20                  25                  30

Tyr Thr Met Gly Trp Phe Arg Gln Ala Pro Gly Lys Glu Arg Glu Phe
        35                  40                  45

Val Ala Ala Ile Ser Pro Ser Gly Val Ser Thr Asp Tyr Ala Asp Ser
    50                  55                  60

Val Arg Gly Arg Phe Thr Ile Ser Arg Asp Asn Ala Lys Asn Thr Met
65                  70                  75                  80

Tyr Leu Gln Met Asn Ser Leu Lys Pro Glu Asp Thr Ala Val Tyr Tyr
                85                  90                  95
```

```
Cys Ala Ala Gly Gly Arg His Tyr Thr Arg His Pro Tyr Asp Tyr Asp
            100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

<210> SEQ ID NO 27

<400> SEQUENCE: 27

000

<210> SEQ ID NO 28
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 28

```
Ala Ile Ser Pro Ser Gly Val Ser Thr Asp
1               5                   10
```

<210> SEQ ID NO 29
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 29

```
Ala Ala Gly Gly Arg His Tyr Thr Arg His Pro Tyr Asp Tyr Asp Tyr
1               5                   10                  15
```

<210> SEQ ID NO 30
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 30

```
Met Gln Val Gln Leu Gln Glu Ser Gly Gly Gly Leu Val Gln Thr Gly
1               5                   10                  15

Gly Ser Leu Arg Leu Ser Cys Ala Ala Ser Gly Arg Ser Phe Ser Ser
            20                  25                  30

Tyr Ser Met Gly Trp Phe Arg Gln Gly Pro Gly Lys Gly Arg Glu Trp
        35                  40                  45

Val Ala Asp Ile Asn Glu Ser Gly Ser Ser Thr Ser Tyr Tyr Asp Pro
    50                  55                  60

Val Lys Gly Arg Phe Thr Ile Ser Arg Asp Asn Ser Lys Asn Thr Val
65                  70                  75                  80

Tyr Leu Gln Met Asn Asp Leu Lys Pro Glu Asp Thr Ala Asp Tyr Tyr
                85                  90                  95

Cys Ala Ala Leu Val Thr Gly Gly Asp Thr Asp Leu Gly Glu Trp Asp
            100                 105                 110

Phe Trp Gly Pro Gly Thr Gln Val Thr Val Ser Ser Ala Ala Ala Tyr
        115                 120                 125

Pro Tyr Asp Val Pro Asp Tyr Gly Ser His His His His His His
```

-continued

```
        130               135               140
```

<210> SEQ ID NO 31
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 31

Gly Arg Ser Phe Ser Ser Tyr Ser
1               5

<210> SEQ ID NO 32
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 32

Ile Asn Glu Ser Gly Ser Ser Thr
1               5

<210> SEQ ID NO 33
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 33

Ala Ala Leu Val Thr Gly Gly Asp Thr Asp Leu Gly Glu Trp Asp Phe
1               5                   10                  15

<210> SEQ ID NO 34
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 34

Met Gln Val Gln Leu Gln Glu Ser Gly Gly Gly Leu Val Gln Ala Gly
1               5                   10                  15

Asp Ser Leu Lys Leu Ser Cys Ala Ala Ser Gly Gly Thr Phe Ser Ser
            20                  25                  30

Tyr Val Met Gly Trp Phe Arg Gln Ala Pro Gly Lys Glu Arg Glu Phe
        35                  40                  45

Val Ala Arg Ile Gly Val Ser Glu Gly Tyr Leu Tyr Tyr Ala Asp Ser
    50                  55                  60

Val Lys Asp Arg Phe Thr Ile Ser Arg Asp Ser Ala Lys Asn Thr Gly
65                  70                  75                  80

Tyr Leu Gln Met Asn Ala Leu Lys Pro Glu Asp Thr Ala Val Tyr Tyr
                85                  90                  95

Cys Ala Ala Gly Pro Arg Arg Tyr Trp Thr Arg Glu Pro Asp Ala Tyr
            100                 105                 110

Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His

-continued

```
        130             135             140
```

```
<210> SEQ ID NO 35
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 35

Gly Gly Thr Phe Ser Ser Tyr Val
1               5

<210> SEQ ID NO 36
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 36

Ile Gly Val Ser Glu Gly Tyr Leu
1               5

<210> SEQ ID NO 37
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 37

Ala Ala Gly Pro Arg Arg Tyr Trp Thr Arg Glu Pro Asp Ala Tyr Asp
1               5                   10                  15

Tyr

<210> SEQ ID NO 38
<211> LENGTH: 145
<212> TYPE: PRT
<213> ORGANISM: Artificial sequence
<220> FEATURE:
<223> OTHER INFORMATION: nanobody amino acid sequence

<400> SEQUENCE: 38

Met Gln Val Gln Leu Gln Glu Ser Gly Gly Gly Leu Val Gln Ala Gly
1               5                   10                  15

Gly Ser Leu Lys Leu Ser Cys Gly Ala Ser Gly Arg Thr Phe Ser Thr
            20                  25                  30

Asn Ala Met Gly Trp Phe Arg Gln Ala Pro Gly Lys Glu Arg Glu Phe
        35                  40                  45

Val Ala Thr Ile Ser Ala Gly Gly Ser Leu Thr Tyr Tyr Ala Asp Ser
    50                  55                  60

Val Lys Gly Arg Phe Thr Ile Ser Arg Asp Asn Ala Lys Asn Thr Val
65                  70                  75                  80

Tyr Leu Arg Met Asn Ser Leu Lys Pro Asp Asp Thr Ala Val Tyr Tyr
                85                  90                  95

Cys Ala Ala Asp Gln Asp Ser Gly Arg Leu Pro Leu Ile Asn Ser Gly
            100                 105                 110

Tyr Glu Tyr Trp Gly Gln Gly Thr Gln Val Thr Val Ser Ser Ala Ala
            115                 120                 125
```

-continued

Ala Tyr Pro Tyr Asp Val Pro Asp Tyr Gly Ser His His His His
    130                 135             140

His
145

<210> SEQ ID NO 39
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 39

Gly Arg Thr Phe Ser Thr Asn Ala
1               5

<210> SEQ ID NO 40
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 40

Ile Ser Ala Gly Gly Ser Leu Thr
1               5

<210> SEQ ID NO 41
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 41

Ala Ala Asp Gln Asp Ser Gly Arg Leu Pro Leu Ile Asn Ser Gly Tyr
1               5                   10                  15

Glu Tyr

<210> SEQ ID NO 42
<211> LENGTH: 145
<212> TYPE: PRT
<213> ORGANISM: Artificial sequence
<220> FEATURE:
<223> OTHER INFORMATION: nanobody amino acid sequence

<400> SEQUENCE: 42

Met Gln Val Gln Leu Gln Glu Ser Gly Gly Gly Leu Val Gln Ala Gly
1               5                   10                  15

Ala Ser Leu Arg Leu Ser Cys Ala Ala Ser Gly Arg Thr Phe Ser Ser
            20                  25                  30

Tyr Gly Thr Ala Met Gly Trp Phe Arg Gln Ala Pro Gly Lys Glu Arg
        35                  40                  45

Glu Phe Val Ala Ala Ile Leu Trp Thr Gly Ser Ser Ser Tyr Asp Ser
    50                  55                  60

Val Lys Gly Arg Phe Thr Ile Ser Arg Asp Asn Ala Lys Asn Thr Val
65                  70                  75                  80

Tyr Leu Gln Met Ile Ser Leu Asn Pro Glu Asp Thr Ala Val Tyr Tyr
                85                  90                  95

```
Cys Ala Ala Arg Ser Arg Tyr Thr Gly Ser Tyr Tyr Glu Glu Ser Thr
            100                 105                 110

Tyr Asn Tyr Trp Gly Gln Gly Thr Gln Val Thr Val Ser Ser Ala Ala
        115                 120                 125

Ala Tyr Pro Tyr Asp Val Pro Asp Tyr Gly Ser His His His His His
    130                 135                 140

His
145
```

<210> SEQ ID NO 43
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 43

```
Gly Arg Thr Phe Ser Ser Tyr Gly Thr Ala
1               5                   10
```

<210> SEQ ID NO 44
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 44

```
Ile Leu Trp Thr Gly Ser Ser Ser
1               5
```

<210> SEQ ID NO 45
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 45

```
Ala Ala Arg Ser Arg Tyr Thr Gly Ser Tyr Tyr Glu Glu Ser Thr Tyr
1               5                   10                  15

Asn Tyr
```

<210> SEQ ID NO 46
<211> LENGTH: 147
<212> TYPE: PRT
<213> ORGANISM: Artificial sequence
<220> FEATURE:
<223> OTHER INFORMATION: nanobody amino acid sequence

<400> SEQUENCE: 46

```
Met Gln Val Gln Leu Gln Glu Ser Gly Gly Gly Val Val Gln Pro Gly
1               5                   10                  15

Gly Ser Leu Arg Leu Ser Cys Ala Ala Ser Gly Arg Asp Phe Ser Asn
            20                  25                  30

Tyr Asn Met Ala Trp Phe Arg Gln Ala Pro Gly Lys Glu Arg Asp Val
        35                  40                  45

Val Ala Thr Ile Arg Arg Ser Gly Asp Ile Thr Ser Tyr Thr Asp Ser
    50                  55                  60

Val Lys Gly Arg Phe Thr Ile Ser Arg Asp Asn Ala Lys Asn Thr Val
```

-continued

```
65                   70                   75                   80

Tyr Leu Gln Met Asn Ser Leu Lys Pro Glu Asp Thr Ala Ala Tyr Tyr
             85                   90                   95

Cys Ala Ala Arg Thr Gly Ser Phe Leu Thr Val Leu Ile Thr Thr Pro
             100                  105                  110

Gly Asn Tyr Asn Tyr Trp Gly Gln Gly Thr Gln Val Thr Val Ser Ser
         115                  120                  125

Ala Ala Ala Tyr Pro Tyr Asp Val Pro Asp Tyr Gly Ser His His His
    130                  135                  140

His His His
145
```

<210> SEQ ID NO 47
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 47

```
Gly Arg Asp Phe Ser Asn Tyr Asn
1               5
```

<210> SEQ ID NO 48
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 48

```
Ile Arg Arg Ser Gly Asp Ile Thr
1               5
```

<210> SEQ ID NO 49
<211> LENGTH: 20
<212> TYPE: PRT
<213> ORGANISM: Artificial sequence
<220> FEATURE:
<223> OTHER INFORMATION: Complementarity-determining region amino acid
      sequence

<400> SEQUENCE: 49

```
Ala Ala Arg Thr Gly Ser Phe Leu Thr Val Leu Ile Thr Thr Pro Gly
1               5                   10                  15

Asn Tyr Asn Tyr
            20
```

<210> SEQ ID NO 50
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 50

```
Met Gln Val Gln Leu Gln Glu Ser Gly Gly Gly Leu Val Gln Ala Gly
1               5                   10                  15

Asp Ser Leu Arg Leu Ser Cys Ala Ala Ser Gly Arg Thr Phe Ser Ala
            20                  25                  30

Phe Arg Met Ala Trp Phe Arg Gln Ala Pro Gly Lys Glu Arg Ala Leu
```

-continued

```
                35                  40                  45
Val Ala Asp Ile Ser Arg Leu Ser Thr Arg Thr Tyr Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Leu Glu Gly Val Gly Pro Met Trp Glu Tyr Trp Val
                100                 105                 110

Gln Gly Thr Gln Val Thr Val Ser Ser Ala Ala Ala Tyr Pro Tyr Asp
        115                 120                 125

Val Pro Asp Tyr Gly Ser His His His His His
    130                 135                 140

<210> SEQ ID NO 51
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 51

Gly Arg Thr Phe Ser Ala Phe Arg
1               5

<210> SEQ ID NO 52
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 52

Ile Ser Arg Leu Ser Thr Arg Thr
1               5

<210> SEQ ID NO 53
<211> LENGTH: 13
<212> TYPE: PRT
<213> ORGANISM: Artificial sequence
<220> FEATURE:
<223> OTHER INFORMATION: Complementarity-determining region amino acid
      sequence

<400> SEQUENCE: 53

Ala Ala Asp Leu Glu Gly Val Gly Pro Met Trp Glu Tyr
1               5                   10

<210> SEQ ID NO 54
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 54

Met Gln Val Gln Leu Gln Glu Ser Gly Gly Gly Ser Val Gln Ala Gly
1               5                   10                  15

Asn Ser Leu Arg Leu Ser Cys Thr Tyr Ser Gly Arg Thr Phe Ser Thr
                20                  25                  30

Arg Ala Met Gly Trp Phe Arg Gln Ala Pro Gly Lys Glu Arg Glu Leu
```

-continued

```
        35                    40                    45
Val Ala Gly Ile Gly Trp Asn Gly Ala Thr Gln Tyr Tyr Ala Asp Ser
    50                    55                    60

Val Lys Gly Arg Phe Thr Ile Ser Arg Asp Ser Ala Ser Asn Thr Val
65                    70                    75                    80

Ala Leu Gln Met Asn Ser Leu Glu Pro Glu Asp Thr Ala Val Tyr Tyr
                85                    90                    95

Cys Ala Ala His Gly Arg Glu Tyr Val Thr Pro Ser Tyr Asn Asn Tyr
            100                   105                   110

Asp Tyr Trp Gly Gln Gly Thr Gln Val Thr Val Ser Ser Ala Ala Ala
        115                   120                   125

Tyr Pro Tyr Asp Val Pro Asp Tyr Gly Ser His His His His His His
    130                   135                   140
```

```
<210> SEQ ID NO 55
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 55

Gly Arg Thr Phe Ser Thr Arg Ala
1               5

<210> SEQ ID NO 56
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 56

Ile Gly Trp Asn Gly Ala Thr Gln
1               5

<210> SEQ ID NO 57
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 57

Ala Ala His Gly Arg Glu Tyr Val Thr Pro Ser Tyr Asn Asn Tyr Asp
1               5                   10                  15

Tyr

<210> SEQ ID NO 58
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 58

Met Gln Val Gln Leu Gln Glu Ser Gly Gly Gly Leu Thr Gln Ala Gly
1               5                   10                  15

Asp Ser Leu Arg Leu Ser Cys Ala Ala Ser Gly Arg Ser Phe Val Arg
            20                  25                  30
```

Tyr Thr Thr Gly Trp Phe Arg Gln Ala Pro Gly Lys Glu Arg Glu Phe
        35              40              45

Val Ala Ser Ile Ser Trp Ser Arg Gly Ser Thr Tyr Tyr Ala Asp Ser
    50              55              60

Val Lys Gly Arg Phe Thr Ile Ser Lys Asp Asn Ala Glu Asn Thr Val
65              70              75              80

Tyr Leu Gln Met Asn Ser Pro Glu Pro Glu Asp Thr Ala Val Tyr Tyr
            85              90              95

Cys Ala Gly Asn Ser Arg Gly Ala Thr Thr Phe Ala Gln Tyr Tyr Asp
            100             105             110

Asp Trp Gly Gln Gly Thr Gln Val Thr Val Ser Ser Ala Ala Ala Tyr
        115             120             125

Pro Tyr Asp Val Pro Asp Tyr Gly Ser His His His His His His
    130             135             140

<210> SEQ ID NO 59
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 59

Gly Arg Ser Phe Val Arg Tyr Thr
1               5

<210> SEQ ID NO 60
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 60

Ile Ser Trp Ser Arg Gly Ser Thr
1               5

<210> SEQ ID NO 61
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 61

Ala Gly Asn Ser Arg Gly Ala Thr Thr Phe Ala Gln Tyr Tyr Asp Asp
1               5               10              15

<210> SEQ ID NO 62
<211> LENGTH: 137
<212> TYPE: PRT
<213> ORGANISM: Artificial sequence
<220> FEATURE:
<223> OTHER INFORMATION: nanobody amino acid sequence

<400> SEQUENCE: 62

Met Gln Val Gln Leu Gln Glu Ser Gly Gly Gly Leu Val Gln Ala Gly
1               5               10              15

Gly Ser Leu Arg Leu Ser Cys Ala Ala Ser Gly Arg Thr Phe Ser Leu
        20              25              30

-continued

```
Thr Arg Met Gly Trp Phe Arg Gln Ala Pro Gly Lys Glu Arg Glu Ile
        35              40              45

Val Ala His Ile Met Arg Ser Ser Asp Ser Thr Phe Tyr Gly Asp Ser
    50              55              60

Val Lys Gly Arg Phe Thr Ile Ser Arg Asp Asn Ala Lys Asn Thr Val
65              70              75              80

Tyr Leu Gln Met Asn Arg Leu Asn Pro Glu Asp Thr Ala Val Tyr Tyr
            85              90              95

Cys Ala Ala Ala Gln Trp Ala Gly Tyr Asp Tyr Trp Gly Gln Gly Thr
            100             105             110

Gln Val Thr Val Ser Ser Ala Ala Ala Tyr Pro Tyr Asp Val Pro Asp
        115             120             125

Tyr Gly Ser His His His His His His
    130             135
```

```
<210> SEQ ID NO 63
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 63

Gly Arg Thr Phe Ser Leu Thr Arg
1               5
```

```
<210> SEQ ID NO 64
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 64

Ile Met Arg Ser Ser Asp Ser Thr
1               5
```

```
<210> SEQ ID NO 65
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 65

Ala Ala Ala Gln Trp Ala Gly Tyr Asp Tyr
1               5               10
```

```
<210> SEQ ID NO 66
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 66

Met Gln Val Gln Leu Gln Glu Ser Gly Gly Gly Leu Val Pro Ala Gly
1               5               10              15

Gly Ser Leu Arg Leu Ser Cys Ala Ala Ser Gly Arg Thr Phe Thr Ser
            20              25              30
```

-continued

```
Ser Thr Met Ala Trp Phe Arg Gln Val Pro Gly Lys Glu Arg Glu Phe
        35              40              45
```

```
Val Ala Ala Ile Ser Pro Arg Gly Leu Ser Gln Asp Tyr Gly His Ser
    50              55              60
```

```
Val Lys Gly Arg Phe Thr Ile Ser Arg Asp Asn Ala Glu Asn Thr Val
65              70              75              80
```

```
Tyr Leu Gln Met Asn Ser Leu Lys Ser Glu Asp Thr Ala Leu Tyr Tyr
            85              90              95
```

```
Cys Ala Ala Thr Ser Gly Ser Tyr Ser Ser Ser Arg Asn Asp Tyr Tyr
            100             105             110
```

```
Tyr Trp Gly Gln Gly Thr Gln Val Thr Val Ser Ser Ala Ala Ala Tyr
        115             120             125
```

```
Pro Tyr Asp Val Pro Asp Tyr Gly Ser His His His His His His
    130             135             140
```

```
<210> SEQ ID NO 67
<211> LENGTH: 8
<212> TYPE: PRT
<213> ORGANISM: Artificial sequence
<220> FEATURE:
<223> OTHER INFORMATION: Complementarity-determining region amino acid
      sequence
```

```
<400> SEQUENCE: 67
```

```
Gly Arg Thr Phe Thr Ser Ser Thr
1               5
```

```
<210> SEQ ID NO 68
<211> LENGTH: 8
<212> TYPE: PRT
<213> ORGANISM: Artificial sequence
<220> FEATURE:
<223> OTHER INFORMATION: Complementarity-determining region amino acid
      sequence
```

```
<400> SEQUENCE: 68
```

```
Ile Ser Pro Arg Gly Leu Ser Gln
1               5
```

```
<210> SEQ ID NO 69
<211> LENGTH: 16
<212> TYPE: PRT
<213> ORGANISM: Artificial sequence
<220> FEATURE:
<223> OTHER INFORMATION: Complementarity-determining region amino acid
      sequence
```

```
<400> SEQUENCE: 69
```

```
Ala Ala Thr Ser Gly Ser Tyr Ser Ser Ser Arg Asn Asp Tyr Tyr Tyr
1               5               10              15
```

```
<210> SEQ ID NO 70
<211> LENGTH: 137
<212> TYPE: PRT
<213> ORGANISM: Artificial sequence
<220> FEATURE:
<223> OTHER INFORMATION: nanobody amino acid sequence
```

```
<400> SEQUENCE: 70
```

```
Met Gln Val Gln Leu Gln Glu Ser Gly Gly Gly Leu Val Gln Pro Gly
1               5               10              15
```

```
Gly Ser Leu Arg Leu Ser Cys Ala Ala Ser Gly Phe Thr Leu Ser Asn
            20              25              30
```

```
Tyr Arg Met Ala Trp Phe Arg Gln Gly Leu Gly Lys Glu Arg Glu Phe
        35              40              45

Val Ala His Ile Met Arg Asn Ser Asp Thr Thr Trp Tyr Thr Glu Ser
    50              55              60

Val Lys Gly Arg Phe Thr Ile Ser Arg Asp Asn Ser Lys Asn Thr Val
65              70              75              80

Tyr Leu Gln Met Asn Ser Leu Lys Pro Glu Asp Thr Ala Val Tyr Tyr
            85              90              95

Cys Ala Ala Ser Asn Ala Gly Thr Phe Asp Tyr Trp Gly Gln Gly Thr
            100             105             110

Gln Val Thr Val Ser Ser Ala Ala Ala Tyr Pro Tyr Asp Val Pro Asp
        115             120             125

Tyr Gly Ser His His His His His His
    130             135
```

```
<210> SEQ ID NO 71
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 71

Gly Phe Thr Leu Ser Asn Tyr Arg
1               5
```

```
<210> SEQ ID NO 72
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 72

Ile Met Arg Asn Ser Asp Thr Thr
1               5
```

```
<210> SEQ ID NO 73
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 73

Ala Ala Ser Asn Ala Gly Thr Phe Asp Tyr
1               5               10
```

```
<210> SEQ ID NO 74
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 74

Met Gln Val Gln Leu Gln Glu Ser Gly Gly Gly Leu Val Gln Pro Gly
1               5               10              15

Gly Ser Leu Arg Leu Ser Cys Ala Ser Ser Gly Ala Asn Ile Arg Leu
            20              25              30
```

-continued

```
Tyr Gly Met Ala Trp Tyr Arg Gln Pro Pro Gly Glu Glu Arg Glu Leu
        35              40              45

Val Ala Ser Ile Thr Val Gly Gly Ser Ile Thr Tyr Ala Glu Ser Val
        50              55              60

Lys Ala Arg Phe Thr Ile Ser Arg Asp Asn Ala Arg Asp Met Val Phe
65              70              75              80

Leu Gln Met Asn Ser Leu Lys Pro Glu Asp Thr Ala Val Tyr Tyr Cys
                85              90              95

Asn Ala Met Asn Pro Trp Tyr Tyr Trp Ala Trp Gly Gln Gly Thr Gln
                100             105             110

Val Thr Val Ser Ser Ala Ala Ala Tyr Pro Tyr Asp Val Pro Asp Tyr
        115             120             125

Gly Ser His His His His His His
    130             135
```

```
<210> SEQ ID NO 75
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 75

Gly Ala Asn Ile Arg Leu Tyr Gly
1               5
```

```
<210> SEQ ID NO 76
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 76

Ile Thr Val Gly Gly Ser Ile
1               5
```

```
<210> SEQ ID NO 77
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 77

Asn Ala Met Asn Pro Trp Tyr Tyr Trp Ala
1               5               10
```

```
<210> SEQ ID NO 78
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 78

Met Gln Val Gln Leu Gln Glu Ser Gly Gly Gly Leu Val Gln Ala Gly
1               5               10              15

Gly Ser Leu Arg Leu Ser Cys Ala Ala Ser Gly Gly Thr Leu Ser Ser
            20              25              30
```

-continued

```
Tyr Asp Met Gly Trp Phe Arg Gln Ala Pro Gly Lys Gly Arg Asp Phe
    35                  40                  45

Val Ala Gly Ile Asp Trp Ser Gly Gly Ser Thr Asn Tyr Glu Arg Ser
    50                  55                  60

Val Lys Gly Arg Phe Thr Ile Thr Arg Asp Asn Ala Lys Asn Thr Val
65                  70                  75                  80

Leu Leu Gln Met Asn Ser Leu Lys Pro Glu Asp Thr Ala Val Tyr Tyr
                85                  90                  95

Cys Ala Ala Ala Arg Ala Asn Ser Asp Leu Gly Ile Tyr Asp Tyr Trp
                100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140
```

<210> SEQ ID NO 79
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 79

```
Gly Gly Thr Leu Ser Ser Tyr Asp
1               5
```

<210> SEQ ID NO 80
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 80

```
Ile Asp Trp Ser Gly Gly Ser Thr
1               5
```

<210> SEQ ID NO 81
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 81

```
Ala Ala Ala Arg Ala Asn Ser Asp Leu Gly Ile Tyr Asp Tyr
1               5                   10
```

<210> SEQ ID NO 82
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 82

```
Met Gln Val Gln Leu Gln Glu Ser Gly Gly Gly Leu Val Glu Ala Gly
1               5                   10                  15

Gly Ser Leu Gly Leu Ala Cys Thr Thr Ser Gly Ile Ile Phe Ser Arg
        20                  25                  30
```

```
Asn Asp Met Gly Trp Phe Arg Gln Ala Pro Gly Glu Gln Arg Thr Ala
        35              40              45

Val Ala Thr Ile Thr Arg Ser Ser Ser Thr Asn Tyr Ala Gly Ser Val
        50              55              60

Lys Gly Arg Phe Thr Ile Ser Arg Asp Asn Ala Glu Asn Thr Val Tyr
65              70              75              80

Leu Gln Met Ser Asn Leu Lys Pro Glu Asp Thr Ala Val Tyr Tyr Cys
                85              90              95

Ala Thr Ile Pro Thr Ala Thr Gln Pro Tyr Val Tyr Trp Gly Gln Gly
                100             105             110

Thr Gln Val Thr Val Ser Ser Ala Ala Ala Tyr Pro Tyr Asp Val Pro
        115             120             125

Asp Tyr Gly Ser His His His His His His
    130             135
```

```
<210> SEQ ID NO 83
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 83

Gly Ile Ile Phe Ser Arg Asn Asp
1               5
```

```
<210> SEQ ID NO 84
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 84

Ile Thr Arg Ser Ser Ser Thr
1               5
```

```
<210> SEQ ID NO 85
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 85

Ala Thr Ile Pro Thr Ala Thr Gln Pro Tyr Val Tyr
1               5               10
```

```
<210> SEQ ID NO 86
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 86

Met Gln Val Gln Leu Gln Glu Ser Gly Gly Gly Leu Val Gln Thr Gly
1               5               10              15

Gly Ser Leu Arg Leu Ser Cys Ala Ala Ser Gly Arg Ser Phe Ser Ser
                20              25              30
```

-continued

```
Tyr Ser Met Gly Trp Phe Arg Gln Gly Pro Gly Lys Gly Arg Glu Trp
        35                  40                  45

Val Ala Asp Ile Asn Glu Ser Gly Thr Thr Thr Asn Tyr Trp Asp Pro
        50                  55                  60

Val Lys Gly Arg Phe Ile Ile Ser Arg Asp Asn Ala Gln Asn Met Val
65                  70                  75                  80

Tyr Leu Gln Met Asn Ser Leu Lys Pro Glu Asp Thr Ala Val Tyr Tyr
                85                  90                  95

Cys Ala Ala Gly Pro Arg Thr Arg Trp Thr Arg Glu Pro Asp Ala Tyr
                100                 105                 110

Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His
        130                 135                 140
```

<210> SEQ ID NO 87
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 87

```
Gly Arg Ser Phe Ser Ser Tyr Ser
1               5
```

<210> SEQ ID NO 88
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 88

```
Ile Asn Glu Ser Gly Thr Thr Thr
1               5
```

<210> SEQ ID NO 89
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 89

```
Ala Ala Gly Pro Arg Thr Arg Trp Thr Arg Glu Pro Asp Ala Tyr Asp
1               5                   10                  15

Tyr
```

<210> SEQ ID NO 90
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 90

```
Met Gln Val Gln Leu Gln Glu Ser Gly Gly Gly Leu Val Gln Ala Gly
1               5                   10                  15
```

```
Gly Ser Leu Arg Leu Ser Cys Val Ala Ser Gly Arg Thr Phe Ser Thr
        20                  25                  30

Tyr Asp Met Gly Trp Phe Arg Gln Ala Pro Gly Lys Gly Arg Glu Phe
        35                  40                  45

Val Ala Gly Ile Asp Trp Ser Gly Gly Ser Thr Asn Tyr Val Asn Phe
    50                  55                  60

Val Lys Gly Arg Phe Thr Ile Ser Arg Asp Asn Ala Lys Asn Thr Met
65                  70                  75                  80

Tyr Leu Gln Met Asn Ser Leu Lys Pro Glu Asp Thr Ala Val Tyr Tyr
                85                  90                  95

Cys Ala Ala Ala Val Gly Asp Ser Glu Met Ala Thr Tyr Asp Tyr Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140
```

```
<210> SEQ ID NO 91
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 91

Gly Arg Thr Phe Ser Thr Tyr Asp
1               5
```

```
<210> SEQ ID NO 92

<400> SEQUENCE: 92

000
```

```
<210> SEQ ID NO 93
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 93

Ala Ala Ala Val Gly Asp Ser Glu Met Ala Thr Tyr Asp Tyr
1               5                   10
```

```
<210> SEQ ID NO 94
<211> LENGTH: 137
<212> TYPE: PRT
<213> ORGANISM: Artificial sequence
<220> FEATURE:
<223> OTHER INFORMATION: nanobody amino acid sequence

<400> SEQUENCE: 94

Met Gln Val Gln Leu Gln Glu Ser Gly Gly Gly Leu Val Gln Val Gly
1               5                   10                  15

Gly Ser Leu Arg Leu Ser Cys Val Ala Ser Glu Pro Thr Phe Arg Pro
        20                  25                  30

Asn Arg Met Gly Trp Phe Arg Gln Ala Pro Gly Lys Glu Arg Glu Leu
        35                  40                  45

Val Ala His Ile Met Trp Ser Ser Gly Ser Thr Trp Tyr Gly Asp Ser
```

```
        50                55                60

Val Lys Gly Arg Phe Thr Ile Ser Arg Asp Asn Ala Lys Asn Thr Val
65                  70                  75                  80

Ile Leu Gln Met Asn Ser Leu Asn Pro Glu Asp Thr Ala Val Tyr Tyr
                85                  90                  95

Cys Ala Ala Ala Gln Arg Ala Gly Tyr Asp Tyr Trp Gly Gln Gly Thr
                100                 105                 110

Gln Val Thr Val Ser Ser Ala Ala Ala Tyr Pro Tyr Asp Val Pro Asp
        115                 120                 125

Tyr Gly Ser His His His His His His
    130                 135

<210> SEQ ID NO 95
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 95

Glu Pro Thr Phe Arg Pro Asn Arg
1               5

<210> SEQ ID NO 96
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 96

Ile Met Trp Ser Ser Gly Ser Thr Trp
1               5

<210> SEQ ID NO 97
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 97

Ala Ala Gln Arg Ala Gly Tyr Asp Tyr
1               5

<210> SEQ ID NO 98
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 98

Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Ser Leu Ser Ser
            20                  25                  30

Tyr Ser Met Gly Trp Ile Arg Gln Ala Pro Gly Lys Glu Arg Asp Phe
        35                  40                  45

Val Thr Ala Ile Arg Trp Ser Gly Gly Ser Thr Tyr Tyr Ala Asp Ser
```

```
        50                    55                    60

Val Lys Gly Arg Phe Thr Ile Ser Arg Asp Ile Ala Lys Asn Ala Val
65                    70                    75                    80

Tyr Leu Gln Met Asn Ser Leu Lys Thr Glu Asp Thr Ala Val Tyr Tyr
                    85                    90                    95

Cys Ala Ala Arg Leu Gly Gly Arg Ser Trp Asp Ala Gly Asp Tyr Gln
                    100                   105                   110

Tyr Trp Gly Gln Gly Thr Gln Val Thr Val Ser Ser Ala Ala Ala Tyr
            115                   120                   125

Pro Tyr Asp Val Pro Asp Tyr Gly Ser His His His His His
        130                   135                   140
```

```
<210> SEQ ID NO 99
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 99

Gly Arg Ser Leu Ser Ser Tyr Ser
1               5
```

```
<210> SEQ ID NO 100
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 100

Ile Arg Trp Ser Gly Gly Ser Thr
1               5
```

```
<210> SEQ ID NO 101
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 101

Ala Ala Arg Leu Gly Gly Arg Ser Trp Asp Ala Gly Asp Tyr Gln Tyr
1               5                   10                  15
```

```
<210> SEQ ID NO 102
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 102

Met Gln Val Gln Leu Gln Glu Ser Gly Gly Gly Ser Val Gln Ser Gly
1               5                   10                  15

Gly Ser Leu Phe Leu Ser Cys Ala Ala Ser Gly Phe Val Phe Glu Thr
            20                    25                    30

Ser Pro Met Thr Trp Val Arg Gln Ala Pro Gly Gln Gly Val Arg Trp
        35                    40                    45

Val Gly Ser Ile Thr Thr Asp Gly Arg Arg Ala Asp Tyr Glu Asp Ala
```

```
        50              55              60

Val Lys Gly Arg Phe Thr Ile Ser Arg Asp Asn Val Lys Asn Met Leu
65                  70                  75                  80

Tyr Leu Glu Met Asn Asn Leu Lys Pro Glu Asp Thr Ala Met Tyr Phe
                85                  90                  95

Cys Arg Glu Ser Arg Asp Leu Asn Ala Val Thr Arg Gly Thr Gln Val
                100                 105                 110

Thr Val Ser Ser Ala Ala Ala Tyr Pro Tyr Asp Val Pro Asp Tyr Gly
            115                 120                 125

Ser His His His His His His
    130                 135
```

<210> SEQ ID NO 103
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 103

```
Gly Phe Val Phe Glu Thr Ser Pro
1               5
```

<210> SEQ ID NO 104
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 104

```
Ile Thr Thr Asp Gly Arg Arg Ala
1               5
```

<210> SEQ ID NO 105
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 105

```
Arg Glu Ser Arg Asp Leu Asn Ala
1               5
```

<210> SEQ ID NO 106
<211> LENGTH: 139
<212> TYPE: PRT
<213> ORGANISM: Artificial sequence
<220> FEATURE:
<223> OTHER INFORMATION: nanobody amino acid sequence

<400> SEQUENCE: 106

```
Met Gln Val Gln Leu Gln Glu Ser Gly Gly Gly Leu Val Gln Thr Gly
1               5                   10                  15

Asp Ser Leu Arg Leu Ser Cys Ala Val Ser Gly Arg Thr Gly Ser Ile
            20                  25                  30

Asn Arg Met Gly Trp Phe Arg Gln Ala Pro Gly Lys Glu Arg Glu Ile
        35                  40                  45

Val Ser His Ile Phe Trp Ser Asn Val Gly Thr Trp Ser Ala Glu Ser
```

-continued

```
        50              55              60

Val Lys Gly Arg Phe Ile Ile Ser Arg Asp Asn Ala Lys Asn Thr Val
65                  70                  75                  80

Tyr Leu Gln Met Asn Ser Leu Lys Pro Glu Asp Thr Ala Val Tyr Ser
                85                  90                  95

Cys Ala Ala Ala Thr Gly Ser Ala Tyr Asn Tyr Trp Val Pro Ser Arg
                    100                 105                 110

Gly Asp Pro Gly His Val Ser Ser Ala Ala Ala Tyr Pro Tyr Asp Val
            115                 120                 125

Pro Asp Tyr Gly Ser His His His His His His
        130                 135
```

```
<210> SEQ ID NO 107
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 107

Gly Arg Thr Gly Ser Ile Asn Arg
1               5
```

```
<210> SEQ ID NO 108
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 108

Ile Phe Trp Ser Asn Val Gly Thr
1               5
```

```
<210> SEQ ID NO 109
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 109

Ala Ala Ala Thr Gly Ser Ala Tyr Asn Tyr
1               5                   10
```

```
<210> SEQ ID NO 110
<211> LENGTH: 133
<212> TYPE: PRT
<213> ORGANISM: Artificial sequence
<220> FEATURE:
<223> OTHER INFORMATION: nanobody amino acid sequence

<400> SEQUENCE: 110

Met Gln Val Gln Leu Gln Glu Ser Gly Gly Gly Gln Val Gln Ala Gly
1               5                   10                  15

Asp Ser Leu Arg Leu Ser Cys Val Thr Ser Gly Met Ser Phe Ser Thr
                20                  25                  30

Ser Ala Met Gly Trp Tyr Arg Gln Ala Ser Gly Lys Gln Arg Glu Trp
        35                  40                  45

Val Ala Ile Ile Arg Glu Asp Ser Thr Thr Asn Tyr Ser Ser Phe Ala
```

-continued

```
     50              55              60

Lys Gly Arg Phe Thr Ile Ser Arg Asp Asn Thr Asn Lys Thr Val Tyr
65                  70              75                  80

Leu Leu Met Asn Ser Leu Glu Pro Asp Asp Thr Ala Val Tyr Tyr Cys
                85              90                  95

Arg Thr Tyr Thr Gly Gly Tyr Trp Gly Gln Gly Thr Gln Val Thr Val
            100             105                 110

Ser Ser Ala Ala Ala Tyr Pro Tyr Asp Val Pro Asp Tyr Gly Ser His
        115             120                 125

His His His His His
    130

<210> SEQ ID NO 111
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 111

Gly Met Ser Phe Ser Thr Ser Ala
1               5

<210> SEQ ID NO 112
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 112

Ile Arg Glu Asp Ser Thr Thr
1               5

<210> SEQ ID NO 113
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 113

Arg Thr Tyr Thr Gly Gly Tyr
1               5

<210> SEQ ID NO 114
<211> LENGTH: 145
<212> TYPE: PRT
<213> ORGANISM: Artificial sequence
<220> FEATURE:
<223> OTHER INFORMATION: nanobody amino acid sequence

<400> SEQUENCE: 114

Met Gln Val Gln Leu Gln Glu Ser Gly Gly Gly Leu Val Gln Ala Gly
1               5               10                  15

Gly Ser Leu Arg Leu Ser Cys Ala Ala Ser Gly Arg Thr Phe Ser Ser
                20              25                  30

Tyr Ala Met Gly Trp Phe Arg Gln Ala Pro Gly Lys Glu Arg Glu Phe
            35              40                  45

Val Ala Gly Ile Ser Trp Ser Gly Arg Ser Thr Tyr Tyr Ala Asp Ser
```

-continued

```
      50               55               60

Val Lys Gly Arg Phe Thr Ile Ser Arg Asp Asp Ala Lys Asn Thr Val
65               70               75               80

Tyr Leu Gln Met Asn Ser Leu Lys Pro Glu Asp Thr Ala Val Tyr Tyr
              85               90               95

Cys Ala Ala Pro Asp Thr Ala Ala Gln Phe Thr Thr Pro Leu Tyr Glu
              100              105              110

Tyr Ala Tyr Trp Gly Gln Gly Thr Gln Val Thr Val Ser Ser Ala Ala
         115              120              125

Ala Tyr Pro Tyr Asp Val Pro Asp Tyr Gly Ser His His His His
    130              135              140

His
145
```

<210> SEQ ID NO 115
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 115

```
Gly Arg Thr Phe Ser Ser Tyr Ala
1               5
```

<210> SEQ ID NO 116
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 116

```
Ile Ser Trp Ser Gly Arg Ser Thr
1               5
```

<210> SEQ ID NO 117
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 117

```
Ala Ala Pro Asp Thr Ala Ala Gln Phe Thr Thr Pro Leu Tyr Glu Tyr
1               5               10               15
```

<210> SEQ ID NO 118
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 118

```
Met Gln Val Gln Leu Gln Glu Ser Gly Gly Gly Leu Val Gln Ala Gly
1               5               10               15

Asp Ser Leu Arg Leu Ala Cys Ala Ser Ser Ser Arg Thr Phe Ser Thr
              20               25               30

Tyr Thr Met Gly Trp Phe Arg Gln Thr Pro Gly Arg Glu Arg Asp Phe
```

-continued

```
        35              40              45

Val Ala Ala Ile Ser Pro Ser Gly Ala Thr Ala Asp Tyr Ala Asp Ser
    50              55              60

Val Lys Gly Arg Phe Thr Ile Ser Arg Asp Asn Ala Lys Asn Thr Leu
65              70              75              80

Tyr Leu Gln Met Asp Ser Leu Lys Pro Glu Asp Thr Ala Val Tyr Tyr
                85              90              95

Cys Ala Ala Arg Tyr Leu Ser Trp Ser Arg Met Asn His Glu Tyr Pro
            100             105             110

Tyr Trp Gly Gln Gly Thr Gln Val Thr Val Ser Ser Ala Ala Ala Tyr
        115             120             125

Pro Tyr Asp Val Pro Asp Tyr Gly Ser His His His His His His
    130             135             140
```

```
<210> SEQ ID NO 119
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 119

Ser Arg Thr Phe Ser Thr Tyr Thr
1               5
```

```
<210> SEQ ID NO 120
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 120

Ile Ser Pro Ser Gly Ala Thr Ala
1               5
```

```
<210> SEQ ID NO 121
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 121

Ala Ala Arg Tyr Leu Ser Trp Ser Arg Met Asn His Glu Tyr Pro Tyr
1               5               10              15
```

```
<210> SEQ ID NO 122
<211> LENGTH: 146
<212> TYPE: PRT
<213> ORGANISM: Artificial sequence
<220> FEATURE:
<223> OTHER INFORMATION: nanobody amino acid sequence

<400> SEQUENCE: 122

Met Gln Val Gln Leu Gln Glu Ser Gly Gly Gly Leu Val Gln Ala Gly
1               5               10              15

Asp Ser Leu Arg Leu Ser Cys Ala Ala Ser Glu Arg Thr Phe Ser Ser
            20              25              30

Tyr Val Met Gly Trp Phe Arg Gln Ala Pro Arg Lys Glu Arg Glu Phe
```

```
          35                    40                    45
Val Ala Ala Met Thr Trp Ser Gly Ser Ser Arg Ile Tyr Tyr Ala Asp
   50                    55                    60

Ser Val Lys Gly Arg Phe Thr Ile Ser Arg Asp Asn Ala Lys Asn Thr
65                    70                    75                    80

Ala Tyr Leu Gln Met Asn Ser Leu Lys Pro Glu Asp Thr Ala Val Tyr
                  85                    90                    95

Tyr Cys Ala Ala Lys Asp Ala Tyr Gly Gly Ile Ser Phe Arg Pro Asn
              100                   105                   110

Thr Tyr His Ser Trp Gly Gln Gly Thr Gln Val Thr Val Ser Ser Ala
          115                   120                   125

Ala Ala Tyr Pro Tyr Asp Val Pro Asp Tyr Gly Ser His His His His
   130                   135                   140

His His
145
```

```
<210> SEQ ID NO 123
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 123

Glu Arg Thr Phe Ser Ser Tyr Val
1               5
```

```
<210> SEQ ID NO 124
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 124

Met Thr Trp Ser Gly Ser Ser Arg Ile
1               5
```

```
<210> SEQ ID NO 125
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 125

Ala Ala Lys Asp Ala Tyr Gly Gly Ile Ser Phe Arg Pro Asn Thr Tyr
1               5                   10                  15

His Ser
```

```
<210> SEQ ID NO 126
<211> LENGTH: 130
<212> TYPE: PRT
<213> ORGANISM: Artificial sequence
<220> FEATURE:
<223> OTHER INFORMATION: nanobody amino acid sequence

<400> SEQUENCE: 126

Met Gln Val Gln Leu Gln Glu Ser Gly Gly Gly Leu Val Gln Pro Gly
1               5                   10                  15
```

Gly Ser Leu Arg Leu Ser Cys Ala Ala Leu Gly Asn Ile Val Asn Ile
        20                  25              30

Asn Asn Met Gly Trp Tyr Arg Gln Ala Pro Gly Gly Gln Arg Glu Leu
        35                  40              45

Val Ala Thr Ile Thr Arg Gly Ala Ile Lys Asn Tyr Ala Asp Ser Val
        50                  55              60

Lys Gly Arg Phe Thr Ile Phe Arg Gly Asn Ala Asn Thr Val Tyr Leu
65                  70              75              80

Gln Met Asn Ser Leu Lys Pro Glu Asp Thr Ala Val Tyr Tyr Cys Val
                85              90              95

Ala Asp Ser Ser Trp Gly Gln Gly Thr Gln Val Thr Val Ser Ser Ala
            100             105             110

Ala Ala Tyr Pro Tyr Asp Val Pro Asp Tyr Gly Ser His His His His
        115             120             125

His His
    130

<210> SEQ ID NO 127
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 127

Gly Asn Ile Val Asn Ile Asn Asn
1               5

<210> SEQ ID NO 128
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 128

Ile Thr Arg Gly Ala Ile Lys
1               5

<210> SEQ ID NO 129
<211> LENGTH: 5
<212> TYPE: PRT
<213> ORGANISM: Artificial sequence
<220> FEATURE:
<223> OTHER INFORMATION: Complementarity-determining region amino acid
      sequence

<400> SEQUENCE: 129

Val Ala Asp Ser Ser
1               5

<210> SEQ ID NO 130
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 130

Met Gln Val Gln Leu Gln Glu Ser Gly Gly Gly Val Val Gln Ala Gly
1               5                   10                  15

```
Gly Phe Leu Arg Leu Ser Cys Ala Ala Ser Gly Leu Ile Phe Asp Asp
             20                  25                  30

Thr Ala Ile Gly Trp Phe Arg Gln Ala Pro Gly Lys Glu Arg Glu Phe
             35                  40                  45

Val Ala Ala Val Ser Pro Ser Gly Val Ser Thr Asp Tyr Thr Asp Ser
    50                  55                  60

Val Lys Gly Arg Phe Thr Ile Ser Arg Asp Asn Ala Lys Lys Thr Val
65                  70                  75                  80

Phe Leu Gln Met Ser Arg Leu Lys Pro Glu Asp Thr Ala Val Tyr Tyr
                 85                  90                  95

Cys Ala Ala Arg Leu Arg His Tyr Ser Asn Asp Gln His Glu Tyr Asp
                100                 105                 110

Ser Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

<210> SEQ ID NO 131
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 131

```
Gly Leu Ile Phe Asp Asp Thr Ala
1               5
```

<210> SEQ ID NO 132
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 132

```
Val Ser Pro Ser Gly Val Ser Thr
1               5
```

<210> SEQ ID NO 133
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 133

```
Ala Ala Arg Leu Arg His Tyr Ser Asn Asp Gln His Glu Tyr Asp Ser
1               5                   10                  15
```

<210> SEQ ID NO 134
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 134

```
Met Gln Val Gln Leu Gln Glu Ser Gly Gly Gly Leu Val Gln Ala Gly
1               5                   10                  15
```

Gly Ser Leu Arg Leu Ser Cys Ala Ala Ser Gly Ile Val Phe Ser Ile
          20                  25                  30

Thr Thr Met Gly Trp Tyr Arg Gln Ala Pro Gly Lys Gln Arg Glu Leu
          35                  40                  45

Val Ala Thr Ile Ala Ser Gly Val Arg Ala Asp Tyr Ala Asp Ser Val
          50                  55                  60

Lys Gly Arg Phe Thr Ile Ser Arg Asp Asn Gly Lys Asn Thr Val Tyr
65                  70                  75                  80

Leu Gln Met Asn Ser Leu Lys Pro Glu Asp Thr Ala Val Tyr Tyr Cys
                  85                  90                  95

Asn Ala Asn Arg Phe Ser Leu Gly Asn Tyr Trp Gly Gln Gly Thr Gln
          100                 105                 110

Val Thr Val Ser Ser Ala Ala Ala Tyr Pro Tyr Asp Val Pro Asp Tyr
          115                 120                 125

Gly Ser His His His His His His
    130                 135

<210> SEQ ID NO 135
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 135

Gly Ile Val Phe Ser Ile Thr Thr
1               5

<210> SEQ ID NO 136
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 136

Ile Ala Ser Gly Val Arg Ala
1               5

<210> SEQ ID NO 137
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 137

Asn Ala Asn Arg Phe Ser Leu Gly Asn Tyr
1               5                   10

<210> SEQ ID NO 138
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 138

Met Gln Val Gln Leu Gln Glu Ser Gly Gly Gly Leu Val Gln Thr Gly
1               5                   10                  15

```
Asp Ser Leu Arg Leu Ser Cys Ala Ala Ser Gly Gly Thr Phe Ser Ala
        20              25              30

Tyr Thr Met Gly Trp Phe Arg Gln Ala Pro Gly Lys Glu Arg Glu Phe
        35              40              45

Val Ala Ala Ile Ser Arg Ser Gly Ser Ser Thr His Tyr Ala Asn Ser
    50              55              60

Val Lys Gly His Phe Thr Ile Ser Arg Asp Asn Ala Lys Lys Thr Val
65              70              75              80

Tyr Leu Gln Met Asn Ser Leu Lys Pro Glu Asp Thr Ala Arg Tyr Tyr
                85              90              95

Cys Ala Gly Glu Arg Thr Gly His Phe Thr Asp Leu Tyr Tyr Glu Tyr
        100             105             110

Asp Tyr Trp Gly Gln Gly Thr Gln Val Thr Val Ser Ser Ala Ala Ala
        115             120             125

Tyr Pro Tyr Asp Val Pro Asp Tyr Gly Ser His His His His His
    130             135             140
```

```
<210> SEQ ID NO 139
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 139

Gly Gly Thr Phe Ser Ala Tyr Thr
1               5
```

```
<210> SEQ ID NO 140
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 140

Ile Ser Arg Ser Gly Ser Ser Thr
1               5
```

```
<210> SEQ ID NO 141
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 141

Ala Gly Glu Arg Thr Gly His Phe Thr Asp Leu Tyr Tyr Glu Tyr Asp
1               5               10              15

Tyr
```

```
<210> SEQ ID NO 142
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 142
```

-continued

```
Met Gln Val Gln Leu Gln Glu Ser Gly Gly Gly Leu Val Gln Ala Gly
1               5                   10                  15

Gly Ser Leu Arg Leu Ser Cys Ala Ala Pro Gly Ser Asn Phe Arg Ile
            20                  25                  30

Asn Thr Met Gly Trp Tyr Arg Gln Ala Pro Gly Lys Gln Arg Glu Leu
        35                  40                  45

Val Ala Thr Ile Ala Asn Ser Gly Arg Ile Asn Ser Ala Asn Ser Val
    50                  55                  60

Lys Gly Arg Phe Thr Ile Phe Arg Gly Asn Ala Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Val Val Glu Ser Ser Asn Tyr Gln Thr Leu Asn Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 143
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 143

```
Gly Ser Asn Phe Arg Ile Asn Thr
1               5
```

<210> SEQ ID NO 144
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 144

```
Ile Ala Asn Ser Gly Arg Ile
1               5
```

<210> SEQ ID NO 145
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 145

```
Asn Ala Asp Val Val Glu Ser Ser Asn Tyr Gln Thr Leu Asn Tyr
1               5                   10                  15
```

<210> SEQ ID NO 146
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 146

```
Met Gln Val Gln Leu Gln Glu Ser Gly Gly Gly Leu Val Gln Ala Gly
1               5                   10                  15

Gly Ser Leu Arg Leu Ser Cys Val Ala Ser Arg Ala Ser Gly Ser Ile
            20                  25                  30

Phe Gly Ala Gln Thr Met Ala Trp Tyr Arg Gln Ala Ser Gly Glu Arg
        35                  40                  45

Arg Glu Leu Val Ala Thr Ile Thr Ser Ser Gly Ser Thr Asn Tyr Ala
    50                  55                  60

Asp Ser Val Lys Gly Arg Phe Thr Ile Ser Arg Asp Asn Ala Lys Ser
65                  70                  75                  80

Thr Met Phe Leu Gln Met Asn Asn Leu Lys Pro Glu Asp Thr Ala Val
                85                  90                  95

Tyr Tyr Cys Asn Val Gly Phe Arg Ser Arg Tyr Ser Tyr Asp Ser Ser
            100                 105                 110

Val Trp Gly Glu Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

<210> SEQ ID NO 147
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 147

```
Arg Ala Ser Gly Ser Ile Phe Gly Ala Gln Thr
1               5                   10
```

<210> SEQ ID NO 148
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 148

```
Ile Thr Ser Ser Gly Ser Thr
1               5
```

<210> SEQ ID NO 149
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 149

```
Asn Val Gly Phe Arg Ser Arg Tyr Ser Tyr Asp Ser Ser Val
1               5                   10
```

<210> SEQ ID NO 150
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 150

-continued

```
Met Gln Val Gln Leu Gln Glu Ser Gly Gly Gly Leu Val Gln Ala Gly
1               5                   10                  15

Gly Ser Leu Arg Leu Ser Cys Ala Ala Ser Gly Arg Thr Phe Ser Thr
            20                  25                  30

Ser Asn Met Gly Trp Phe Arg Gln Ala Pro Gly Lys Glu Arg Glu Phe
        35                  40                  45

Val Gly Ala Ile Ser Pro Ser Gly Arg Ser Thr Asp Tyr Ala Ser Ser
    50                  55                  60

Val Glu Gly Arg Phe Thr Ile Ser Arg Asp Asn Pro Lys Asn Thr Met
65                  70                  75                  80

Tyr Leu Gln Met Asn Ser Leu Lys Pro Glu Asp Thr Ala Val Tyr Tyr
                85                  90                  95

Cys Ala Ala Arg Arg Ser Pro Ser Tyr Thr Arg Val Gly Asp Glu Tyr
            100                 105                 110

Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140
```

<210> SEQ ID NO 151
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 151

```
Gly Arg Thr Phe Ser Thr Ser Asn
1               5
```

<210> SEQ ID NO 152
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 152

```
Ile Ser Pro Ser Gly Arg Ser Thr
1               5
```

<210> SEQ ID NO 153
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 153

```
Ala Ala Arg Arg Ser Pro Ser Tyr Thr Arg Val Gly Asp Glu Tyr Asp
1               5                   10                  15

Tyr
```

<210> SEQ ID NO 154
<211> LENGTH: 148
<212> TYPE: PRT
<213> ORGANISM: Artificial sequence
<220> FEATURE:
<223> OTHER INFORMATION: nanobody amino acid sequence

<400> SEQUENCE: 154

```
Met Gln Val Gln Leu Gln Glu Ser Gly Gly Gly Leu Val Gln Ala Gly
1               5                   10                  15

Asp Ser Leu Arg Leu Ser Cys Ala Ala Ser Gly Arg Ser Phe Ser Ile
            20                  25                  30

Tyr Thr Met Gly Trp Phe Arg Gln Ala Pro Gly Lys Glu Arg Glu Phe
        35                  40                  45

Val Ser Leu Ile Met Arg Ser Gly Gly Ile Ile Tyr Ala Asp Phe Val
    50                  55                  60

Lys Gly Arg Phe Thr Ile Ser Arg Asp Asn Ala Lys Asn Leu Val Tyr
65                  70                  75                  80

Leu Gln Met Asn Ser Leu Lys Pro Glu Asp Thr Ala Val Tyr Tyr Cys
                85                  90                  95

Ala Ala Gly Gly Ser Thr Asn Ser Arg Ala Tyr Asn Tyr Tyr Lys Leu
            100                 105                 110

Ser Leu Ala Tyr Asp Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145
```

<210> SEQ ID NO 155

<400> SEQUENCE: 155

000

<210> SEQ ID NO 156
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 156

```
Ile Met Arg Ser Gly Gly Ile Ile
1               5
```

<210> SEQ ID NO 157
<211> LENGTH: 22
<212> TYPE: PRT
<213> ORGANISM: Artificial sequence
<220> FEATURE:
<223> OTHER INFORMATION: Complementarity-determining region amino acid
      sequence

<400> SEQUENCE: 157

```
Ala Ala Gly Gly Ser Thr Asn Ser Arg Ala Tyr Asn Tyr Tyr Lys Leu
1               5                   10                  15

Ser Leu Ala Tyr Asp Tyr
            20
```

<210> SEQ ID NO 158
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 158

```
Met Gln Val Gln Leu Gln Glu Ser Gly Gly Gly Leu Val Gln Ala Gly
1               5                   10                  15

Asp Ser Leu Arg Leu Ser Cys Ala Ala Ser Gly Gly Thr Phe Ser Thr
            20                  25                  30

Tyr Thr Met Gly Trp Phe Arg Gln Ala Pro Gly Lys Glu Arg Glu Phe
        35                  40                  45

Val Ala Ala Ile Ser Arg Thr Gly Arg Gly Thr Asp Tyr Ala Asp Ser
    50                  55                  60

Val Lys Gly Arg Phe Thr Ile Ser Arg Asp Asn Val Lys Asn Thr Val
65                  70                  75                  80

Ser Leu Gln Met Asn Ser Leu Lys Pro Glu Asp Thr Ala Val Tyr Tyr
                85                  90                  95

Cys Ala Glu Arg Ser Ser Val His Tyr Ser Gly Ile Ala Ala Asp Tyr
            100                 105                 110

Asp Tyr Trp Ser Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140
```

<210> SEQ ID NO 159
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 159

```
Gly Gly Thr Phe Ser Thr Tyr Thr
1               5
```

<210> SEQ ID NO 160
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 160

```
Ile Ser Arg Thr Gly Arg Gly Thr
1               5
```

<210> SEQ ID NO 161
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 161

```
Ala Glu Arg Ser Ser Val His Tyr Ser Gly Ile Ala Ala Asp Tyr Asp
1               5                   10                  15

Tyr
```

<210> SEQ ID NO 162
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 162

Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Arg Asn Leu Ser Arg
            20                  25                  30

Ser Ala Met Gly Trp Phe Arg Gln Asn Pro Gly Glu Glu Arg Glu Phe
        35                  40                  45

Val Ala Ala Ile Asp Trp Trp Gly Asp Ser Thr Tyr Tyr Gly Asp Ser
        50                  55                  60

Val Thr Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Val Tyr Tyr
                85                  90                  95

Cys Ala Ala Gly Leu Arg Pro Phe Asp Gly Ser Trp Glu Arg Arg Tyr
            100                 105                 110

Asp Tyr Trp Gly Gln Gly Thr Gln Val Thr Val Ser Ser Ala Ala Ala
            115                 120                 125

Tyr Pro Tyr Asp Val Pro Asp Tyr Gly Ser His His His His His His
    130                 135                 140

<210> SEQ ID NO 163
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 163

Gly Arg Asn Leu Ser Arg Ser Ala
1               5

<210> SEQ ID NO 164
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 164

Ile Asp Trp Trp Gly Asp Ser Thr
1               5

<210> SEQ ID NO 165
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 165

Ala Ala Gly Leu Arg Pro Phe Asp Gly Ser Trp Glu Arg Arg Tyr Asp
1               5                   10                  15

Tyr

<210> SEQ ID NO 166
<211> LENGTH: 135
<212> TYPE: PRT
<213> ORGANISM: Artificial sequence -continued
<220> FEATURE:
<223> OTHER INFORMATION: nanobody amino acid sequence

<400> SEQUENCE: 166

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Gly Tyr
            20                  25                  30

Ile Met Ser Trp Phe Arg Gln Pro Pro Gly Lys Glu Arg Glu Leu Val
        35                  40                  45

Ala Ala Ile Thr Tyr Val Gly Ser Thr Tyr Val Glu Asp Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Arg
                85                  90                  95

Ala Arg Glu Gly Glu Gln Leu Asp Phe Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135
```

<210> SEQ ID NO 167
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 167

```
Gly Ser Thr Phe Ser Gly Tyr Ile
1               5
```

<210> SEQ ID NO 168
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 168

```
Ile Thr Tyr Val Gly Ser Thr
1               5
```

<210> SEQ ID NO 169
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 169

```
Arg Ala Arg Glu Gly Glu Gln Leu Asp Phe
1               5                   10
```

<210> SEQ ID NO 170
<211> LENGTH: 135
<212> TYPE: PRT
<213> ORGANISM: Artificial sequence -continued
<220> FEATURE:
<223> OTHER INFORMATION: nanobody amino acid sequence

<400> SEQUENCE: 170

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Leu Ser Gly Tyr
            20                  25                  30

Ile Met Ser Trp Phe Arg Gln Pro Pro Gly Lys Glu Arg Glu Leu Val
        35                  40                  45

Ala Ala Ile Thr Tyr Val Gly Ser Thr Tyr Val Glu Asp Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Arg
                85                  90                  95

Ala Arg Glu Gly Glu Gln Leu Asp Phe Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135

<210> SEQ ID NO 171
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 171

Ser Gly Ser Thr Phe Ser Gly Tyr
1               5

<210> SEQ ID NO 172
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 172

Gln Val Gln Leu Gln Glu Ser Gly Gly Gly Leu Val Gln Ser Gly Asp
1               5                   10                  15

Ser Leu Arg Leu Ser Cys Ala Ala Ser Gly Ser Thr Phe Ser Gly Tyr
            20                  25                  30

Ile Met Ser Trp Phe Arg Gln Pro Pro Gly Lys Glu Arg Glu Leu Val
        35                  40                  45

Ala Ala Ile Thr Tyr Val Gly Ser Thr Tyr Val Glu Asp Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Arg
                85                  90                  95

Ala Arg Glu Gly Glu Gln Leu Asp Phe Trp Gly Gln Gly Thr Gln Val
            100                 105                 110

Thr Val Ser Ser Ala Ala Ala Tyr Pro Tyr Asp Val Pro Asp Tyr Gly
        115                 120                 125

-continued

```
Ser His His His His His
    130                 135

<210> SEQ ID NO 173
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 173

Gln Val Gln Leu Gln Glu Ser Gly Gly Gly Leu Val Gln Pro Gly Gly
1               5                   10                  15

Ser Leu Arg Leu Ser Cys Val Ala Ser Gly Ser Thr Phe Ser Gly Tyr
            20                  25                  30

Ile Met Ser Trp Phe Arg Gln Pro Pro Gly Lys Glu Arg Glu Leu Val
            35                  40                  45

Ala Ala Ile Thr Tyr Val Gly Ser Thr Tyr Val Glu Asp Ser Val Lys
        50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Arg
                85                  90                  95

Ala Arg Glu Gly Glu Gln Leu Asp Phe Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His His
    130                 135

<210> SEQ ID NO 174
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 174

Ala Ser Gly Ser Thr Phe Ser Gly Tyr Ile Met Ser
1               5                   10

<210> SEQ ID NO 175
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 175

Gln Val Gln Leu Gln Glu Ser Gly Gly Gly Leu Val Gln Ala Gly Asp
1               5                   10                  15

Ser Leu Arg Leu Ser Cys Ala Ala Ser Gly Ser Thr Phe Ser Gly Tyr
            20                  25                  30

Ile Met Ser Trp Phe Arg Gln Pro Pro Gly Lys Glu Arg Glu Leu Val
            35                  40                  45

Ala Ala Ile Thr Tyr Val Gly Ser Thr Tyr Val Glu Asp Ser Val Lys
        50                  55                  60

Gly Arg Phe Thr Ile Ser Arg Asp Asn Ala Lys Asn Thr Val Ser Leu
65                  70                  75                  80
```

Gln Met Asn Ser Leu Lys Pro Glu Asp Thr Ala Val Tyr Tyr Cys Arg
                85              90              95

Ala Arg Glu Gly Glu Gln Leu Asp Phe Trp Gly Gln Gly Thr Gln Val
            100             105             110

Thr Val Ser Ser Ala Ala Ala Tyr Pro Tyr Asp Val Pro Asp Tyr Gly
        115             120             125

Ser His His His His His His
    130             135

<210> SEQ ID NO 176
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 176

Gln Val Gln Leu Gln Glu Ser Gly Gly Gly Thr Val Gln Ala Gly Gly
1               5               10              15

Ser Leu Arg Leu Ser Cys Ala Ala Ser Gly Ser Thr Phe Ser Gly Tyr
            20              25              30

Ile Met Ser Trp Phe Arg Gln Pro Pro Gly Lys Glu Arg Glu Leu Val
        35              40              45

Ala Ala Ile Thr Tyr Val Gly Ser Thr Tyr Val Glu Asp Ser Val Lys
    50              55              60

Gly Arg Phe Thr Ile Ser Arg Asp Asn Ala Lys Asn Thr Val Ser Leu
65              70              75              80

Gln Met Asn Ser Leu Lys Pro Glu Asp Thr Ala Val Tyr Tyr Cys Arg
                85              90              95

Ala Arg Glu Gly Glu Gln Leu Asp Phe Trp Gly Gln Gly Thr Gln Val
            100             105             110

Thr Val Ser Ser Ala Ala Ala Tyr Pro Tyr Asp Val Pro Asp Tyr Gly
        115             120             125

Ser His His His His His His
    130             135

<210> SEQ ID NO 177
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 177

Gln Val Gln Leu Gln Glu Ser Gly Gly Gly Leu Val Gln Ala Gly Gly
1               5               10              15

Ser Leu Arg Leu Ser Cys Ala Ala Ser Gly Ser Thr Phe Ser Gly Tyr
            20              25              30

Ile Met Ser Trp Phe Arg Gln Pro Pro Gly Lys Glu Arg Glu Leu Val
        35              40              45

Ala Ala Ile Thr Tyr Val Gly Ser Thr Trp Tyr Gln Asp Ser Val Lys
    50              55              60

Gly Arg Phe Thr Ile Ser Arg Asp Asn Ala Lys Asn Thr Val Ser Leu
65              70              75              80

Gln Met Asn Ser Leu Lys Pro Glu Asp Thr Ala Val Tyr Tyr Cys Arg
                85              90              95

Ala Arg Glu Gly Glu Gln Leu Asp Phe Trp Gly Gln Gly Thr Gln Val

-continued

```
              100                   105                   110
Thr Val Ser Ser Ala Ala Ala Tyr Pro Tyr Asp Val Pro Asp Tyr Gly
         115                   120                   125

Ser His His His His His
    130                   135

<210> SEQ ID NO 178
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 178

Ala Ile Thr Tyr Val Gly Ser Thr Trp Tyr Gln
1               5                   10

<210> SEQ ID NO 179
<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 179

Gln Val Gln Leu Gln Glu Ser Gly Gly Gly Thr Val Gln Pro Gly Gly
1               5                   10                  15

Ser Leu Lys Leu Ser Cys Ala Ala Ser Gly Asn Leu Asn Tyr Ile Asn
             20                  25                  30

Val Trp Ser Trp Tyr Arg Gln Ala Pro Gly Lys Gln Arg Glu Arg Val
             35                  40                  45

Ala Gly Ile Ala Thr Gly Gly Gly Arg Ile Ser Tyr Ser Glu Ser Val
         50                  55                  60

Lys Gly Arg Phe Ile Ile Ser Arg Asp Asp Ala Thr Asn Thr Val Ser
65                  70                  75                  80

Leu Gln Met Ser Gly Leu Thr Pro Glu Asp Thr Ala Val Tyr Tyr Cys
                 85                  90                  95

Asn Ala Phe Gly Ser Asp Pro Asp Phe Ser Asp Tyr Lys His Asp Tyr
             100                 105                 110

Trp Gly Gln Gly Thr Gln Val Thr Val Ser Ser Ala Ala Ala Tyr Pro
         115                 120                 125

Tyr Asp Val Pro Asp Tyr Gly Ser His His His His His
    130                 135                 140

<210> SEQ ID NO 180
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 180

Gly Asn Leu Asn Tyr Ile Asn Val
1               5

<210> SEQ ID NO 181
<211> LENGTH: 8
<212> TYPE: PRT
<213> ORGANISM: Artificial sequence
<220> FEATURE:
```

-continued

<223> OTHER INFORMATION: Complementarity-determining region amino acid
      sequence

<400> SEQUENCE: 181

Ile Ala Thr Gly Gly Gly Arg Ile
1               5

<210> SEQ ID NO 182
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 182

Asn Ala Phe Gly Ser Asp Pro Asp Phe Ser Asp Tyr Lys His Asp Tyr
1               5                   10                  15

<210> SEQ ID NO 183
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 183

Gln Val Gln Leu Gln Glu Ser Gly Gly Gly Leu Val Gln Thr Gly Gly
1               5                   10                  15

Ser Leu Arg Leu Ser Cys Ala Ala Ser Gly Ser Thr Phe Ser Gly Tyr
            20                  25                  30

Ile Met Ser Trp Phe Arg Gln Pro Pro Gly Lys Glu Arg Glu Leu Val
        35                  40                  45

Ala Ala Ile Thr Tyr Val Gly Ser Thr Tyr Val Glu Asp Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Arg
                85                  90                  95

Ala Arg Glu Gly Glu Gln Leu Asp Phe Trp Gly Gln Gly Thr Gln Val
            100                 105                 110

Thr Val Ser Ser Ala Ala Ala Tyr Pro Tyr Asp Val Pro Asp Tyr Gly
            115                 120                 125

Ser His His His His His His
        130                 135

<210> SEQ ID NO 184

<400> SEQUENCE: 184

000

<210> SEQ ID NO 185
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 185

Gln Val Gln Leu Gln Glu Ser Gly Gly Gly Leu Val Gln Ala Gly Gly
1               5                   10                  15

-continued

```
Ser Leu Arg Leu Ser Cys Ala Ala Ser Gly Ser Thr Phe Ser Gly Tyr
        20                  25                  30

Ile Met Ser Trp Phe Arg Gln Pro Pro Gly Lys Glu Arg Glu Leu Val
        35                  40                  45

Ala Ala Ile Thr Tyr Val Gly Ser Thr Tyr Val Glu Asp Ser Val Lys
        50                  55                  60

Gly Arg Phe Thr Ile Ser Arg Asp Asn Val Lys Asn Thr Val Ser Leu
65                  70                  75                  80

Gln Met Asn Ser Leu Lys Pro Glu Asp Thr Ala Val Tyr Tyr Cys Arg
                85                  90                  95

Ala Arg Glu Gly Glu Gln Leu Asp Phe Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135
```

<210> SEQ ID NO 186
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 186

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Thr Ile Phe Ser Ala Lys
        20                  25                  30

Ala Leu Gly Trp His Arg Gln Ala Pro Gly Lys Gln Arg Glu Val Val
        35                  40                  45

Ala Gly Ile Thr Ser Gly Gly Ser Thr Asn Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Val Lys Phe Glu Asp Thr Ala Val Tyr Tyr Cys Val
                85                  90                  95

Leu Tyr Asp Leu Ile Lys Asp Arg Thr Tyr Trp Gly Gln Gly Thr Gln
            100                 105                 110

Val Thr Val Ser Ser Ala Ala Ala Tyr Pro Tyr Asp Val Pro Asp Tyr
        115                 120                 125

Gly Ser His His His His His His
    130                 135
```

<210> SEQ ID NO 187
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 187

```
Gly Thr Ile Phe Ser Ala Lys Ala
1               5
```

<210> SEQ ID NO 188
<211> LENGTH: 7
<212> TYPE: PRT

<213> ORGANISM: Artificial sequence
<220> FEATURE:
<223> OTHER INFORMATION: Complementarity-determining region amino acid
      sequence

<400> SEQUENCE: 188

Ile Thr Ser Gly Gly Ser Thr
1               5

<210> SEQ ID NO 189
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 189

Val Leu Tyr Asp Leu Ile Lys Asp Arg Thr Tyr
1               5                   10

<210> SEQ ID NO 190
<211> LENGTH: 137
<212> TYPE: PRT
<213> ORGANISM: Artificial sequence
<220> FEATURE:
<223> OTHER INFORMATION: nanobody amino acid sequence

<400> SEQUENCE: 190

Gln Val Gln Leu Gln Glu Ser Gly Gly Gly Leu Val Gln Pro Gly Gly
1               5                   10                  15

Ser Leu Arg Leu Ser Cys Ala Thr Ser Thr Ser Ile Phe Ser Ile Asn
            20                  25                  30

Val Met Asp Trp Tyr Arg Gln Ala Pro Gly Lys Gln Arg Glu Leu Val
        35                  40                  45

Ala Gly Ile Thr Ser Gly Asp Asn Thr Asn Tyr Ala Asp Ser Val Lys
    50                  55                  60

Gly Arg Phe Thr Ile Ser Arg Asp Asn Ala Asn Asn Thr Val Trp Leu
65                  70                  75                  80

Gln Met Asn Ser Leu Lys Pro Glu Asp Thr Ala Val Tyr Tyr Cys Arg
                85                  90                  95

Gly Arg Val Tyr Asn Gly Gly Trp Tyr Asp Tyr Trp Gly Gln Gly Thr
            100                 105                 110

Gln Val Thr Val Ser Ser Ala Ala Ala Tyr Pro Tyr Asp Val Pro Asp
        115                 120                 125

Tyr Gly Ser His His His His His His
    130                 135

<210> SEQ ID NO 191
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 191

Thr Ser Ile Phe Ser Gly Thr
1               5

<210> SEQ ID NO 192
<211> LENGTH: 7
<212> TYPE: PRT

<213> ORGANISM: Artificial sequence
<220> FEATURE:
<223> OTHER INFORMATION: Complementarity-determining region amino acid
      sequence

<400> SEQUENCE: 192

Ile Thr Ser Gly Asp Asn Thr
1               5

<210> SEQ ID NO 193
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 193

Arg Gly Arg Val Tyr Asn Gly Gly Trp Tyr Asp Tyr
1               5                   10

<210> SEQ ID NO 194
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 194

Gln Val Gln Leu Gln Glu Ser Gly Gly Gly Leu Val Gln Ala Gly Gly
1               5                   10                  15

Ser Leu Arg Leu Ala Cys Ala Ala Ser Glu Arg Thr Phe Ser Ser Tyr
            20                  25                  30

Val Met Gly Trp Phe Arg Gln Gly Pro Gly Lys Glu Arg Glu Phe Val
        35                  40                  45

Ala Ala Ile Ser Trp Ser Gly Gly Ala Arg Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Val Cys
                85                  90                  95

Ala Ala Arg Arg Thr Tyr Ser Pro Arg Thr Leu Glu Tyr Asp Phe Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 195
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 195

Glu Arg Thr Phe Ser Ser Tyr Val
1               5

<210> SEQ ID NO 196
<211> LENGTH: 8
<212> TYPE: PRT

<213> ORGANISM: Artificial sequence
<220> FEATURE:
<223> OTHER INFORMATION: Complementarity-determining region amino acid
      sequence

<400> SEQUENCE: 196

Ile Ser Trp Ser Gly Gly Ala Arg
1               5

<210> SEQ ID NO 197
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 197

Ala Ala Arg Arg Thr Tyr Ser Pro Arg Thr Leu Glu Tyr Asp Phe
1               5                   10                  15

<210> SEQ ID NO 198
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 198

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asp Thr Phe Ser Thr Tyr
            20                  25                  30

Val Met Gly Trp Phe Arg Gln Gly Pro Gly Lys Glu Arg Glu Phe Val
        35                  40                  45

Ala Ala Ile Ser Trp Ser Gly Gly Ala Arg Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Val Cys
                85                  90                  95

Ala Ala Arg Arg Thr Tyr Ser Pro Arg Thr Leu Glu Tyr Asp Phe Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 199
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 199

Gly Asp Thr Phe Ser Thr Tyr Val
1               5

<210> SEQ ID NO 200
<211> LENGTH: 140
<212> TYPE: PRT

```
<213> ORGANISM: Artificial sequence
<220> FEATURE:
<223> OTHER INFORMATION: nanobody amino acid sequence

<400> SEQUENCE: 200

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Ser Trp Val Arg Gln Ala Pro Gly Lys Gly Phe Glu Trp Val
        35                  40                  45

Ser Ile Ile Asn Thr Asp Gly Ile Gly Ser Arg Tyr Ala Asp Ser Val
    50                  55                  60

Met Gly Arg Phe Thr Ile Ser Arg Asp Asn Glu Lys Lys Met Met Tyr
65                  70                  75                  80

Leu Gln Met Asn Ser Leu Lys Pro Glu Asp Thr Ala Met Tyr Tyr Cys
                85                  90                  95

Ala Arg Gly Asn Ala Ala Leu Thr Val Ile Arg Gly Arg Pro Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His
    130                 135                 140

<210> SEQ ID NO 201
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 201

Gly Phe Thr Phe Ser Asp Tyr Val
1               5

<210> SEQ ID NO 202
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 202

Ile Asn Thr Asp Gly Ile Gly Ser
1               5

<210> SEQ ID NO 203
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 203

Ala Arg Gly Asn Ala Ala Leu Thr Val Ile Arg Gly Arg Pro
1               5                   10

<210> SEQ ID NO 204
<211> LENGTH: 140
<212> TYPE: PRT
```

-continued

<213> ORGANISM: Artificial sequence
<220> FEATURE:
<223> OTHER INFORMATION: nanobody amino acid sequence

<400> SEQUENCE: 204

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Ser Trp Val Arg Gln Ala Pro Gly Lys Gly Phe Glu Trp Val
            35                  40                  45

Ser Ile Ile Asn Thr Asp Gly Asn Gly Ser Arg Tyr Ala Asp Ser Val
    50                  55                  60

Met Gly Arg Phe Thr Ile Ser Arg Asp Asn Asp Lys Lys Met Met Tyr
65                  70                  75                  80

Leu Gln Met Asn Ser Leu Lys Pro Glu Asp Thr Ala Met Tyr Tyr Cys
                85                  90                  95

Ala Lys Gly Asn Ala Ala Leu Ser Leu Ile Arg Gly Arg Pro Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His
    130                 135                 140

<210> SEQ ID NO 205
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 205

Ile Asn Thr Asp Gly Asn Gly Ser
1               5

<210> SEQ ID NO 206
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 206

Ala Lys Gly Asn Ala Ala Leu Ser Leu Ile Arg Gly Arg Pro
1               5                   10

<210> SEQ ID NO 207
<211> LENGTH: 147
<212> TYPE: PRT
<213> ORGANISM: Artificial sequence
<220> FEATURE:
<223> OTHER INFORMATION: nanobody amino acid sequence

<400> SEQUENCE: 207

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala His Gly Lys Glu Arg Glu Phe Val
            35                  40                  45

```
Ala Ala Ile Ser Trp Gly Arg Gly Asn Thr Tyr Tyr Gly Asp Ser Leu
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Asp Pro Gly Arg Ala Tyr Val Ser Gly Asn Tyr Tyr Ser Ala
            100                 105                 110

Ala Thr Tyr Asp Tyr Trp Gly Gln Gly Thr Gln Val Thr Val Ser Ser
        115                 120                 125

Ala Ala Ala Tyr Pro Tyr Asp Val Pro Asp Tyr Gly Ser His His His
    130                 135                 140

His His His
145
```

```
<210> SEQ ID NO 208
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 208

Gly Arg Thr Phe Ser Thr Tyr Ala
1               5
```

```
<210> SEQ ID NO 209
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 209

Ile Ser Trp Gly Arg Gly Asn Thr
1               5
```

```
<210> SEQ ID NO 210
<211> LENGTH: 21
<212> TYPE: PRT
<213> ORGANISM: Artificial sequence
<220> FEATURE:
<223> OTHER INFORMATION: Complementarity-determining region amino acid
      sequence

<400> SEQUENCE: 210

Ala Ala Asp Pro Gly Arg Ala Tyr Val Ser Gly Asn Tyr Tyr Ser Ala
1               5                   10                  15

Ala Thr Tyr Asp Tyr
            20
```

```
<210> SEQ ID NO 211
<211> LENGTH: 147
<212> TYPE: PRT
<213> ORGANISM: Artificial sequence
<220> FEATURE:
<223> OTHER INFORMATION: nanobody amino acid sequence

<400> SEQUENCE: 211

Gln Val Gln Leu Gln Glu Ser Gly Gly Gly Leu Val Gln Ala Gly Gly
1               5                   10                  15
```

-continued

```
Ser Leu Arg Leu Ser Cys Ala Ala Ser Gly Arg Thr Phe Ser Ser Tyr
        20                  25                  30

Ala Met Gly Trp Phe Arg Arg Phe Pro Gly Lys Glu Arg Glu Phe Val
        35                  40                  45

Ala Ala Ile Ser Trp Gly Arg Gly Asn Thr Tyr Tyr Gly Asp Ser Leu
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Asp Pro Gly Arg Ala Tyr Val Ser Gly Asn Tyr Tyr Ser Ala
                100                 105                 110

Ala Thr Tyr Asp Tyr Trp Gly Gln Gly Thr Gln Val Thr Val Ser Ser
        115                 120                 125

Ala Ala Ala Tyr Pro Tyr Asp Val Pro Asp Tyr Gly Ser His His His
    130                 135                 140

His His His
145
```

```
<210> SEQ ID NO 212
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 212

Gly Arg Thr Phe Ser Ser Tyr Ala
1               5
```

```
<210> SEQ ID NO 213
<211> LENGTH: 147
<212> TYPE: PRT
<213> ORGANISM: Artificial sequence
<220> FEATURE:
<223> OTHER INFORMATION: nanobody amino acid sequence

<400> SEQUENCE: 213

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
        20                  25                  30

Ala Met Gly Trp Phe Arg Gln Ala His Gly Lys Glu Arg Glu Phe Val
        35                  40                  45

Ala Ala Ile Ser Trp Gly Arg Gly Asn Thr Tyr Tyr Gly Asp Ser Leu
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Asp Pro Gly Arg Ala Tyr Val Ser Gly Asn Tyr Tyr Ser Ala
                100                 105                 110

Ala Thr Tyr Asp Tyr Trp Gly Gln Gly Thr Gln Val Thr Val Ser Ser
        115                 120                 125

Ala Ala Ala Tyr Pro Tyr Asp Val Pro Asp Tyr Gly Ser His His His
    130                 135                 140
```

His His His
145

<210> SEQ ID NO 214
<211> LENGTH: 145
<212> TYPE: PRT
<213> ORGANISM: Artificial sequence
<220> FEATURE:
<223> OTHER INFORMATION: nanobody amino acid sequence

<400> SEQUENCE: 214

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Ser Phe Ser Thr Ile
            20                  25                  30

Pro Met Gly Trp Phe Arg Gln Ala Pro Glu Met Glu Arg Gly Phe Val
        35                  40                  45

Ala Ala Ile Ser Tyr Arg Gly Thr Tyr Thr Tyr Tyr Thr Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Ser Pro Gly Ile Ser Ala Tyr Trp Gly Asp Leu Ser Asn
            100                 105                 110

Trp Lys Asn Trp Gly Gln Gly Thr Gln Val Thr Val Ser Ser Ala Ala
        115                 120                 125

Ala Tyr Pro Tyr Asp Val Pro Asp Tyr Gly Ser His His His His His
    130                 135                 140

His
145

<210> SEQ ID NO 215
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 215

Gly Gly Ser Phe Ser Thr Ile Pro
1               5

<210> SEQ ID NO 216
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 216

Ile Ser Tyr Arg Gly Thr Tyr Thr
1               5

<210> SEQ ID NO 217
<211> LENGTH: 19
<212> TYPE: PRT
<213> ORGANISM: Artificial sequence
<220> FEATURE:
<223> OTHER INFORMATION: Complementarity-determining region amino acid
      sequence

<400> SEQUENCE: 217

Ala Ala Gly Ser Pro Gly Ile Ser Ala Tyr Trp Gly Asp Leu Ser Asn
1               5                   10                  15

Trp Lys Asn

<210> SEQ ID NO 218
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 218

Gln Val Gln Leu Gln Glu Ser Gly Gly Gly Val Val Gln Ala Gly Gly
1               5                   10                  15

Ser Leu Arg Leu Ser Cys Val Ala Ser Gly Arg Ser Phe Ser Ser His
            20                  25                  30

Ala Met Gly Trp Phe Arg Gln Ala Thr Gly Lys Glu Arg Glu Phe Val
            35                  40                  45

Ala Thr Ile Ser Trp Asn Ser Gly Ser Thr Phe Tyr Ala Asp Ser Leu
        50                  55                  60

Arg Gly Arg Phe Thr Ile Ser Arg Asp Asn Ala Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Ala Ala Ser Gly Arg Gly Ile Thr Ala Ser Ala Phe Arg Tyr Asp
            100                 105                 110

Val Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 219
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 219

Gly Arg Ser Phe Ser Ser His Ala
1               5

<210> SEQ ID NO 220
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 220

Ile Ser Trp Asn Ser Gly Ser Thr
1               5

<210> SEQ ID NO 221
<211> LENGTH: 17
<212> TYPE: PRT
<213> ORGANISM: Artificial sequence
<220> FEATURE:

<223> OTHER INFORMATION: Complementarity-determining region amino acid
     sequence

<400> SEQUENCE: 221

Ala Ala Ala Ser Gly Arg Gly Ile Thr Ala Ser Ala Phe Arg Tyr Asp
1               5                   10                  15

Val

<210> SEQ ID NO 222
<211> LENGTH: 148
<212> TYPE: PRT
<213> ORGANISM: Artificial sequence
<220> FEATURE:
<223> OTHER INFORMATION: nanobody amino acid sequence

<400> SEQUENCE: 222

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Lys Glu Arg Glu Phe Val
        35                  40                  45

Ala Ala Ile Arg Trp Ser Gly Ser Ile Thr Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Gly Arg Ile Phe Gly Ser Gly Ser Tyr Tyr Gly Asn
            100                 105                 110

Arg Asn Thr Tyr Asp Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145

<210> SEQ ID NO 223
<211> LENGTH: 8
<212> TYPE: PRT
<213> ORGANISM: Artificial sequence
<220> FEATURE:
<223> OTHER INFORMATION: Complementarity-determining region amino acid
     sequence

<400> SEQUENCE: 223

Gly Arg Thr Phe Ser Ser Tyr Thr
1               5

<210> SEQ ID NO 224
<211> LENGTH: 8
<212> TYPE: PRT
<213> ORGANISM: Artificial sequence
<220> FEATURE:
<223> OTHER INFORMATION: Complementarity-determining region amino acid
     sequence

<400> SEQUENCE: 224

Ile Arg Trp Ser Gly Ser Ile Thr
1               5

```
<210> SEQ ID NO 225
<211> LENGTH: 22
<212> TYPE: PRT
<213> ORGANISM: Artificial sequence
<220> FEATURE:
<223> OTHER INFORMATION: Complementarity-determining region amino acid
      sequence

<400> SEQUENCE: 225

Ala Ala Asp Pro Gly Arg Ile Phe Gly Ser Gly Ser Tyr Tyr Gly Asn
1               5                   10                  15

Arg Asn Thr Tyr Asp Tyr
            20

<210> SEQ ID NO 226
<211> LENGTH: 146
<212> TYPE: PRT
<213> ORGANISM: Artificial sequence
<220> FEATURE:
<223> OTHER INFORMATION: nanobody amino acid sequence

<400> SEQUENCE: 226

Gln Val Gln Leu Gln Glu Ser Gly Gly Gly Leu Val Gln Ala Gly Gly
1               5                   10                  15

Ser Leu Arg Leu Ser Cys Ala Val Ser Glu Arg Thr Phe Arg Thr Tyr
            20                  25                  30

Thr Met Ala Trp Phe Arg Gln Ala Pro Gly Lys Glu Arg Glu Phe Val
        35                  40                  45

Ala Ala Ile Arg Trp Asn Gly Asp Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Asn Cys
                85                  90                  95

Ala Ala Arg Ala Pro Ser Gly Gly Tyr Tyr Tyr Pro Asn Ala Leu Ser
            100                 105                 110

Glu Tyr Asn Tyr Trp Gly Gln Gly Thr Gln Val Thr Val Ser Ser Ala
        115                 120                 125

Ala Ala Tyr Pro Tyr Asp Val Pro Asp Tyr Gly Ser His His His His
    130                 135                 140

His His
145

<210> SEQ ID NO 227
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 227

Glu Arg Thr Phe Arg Thr Tyr Thr
1               5

<210> SEQ ID NO 228
<211> LENGTH: 8
<212> TYPE: PRT
<213> ORGANISM: Artificial sequence
<220> FEATURE:
<223> OTHER INFORMATION: Complementarity-determining region amino acid
      sequence
```

<400> SEQUENCE: 228

Ile Arg Trp Asn Gly Asp Ser Thr
1               5

<210> SEQ ID NO 229
<211> LENGTH: 20
<212> TYPE: PRT
<213> ORGANISM: Artificial sequence
<220> FEATURE:
<223> OTHER INFORMATION: Complementarity-determining region amino acid
      sequence

<400> SEQUENCE: 229

Ala Ala Arg Ala Pro Ser Gly Gly Tyr Tyr Tyr Pro Asn Ala Leu Ser
1               5                   10                  15

Glu Tyr Asn Tyr
            20

<210> SEQ ID NO 230
<211> LENGTH: 146
<212> TYPE: PRT
<213> ORGANISM: Artificial sequence
<220> FEATURE:
<223> OTHER INFORMATION: nanobody amino acid sequence

<400> SEQUENCE: 230

Gln Val Gln Leu Gln Glu Ser Gly Gly Gly Leu Val Gln Pro Gly Gly
1               5                   10                  15

Ser Leu Arg Leu Ser Cys Ala Ala Ser Glu Arg Thr Phe Arg Thr Tyr
            20                  25                  30

Thr Met Gly Trp Phe Arg Gln Ala Pro Gly Lys Glu Arg Glu Phe Val
        35                  40                  45

Ala Ala Ile Arg Trp Asn Gly Asp Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Ser Cys
                85                  90                  95

Ala Ala Arg Ala Tyr Ser Ile Gly Tyr Tyr Tyr Pro Asn Ala Leu Ser
            100                 105                 110

Glu Tyr Asn Tyr Trp Gly Gln Gly Thr Gln Val Thr Val Ser Ser Ala
        115                 120                 125

Ala Ala Tyr Pro Tyr Asp Val Pro Asp Tyr Gly Ser His His His His
    130                 135                 140

His His
145

<210> SEQ ID NO 231
<211> LENGTH: 13
<212> TYPE: PRT
<213> ORGANISM: Artificial sequence
<220> FEATURE:
<223> OTHER INFORMATION: Complementarity-determining region amino acid
      sequence

<400> SEQUENCE: 231

Ala Ala Ser Glu Arg Thr Phe Arg Thr Tyr Thr Met Gly
1               5                   10

<210> SEQ ID NO 232
<211> LENGTH: 20

```
<212> TYPE: PRT
<213> ORGANISM: Artificial sequence
<220> FEATURE:
<223> OTHER INFORMATION: Complementarity-determining region amino acid
      sequence

<400> SEQUENCE: 232

Ala Ala Arg Ala Tyr Ser Ile Gly Tyr Tyr Tyr Pro Asn Ala Leu Ser
1               5                   10                  15

Glu Tyr Asn Tyr
            20
```

```
<210> SEQ ID NO 233
<211> LENGTH: 145
<212> TYPE: PRT
<213> ORGANISM: Artificial sequence
<220> FEATURE:
<223> OTHER INFORMATION: nanobody amino acid sequence

<400> SEQUENCE: 233

Gln Val Gln Leu Gln Glu Ser Gly Gly Gly Leu Val Gln Ala Gly Asp
1               5                   10                  15

Ser Leu Arg Leu Ser Cys Ala Ala Ser Gly Val Thr Ile Ser Arg Tyr
            20                  25                  30

Thr Met Gly Trp Phe Arg Gln Ala Pro Gly Lys Glu Arg Glu Phe Val
        35                  40                  45

Gly Leu Ile Arg Trp Ser Asn Gly Asn Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Leu Arg Ser Gly Tyr Val Gly Ser Ala Tyr Ser Gln Gln Ala
            100                 105                 110

Tyr Asp Tyr Trp Gly Gln Gly Thr Gln Val Thr Val Ser Ser Ala Ala
            115                 120                 125

Ala Tyr Pro Tyr Asp Val Pro Asp Tyr Gly Ser His His His His His
    130                 135                 140

His
145
```

```
<210> SEQ ID NO 234
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 234

Gly Val Thr Ile Ser Arg Tyr Thr
1               5
```

```
<210> SEQ ID NO 235
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 235
```

```
Ile Arg Trp Ser Asn Gly Asn Thr
1               5

<210> SEQ ID NO 236
<211> LENGTH: 19
<212> TYPE: PRT
<213> ORGANISM: Artificial sequence
<220> FEATURE:
<223> OTHER INFORMATION: Complementarity-determining region amino acid
      sequence

<400> SEQUENCE: 236

Ala Thr Leu Arg Ser Gly Tyr Val Gly Ser Ala Tyr Ser Gln Gln Ala
1               5                   10                  15

Tyr Asp Tyr

<210> SEQ ID NO 237
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 237

Gln Val Gln Leu Gln Glu Ser Gly Gly Gly Leu Val Gln Ala Gly Gly
1               5                   10                  15

Ser Leu Arg Leu Ser Cys Ala Ala Ser Thr Ser Thr Val Ser Asp Tyr
            20                  25                  30

His Met Gly Trp Phe Arg Gln Gly Pro Gly Lys Glu Arg Glu Phe Val
        35                  40                  45

Ala Ala Ile Ser Trp Ser Gly Asp Ser Thr Asp Tyr Ala Asp Ser Val
    50                  55                  60

Lys Ala Arg Phe Thr Ile Ser Arg Asp Asn Ala Lys Lys Thr Met Ser
65                  70                  75                  80

Leu Gln Met Asn Ser Leu Lys Pro Glu Asp Thr Ala Ala Tyr Tyr Cys
                85                  90                  95

Ala Ala Arg Arg Val Phe Lys Ala Thr Trp Asp Tyr Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 238
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 238

Thr Ser Thr Val Ser Asp Tyr His
1               5

<210> SEQ ID NO 239
<211> LENGTH: 8
<212> TYPE: PRT
<213> ORGANISM: Artificial sequence
<220> FEATURE:
<223> OTHER INFORMATION: Complementarity-determining region amino acid
      sequence
```

<400> SEQUENCE: 239

Ile Ser Trp Ser Gly Asp Ser Thr
1               5

<210> SEQ ID NO 240
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 240

Ala Ala Arg Arg Val Phe Lys Ala Thr Trp Asp Tyr
1               5                   10

<210> SEQ ID NO 241
<211> LENGTH: 147
<212> TYPE: PRT
<213> ORGANISM: Artificial sequence
<220> FEATURE:
<223> OTHER INFORMATION: nanobody amino acid sequence

<400> SEQUENCE: 241

Gln Val Gln Leu Gln Glu Ser Gly Gly Gly Leu Val Gln Ala Gly Gly
1               5                   10                  15

Ser Leu Arg Leu Thr Cys Ala Ala Thr Val Arg Ile Phe Ser Ser Tyr
            20                  25                  30

Thr Met Gly Trp Phe Arg Gln Ser Pro Gly Lys Glu Arg Glu Phe Val
        35                  40                  45

Gly Ala Ile Thr Trp Ser Gly Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ala Asp Pro Gly Arg Ser Tyr Val Leu Ser Arg Tyr Tyr Asp Gln
            100                 105                 110

Ala Ser Tyr Asp Tyr Trp Gly Gln Gly Thr Gln Val Thr Val Ser Ser
            115                 120                 125

Ala Ala Ala Tyr Pro Tyr Asp Val Pro Asp Tyr Gly Ser His His His
    130                 135                 140

His His His
145

<210> SEQ ID NO 242
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 242

Val Arg Ile Phe Ser Ser Tyr Thr
1               5

<210> SEQ ID NO 243
<211> LENGTH: 8
<212> TYPE: PRT
<213> ORGANISM: Artificial sequence
<220> FEATURE:

<223> OTHER INFORMATION: Complementarity-determining region amino acid
      sequence

<400> SEQUENCE: 243

Ile Thr Trp Ser Gly Gly Asn Thr
1               5

<210> SEQ ID NO 244
<211> LENGTH: 21
<212> TYPE: PRT
<213> ORGANISM: Artificial sequence
<220> FEATURE:
<223> OTHER INFORMATION: Complementarity-determining region amino acid
      sequence

<400> SEQUENCE: 244

Ala Ala Asp Pro Gly Arg Ser Tyr Val Leu Ser Arg Tyr Tyr Asp Gln
1               5                   10                  15

Ala Ser Tyr Asp Tyr
            20

<210> SEQ ID NO 245
<211> LENGTH: 148
<212> TYPE: PRT
<213> ORGANISM: Artificial sequence
<220> FEATURE:
<223> OTHER INFORMATION: nanobody amino acid sequence

<400> SEQUENCE: 245

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Pro Phe Ser Ser Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Gly Thr Thr Tyr Tyr Thr Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Arg Leu Lys Pro Glu Asp Thr Ala Val Tyr Tyr Cys
                85                  90                  95

Ala Thr Asp Val Gly Arg Ile Tyr Gly Gly Gly Ser Leu Tyr Ser Ser
            100                 105                 110

Ala Phe Ser Tyr Asp Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145

<210> SEQ ID NO 246
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 246

Gly Arg Pro Phe Ser Ser Tyr Thr
1               5

```
<210> SEQ ID NO 247
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 247

Ile Ser Trp Ser Gly Gly Thr Thr
1               5

<210> SEQ ID NO 248
<211> LENGTH: 22
<212> TYPE: PRT
<213> ORGANISM: Artificial sequence
<220> FEATURE:
<223> OTHER INFORMATION: Complementarity-determining region amino acid
      sequence

<400> SEQUENCE: 248

Ala Thr Asp Val Gly Arg Ile Tyr Gly Gly Gly Ser Leu Tyr Ser Ser
1               5                   10                  15

Ala Phe Ser Tyr Asp Tyr
            20

<210> SEQ ID NO 249
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 249

Gln Val Gln Leu Gln Glu Ser Gly Gly Gly Leu Val Gln Ala Gly Ala
1               5                   10                  15

Ser Leu Arg Leu Ser Cys Ala Ala Ser Gly Gly Thr Phe Ser Asp Tyr
            20                  25                  30

Val Met Gly Trp Phe Arg Gln Pro Pro Gly Lys Glu Arg Glu Phe Val
        35                  40                  45

Ala Ser Ile Asn Tyr Gly Gly Asp Lys Ile Ser Tyr Ala Asp Ser Leu
    50                  55                  60

Glu Gly Arg Phe Thr Ile Leu Arg Asp Asn Thr Lys Asp Thr Thr Ser
65                  70                  75                  80

Leu Gln Met Asn Thr Leu Lys Pro Asp Asp Thr Ala Val Tyr Tyr Cys
                85                  90                  95

Ala Ala Lys Trp Gly Tyr Lys Thr Gly Pro Thr Tyr Ser Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140

<210> SEQ ID NO 250
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 250
```

```
Gly Gly Thr Phe Ser Asp Tyr Val
1               5

<210> SEQ ID NO 251
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 251

Ile Asn Tyr Gly Gly Asp Lys Ile
1               5

<210> SEQ ID NO 252
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 252

Ala Ala Lys Trp Gly Tyr Lys Thr Gly Pro Thr Tyr Ser Tyr
1               5                   10

<210> SEQ ID NO 253
<211> LENGTH: 132
<212> TYPE: PRT
<213> ORGANISM: Artificial sequence
<220> FEATURE:
<223> OTHER INFORMATION: nanobody amino acid sequence

<400> SEQUENCE: 253

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Val
            20                  25                  30

Ala Met Gly Trp Phe Arg Gln Ala Pro Gly Lys Glu Arg Glu Phe Ala
        35                  40                  45

Ala Ala Ile Ser Gly Ser Gly Gly Thr Thr Tyr Tyr Ala Ala Ser Val
    50                  55                  60

Lys Gly Arg Phe Thr Ile Ser Arg Asp Asn Gly Lys Lys Met Val Tyr
65                  70                  75                  80

Leu Gln Met Asn Ser Leu Lys Pro Glu Asp Thr Ala Val Tyr Tyr Cys
                85                  90                  95

Ser Thr Tyr Asp Gly Arg Arg Gly Gln Gly Thr Gln Val Thr Val Ser
            100                 105                 110

Ser Ala Ala Ala Tyr Pro Tyr Asp Val Pro Asp Tyr Gly Ser His His
        115                 120                 125

His His His His
    130

<210> SEQ ID NO 254
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 254
```

Gly Arg Thr Phe Ser Asn Val Ala
1               5

<210> SEQ ID NO 255
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 255

Ile Ser Gly Ser Gly Gly Thr Thr
1               5

<210> SEQ ID NO 256
<211> LENGTH: 6
<212> TYPE: PRT
<213> ORGANISM: Artificial sequence
<220> FEATURE:
<223> OTHER INFORMATION: Complementarity-determining region amino acid
      sequence

<400> SEQUENCE: 256

Ser Thr Tyr Asp Gly Arg
1               5

<210> SEQ ID NO 257
<211> LENGTH: 145
<212> TYPE: PRT
<213> ORGANISM: Artificial sequence
<220> FEATURE:
<223> OTHER INFORMATION: nanobody amino acid sequence

<400> SEQUENCE: 257

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe Ser Arg Asn
            20                  25                  30

Ala Ile Ala Trp Phe Arg Gln Ala Pro Gly Lys Glu Arg Glu Phe Val
        35                  40                  45

Ala Ala Ile Ser Trp Asn Ala Ile Thr Thr Ala Tyr Gly Asp Ser Val
    50                  55                  60

Lys Gly Arg Phe Thr Ile Phe Arg Gly Asn Thr Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Tyr Ser Ser Gly Ser Tyr Tyr Tyr Ala Arg Thr Tyr Glu
            100                 105                 110

Tyr Asp Tyr Trp Gly Gln Gly Thr Gln Val Thr Val Ser Ser Ala Ala
            115                 120                 125

Ala Tyr Pro Tyr Asp Val Pro Asp Tyr Gly Ser His His His His His
    130                 135                 140

His
145

<210> SEQ ID NO 258
<211> LENGTH: 8
<212> TYPE: PRT
<213> ORGANISM: Artificial sequence
<220> FEATURE:
<223> OTHER INFORMATION: Complementarity-determining region amino acid
      sequence -continued

<400> SEQUENCE: 258

Gly Leu Thr Phe Ser Arg Asn Ala
1               5

<210> SEQ ID NO 259
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 259

Ile Ser Trp Asn Ala Ile Thr Thr Ala
1               5

<210> SEQ ID NO 260
<211> LENGTH: 19
<212> TYPE: PRT
<213> ORGANISM: Artificial sequence
<220> FEATURE:
<223> OTHER INFORMATION: Complementarity-determining region amino acid
      sequence

<400> SEQUENCE: 260

Ala Ala Arg Tyr Ser Ser Gly Ser Tyr Tyr Tyr Ala Arg Thr Tyr Glu
1               5                   10                  15

Tyr Asp Tyr

<210> SEQ ID NO 261
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 261

Gln Val Gln Leu Gln Glu Ser Gly Gly Gly Leu Val Gln Thr Gly Gly
1               5                   10                  15

Ser Leu Arg Leu Ser Cys Ala Ala Ser Gly Arg Thr Ser Arg Ser Tyr
            20                  25                  30

Ala Met Gly Trp Phe Arg Gln Ala Pro Gly Lys Glu Arg Glu Leu Val
        35                  40                  45

Ala Asp Ile Ala Trp Ser Asp Gly Arg Ile Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Glu Ile Asp Ser Leu Lys Pro Gly Asp Thr Ala Val Tyr Tyr Cys
                85                  90                  95

Ala Ser Arg Ala Arg Gly Thr Val Leu Tyr Asn Tyr Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 262
<211> LENGTH: 8
<212> TYPE: PRT
<213> ORGANISM: Artificial sequence
<220> FEATURE:

<223> OTHER INFORMATION: Complementarity-determining region amino acid
      sequence

<400> SEQUENCE: 262

Gly Arg Thr Ser Arg Ser Tyr Ala
1               5

<210> SEQ ID NO 263
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 263

Ile Ala Trp Ser Asp Gly Arg Ile
1               5

<210> SEQ ID NO 264
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 264

Ala Ser Arg Ala Arg Gly Thr Val Leu Tyr Asn Tyr
1               5                   10

<210> SEQ ID NO 265
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 265

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Ser Arg Ser Tyr
            20                  25                  30

Ala Met Gly Trp Phe Arg Gln Ala Pro Gly Lys Glu Arg Glu His Val
        35                  40                  45

Ala Asp Ile Ala Trp Ser Asp Gly Arg Ile Tyr Tyr Ser Asp Ser Val
    50                  55                  60

Lys Asp Arg Phe Thr Ile Ser Arg Asp Asn Ala Lys Asn Thr Val Tyr
65                  70                  75                  80

Leu Glu Ile Asp Ser Leu Lys Pro Gly Asp Thr Ala Val Tyr Tyr Cys
                85                  90                  95

Ala Ser Arg Ala Arg Gly Thr Val Ser Tyr Asn Tyr Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 266
<211> LENGTH: 12
<212> TYPE: PRT
<213> ORGANISM: Artificial sequence
<220> FEATURE:

<223> OTHER INFORMATION: Complementarity-determining region amino acid
      sequence

<400> SEQUENCE: 266

Ala Ser Arg Ala Arg Gly Thr Val Ser Tyr Asn Tyr
1               5                   10

<210> SEQ ID NO 267
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 267

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ser Arg Ser Tyr
                20                  25                  30

Ala Met Gly Trp Phe Arg Gln Ala Pro Gly Lys Glu Arg Glu Leu Val
            35                  40                  45

Ala Asp Ile Ala Trp Ser Asp Gly Arg Ile Tyr Tyr Ser Asp Ser Val
        50                  55                  60

Lys Gly Arg Phe Thr Ile Ser Arg Asp Asn Ala Lys Asn Thr Val Tyr
65                  70                  75                  80

Leu Glu Ile Asp Ser Leu Lys Pro Gly Asp Thr Ala Val Tyr Tyr Cys
                85                  90                  95

Ala Ser Arg Ala Arg Gly Thr Val Leu Tyr Asn Tyr Trp Gly Gln Gly
                100                 105                 110

Thr Gln Val Thr Val Ser Ser Ala Ala Ala Tyr Pro Tyr Asp Val Pro
        115                 120                 125

Asp Tyr Gly Ser His His His His His His
        130                 135

<210> SEQ ID NO 268
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 268

Gln Val Gln Leu Gln Glu Ser Gly Gly Gly Leu Val Gln Ala Gly Gly
1               5                   10                  15

Ser Leu Thr Leu Ser Cys Ala Ala Ser Gly Arg Thr Ser Arg Ser Tyr
                20                  25                  30

Ala Met Gly Trp Phe Arg Gln Ala Pro Gly Lys Glu Arg Glu Leu Val
            35                  40                  45

Ala Asp Ile Ala Trp Ser Asp Gly Arg Ile Tyr Tyr Ser Asp Ser Val
        50                  55                  60

Lys Gly Arg Phe Thr Ile Ser Arg Asp Asn Ala Lys Asn Thr Val Tyr
65                  70                  75                  80

Leu Glu Ile Asp Ser Leu Lys Pro Gly Asp Thr Ala Val Tyr Tyr Cys
                85                  90                  95

Ala Ser Arg Ala Arg Gly Thr Val Ser Tyr Asn Tyr Trp Gly Gln Gly
                100                 105                 110

Thr Gln Val Thr Val Ser Ser Ala Ala Ala Tyr Pro Tyr Asp Val Pro
        115                 120                 125

-continued

```
Asp Tyr Gly Ser His His His His His His
    130                 135
```

```
<210> SEQ ID NO 269
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 269
```

```
Gln Val Gln Leu Gln Glu Ser Gly Gly Gly Leu Val Gln Ala Gly Asp
1               5                   10                  15
```

```
Ser Leu Arg Leu Ser Cys Ala Ala Ser Gly Arg Thr Ser Arg Ser Tyr
            20                  25                  30
```

```
Ala Met Gly Trp Phe Arg Gln Ala Pro Gly Lys Glu Arg Glu Leu Val
        35                  40                  45
```

```
Ala Asp Ile Ser Trp Ser Asp Gly Arg Ile Tyr Tyr Ser Asp Ser Val
    50                  55                  60
```

```
Lys Gly Arg Phe Thr Ile Ser Arg Asp Asn Ala Lys Asn Thr Val Tyr
65                  70                  75                  80
```

```
Leu Glu Ile Asp Ser Leu Lys Pro Gly Asp Thr Ala Val Tyr Tyr Cys
                85                  90                  95
```

```
Ala Ser Arg Ala Arg Gly Ser Val Leu Tyr Asn Tyr Trp Gly Gln Gly
            100                 105                 110
```

```
Thr Gln Val Thr Val Ser Ser Ala Ala Ala Tyr Pro Tyr Asp Val Pro
        115                 120                 125
```

```
Asp Tyr Gly Ser His His His His His His
    130                 135
```

```
<210> SEQ ID NO 270
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 270
```

```
Ile Ser Trp Ser Asp Gly Arg Ile
1               5
```

```
<210> SEQ ID NO 271
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 271
```

```
Gln Val Gln Leu Gln Glu Ser Gly Gly Gly Ser Val Gln Ala Gly Gly
1               5                   10                  15
```

```
Ser Leu Arg Leu Ser Cys Ala Ala Ser Gly Arg Thr Ser Arg Ser Tyr
            20                  25                  30
```

```
Ala Met Gly Trp Phe Arg Gln Ala Pro Gly Lys Glu Arg Glu Leu Val
        35                  40                  45
```

```
Ala Asp Ile Ala Trp Ser Asp Gly Arg Ile Tyr Tyr Ser Asp Ser Val
    50                  55                  60
```

```
Lys Gly Arg Phe Thr Ile Ser Arg Asp Asn Ala Lys Asn Thr Val Tyr
65                  70                  75                  80
```

-continued

Leu Glu Ile Asp Ser Leu Lys Pro Gly Asp Thr Ala Val Tyr Tyr Cys
                85                  90                  95

Ala Ser Arg Ala Arg Gly Thr Val Ser Tyr Asn Tyr Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 272
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 272

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ser Arg Ser Tyr
            20                  25                  30

Ala Met Gly Trp Phe Arg Gln Ala Pro Gly Lys Glu Arg Glu Leu Val
        35                  40                  45

Ala Asp Ile Ala Trp Ser Asp Gly Arg Ile Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Glu Ile Asp Ser Leu Lys Pro Gly Asp Thr Ala Val Tyr Tyr Cys
                85                  90                  95

Ala Ser Arg Ala Arg Gly Thr Val Ser Tyr Asn Tyr Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 273
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 273

Gln Val Gln Leu Gln Glu Ser Gly Gly Gly Leu Val Gln Ala Gly Gly
1               5                   10                  15

Ser Leu Arg Leu Ser Cys Val Tyr Ser Gly Asn Val Phe Ser Ile Asn
            20                  25                  30

Leu Met Gly Trp Tyr Arg Gln Ala Pro Gly Lys Gln Arg Glu Leu Leu
        35                  40                  45

Ala Gly Ile Asn Arg Gly Gly Arg Thr Asn Tyr Thr Asp Val Val Lys
    50                  55                  60

Gly Arg Phe Thr Ile Ser Arg Glu Asn Ala Lys Asn Thr Ile Tyr Leu
65                  70                  75                  80

Gln Met Asn Gly Leu Lys Pro Glu Asp Thr Gly Val Tyr Tyr Cys Ala
                85                  90                  95

Ala Ser Arg Asp Pro Tyr Thr Gly Tyr Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135

<210> SEQ ID NO 274
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 274

Gly Asn Val Phe Ser Ile Asn Leu
1               5

<210> SEQ ID NO 275
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 275

Ile Asn Arg Gly Gly Arg Thr
1               5

<210> SEQ ID NO 276
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 276

Ala Ala Ser Arg Asp Pro Tyr Thr Gly Tyr
1               5                   10

<210> SEQ ID NO 277
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 277

Gln Val Gln Leu Gln Glu Ser Gly Gly Gly Leu Val Gln Ala Gly Gly
1               5                   10                  15

Ser Leu Arg Leu Ser Cys Val Tyr Ser Gly Asn Val Phe Ser Ile Asn
            20                  25                  30

Leu Met Gly Trp Tyr Arg Gln Ala Pro Gly Lys Gln Arg Glu Leu Leu
        35                  40                  45

Ala Gly Ile Asn Arg Gly Gly Arg Thr Asn Tyr Thr Asp Val Val Lys
    50                  55                  60

Gly Arg Phe Thr Ile Ser Lys Glu Asn Ala Lys Asn Thr Ile Tyr Leu
65                  70                  75                  80

Gln Met Asn Ser Leu Lys Pro Glu Asp Thr Gly Val Tyr Tyr Cys Ala
                85                  90                  95

Ala Ser Arg Asp Pro Tyr Thr Gly Tyr Trp Gly Gln Gly Thr Gln Val
        100                 105                 110

```
Thr Val Ser Ser Ala Ala Ala Tyr Pro Tyr Asp Val Pro Asp Tyr Gly
        115                 120                 125

Ser His His His His His His
    130                 135
```

```
<210> SEQ ID NO 278
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 278
```

```
Gln Val Gln Leu Gln Glu Ser Gly Gly Gly Leu Val Gln Ala Gly Gly
1               5                   10                  15

Ser Leu Arg Leu Ser Cys Val Tyr Ser Gly Asn Val Phe Ser Ile Asn
        20                  25                  30

Leu Met Gly Trp Tyr Arg Gln Ala Pro Gly Lys Gln Arg Glu Leu Leu
        35                  40                  45

Ala Gly Ile Asn Arg Gly Gly Arg Thr Asn Tyr Thr Asp Val Val Lys
    50                  55                  60

Gly Arg Phe Thr Ile Ser Arg Glu Asn Ala Lys Asn Thr Ile Tyr Leu
65                  70                  75                  80

Gln Met Asn Ser Leu Lys Pro Glu Asp Thr Gly Val Tyr Tyr Cys Ala
                85                  90                  95

Ala Ser Arg Asp Pro Tyr Thr Gly Tyr Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135
```

```
<210> SEQ ID NO 279
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 279
```

```
Gln Val Gln Leu Gln Glu Ser Gly Gly Gly Leu Val Gln Pro Gly Gly
1               5                   10                  15

Ser Leu Arg Leu Ser Cys Val Ala Ser Gly Ser Val Asp Ser Ile Asn
        20                  25                  30

Leu Met Gly Trp Tyr Arg Gln Ala Pro Gly Lys Gln Arg Glu Leu Leu
        35                  40                  45

Ala Gly Ile Asn Arg Gly Gly Arg Thr Asn Tyr Thr Asp Val Val Lys
    50                  55                  60

Gly Arg Phe Thr Ile Ser Arg Glu Asn Ala Lys Asn Thr Ile Tyr Leu
65                  70                  75                  80

Gln Met Asn Ser Leu Lys Pro Glu Asp Thr Gly Val Tyr Tyr Cys Ala
                85                  90                  95

Ala Ser Arg Asp Pro Tyr Thr Gly Tyr Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His His
```

```
        130                     135
```

```
<210> SEQ ID NO 280
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 280

Gly Ser Val Asp Ser Ile Asn Leu
1               5

<210> SEQ ID NO 281
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 281

Gln Val Gln Leu Gln Glu Ser Gly Gly Gly Leu Val Pro Ser Gly Gly
1               5                   10                  15

Ser Leu Arg Leu Ser Cys Val Tyr Ser Gly Asn Val Phe Ser Ile Asn
            20                  25                  30

Leu Met Gly Trp Tyr Arg Gln Ala Pro Gly Lys Gln Arg Glu Leu Leu
        35                  40                  45

Ala Gly Ile Asn Arg Gly Gly Arg Thr Asn Tyr Thr Asp Val Val Lys
    50                  55                  60

Gly Arg Phe Thr Ile Ser Arg Glu Asn Ala Lys Asn Thr Ile Tyr Leu
65                  70                  75                  80

Gln Met Asn Gly Leu Lys Pro Glu Asp Thr Gly Val Tyr Tyr Cys Ala
                85                  90                  95

Ala Ser Arg Asp Pro Tyr Thr Gly Tyr Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135

<210> SEQ ID NO 282
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 282

Asn Val Phe Ser Ile Asn Leu
1               5

<210> SEQ ID NO 283
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 283

Gln Val Gln Leu Gln Glu Ser Gly Gly Gly Leu Val Gln Ala Gly Gly
1               5                   10                  15
```

```
Ser Leu Arg Leu Ser Cys Val Tyr Ser Gly Asn Val Phe Ser Ile Asn
        20                  25                  30

Leu Met Gly Trp Tyr Arg Gln Ala Pro Gly Lys Gln Arg Glu Leu Leu
        35                  40                  45

Ala Gly Ile Thr Arg Gly Gly Arg Thr Asn Tyr Thr Asp Val Val Lys
    50                  55                  60

Gly Arg Phe Thr Ile Ser Arg Glu Ser Ala Lys Asn Thr Ile Tyr Leu
65                  70                  75                  80

Gln Met Asn Ser Leu Lys Pro Glu Asp Thr Gly Val Tyr Tyr Cys Ala
                85                  90                  95

Ala Ser Arg Asp Pro Tyr Thr Gly Tyr Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135
```

```
<210> SEQ ID NO 284
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 284
```

```
Gln Val Gln Leu Gln Glu Ser Gly Gly Gly Leu Val Gln Ala Gly Gly
1               5                   10                  15

Ser Leu Arg Leu Ser Cys Val Tyr Ser Gly Asn Val Phe Ser Ile Asn
        20                  25                  30

Leu Met Gly Trp Tyr Arg Gln Ala Pro Gly Lys Gln Arg Glu Leu Leu
        35                  40                  45

Ala Gly Ile Thr Arg Gly Gly Arg Thr Asn Tyr Thr Asp Val Val Lys
    50                  55                  60

Gly Arg Phe Thr Ile Ser Arg Glu Asn Ala Lys Asn Thr Ile Tyr Leu
65                  70                  75                  80

Gln Met Asn Ser Leu Lys Pro Glu Asp Thr Gly Val Tyr Tyr Cys Ala
                85                  90                  95

Ala Ser Arg Asp Pro Tyr Thr Gly Tyr Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135
```

```
<210> SEQ ID NO 285
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 285
```

```
Cys Ala Ala Ser Arg Asp Pro Tyr Thr Gly Tyr
1               5                   10
```

```
<210> SEQ ID NO 286
<211> LENGTH: 143
```

```
<212> TYPE: PRT
<213> ORGANISM: Artificial sequence
<220> FEATURE:
<223> OTHER INFORMATION: nanobody amino acid sequence

<400> SEQUENCE: 286

Gln Val Gln Leu Gln Glu Ser Gly Gly Gly Leu Val Gln Ala Gly Asp
1               5                   10                  15

Ser Leu Arg Leu Ser Cys Val Ala Ser Lys Arg Ser Phe Ser Ser His
            20                  25                  30

Ala Met Gly Trp Phe Arg Gln Ala Pro Gly Lys Ala Arg Glu Phe Val
        35                  40                  45

Ala Thr Ile Ser Trp Asn Ser Gly Ser Thr Phe Tyr Ser Asp Ser Ser
    50                  55                  60

Arg Gly Arg Phe Thr Ile Ser Arg Asp Asn Gly Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Ala Ser Gly Arg Gly Ile Thr Ala Ser Asp Phe Arg Tyr Asp
            100                 105                 110

Ala Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 287
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 287

Lys Arg Ser Phe Ser Ser His Ala
1               5

<210> SEQ ID NO 288

<400> SEQUENCE: 288

000

<210> SEQ ID NO 289
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 289

Ala Ala Ala Ser Gly Arg Gly Ile Thr Ala Ser Asp Phe Arg Tyr Asp
1               5                   10                  15

Ala

<210> SEQ ID NO 290
<211> LENGTH: 143
<212> TYPE: PRT
<213> ORGANISM: Artificial sequence
<220> FEATURE:
<223> OTHER INFORMATION: nanobody amino acid sequence
```

<400> SEQUENCE: 290

```
Gln Val Gln Leu Gln Glu Ser Gly Gly Gly Val Val Gln Ala Gly Gly
1               5                   10                  15

Ser Leu Arg Leu Ser Cys Val Gly Ser Gly Arg Thr Phe Ser Ser His
            20                  25                  30

Ala Met Gly Trp Phe Arg Gln Ala Pro Gly Lys Glu Arg Glu Phe Val
        35                  40                  45

Ala Thr Ile Ser Trp Asn Ser Gly Ser Thr Phe Tyr Ala Asp Ser Val
    50                  55                  60

Arg Gly Arg Phe Thr Ile Ser Arg Asp Asn Ala Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Ala Ala Ser Gly Arg Gly Ile Thr Ala Ser Asp Phe Arg Tyr Asp
            100                 105                 110

Ala Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

<210> SEQ ID NO 291
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 291

```
Gly Arg Thr Phe Ser Ser His Ala
1               5
```

<210> SEQ ID NO 292
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 292

```
Gln Val Gln Leu Gln Glu Ser Gly Gly Gly Ser Val Gln Ala Gly Gly
1               5                   10                  15

Ser Leu Arg Leu Ser Cys Val Ala Ser Gly Arg Ser Phe Ser Arg His
            20                  25                  30

Ala Met Ala Trp Phe Arg Gln Ala Pro Gly Lys Glu Arg Glu Phe Val
        35                  40                  45

Ala Thr Ile Ser Trp Asn Ala Gly Ser Thr Tyr Tyr Ala Asp Ser Val
    50                  55                  60

Lys Gly Arg Phe Thr Ile Ser Arg Asp Asn Ala Lys Asn Thr Val Thr
65                  70                  75                  80

Leu Gln Met Asn Ser Leu Lys Pro Glu Asp Thr Ala Val Tyr Tyr Cys
                85                  90                  95

Ala Ala Ala Ser Gly Arg Gly Ile Thr Ala Ser Asp Phe Arg Tyr Asp
            100                 105                 110

Ala Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

<210> SEQ ID NO 293
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 293

Gly Arg Ser Phe Ser Arg His Ala
1               5

<210> SEQ ID NO 294
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 294

Ile Ser Trp Asn Ala Gly Ser Thr
1               5

<210> SEQ ID NO 295
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 295

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Ile
                20                  25                  30

Asn Met Gly Trp Phe Arg Gln Ala Pro Gly Lys Glu Arg Glu Phe Val
            35                  40                  45

Ala Val Ile Ser Trp Asn Ser Ile Ala Asp Tyr Ala Asp Ser Val Lys
        50                  55                  60

Ala Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Ser Ala Pro Phe Arg Ser Lys Asn Pro Thr Leu Tyr Leu Tyr Trp
            100                 105                 110

Gly Arg Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 296
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 296

Gly Arg Thr Phe Ser Arg Ile Asn
1               5

```
<210> SEQ ID NO 297
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 297

Ile Ser Trp Asn Ser Ile Ala
1               5

<210> SEQ ID NO 298
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 298

Ala Ala Ser Ala Pro Phe Arg Ser Lys Asn Pro Thr Leu Tyr Leu Tyr
1               5                   10                  15

<210> SEQ ID NO 299
<211> LENGTH: 147
<212> TYPE: PRT
<213> ORGANISM: Artificial sequence
<220> FEATURE:
<223> OTHER INFORMATION: nanobody amino acid sequence
<220> FEATURE:
<221> NAME/KEY: misc_feature
<222> LOCATION: (39)..(39)
<223> OTHER INFORMATION: Xaa can be any naturally occurring amino acid

<400> SEQUENCE: 299

Gln Val Gln Leu Gln Glu Ser Gly Gly Gly Leu Val Gln Ser Gly Asp
1               5                   10                  15

Ser Leu Arg Leu Ser Cys Ser Ala Ser Gly Arg Thr Phe Asn Pro Val
            20                  25                  30

Ala Met Ala Trp Phe Arg Xaa Ala Pro Gly Lys Glu Arg Glu Phe Val
            35                  40                  45

Gly Thr Ile Thr Trp Gly Ile Gly Ser Thr His Tyr Ala Val Pro Val
    50                  55                  60

Lys Gly Arg Phe Thr Ile Ser Lys Glu Asn Ala Lys Asn Thr Val Tyr
65                  70                  75                  80

Leu Gln Met Asn Arg Leu Gln Pro Glu Asp Thr Ala Val Tyr Tyr Cys
                85                  90                  95

Ala Ala Arg Thr Ser Leu Leu Arg Arg Ala Asp Glu Ile Pro Ser Val
            100                 105                 110

Ala Asn Tyr Asp Ser Trp Gly Gln Gly Thr Gln Val Thr Val Ser Ser
        115                 120                 125

Ala Ala Ala Tyr Pro Tyr Asp Val Pro Asp Tyr Gly Ser His His His
    130                 135                 140

His His His
145

<210> SEQ ID NO 300
<211> LENGTH: 8
<212> TYPE: PRT
<213> ORGANISM: Artificial sequence
<220> FEATURE:
```

-continued

<223> OTHER INFORMATION: Complementarity-determining region amino acid
      sequence

<400> SEQUENCE: 300

Gly Arg Thr Phe Asn Pro Val Ala
1               5

<210> SEQ ID NO 301
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 301

Ile Thr Trp Gly Ile Gly Ser Thr
1               5

<210> SEQ ID NO 302
<211> LENGTH: 21
<212> TYPE: PRT
<213> ORGANISM: Artificial sequence
<220> FEATURE:
<223> OTHER INFORMATION: Complementarity-determining region amino acid
      sequence

<400> SEQUENCE: 302

Ala Ala Arg Thr Ser Leu Leu Arg Arg Ala Asp Glu Ile Pro Ser Val
1               5                   10                  15

Ala Asn Tyr Asp Ser
            20

<210> SEQ ID NO 303
<211> LENGTH: 143
<212> TYPE: PRT
<213> ORGANISM: Artificial sequence
<220> FEATURE:
<223> OTHER INFORMATION: nanobody amino acid sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 303

Gln Val Xaa Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Met Tyr
            20                  25                  30

Thr Met Gly Trp Phe Arg Gln Ala Pro Gly Lys Glu Arg Glu Phe Val
        35                  40                  45

Ala Lys Ile Ser Thr Ser Gly Arg Tyr Thr Asp Tyr Val Asp Ser Val
    50                  55                  60

Arg Gly Arg Phe Thr Leu Ser Arg Asp Asn Val Lys Asn Thr Ile Tyr
65                  70                  75                  80

Leu Gln Met Asn Ser Leu Lys Pro Asp Asp Thr Ala Val Tyr Tyr Cys
                85                  90                  95

Ala Ala Arg Leu Pro Arg Pro Asp Thr Trp Ser Gln Gly Lys Thr Asp
            100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 304
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 304

Gly Arg Thr Phe Ser Met Tyr Thr
1               5

<210> SEQ ID NO 305
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 305

Ile Ser Thr Ser Gly Arg Tyr Thr
1               5

<210> SEQ ID NO 306
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 306

Ala Ala Arg Leu Pro Arg Pro Asp Thr Trp Ser Gln Gly Lys Thr Asp
1               5                   10                  15

Tyr

<210> SEQ ID NO 307
<211> LENGTH: 144
<212> TYPE: PRT
<213> ORGANISM: Artificial sequence
<220> FEATURE:
<223> OTHER INFORMATION: nanobody amino acid sequence
<220> FEATURE:
<221> NAME/KEY: misc_feature
<222> LOCATION: (39)..(39)
<223> OTHER INFORMATION: Xaa can be any naturally occurring amino acid

<400> SEQUENCE: 307

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Asn
            20                  25                  30

Pro Met Gly Trp Phe Arg Xaa Ala Pro Gly Lys Glu Arg Glu Phe Val
        35                  40                  45

Ala Thr Lys Thr Gly Gly Asn Ser Gly Ile Thr Val Tyr Ser Asn Ser
    50                  55                  60

Val Lys Gly Arg Phe Thr Ile Ser Arg Asp Leu Ala Lys Asn Thr Val
65                  70                  75                  80

Tyr Leu Gln Met Asp Gly Leu Lys Leu Glu Asp Thr Ala Ile Tyr Tyr
                85                  90                  95

Cys Ala Ala Ser Gly Thr Pro Leu Ala Leu Arg Ser Glu Lys Asn Tyr
            100                 105                 110

Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140

<210> SEQ ID NO 308
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 308

Gly Arg Thr Phe Ser Asn Asn Pro
1               5

<210> SEQ ID NO 309
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 309

Lys Thr Gly Gly Asn Ser Gly Ile Thr
1               5

<210> SEQ ID NO 310
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 310

Ala Ala Ser Gly Thr Pro Leu Ala Leu Arg Ser Glu Lys Asn Tyr Asp
1               5                   10                  15

Tyr

<210> SEQ ID NO 311
<211> LENGTH: 136
<212> TYPE: PRT
<213> ORGANISM: Artificial sequence
<220> FEATURE:
<223> OTHER INFORMATION: nanobody amino acid sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 311

Gln Val Xaa Leu Gln Glu Ser Gly Gly Gly Leu Val Gln Pro Gly Gly
1               5                   10                  15

Ser Leu Arg Leu Ser Cys Ala Ala Ser Gly Ser Ile Phe Asn Ile Asn
            20                  25                  30

Thr Met Gly Trp Tyr Arg Gln Ala Pro Gly Asn Gln Arg Glu Leu Val
        35                  40                  45

Ala Ala Ile Ser Ser Asp Gly Arg Pro Asn His Arg Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Val Pro Ala Ser Arg Ala Gly Gly Tyr Trp Gly Gln Gly Thr Gln
            100                 105                 110

Val Thr Val Ser Ser Ala Ala Ala Tyr Pro Tyr Asp Val Pro Asp Tyr
        115                 120                 125

Gly Ser His His His His His His
    130                 135

<210> SEQ ID NO 312
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 312

Gly Ser Ile Phe Asn Ile Asn Thr
1               5

<210> SEQ ID NO 313
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 313

Ile Ser Ser Asp Gly Arg Pro
1               5

<210> SEQ ID NO 314
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 314

Asn Thr Val Pro Ala Ser Arg Ala Gly Gly Tyr
1               5                   10

<210> SEQ ID NO 315
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 315

Gln Val Gln Leu Gln Glu Ser Gly Gly Gly Leu Ala Gln Ala Gly Asp
1               5                   10                  15

Ser Leu Arg Leu Ser Cys Val Ala Ser Gly Arg Thr Ile Asp Asn Gly
            20                  25                  30

Ala Met Gly Trp Phe Arg Gln Ala Pro Gly Lys Glu Arg Glu Ser Val
        35                  40                  45

Ala Ala Ile Asn Trp Ser Gly Ser Ser Thr Tyr Tyr Ala Asp Ser Val
    50                  55                  60

Lys Gly Arg Phe Ala Ile Ser Arg Asp Asn Val Lys His Glu Val Tyr
65                  70                  75                  80

```
Leu Gln Met Asn Arg Leu Arg Arg Glu Asp Thr Ala Val Tyr Tyr Cys
            85              90                  95

Ala Ala Ala Lys Ser Ile Gly Thr Tyr Ser Ser Ser Ser Ala Tyr Asp
            100             105             110

Tyr Trp Gly Gln Gly Thr Gln Val Thr Val Ser Ser Ala Ala Ala Tyr
        115             120             125

Pro Tyr Asp Val Pro Asp Tyr Gly Ser His His His His His His
    130             135             140
```

<210> SEQ ID NO 316
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 316

```
Gly Arg Thr Ile Asp Asn Gly Ala
1               5
```

<210> SEQ ID NO 317
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 317

```
Ile Asn Trp Ser Gly Ser Ser Thr
1               5
```

<210> SEQ ID NO 318
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 318

```
Ala Ala Ala Lys Ser Ile Gly Thr Tyr Ser Ser Ser Ser Ala Tyr Asp
1               5               10              15

Tyr
```

<210> SEQ ID NO 319
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 319

```
Gln Val Gln Leu Gln Glu Ser Gly Gly Gly Leu Val Gln Ala Gly Gly
1               5               10              15

Ser Leu Arg Leu Ser Cys Ala Ala Ser Gly Arg Thr Phe Asn Thr Tyr
            20              25              30

Ala Met Gly Trp Phe Arg Gln Ala Pro Gly Lys Glu Arg Glu Phe Val
        35              40              45

Ala Ala Met Asn Arg Asp Gly Ser Thr Val Leu Tyr Ala Asp Ser Val
    50              55              60
```

-continued

```
Lys Gly Arg Phe Ala Ile Ser Lys Asp Asn Ala Lys Asn Thr Gly Tyr
65                  70                  75                  80

Leu Gln Met Asn Ser Leu Lys Pro Glu Asp Thr Ala Ile Tyr Tyr Cys
                85                  90                  95

Ala Ala Asn Ala Arg Tyr Ser Asp Tyr Thr Asp Gly Gln Ser Phe Val
                100                 105                 110

Ser Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

```
<210> SEQ ID NO 320
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 320

Gly Arg Thr Phe Asn Thr Tyr Ala
1               5
```

```
<210> SEQ ID NO 321
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 321

Met Asn Arg Asp Gly Ser Thr Val
1               5
```

```
<210> SEQ ID NO 322
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 322

Ala Ala Asn Ala Arg Tyr Ser Asp Tyr Thr Asp Gly Gln Ser Phe Val
1               5                   10                  15

Ser
```

```
<210> SEQ ID NO 323
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 323

Gln Val Gln Leu Gln Glu Ser Gly Gly Gly Leu Val Gln Ala Gly Gly
1               5                   10                  15

Ser Leu Arg Leu Ser Cys Gln Ala Ser Gly Arg Thr Phe Asn Thr Tyr
                20                  25                  30

Ala Met Gly Trp Phe Arg Gln Ala Pro Gly Lys Glu Arg Glu Phe Val
        35                  40                  45

Ala Ala Met Asn Arg Asp Gly Ser Thr Ile Leu Tyr Gly Asp Ser Val
```

-continued

```
        50              55              60

Lys Gly Arg Phe Ala Ile Ser Arg Asp Asn Ala Lys Asn Thr Gly Tyr
65              70              75              80

Leu Gln Met Asn Ser Leu Lys Pro Glu Asp Thr Ala Ile Tyr Tyr Cys
                85              90              95

Ala Ala Asn Ala Arg Tyr Ser Asp Tyr Thr His Gly Gln Ser Phe Val
        100             105             110

Ser Trp Gly Gln Gly Thr Gln Val Thr Val Ser Ser Ala Ala Ala Tyr
        115             120             125

Pro Tyr Asp Val Pro Asp Tyr Gly Ser His His His His His His
    130             135             140
```

```
<210> SEQ ID NO 324
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 324

Met Asn Arg Asp Gly Ser Thr Ile
1               5
```

```
<210> SEQ ID NO 325
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 325

Ala Ala Asn Ala Arg Tyr Ser Asp Tyr Thr His Gly Gln Ser Phe Val
1               5               10              15

Ser
```

```
<210> SEQ ID NO 326
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 326

Gln Val Gln Leu Gln Glu Ser Gly Gly Gly Leu Val Gln Ala Gly Gly
1               5               10              15

Ser Leu Arg Leu Ser Cys Gln Ala Ser Gly Arg Thr Phe Asp Ala Tyr
        20              25              30

Ala Met Gly Trp Phe Arg Gln Ala Pro Gly Lys Glu Arg Glu Phe Val
        35              40              45

Ala Ala Met Asn Arg Asp Gly Ser Thr Val Leu Tyr Ala Asp Ser Val
    50              55              60

Lys Gly Arg Phe Ala Ile Ser Lys Asp Asn Ala Lys Asn Thr Gly Tyr
65              70              75              80

Leu Gln Met Asn Ser Leu Lys Pro Glu Asp Thr Ala Ile Tyr Tyr Cys
                85              90              95

Ala Ala Asn Ala Arg Tyr Ser Asp Tyr Thr Asp Gly Gln Ser Phe Ile
        100             105             110

Ser Trp Gly Gln Gly Thr Gln Val Thr Val Ser Ser Ala Ala Ala Tyr
```

-continued

```
             115                 120                 125

Pro Tyr Asp Val Pro Asp Tyr Gly Ser His His His His His
    130                 135                 140

<210> SEQ ID NO 327
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 327

Gly Arg Thr Phe Asp Ala Tyr Ala
1               5

<210> SEQ ID NO 328
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 328

Ala Ala Asn Ala Arg Tyr Ser Asp Tyr Thr Asp Gly Gln Ser Phe Ile
1               5                   10                  15

Ser

<210> SEQ ID NO 329
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 329

Gln Val Gln Leu Gln Glu Ser Gly Gly Gly Leu Val Gln Ala Gly Gly
1               5                   10                  15

Ser Leu Arg Leu Ser Cys Gln Ala Ser Gly Arg Thr Phe Asn Thr Tyr
            20                  25                  30

Ala Met Gly Trp Phe Arg Gln Ala Pro Gly Lys Glu Arg Glu Phe Val
        35                  40                  45

Ala Ala Met Asn Arg Asp Gly Ser Thr Val Leu Tyr Ala Asp Ser Val
    50                  55                  60

Lys Gly Arg Phe Ala Ile Ser Lys Asp Asn Ala Lys Asn Thr Gly Tyr
65                  70                  75                  80

Leu Gln Met Asn Ser Leu Lys Pro Glu Asp Thr Ala Ile Tyr Tyr Cys
                85                  90                  95

Ala Ala Asn Ala Arg Tyr Ser Asp Tyr Thr Asp Gly Gln Ser Phe Val
            100                 105                 110

Ser Trp Gly Gln Gly Thr Gln Val Thr Val Ser Ser Ala Ala Ala Tyr
        115                 120                 125

Pro Tyr Asp Val Pro Asp Tyr Gly Ser His His His His His
    130                 135                 140

<210> SEQ ID NO 330

<400> SEQUENCE: 330

000
```

-continued

<210> SEQ ID NO 331
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 331

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Phe Asn Thr Tyr
                20                  25                  30

Ala Met Gly Trp Phe Arg Gln Ala Pro Gly Lys Glu Arg Glu Phe Val
            35                  40                  45

Ala Ala Met Asn Arg Asp Gly Ser Thr Val Leu Tyr Ala Asp Tyr Val
        50                  55                  60

Lys Gly Arg Phe Ala Ile Ser Lys Asp Asn Ala Lys Asn Thr Gly Tyr
65                  70                  75                  80

Leu Gln Met Asn Ser Leu Lys Pro Glu Asp Thr Ala Ile Tyr Tyr Cys
                85                  90                  95

Ala Ala Asn Ala Arg Tyr Ser Asp Tyr Thr Asp Glu Gln Ser Phe Val
            100                 105                 110

Ser Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 332
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 332

Ala Ala Asn Ala Arg Tyr Ser Asp Tyr Thr Asp Glu Gln Ser Phe Val
1               5                   10                  15

Ser

<210> SEQ ID NO 333
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 333

Gln Val Gln Leu Gln Glu Ser Gly Gly Gly Leu Val Gln Ala Gly Gly
1               5                   10                  15

Ser Leu Arg Leu Ser Cys Gln Ala Ser Gly Arg Thr Phe Asn Thr Tyr
                20                  25                  30

Ala Met Gly Trp Phe Arg Gln Ala Pro Gly Lys Glu Arg Glu Phe Val
            35                  40                  45

Ala Ala Met Asn Arg Asp Gly Ser Thr Val Leu Tyr Ala Asp Ser Val
        50                  55                  60

Lys Gly Arg Phe Ala Ile Ser Lys Asp Asn Ala Lys Ser Thr Gly Tyr
65                  70                  75                  80

Leu Gln Met Asn Ser Leu Lys Pro Glu Asp Thr Ala Ile Tyr Tyr Cys

-continued

```
                        85                90                95

Ala Ala Asn Ala Arg Tyr Ser Asp Tyr Thr Asp Gly Gln Ser Phe Val
                100                105                110

Ser Trp Gly Gln Gly Thr Gln Val Thr Val Ser Ser Ala Ala Ala Tyr
            115                120                125

Pro Tyr Asp Val Pro Asp Tyr Gly Ser His His His His His His
    130                135                140

<210> SEQ ID NO 334
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 334

Gln Val Gln Leu Gln Glu Ser Gly Gly Gly Leu Val Gln Ala Gly Gly
1               5                10                15

Ser Leu Arg Leu Ser Cys Lys Ala Ser Gly Arg Thr Phe Ser Thr Tyr
            20                25                30

Ala Val Gly Trp Phe Arg Gln Ala Pro Gly Lys Pro Arg Glu Phe Val
        35                40                45

Ala Ala Met Asn Ser Arg Gly Ser Thr Ile Asn Tyr Ala Asp Ser Val
    50                55                60

Lys Gly Arg Phe Ala Ile Ser Arg Asp Asn Ala Lys Asn Thr Gly Tyr
65                70                75                80

Leu Gln Met Asp Ser Leu Lys Pro Glu Asp Thr Ala Ile Tyr Tyr Cys
                85                90                95

Ala Ala Asp Ala Arg Tyr Ser Asp Tyr Thr Asp Gly Gln Ser Phe Lys
                100                105                110

Ser Trp Gly Gln Gly Thr Gln Val Thr Val Ser Ser Ala Ala Ala Tyr
            115                120                125

Pro Tyr Asp Val Pro Asp Tyr Gly Ser His His His His His His
    130                135                140

<210> SEQ ID NO 335

<400> SEQUENCE: 335

000

<210> SEQ ID NO 336
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 336

Met Asn Ser Arg Gly Ser Thr Ile
1               5

<210> SEQ ID NO 337
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 337
```

-continued

Ala Ala Asp Ala Arg Tyr Ser Asp Tyr Thr Asp Gly Gln Ser Phe Lys
1               5                   10                  15

Ser

<210> SEQ ID NO 338
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 338

Gln Val Gln Leu Gln Glu Ser Gly Gly Gly Leu Val Gln Ala Gly Gly
1               5                   10                  15

Ser Leu Arg Leu Ser Cys Gln Ala Ser Gly Arg Thr Phe Asn Thr Tyr
            20                  25                  30

Ala Met Gly Trp Phe Arg Gln Ala Pro Gly Lys Glu Arg Glu Phe Val
        35                  40                  45

Ala Ala Met Asn Arg Asp Gly Ser Thr Ile Leu Tyr Ala Asp Ser Val
    50                  55                  60

Lys Gly Arg Phe Ala Ile Ser Lys Asp Asn Ala Lys Asn Thr Gly Tyr
65                  70                  75                  80

Leu Gln Met Asn Ser Leu Lys Pro Glu Asp Thr Ala Ile Tyr Tyr Cys
                85                  90                  95

Ala Ala Asn Ala Arg Tyr Ser Asp Tyr Thr Asn Gly His Ser Phe Val
            100                 105                 110

Ser Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 339
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 339

Ala Ala Asn Ala Arg Tyr Ser Asp Tyr Thr Asn Gly His Ser Phe Val
1               5                   10                  15

Ser

<210> SEQ ID NO 340
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 340

Gln Val Gln Leu Gln Glu Ser Gly Gly Gly Leu Val Gln Pro Gly Gly
1               5                   10                  15

Ser Leu Arg Leu Ser Cys Gln Ala Ser Gly Arg Thr Phe Asn Thr Tyr
            20                  25                  30

Ala Met Gly Trp Phe Arg Gln Ala Pro Gly Lys Glu Arg Glu Phe Val
        35                  40                  45

Ala Ala Met Asn Arg Asp Gly Ser Thr Val Leu Tyr Ala Asp Ser Val

-continued

```
        50              55              60

Lys Gly Arg Phe Ala Ile Ser Lys Asp Asn Ala Arg Asn Thr Gly Tyr
65              70              75              80

Leu Gln Met Asn Ser Leu Lys Pro Glu Asp Thr Ala Ile Tyr Tyr Cys
                85              90              95

Ala Ala Asn Ala Arg Tyr Ser Asp Tyr Thr Asp Gly Gln Ser Phe Val
                100             105             110

Ser Trp Gly Gln Gly Thr Gln Val Thr Val Ser Ser Ala Ala Ala Tyr
                115             120             125

Pro Tyr Asp Val Pro Asp Tyr Gly Ser His His His His His
    130             135             140
```

<210> SEQ ID NO 341
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 341

```
Gln Val Gln Leu Gln Glu Ser Gly Gly Gly Leu Val Gln Ala Gly Gly
1               5               10              15

Ser Leu Arg Leu Ser Cys Gln Ala Ser Gly Arg Thr Phe Asn Thr Tyr
                20              25              30

Ala Met Gly Trp Phe Arg Gln Ala Pro Gly Lys Glu Arg Glu Phe Val
                35              40              45

Ala Ala Met Asn Arg Asp Gly Ser Thr Val Leu Tyr Arg Asp Ser Val
    50              55              60

Lys Gly Arg Phe Ala Ile Ser Lys Asp Asn Ala Arg Asn Thr Gly Tyr
65              70              75              80

Leu Gln Met Asn Asn Leu Lys Pro Glu Asp Thr Ala Ile Tyr Tyr Cys
                85              90              95

Ala Ala Asn Ala Arg Tyr Ser Asp Tyr Thr Asp Gly Gln Ser Phe Val
                100             105             110

Ser Trp Gly Gln Gly Thr Gln Val Thr Val Ser Ser Ala Ala Ala Tyr
                115             120             125

Pro Tyr Asp Val Pro Asp Tyr Gly Ser His His His His His
    130             135             140
```

<210> SEQ ID NO 342
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 342

```
Gln Val Gln Leu Gln Glu Ser Gly Gly Gly Leu Val Gln Ala Gly Gly
1               5               10              15

Ser Leu Arg Leu Ser Cys Gln Ala Ser Glu Arg Ser Phe Ser Thr Tyr
                20              25              30

Ala Met Gly Trp Phe Arg Gln Ala Pro Gly Lys Glu Arg Glu Phe Val
                35              40              45

Ala Ala Met Asn Arg Asn Gly Asn Thr Ile Asn Tyr Leu Asp Ser Val
    50              55              60

Lys Gly Arg Phe Ala Ile Ser Arg Asp Asn Ala Lys Ser Thr Gly Tyr
65              70              75              80
```

```
Leu Gln Met Asn Ser Leu Lys Pro Glu Asp Thr Ala Thr Tyr Tyr Cys
                85                  90                  95

Ser Ala Asn Ala Arg Leu Ser Asp Tyr Thr Asn Pro Gln Ser Phe Val
            100                 105                 110

Ser Trp Gly Gln Gly Thr Gln Val Thr Val Ser Ser Ala Ala Ala Tyr
        115                 120                 125

Pro Tyr Asp Val Pro Asp Tyr Gly Ser His His His His His
    130                 135                 140
```

```
<210> SEQ ID NO 343
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 343

Glu Arg Ser Phe Ser Thr Tyr Ala
1               5
```

```
<210> SEQ ID NO 344
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 344

Met Asn Arg Asn Gly Asn Thr Ile
1               5
```

```
<210> SEQ ID NO 345
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 345

Ser Ala Asn Ala Arg Leu Ser Asp Tyr Thr Asn Pro Gln Ser Phe Val
1               5                   10                  15

Ser
```

```
<210> SEQ ID NO 346
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 346

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ala Phe Ser Ser Tyr
            20                  25                  30

Gly Met Ala Trp Phe Arg Gln Ala Pro Gly Lys Glu Arg Glu Phe Val
        35                  40                  45

Ala Ala Ile Asn Ser Asn Gly Arg Ser Thr Tyr Tyr Ala Asp Thr Val
    50                  55                  60

Lys Gly Arg Phe Thr Ile Ser Arg Asp Asp Gly Arg Asn Thr Leu Tyr
```

```
       65                    70                    75                    80
Leu Gln Met Asn Ser Leu Lys Pro Glu Asp Thr Ala Val Tyr Tyr Cys
                    85                    90                    95

Ala Ala Asp Arg Gln Ser Met Lys Gly Tyr Glu Tyr Gly Tyr Trp Gly
                100                   105                   110

Gln Gly Thr Gln Val Thr Val Ser Ser Ala Ala Ala Tyr Pro Tyr Asp
            115                   120                   125

Val Pro Asp Tyr Gly Ser His His His His His His
        130                   135                   140

<210> SEQ ID NO 347
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 347

Gly Arg Ala Phe Ser Ser Tyr Gly
1               5

<210> SEQ ID NO 348
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 348

Ile Asn Ser Asn Gly Arg Ser Thr
1               5

<210> SEQ ID NO 349
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 349

Ala Ala Asp Arg Gln Ser Met Lys Gly Tyr Glu Tyr Gly Tyr
1               5                   10

<210> SEQ ID NO 350
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 350

Gln Val Gln Leu Gln Glu Ser Gly Gly Gly Leu Val Gln Ala Gly Gly
1               5                   10                   15

Ser Leu Arg Leu Ser Cys Ala Ala Ser Gly Arg Ala Phe Ser Arg Tyr
                20                   25                   30

Gly Met Ala Trp Phe Arg Gln Ala Pro Gly Lys Glu Arg Glu Phe Val
            35                   40                   45

Ala Ala Ile Thr Ser Asn Gly Arg Ser Thr Tyr Tyr Ala Asp Thr Val
        50                   55                   60

Lys Gly Arg Phe Thr Ile Ser Arg Asp Asn Gly Arg Asn Thr Leu Tyr
```

-continued

```
65                    70                    75                    80

Leu Gln Met Asn Thr Leu Lys Pro Glu Asp Thr Ala Val Tyr Tyr Cys
                85                    90                    95

Ala Ala Asp Arg Lys Ser Met Thr Gly Tyr Glu Tyr Gly Tyr Trp Gly
            100                   105                   110

Gln Gly Thr Gln Val Thr Val Ser Ser Ala Ala Ala Tyr Pro Tyr Asp
        115                   120                   125

Val Pro Asp Tyr Gly Ser His His His His His His
    130                   135                   140
```

```
<210> SEQ ID NO 351
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 351

Gly Arg Ala Phe Ser Arg Tyr Gly
1               5
```

```
<210> SEQ ID NO 352
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 352

Ile Thr Ser Asn Gly Arg Ser Thr
1               5
```

```
<210> SEQ ID NO 353
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 353

Ala Ala Asp Arg Lys Ser Met Thr Gly Tyr Glu Tyr Gly Tyr
1               5                   10
```

```
<210> SEQ ID NO 354
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 354

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ala Phe Ser Arg Tyr
            20                  25                  30

Gly Met Ala Trp Phe Arg Gln Ala Pro Gly Lys Glu Arg Glu Phe Val
        35                  40                  45

Ala Ala Ile Thr Ser Asn Gly Arg Ser Thr Tyr Tyr Ala Asp Thr Val
    50                  55                  60

Lys Gly Arg Phe Thr Ile Ser Arg Asp Asn Gly Arg Asn Thr Leu Tyr
```

-continued

```
65              70              75              80
Leu Gln Met Asn Thr Leu Lys Pro Glu Asp Thr Ala Val Tyr Tyr Cys
            85              90              95

Ala Ala Asp Arg Lys Ser Met Thr Gly Tyr Glu Tyr Gly Tyr Trp Gly
            100             105             110

Gln Gly Thr Gln Val Thr Val Ser Ser Ala Ala Ala Tyr Pro Tyr Asp
        115             120             125

Val Pro Asp Tyr Gly Ser His His His His His
    130             135             140

<210> SEQ ID NO 355
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 355

Gln Val Gln Leu Gln Glu Ser Gly Gly Gly Leu Val Gln Ala Gly Gly
1               5               10              15

Ser Leu Arg Leu Ser Cys Ala Ala Ser Gly Arg Ala Phe Ser Arg Tyr
            20              25              30

Gly Met Ala Trp Phe Arg Gln Ala Pro Gly Lys Glu Arg Glu Phe Val
            35              40              45

Gly Ala Ile Asn Ser Asn Gly Arg Ser Thr Tyr Tyr Ala Asp Thr Val
        50              55              60

Lys Gly Arg Phe Thr Ile Ser Arg Asp Asn Asp Arg Asn Thr Leu Tyr
65              70              75              80

Leu Gln Met Asn Ser Leu Lys Pro Glu Asp Thr Ala Val Tyr Tyr Cys
            85              90              95

Ala Ala Asp Arg Gln Ser Met Thr Arg Tyr Glu Tyr Gly Tyr Trp Gly
            100             105             110

Gln Gly Thr Gln Val Thr Val Ser Ser Ala Ala Ala Tyr Pro Tyr Asp
        115             120             125

Val Pro Asp Tyr Gly Ser His His His His His
    130             135             140

<210> SEQ ID NO 356
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 356

Ala Ala Asp Arg Gln Ser Met Thr Arg Tyr Glu Tyr Gly Tyr
1               5               10

<210> SEQ ID NO 357
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 357

Gln Val Gln Leu Gln Glu Ser Gly Gly Gly Leu Val Gln Pro Gly Gly
1               5               10              15

Ser Leu Arg Leu Ser Cys Ala Ala Ser Gly Phe Thr Phe Ser Asn Tyr
```

-continued

```
                20                    25                    30

Ala Met Gly Trp Phe Arg Gln Ala Pro Gly Lys Glu Arg Asp Phe Val
        35                    40                    45

Ala Ala Val Ser Gly Ile Ala Arg Arg Thr Tyr Tyr Ala Asp Ser Val
    50                    55                    60

Lys Gly Arg Ser Thr Ile Ser Arg Asp Asn Gly Arg Asn Thr Leu Tyr
65                    70                    75                    80

Leu Gln Met Asn Asn Leu Lys Pro Glu Asp Thr Ala Val Tyr Tyr Cys
                85                    90                    95

Ala Arg Ala Thr Ser Arg Met Thr Ser Val Thr Thr Leu Asn Asp Tyr
            100                   105                   110

Gly Tyr Trp Gly Gln Gly Thr Pro Val Thr Val Ser Ser Ala Ala Ala
            115                   120                   125

Tyr Pro Tyr Asp Val Pro Asp Tyr Gly Ser His His His His His His
    130                   135                   140
```

<210> SEQ ID NO 358
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 358

```
Gly Phe Thr Phe Ser Asn Tyr Ala
1               5
```

<210> SEQ ID NO 359
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 359

```
Val Ser Gly Ile Ala Arg Arg Thr
1               5
```

<210> SEQ ID NO 360
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 360

```
Ala Arg Ala Thr Ser Arg Met Thr Ser Val Thr Thr Leu Asn Asp Tyr
1               5                   10                  15

Gly Tyr
```

<210> SEQ ID NO 361
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 361

```
Gln Val Gln Leu Gln Glu Ser Gly Gly Gly Leu Val Gln Pro Gly Glu
1               5                   10                  15
```

Ser Leu Arg Leu Ser Cys Ala Ala Ser Gly Phe Thr Phe Ser Asn Tyr
        20                  25                  30

Ala Met Gly Trp Phe Arg Gln Ala Pro Gly Lys Glu Arg Asp Phe Val
        35                  40                  45

Ala Ala Val Ser Gly Ile Ala Arg Arg Thr Tyr Tyr Ala Asp Ser Val
    50                  55                  60

Lys Gly Arg Ser Thr Ile Ser Arg Asp Asn Gly Arg Asn Thr Val Tyr
65                  70                  75                  80

Leu Gln Met Asn Ser Leu Lys Pro Glu Asp Thr Ala Val Tyr Tyr Cys
                85                  90                  95

Ala Arg Ala Thr Ser Arg Met Thr Ser Val Thr Thr Leu Asp Asp Tyr
            100                 105                 110

Gly Tyr Trp Gly Gln Gly Thr Gln Val Thr Val Ser Ser Ala Ala Ala
            115                 120                 125

Tyr Pro Tyr Asp Val Pro Asp Tyr Gly Ser His His His His His His
    130                 135                 140

<210> SEQ ID NO 362
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 362

Ala Arg Ala Thr Ser Arg Met Thr Ser Val Thr Thr Leu Asp Asp Tyr
1               5                   10                  15

Gly Tyr

<210> SEQ ID NO 363
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 363

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
        20                  25                  30

Ala Met Gly Trp Phe Arg Gln Ala Pro Gly Lys Glu Arg Asp Phe Val
        35                  40                  45

Ala Ala Val Ser Gly Ile Ala Arg Arg Thr Tyr Tyr Ala Asp Ser Val
    50                  55                  60

Lys Gly Arg Ser Thr Ile Ser Arg Asp Asn Gly Arg Asn Thr Val Tyr
65                  70                  75                  80

Leu Gln Met Asn Ser Leu Lys Pro Glu Asp Thr Ala Val Tyr Tyr Cys
                85                  90                  95

Ala Arg Ala Thr Ser Arg Met Thr Ser Val Thr Thr Leu Asn Asp Tyr
            100                 105                 110

Gly Tyr Trp Gly Gln Gly Thr Gln Val Thr Val Ser Ser Ala Ala Ala
            115                 120                 125

Tyr Pro Tyr Asp Val Pro Asp Tyr Gly Ser His His His His His His
    130                 135                 140

<210> SEQ ID NO 364
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 364

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Phe Arg Gln Ala Pro Gly Lys Glu Arg Glu Phe Val
        35                  40                  45

Ala Ala Val Ser Gly Ile Ala Arg Arg Thr Tyr Tyr Ala Asp Ser Val
    50                  55                  60

Lys Gly Arg Ser Thr Ile Ser Arg Asp Asn Gly Arg Asn Thr Val Tyr
65                  70                  75                  80

Leu Gln Met Asn Ser Leu Lys Pro Glu Asp Thr Ala Val Tyr Tyr Cys
                85                  90                  95

Ala Arg Ala Thr Ser Arg Met Thr Ser Val Thr Thr Leu Asn Asp Tyr
            100                 105                 110

Ala Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140
```

<210> SEQ ID NO 365
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 365

```
Gly Phe Thr Phe Ser Ser Tyr Ala
1               5
```

<210> SEQ ID NO 366
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 366

```
Ala Arg Ala Thr Ser Arg Met Thr Ser Val Thr Thr Leu Asn Asp Tyr
1               5                   10                  15

Ala Tyr
```

<210> SEQ ID NO 367
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 367

```
Gln Val Gln Leu Gln Glu Ser Gly Gly Gly Ser Val Gln Ser Gly Gly
1               5                   10                  15
```

-continued

```
Ser Leu Thr Leu Ser Cys Ser Ala Ser Gly Ser Leu Phe Ser Ile Asn
        20                  25                  30

Ala Met Gly Trp Tyr Arg Gln Ala Pro Arg Lys Gln His Glu Leu Val
        35                  40                  45

Ala Thr Met Met Asp Gly Gly Ser Thr Ser Tyr Ala Asp Ser Val Lys
    50                  55                  60

Gly Arg Phe Thr Ile Ser Arg Asp Asn Asp Lys Lys Thr Val Tyr Leu
65                  70                  75                  80

Gln Met Asn Ser Leu Lys Pro Glu Asp Thr Gly Val Tyr Tyr Cys Val
                85                  90                  95

Ala Asp Arg Leu Gly Ser Gly Arg Tyr Ala Tyr Gly Ile Asp Tyr Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140
```

```
<210> SEQ ID NO 368
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 368

Gly Ser Leu Phe Ser Ile Asn Ala
1               5
```

```
<210> SEQ ID NO 369
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 369

Met Met Asp Gly Gly Ser Thr
1               5
```

```
<210> SEQ ID NO 370
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 370

Val Ala Asp Arg Leu Gly Ser Gly Arg Tyr Ala Tyr Gly Ile Asp Tyr
1               5                   10                  15
```

```
<210> SEQ ID NO 371
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 371

Gln Val Gln Leu Gln Glu Ser Gly Gly Gly Leu Val Gln Pro Gly Gly
1               5                   10                  15
```

```
Ser Leu Arg Leu Ala Cys Ala Ala Ser Gly Ser Ile Phe Ser Ile Asn
        20                  25                  30

Ala Met Gly Trp Tyr Arg Gln Ala Pro Arg Lys Gln Arg Glu Leu Val
        35                  40                  45

Ala Thr Met Met Asp Gly Gly Ser Thr Ser Tyr Ala Asp Ser Val Lys
    50                  55                  60

Gly Arg Phe Thr Ile Ser Arg Asp Asn Asp Lys Lys Thr Val Tyr Leu
65                  70                  75                  80

Gln Met Asn Ser Leu Lys Pro Glu Asp Thr Gly Val Tyr Tyr Cys Val
                85                  90                  95

Ala Asp Arg Leu Gly Ser Gly Arg Tyr Ala Tyr Gly Ile Asp Tyr Trp
            100                 105                 110

Gly Gln Gly Thr Gln Val Thr Val Ser Ser Ala Ala Ala Tyr Pro Tyr
            115                 120                 125

Asp Val Pro Asp Tyr Gly Ser His His His His His His
    130                 135                 140
```

```
<210> SEQ ID NO 372
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 372

Gly Ser Ile Phe Ser Ile Asn Ala
1               5
```

```
<210> SEQ ID NO 373
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 373

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Val Ser Ile Asn
        20                  25                  30

Gly Met Gly Trp Tyr Arg Gln Ala Pro Arg Lys Gln Arg Glu Leu Val
        35                  40                  45

Ala Thr Met Met Asp Gly Gly Ser Thr Ser Tyr Ala Asp Ser Val Lys
    50                  55                  60

Gly Arg Phe Thr Ile Ser Arg Asp Asn Asp Lys Lys Thr Val Tyr Leu
65                  70                  75                  80

Gln Met Asn Ser Leu Lys Pro Glu Asp Thr Gly Val Tyr Tyr Cys Ala
                85                  90                  95

Ala Asp Arg Leu Gly Ser Gly Arg Tyr Ala Tyr Ala Ile Asp Tyr Trp
            100                 105                 110

Gly Gln Gly Thr Gln Val Thr Val Ser Ser Ala Ala Ala Tyr Pro Tyr
            115                 120                 125

Asp Val Pro Asp Tyr Gly Ser His His His His His His
    130                 135                 140
```

```
<210> SEQ ID NO 374
<211> LENGTH: 8
<212> TYPE: PRT
```

```
<213> ORGANISM: Artificial sequence
<220> FEATURE:
<223> OTHER INFORMATION: Complementarity-determining region amino acid
      sequence

<400> SEQUENCE: 374

Gly Ser Ile Val Ser Ile Asn Gly
1               5

<210> SEQ ID NO 375
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 375

Ala Ala Asp Arg Leu Gly Ser Gly Arg Tyr Ala Tyr Ala Ile Asp Tyr
1               5                   10                  15

<210> SEQ ID NO 376
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 376

Gln Val Gln Leu Gln Glu Ser Gly Gly Gly Leu Val Gln Pro Gly Gly
1               5                   10                  15

Ser Leu Arg Leu Ser Cys Thr Ala Ser Gly Arg Thr Val Ser Asn Tyr
            20                  25                  30

Gly Met Ala Trp Phe Arg Gln Val Ala Gly Lys Glu Arg Ala Phe Val
        35                  40                  45

Ala Ala Ile Asn Asn Arg Gly Asp Ser Lys Tyr Tyr Ala Glu Ser Val
    50                  55                  60

Lys Gly Arg Phe Thr Ile Ala Arg Asp Asn Ala Lys Asn Thr Val Tyr
65                  70                  75                  80

Leu Gln Met Asn Val Leu Lys Pro Glu Asp Thr Ala Val Tyr Tyr Cys
                85                  90                  95

Ala Ala Asp Arg Arg Ser Leu Val Arg Tyr Glu Tyr Asn Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140

<210> SEQ ID NO 377
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 377

Gly Arg Thr Val Ser Asn Tyr Gly
1               5

<210> SEQ ID NO 378
<211> LENGTH: 8
<212> TYPE: PRT
```

-continued

<213> ORGANISM: Artificial sequence
<220> FEATURE:
<223> OTHER INFORMATION: Complementarity-determining region amino acid
      sequence

<400> SEQUENCE: 378

Ile Asn Asn Arg Gly Asp Ser Lys
1               5

<210> SEQ ID NO 379
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 379

Ala Ala Asp Arg Arg Ser Leu Val Arg Tyr Glu Tyr Asn Tyr
1               5                   10

<210> SEQ ID NO 380
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 380

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Arg Trp Ser Ser Gly Asn Thr Tyr Tyr Thr Asp Ala Val
    50                  55                  60

Lys Gly Arg Phe Thr Ile Ser Arg Asp Asn Thr Glu Asn Thr Val Tyr
65                  70                  75                  80

Leu Gln Met Asn Ser Leu Lys Pro Glu Asp Thr Ala Val Tyr Tyr Cys
                85                  90                  95

Val Ala Asp Asp Gly Leu Ser Tyr Ala Ser Ser Ser Tyr Leu Tyr Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 381
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 381

Gly Arg Thr Phe Ser Arg Tyr Thr
1               5

<210> SEQ ID NO 382
<211> LENGTH: 8
<212> TYPE: PRT

<213> ORGANISM: Artificial sequence
<220> FEATURE:
<223> OTHER INFORMATION: Complementarity-determining region amino acid
      sequence

<400> SEQUENCE: 382

Ile Arg Trp Ser Ser Gly Asn Thr
1               5

<210> SEQ ID NO 383
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 383

Val Ala Asp Asp Gly Leu Ser Tyr Ala Ser Ser Ser Tyr Leu Tyr
1               5                   10                  15

<210> SEQ ID NO 384
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 384

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Arg Trp Ser Ser Gly Asn Thr Tyr Tyr Thr Asp Ala Val
    50                  55                  60

Lys Gly Arg Phe Thr Ile Ser Arg Asp Asn Thr Glu Asn Thr Val Tyr
65                  70                  75                  80

Leu Gln Met Asn Ser Leu Lys Pro Glu Asp Thr Ala Val Tyr Tyr Cys
                85                  90                  95

Val Ala Asp Asp Gly Leu Ser Tyr Ala Ser Ser Ser Tyr Leu Tyr Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 385
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 385

Gly Phe Thr Phe Ser Arg Tyr Thr
1               5

<210> SEQ ID NO 386
<211> LENGTH: 140
<212> TYPE: PRT

<213> ORGANISM: Artificial sequence
<220> FEATURE:
<223> OTHER INFORMATION: nanobody amino acid sequence

<400> SEQUENCE: 386

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Phe Gly Asn Tyr
                20                  25                  30

Gly Leu Ala Trp Phe Arg Gln Pro Pro Gly Lys Glu Arg Glu Phe Val
            35                  40                  45

Ala Ala Ile Asn Asn Arg Gly Gly Asn Thr Tyr Tyr Ala Asp Ser Val
        50                  55                  60

Lys Gly Arg Phe Thr Ile Ser Arg Asp Asn Ala Ala Asn Thr Leu Tyr
65                  70                  75                  80

Leu Gln Met Ser Ser Leu Lys Pro Glu Asp Thr Ala Val Tyr Tyr Cys
                85                  90                  95

Ala Ala Asp Arg Thr Ser Leu His Ser Tyr Arg Tyr Thr Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140

<210> SEQ ID NO 387
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 387

Gly Arg Thr Phe Gly Asn Tyr Gly
1               5

<210> SEQ ID NO 388
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 388

Ile Asn Asn Arg Gly Gly Asn Thr
1               5

<210> SEQ ID NO 389
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 389

Ala Ala Asp Arg Thr Ser Leu His Ser Tyr Arg Tyr Thr Tyr
1               5                   10

<210> SEQ ID NO 390
<211> LENGTH: 140
<212> TYPE: PRT

```
<213> ORGANISM: Artificial sequence
<220> FEATURE:
<223> OTHER INFORMATION: nanobody amino acid sequence

<400> SEQUENCE: 390

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Phe Gly Asn Tyr
            20                  25                  30

Gly Leu Ala Trp Phe Arg Gln Pro Pro Gly Lys Glu Arg Glu Phe Val
        35                  40                  45

Ala Ala Ile Ser Asn Arg Gly Gly Asn Thr Tyr Tyr Ala Asp Ser Val
    50                  55                  60

Lys Gly Arg Phe Thr Ile Ser Arg Asp Asn Ala Ala Asn Thr Leu Tyr
65                  70                  75                  80

Leu Gln Met Ser Ser Leu Lys Pro Glu Asp Thr Ala Val Tyr Tyr Cys
                85                  90                  95

Ala Ala Asp Arg Thr Ser Leu His Ser Tyr Arg Tyr Thr Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140

<210> SEQ ID NO 391
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 391

Ile Ser Asn Arg Gly Gly Asn Thr
1               5

<210> SEQ ID NO 392
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 392

Gln Val Gln Leu Gln Glu Ser Gly Gly Gly Leu Val Gln Ala Gly Asp
1               5                   10                  15

Ser Pro Lys Leu Ser Cys Val Ala Ser Gly Arg Thr Phe Gly Asn Tyr
            20                  25                  30

Gly Leu Ala Trp Phe Arg Gln Pro Pro Gly Lys Glu Arg Glu Phe Val
        35                  40                  45

Ala Ala Ile Ser Asn Arg Gly Gly Asn Thr Tyr Tyr Ala Asp Ser Val
    50                  55                  60

Lys Gly Arg Phe Thr Ile Ser Arg Asp Asn Ala Ala Asn Thr Leu Tyr
65                  70                  75                  80

Leu Gln Met Ser Ser Leu Lys Pro Glu Asp Thr Ala Val Tyr Tyr Cys
                85                  90                  95

Ala Ala Asp Arg Thr Ser Leu His Ser Tyr Arg Tyr Thr Tyr Trp Gly
            100                 105                 110

Gln Gly Thr Gln Val Thr Val Ser Ser Ala Ala Ala Tyr Pro Tyr Asp
```

-continued

```
                115             120             125

Val Pro Asp Tyr Gly Ser His His His His His
    130             135             140

<210> SEQ ID NO 393
<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 393

Gln Val Gln Leu Gln Glu Ser Gly Gly Gly Leu Val Gln Ala Gly Gly
1               5                   10                  15

Ser Leu Arg Leu Ser Cys Ala Ala Ser Glu Arg Thr Phe Ser Thr Tyr
            20                  25                  30

Asn Met Ala Trp Phe Arg Gln Ala Pro Gly Lys Glu Arg Glu Ser Val
        35                  40                  45

Ser Arg Ile Asn Trp Asn Gly Gly Phe Thr Gly Tyr Ala Asp Ser Val
    50                  55                  60

Lys Gly Arg Phe Thr Ile Ser Arg Asp Asn Ala Lys Lys Ala Met Tyr
65                  70                  75                  80

Leu Gln Met Asn Ser Leu Lys Ser Glu Asp Thr Ala Val Tyr Tyr Cys
                85                  90                  95

Ala Ala Cys Gly Ser Ala Tyr Pro Cys Arg Pro Glu Glu Tyr Thr Tyr
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140

<210> SEQ ID NO 394
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 394

Glu Arg Thr Phe Ser Thr Tyr Asn
1               5

<210> SEQ ID NO 395
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 395

Ile Asn Trp Asn Gly Gly Phe Thr
1               5

<210> SEQ ID NO 396
<211> LENGTH: 14
<212> TYPE: PRT
<213> ORGANISM: Artificial sequence
<220> FEATURE:
<223> OTHER INFORMATION: Complementarity-determining region amino acid
      sequence
```

-continued

<400> SEQUENCE: 396

Ala Ala Cys Gly Ser Ala Tyr Pro Cys Arg Pro Glu Glu Tyr
1               5                   10

<210> SEQ ID NO 397
<211> LENGTH: 139
<212> TYPE: PRT
<213> ORGANISM: Artificial sequence
<220> FEATURE:
<223> OTHER INFORMATION: nanobody amino acid sequence

<400> SEQUENCE: 397

Gln Val Gln Leu Gln Glu Ser Gly Gly Gly Leu Val Gln Thr Gly Glu
1               5                   10                  15

Ser Leu Arg Leu Ser Cys Ala Ala Ser Gly Arg Thr Leu Ser Ser Tyr
            20                  25                  30

Thr Met Gly Trp Phe Arg Gln Ala Pro Gly Lys Glu Arg Glu Ile Val
            35                  40                  45

Ala Ala Ser Ser Trp Ser Gly Gly Arg Thr Tyr Tyr Ala Asp Ser Val
        50                  55                  60

Lys Gly Arg Phe Thr Met Ser Arg Asn Asn Ala Glu Asn Thr Val Tyr
65                  70                  75                  80

Leu Gln Met Asn Ser Leu Asn Pro Glu Asp Thr Ala Val Tyr Tyr Cys
                85                  90                  95

Ala Ala Asp Ser Ser Arg Ala Pro Arg Thr Tyr Asn Tyr Trp Gly Gln
            100                 105                 110

Gly Thr Gln Val Thr Val Ser Ser Ala Ala Ala Tyr Pro Tyr Asp Val
        115                 120                 125

Pro Asp Tyr Gly Ser His His His His His His
    130                 135

<210> SEQ ID NO 398
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 398

Gly Arg Thr Leu Ser Ser Tyr Thr
1               5

<210> SEQ ID NO 399
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 399

Ser Ser Trp Ser Gly Gly Arg Thr
1               5

<210> SEQ ID NO 400
<211> LENGTH: 13
<212> TYPE: PRT
<213> ORGANISM: Artificial sequence
<220> FEATURE:
<223> OTHER INFORMATION: Complementarity-determining region amino acid
      sequence

```
<400> SEQUENCE: 400

Ala Ala Asp Ser Ser Arg Ala Pro Arg Thr Tyr Asn Tyr
1               5                   10

<210> SEQ ID NO 401
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 401

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Asn Met Ser Trp Phe Arg Gln Gly Pro Gly Lys Glu Arg Ile Phe Val
        35                  40                  45

Ala Thr Ile Ser Trp Ser Gly Arg Val Thr Asp Tyr Ala Asp Ser Val
    50                  55                  60

Arg Gly Arg Phe Thr Ile Ser Arg Asp Asn Ala Lys Lys Met Val Tyr
65                  70                  75                  80

Leu Gln Met Asn Ser Leu Lys Pro Glu Asp Thr Ala Val Tyr Tyr Cys
                85                  90                  95

Ala Ala Asp Ser Asn Ser Arg Arg Ser Arg Asp Tyr Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140

<210> SEQ ID NO 402
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 402

Gly Arg Thr Phe Ser Thr Tyr Asn
1               5

<210> SEQ ID NO 403
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 403

Ile Ser Trp Ser Gly Arg Val Thr
1               5

<210> SEQ ID NO 404
<211> LENGTH: 14
<212> TYPE: PRT
<213> ORGANISM: Artificial sequence
<220> FEATURE:
<223> OTHER INFORMATION: Complementarity-determining region amino acid
      sequence
```

```
<400> SEQUENCE: 404

Ala Ala Asp Ser Asn Ser Arg Arg Ser Arg Asp Tyr Asp Tyr
1               5                   10

<210> SEQ ID NO 405
<211> LENGTH: 134
<212> TYPE: PRT
<213> ORGANISM: Artificial sequence
<220> FEATURE:
<223> OTHER INFORMATION: nanobody amino acid sequence

<400> SEQUENCE: 405

Gln Val Gln Leu Gln Glu Ser Gly Gly Gly Leu Val Gln Pro Gly Gly
1               5                   10                  15

Ser Leu Arg Leu Ser Cys Ala Ala Ser Gly Thr Thr Arg Arg Ile Asn
            20                  25                  30

Ser Met Arg Trp Tyr Arg Gln Thr Pro Gly Asn Glu Arg Asp Leu Val
        35                  40                  45

Ala Gly Ile Thr Glu Gly Gly Phe Thr Ala Tyr Val Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Ala Tyr Leu Gly Ala Ala Tyr Trp Gly Gln Gly Thr Gln Val Thr
            100                 105                 110

Val Ser Ser Ala Ala Ala Tyr Pro Tyr Asp Val Pro Asp Tyr Gly Ser
        115                 120                 125

His His His His His His
    130

<210> SEQ ID NO 406
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 406

Gly Thr Thr Arg Arg Ile Asn Ser
1               5

<210> SEQ ID NO 407
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 407

Ile Thr Glu Gly Gly Phe Thr
1               5

<210> SEQ ID NO 408
<211> LENGTH: 6
<212> TYPE: PRT
<213> ORGANISM: Artificial sequence
<220> FEATURE:
<223> OTHER INFORMATION: Complementarity-determining region amino acid
      sequence
```

-continued

```
<400> SEQUENCE: 408

Tyr Leu Gly Ala Ala Tyr
1               5

<210> SEQ ID NO 409
<211> LENGTH: 133
<212> TYPE: PRT
<213> ORGANISM: Artificial sequence
<220> FEATURE:
<223> OTHER INFORMATION: type 2 chitin-binding domain (ChtBD2)
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (43)..(47)
<223> OTHER INFORMATION: Xaa can be any naturally occurring amino acid
<220> FEATURE:
<221> NAME/KEY: misc_feature
<222> LOCATION: (54)..(62)
<223> OTHER INFORMATION: Xaa can be any naturally occurring amino acid
<220> FEATURE:
<221> NAME/KEY: misc_feature
<222> LOCATION: (87)..(98)
<223> OTHER INFORMATION: Xaa can be any naturally occurring amino acid
<220> FEATURE:
<221> NAME/KEY: misc_feature
<222> LOCATION: (116)..(121)
<223> OTHER INFORMATION: Xaa can be any naturally occurring amino acid

<400> SEQUENCE: 409

Cys Xaa Xaa Xaa Xaa Xaa Xaa Xaa Xaa Xaa Xaa Xaa Cys Cys Cys Cys
1               5                   10                  15

Cys Cys Cys Cys Cys Cys Cys Cys Cys Cys Cys Cys Cys Cys Cys Cys
                20                  25                  30

Cys Cys Cys Cys Cys Cys Cys Cys Cys Cys Xaa Xaa Xaa Xaa Xaa Cys
            35                  40                  45

Cys Cys Cys Cys Cys Xaa Xaa Xaa Xaa Xaa Xaa Xaa Xaa Xaa Cys Cys
    50                  55                  60

Cys Cys Cys Cys Cys Cys Cys Cys Cys Cys Cys Cys Cys Cys Cys Cys
65                  70                  75                  80

Cys Cys Cys Cys Cys Cys Xaa Xaa Xaa Xaa Xaa Xaa Xaa Xaa Xaa Xaa
                85                  90                  95

Xaa Xaa Cys Cys Cys Cys Cys Cys Cys Cys Cys Cys Cys Cys Cys Cys
            100                 105                 110

Cys Cys Cys Xaa Xaa Xaa Xaa Xaa Xaa Cys Cys Cys Cys Cys Cys Cys
        115                 120                 125

Cys Cys Cys Cys Cys
        130

<210> SEQ ID NO 410
<211> LENGTH: 1137
<212> TYPE: PRT
<213> ORGANISM: Artificial sequence
<220> FEATURE:
<223> OTHER INFORMATION: type 2 chitin-binding domain (ChtBD2)

<400> SEQUENCE: 410

Met Lys Asp Ala Val Ile Leu Leu Leu Cys Ala Ile Ala Leu Ala Asp
1               5                   10                  15

Gly Phe Asn His Glu Leu Leu Ser Asn Ser Arg Ser Cys Asn Cys Asn
                20                  25                  30

Pro Ser Glu Ala Gln Gln Ile Cys Glu Ala Asn Tyr Gly Lys Asp Asp
```

-continued

```
              35                    40                    45

Val Leu Ile Ala His Glu Asn Cys Asp Lys Phe Tyr Lys Cys Ala Asn
        50                    55                    60

Gly Lys Pro Phe Pro Tyr Lys Cys Pro Asn Asn Leu Leu Tyr Asp Pro
    65                    70                    75                    80

Tyr Lys Glu Glu Cys Glu Trp Pro Trp Leu Val Asp Cys Gly Asp Arg
                      85                    90                    95

Pro Ile Ser Glu Gly Ser Asp Gln Glu Asp Gly Gly Val Asp Asn Asp
                     100                   105                   110

Asn Asn Asp Ser Asn Asp Asn Asn Gly Val Asp Asp Gly Trp Thr Cys
                     115                   120                   125

Asn Cys Asn Pro Ser Glu Ala Pro Ser Ile Cys Ala Ala Glu Gly Ser
        130                   135                   140

Ser Gly Val Leu Val Ala His Glu Asn Cys Asp Gln Phe Tyr Met Cys
    145                   150                   155                   160

Asp Ala Gly Arg Pro Val Thr Phe Asp Cys Pro Pro Thr Leu Met Tyr
                     165                   170                   175

Asp Pro His Arg Glu Glu Cys Tyr Trp Pro His Glu Val Asp Cys Gly
                     180                   185                   190

Asp Arg Gly Ile Ser Glu Pro Gly Asn Asp Gln Gly Asn Asp Asn Asp
                     195                   200                   205

Gly Asn Asp Asn Asn Ser Ser Asn Glu Gln Gly Gly Val Cys Asn Cys
        210                   215                   220

Asn Pro Glu Glu Ala Pro Ala Ile Cys Ala Ser Pro Gly Ser Glu Gly
    225                   230                   235                   240

Val Leu Val Ala His Glu Asn Cys Glu Lys Tyr Tyr Ile Cys Asn His
                     245                   250                   255

Gly Arg Pro Val Val Ala Ser Cys Ser Gly Asn Leu Leu Phe Asn Pro
                     260                   265                   270

Tyr Thr Asn Glu Cys Gly Trp Pro Arg Asp Val Asp Cys Gly Asp Arg
                     275                   280                   285

Ile Glu Pro Gly Cys Thr Gly Cys Asn Asp Asn Asn Asn Asn Asp Asp
        290                   295                   300

Asn Asp Ser Asp Cys Asp Gly Asp Asp Pro Val Pro Pro Ala Asp
    305                   310                   315                   320

Asn Asp Asp Ser Glu Ser Ala Asp Ile Asp Asp Leu Pro Pro Pro Gly
                     325                   330                   335

Asp Asp Ala Ser Val Arg Pro Pro Val Asp Glu Gly Thr Cys Asn Cys
                     340                   345                   350

Asn Pro Glu Gln Ala Pro Ser Ile Cys Ala Glu Asp Asp Ser Asp Gly
                     355                   360                   365

Val Leu Val Ala His Glu Asp Cys Asn Lys Phe Tyr Lys Cys His Asn
        370                   375                   380

Gly Lys Pro Val Ala Leu Tyr Cys Pro Gly Asn Leu Leu Tyr Asn Pro
    385                   390                   395                   400

Asn Thr Glu Gln Cys Asp Trp Pro Glu Lys Val Asp Cys Gly Asp Arg
                     405                   410                   415

Val Ile Pro Asp Pro Glu Asp Asn Asn Asn Asn Asp Ser Ser Gly Gly
                     420                   425                   430

Asn Asn Asp Gly Gly Asn Asp Gly Gly Asn Gly Gly Gly Gly Asn Cys
        435                   440                   445

Asp Pro Ser Glu Ala Pro Ala Ile Cys Ala Glu Asp Asp Ser Glu Gly
    450                   455                   460
```

```
Val Leu Val Ala His Glu Asn Cys Asn Gln Phe Tyr Lys Cys Ser Gly
465             470             475             480

Gly Lys Pro Val Ala Leu Leu Cys Pro Gly Asn Leu Leu Phe Asn Pro
                485             490             495

Asn Thr Asp Gln Cys Asp Trp Pro Trp Glu Val Asp Cys Gly Asp Arg
            500             505             510

Ile Ile Pro Asp Pro Asp Gln Lys Pro Asp Pro Glu Asp Ser Ser Asp
            515             520             525

Asp Ser Ser Ala Asp Ile Asp Asp Leu Pro Pro Pro Gly Asp Asp Val
            530             535             540

Thr Thr Arg Pro Pro Gly Thr Cys Asn Cys Asn Pro Glu Glu Ala Pro
545             550             555             560

Ser Ile Cys Ala Gln Asp Gly Ser Asn Gly Thr Leu Ile Ala His Glu
                565             570             575

Asp Cys Asn Lys Phe Tyr Ile Cys Asp His Gly Lys Pro Val Ala Leu
                580             585             590

Ser Cys Pro Gly Asn Leu Leu Tyr Asn Pro Tyr Thr Glu Lys Cys Asp
                595             600             605

Trp Pro Glu Asn Val Glu Cys Gly Asp Ser Asp Gly Ile Leu Ile Ala
            610             615             620

His Glu Asp Cys Asn Lys Phe Tyr Ile Cys Asp His Gly Lys Pro Val
625             630             635             640

Val Leu Ser Cys Pro Gly Asn Leu Phe Tyr Asn Pro Tyr Thr Glu Gln
                645             650             655

Cys Asp Trp Pro Val Asn Val Glu Cys Gly Asp Arg Val Thr Pro Asp
                660             665             670

Pro Asp Ala Thr Pro Ala Pro Thr Ala Ala Pro Thr Ser Thr Thr Thr
            675             680             685

Val Ala Pro Thr Ala Ala Pro Ser Thr Thr Thr Thr Val Ala Pro Thr
            690             695             700

Ala Ala Pro Thr Thr Thr Thr Thr Val Ala Pro Thr Thr Thr Thr Thr
705             710             715             720

Val Ala Pro Thr Thr Thr Thr Thr Val Ala Pro Thr Ala Ala Pro Thr
                725             730             735

Thr Thr Thr Thr Val Ala Pro Thr Ala Ala Pro Thr Thr Thr Thr Thr
            740             745             750

Val Ala Pro Thr Ala Ala Pro Thr Thr Thr Thr Thr Val Ala Ser Thr
            755             760             765

Ala Ala Pro Thr Ala Ala Pro Thr Ala Ala Pro Thr Ala Ala Ser Thr
            770             775             780

Pro Asp Asp Ser Asp Cys Asp Asp Asp Asn Asn Gly Gly Asp Asp Thr
785             790             795             800

Cys Asn Cys Asn Pro Asp Glu Ala Ala Ser Ile Cys Ser Val Gly Asn
                805             810             815

Ser Asp Gly Ile His Val Ala His Glu Asn Cys Asn Trp Phe Tyr Lys
            820             825             830

Cys Asp Asn Gly Arg Pro Val Pro Phe Arg Cys Pro Ser Gly Leu Met
            835             840             845

Tyr Asn Pro Tyr Thr Gln Ile Cys Asp Trp Pro Trp Asp Val Glu Cys
            850             855             860

Gly Asp Arg Val Ile Ala Asp Asp Asp Ser Ser Glu Glu Asp Asn
865             870             875             880
```

```
Asp Asn Asp Asn Asp Ser Gly Val Val Gly Pro Cys Asn Cys Asn Pro
            885                     890                 895

Glu Glu Ala Pro Ala Ile Cys Ala Ala Glu Gly Ser Asn Gly Val His
            900                 905                 910

Val Ala His Gln Asn Cys Asn Gln Tyr Tyr Met Cys Asp Asn Gly Arg
            915                 920                 925

Pro Val Ala Phe Thr Cys Asn Gly Phe Leu Leu Tyr Asn Pro Tyr Thr
    930                 935                 940

Gln Gln Cys Asp Trp Pro His Leu Val Glu Cys Gly Asp Arg Val Ile
945                 950                 955                 960

Pro Glu Pro Gly Asp Glu Asp Glu Asp Cys Asp Asp Asp Asp
            965                 970                 975

Asn Ser Asn Asn Val Ile Asn Asp Asp Pro Ser Gln Ala Pro Ala Ile
            980                 985                 990

Cys Ala Asp Ser Gly Ser Glu Gly Val Leu Val Ala His Glu Asn Cys
            995             1000                1005

Asp Gln  Tyr Tyr Ile Cys Asp  Gly Gly Arg Pro Val  Ala Arg Pro
    1010                1015                1020

Cys Gln  Gly Gly Leu Leu Tyr  Asn Pro Leu Thr Gln  Tyr Cys Asp
    1025                1030                1035

Trp Pro  Gly Asn Val Asn Cys  Gly Asp Arg Ile Ile  Pro Asp Asp
    1040                1045                1050

Cys Ala  Cys Asn Pro Arg Asn  Ala Pro Arg Leu Cys  Ser Lys Pro
    1055                1060                1065

Asp Ser  Glu Gly Ser Leu Val  Ala His Glu Asn Cys  Asn Gln Phe
    1070                1075                1080

Tyr Ile  Cys Ala His Ser Val  Pro Val Glu His Phe  Cys Pro Val
    1085                1090                1095

Gly Leu  Tyr Tyr Asn Ile Glu  Leu Glu Leu Cys Asp  Trp Ala Gln
    1100                1105                1110

Asn Val  Asn Cys Glu Asn Arg  Asn Leu Pro Ser Leu  Asn Lys His
    1115                1120                1125

Trp Glu  Ser Arg Gln Thr Leu  Arg Lys
    1130                1135

<210> SEQ ID NO 411
<211> LENGTH: 134
<212> TYPE: PRT
<213> ORGANISM: Artificial sequence
<220> FEATURE:
<223> OTHER INFORMATION: nanobody amino acid sequence

<400> SEQUENCE: 411

Gln Val Gln Leu Gln Glu Ser Gly Gly Gly Leu Val Gln Ala Gly Gly
1               5                   10                  15

Ser Leu Arg Leu Ser Cys Ser Ala Ser Thr Ser Ile Ala Ser Ile Asn
            20                  25                  30

Ala Val Gly Trp Tyr Arg Gln Ala Pro Gly Lys Gln Arg Glu Leu Val
            35                  40                  45

Ala Val Ile Val Asn Gly Ser Thr Thr Arg Tyr Ala Asp Ser Val Lys
    50                  55                  60

Gly Arg Phe Thr Ile Ser Gly Asp Asn Ala Glu Asn Thr Val Pro Leu
65                  70                  75                  80

Leu Met Ser Ser Leu Lys Pro Glu Asp Thr Ala Ile Tyr Tyr Cys Gly
                85                  90                  95
```

Ala Arg Asp Leu Ser Gly Thr Tyr Trp Gly Gln Gly Thr Gln Val Thr
            100                 105                 110

Val Ser Ser Ala Ala Ala Tyr Pro Tyr Asp Val Pro Asp Tyr Gly Ser
        115                 120                 125

His His His His His His
    130

<210> SEQ ID NO 412
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 412

Thr Ser Ile Ala Ser Ile Asn Ala
1               5

<210> SEQ ID NO 413
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 413

Ile Val Asn Gly Ser Thr Thr
1               5

<210> SEQ ID NO 414
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 414

Gly Ala Arg Asp Leu Ser Gly Thr Tyr
1               5

<210> SEQ ID NO 415
<211> LENGTH: 134
<212> TYPE: PRT
<213> ORGANISM: Artificial sequence
<220> FEATURE:
<223> OTHER INFORMATION: nanobody amino acid sequence

<400> SEQUENCE: 415

Gln Val Gln Leu Gln Glu Ser Gly Gly Gly Leu Val Gln Pro Gly Gly
1               5                   10                  15

Ser Leu Arg Leu Ser Cys Ser Ala Ser Thr Ser Ile Ala Ser Ile Asn
            20                  25                  30

Ala Val Gly Trp Tyr Arg Gln Ala Pro Gly Lys Gln Arg Glu Leu Val
            35                  40                  45

Ala Val Ile Val Asn Gly Ser Thr Thr Arg Tyr Ala Asp Ser Val Lys
        50                  55                  60

Gly Arg Phe Thr Ile Ser Gly Asp Asn Ala Lys Asn Thr Val Pro Leu
65                  70                  75                  80

Gln Met Ser Ser Leu Lys Pro Glu Asp Thr Ala Ile Tyr Tyr Cys Gly
                85                  90                  95

-continued

```
Ala Arg Asp Leu Ser Gly Thr Tyr Trp Gly Gln Gly Thr Gln Val Thr
            100                 105                 110

Val Ser Ser Ala Ala Ala Tyr Pro Tyr Asp Val Pro Asp Tyr Gly Ser
        115                 120                 125

His His His His His His
    130

<210> SEQ ID NO 416
<211> LENGTH: 134
<212> TYPE: PRT
<213> ORGANISM: Artificial sequence
<220> FEATURE:
<223> OTHER INFORMATION: nanobody amino acid sequence

<400> SEQUENCE: 416

Gln Val Gln Leu Gln Glu Ser Gly Gly Gly Leu Val Gln Ala Gly Gly
1               5                   10                  15

Ser Leu Arg Leu Ser Cys Ser Ala Ser Thr Ser Ile Ala Ser Ile Asn
            20                  25                  30

Ala Val Gly Trp Tyr Arg Gln Ala Pro Gly Lys Gln Arg Glu Leu Val
        35                  40                  45

Ala Val Ile Val Asn Gly Ser Thr Thr Arg Tyr Ala Asp Ser Val Lys
    50                  55                  60

Gly Arg Phe Thr Ile Ser Gly Asp Asn Ala Lys Asn Thr Val Pro Leu
65                  70                  75                  80

Gln Met Ser Ser Leu Lys Pro Glu Asp Thr Ala Ile Tyr Tyr Cys Gly
                85                  90                  95

Ala Arg Asp Leu Ser Gly Thr Tyr Trp Gly Gln Gly Thr Gln Val Thr
            100                 105                 110

Val Ser Ser Ala Ala Ala Tyr Pro Tyr Asp Val Pro Asp Tyr Gly Ser
        115                 120                 125

His His His His His His
    130

<210> SEQ ID NO 417
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 417

Gln Val Gln Leu Gln Glu Ser Gly Gly Gly Leu Val Gln Ala Gly Gly
1               5                   10                  15

Ser Leu Arg Leu Ser Cys Ala Ala Ser Arg Gly Thr Phe Ser Arg Tyr
            20                  25                  30

Val Met Gly Trp Phe Arg Gln Gly Pro Gly Lys Glu Arg Glu Phe Val
        35                  40                  45

Ala Gly Ile Ser Trp Ser Gly Ile Ser Thr Tyr Tyr Ala Asp Phe Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Gly Arg Gly Tyr Asp Tyr Trp Gly Gln Gly Thr Gln
            100                 105                 110

Val Thr Val Ser Ser Ala Ala Ala Tyr Pro Tyr Asp Val Pro Asp Tyr
        115                 120                 125
```

```
Gly Ser His His His His His His
    130                 135

<210> SEQ ID NO 418
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 418

Arg Gly Thr Phe Ser Arg Tyr Val
1               5

<210> SEQ ID NO 419
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 419

Ile Ser Trp Ser Gly Ile Ser Thr
1               5

<210> SEQ ID NO 420
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 420

Ala Ala Asp Pro Gly Arg Gly Tyr Asp Tyr
1               5                   10

<210> SEQ ID NO 421
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 421

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ser Phe Ser Arg Ser
            20                  25                  30

Val Met Gly Trp Phe Arg Gln Ala Pro Gly Lys Glu Arg Glu Phe Val
            35                  40                  45

Ala Ala Thr Ser Trp Ser Gly Gly Thr Tyr Tyr Ala Asp Ser Val
    50                  55                  60

Lys Gly Arg Phe Thr Ile Ser Arg Asp Asn Ala Gln Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Val Gly Arg Gly Tyr His Tyr Trp Gly Gln Gly Thr Gln
            100                 105                 110

Val Thr Val Ser Ser Ala Ala Ala Tyr Pro Tyr Asp Val Pro Asp Tyr
            115                 120                 125
```

-continued

```
Gly Ser His His His His His His
    130                 135

<210> SEQ ID NO 422
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 422

Gly Arg Ser Phe Ser Arg Ser Val
1               5

<210> SEQ ID NO 423
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 423

Thr Ser Trp Ser Gly Gly Gly Thr
1               5

<210> SEQ ID NO 424
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 424

Ala Ala Asp Val Gly Arg Gly Tyr His Tyr
1               5               10

<210> SEQ ID NO 425
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 425

Gln Val Gln Leu Gln Glu Ser Gly Gly Gly Leu Val Gln Ala Gly Gly
1               5                   10                  15

Ser Leu Arg Leu Ser Cys Val Ala Ser Gly Gly Thr Phe Ser Gly Leu
            20                  25                  30

Thr Met Gly Trp Phe Arg Gln Ala Pro Gln Lys Glu Arg Glu Phe Val
            35                  40                  45

Ala Ala Ile Ser Trp Thr Gly Arg Ser Thr Tyr Tyr Ala Asp Ser Val
    50                  55                  60

Lys Gly Arg Phe Thr Ile Ser Arg Asp Asn Val Lys Asn Met Val Tyr
65                  70                  75                  80

Leu Gln Met Asn Ser Leu Lys Pro Glu Asp Thr Gly Val Tyr Phe Cys
                85                  90                  95

Ala Ala Asp Trp Ala Ser Gly Thr Pro Tyr Trp Gly Gln Gly Thr Gln
            100                 105                 110

Val Thr Val Ser Ser Ala Ala Ala Tyr Pro Tyr Asp Val Pro Asp Tyr
            115                 120                 125
```

```
Gly Ser His His His His His His
    130                 135

<210> SEQ ID NO 426
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 426

Gly Gly Thr Phe Ser Gly Leu Thr
1               5

<210> SEQ ID NO 427
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 427

Ile Ser Trp Thr Gly Arg Ser Thr
1               5

<210> SEQ ID NO 428
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 428

Ala Ala Asp Trp Ala Ser Gly Thr Pro Tyr
1               5                   10

<210> SEQ ID NO 429
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 429

Gln Val Gln Leu Gln Glu Ser Gly Gly Gly Leu Val Gln Ala Gly Thr
1               5                   10                  15

Ser Leu Arg Leu Ser Cys Ala Ala Ser Gly Gly Thr Phe Ser Gly Leu
            20                  25                  30

Thr Met Gly Trp Phe Arg Gln Ala Pro Gln Lys Glu Arg Glu Phe Val
        35                  40                  45

Ala Ala Ile Ser Trp Thr Gly Arg Ser Thr Tyr Tyr Ala Asp Ser Val
    50                  55                  60

Lys Gly Arg Phe Thr Ile Ser Arg Asp Asn Val Lys Asn Met Val Tyr
65                  70                  75                  80

Leu Gln Met Val Ala Leu Asn Pro Glu Asp Thr Ala Val Tyr Tyr Cys
                85                  90                  95

Ala Ala Asp Trp Ala Ser Ala Thr Pro Tyr Trp Gly Gln Gly Thr Gln
            100                 105                 110

Val Thr Val Ser Ser Ala Ala Ala Tyr Pro Tyr Asp Val Pro Asp Tyr
            115                 120                 125
```

-continued

```
Gly Ser His His His His His His
    130                 135

<210> SEQ ID NO 430
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 430

Ala Ala Asp Trp Ala Ser Ala Thr Pro Tyr
1               5                   10

<210> SEQ ID NO 431
<211> LENGTH: 149
<212> TYPE: PRT
<213> ORGANISM: Artificial sequence
<220> FEATURE:
<223> OTHER INFORMATION: nanobody amino acid sequence

<400> SEQUENCE: 431

Gln Val Gln Leu Gln Glu Ser Gly Gly Gly Leu Val Gln Ser Gly Glu
1               5                   10                  15

Ser Leu Thr Leu Ala Cys Val Ile Ser Gly Ile Thr Leu Glu Arg Tyr
            20                  25                  30

Thr Val Gly Trp Phe His Gln Ala Pro Gly Lys Asn Pro Glu Gly Val
        35                  40                  45

Ser Cys Ile Gly Lys Ser Asn Asp Glu Thr Phe Tyr Thr Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Thr Pro Ser Asp Ala Gly Val Tyr Tyr Cys
                85                  90                  95

Ala Ala Ala Lys Ala Pro Val Thr Ala Tyr Asp Cys Ser Leu Tyr Leu
                100                 105                 110

Tyr Thr Trp Arg Ser Thr Tyr Arg Gly Gln Gly Thr Gln Val Thr Val
                115                 120                 125

Ser Ser Ala Ala Ala Tyr Pro Tyr Asp Val Pro Asp Tyr Gly Ser His
    130                 135                 140

His His His His His
145

<210> SEQ ID NO 432
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 432

Gly Ile Thr Leu Glu Arg Tyr Thr
1               5

<210> SEQ ID NO 433
<211> LENGTH: 8
<212> TYPE: PRT
<213> ORGANISM: Artificial sequence
<220> FEATURE:
<223> OTHER INFORMATION: Complementarity-determining region amino acid
``` sequence

<400> SEQUENCE: 433

Ile Gly Lys Ser Asn Asp Glu Thr
1               5

<210> SEQ ID NO 434
<211> LENGTH: 23
<212> TYPE: PRT
<213> ORGANISM: Artificial sequence
<220> FEATURE:
<223> OTHER INFORMATION: Complementarity-determining region amino acid
      sequence

<400> SEQUENCE: 434

Ala Ala Ala Lys Ala Pro Val Thr Ala Tyr Asp Cys Ser Leu Tyr Leu
1               5                   10                  15

Tyr Thr Trp Arg Ser Thr Tyr
            20

<210> SEQ ID NO 435
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 435

Gln Val Gln Leu Gln Glu Ser Gly Gly Gly Leu Val Gln Ala Gly Gly
1               5                   10                  15

Ser Leu Thr Leu Ser Cys Ala Ala Ser Ala Arg Thr Phe Ser Thr Tyr
            20                  25                  30

Ala Leu Ala Trp Phe Arg Gln Thr Pro Gly Lys Gly Arg Glu Phe Val
        35                  40                  45

Gly Ala Ile Ser Arg Ser Gly Ser Ser Thr Arg Tyr Ala Asp Ser Val
    50                  55                  60

Lys Gly Arg Phe Ala Ile Ser Arg Asp Asn Ala Gln Arg Ala Ile Tyr
65                  70                  75                  80

Leu Gln Met Asn Ser Leu Lys Pro Glu Asp Thr Ala Val Tyr Tyr Cys
                85                  90                  95

Ala Ala Gly Ser Arg Ser Tyr Tyr Asn Ile Pro Tyr Tyr Asp Tyr Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 436
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 436

Ala Arg Thr Phe Ser Thr Tyr Ala
1               5

<210> SEQ ID NO 437
<211> LENGTH: 15
<212> TYPE: PRT

<213> ORGANISM: Artificial sequence
<220> FEATURE:
<223> OTHER INFORMATION: Complementarity-determining region amino acid
      sequence

<400> SEQUENCE: 437

Ala Ala Gly Ser Arg Ser Tyr Tyr Asn Ile Pro Tyr Tyr Asp Tyr
1               5                   10                  15

<210> SEQ ID NO 438
<211> LENGTH: 147
<212> TYPE: PRT
<213> ORGANISM: Artificial sequence
<220> FEATURE:
<223> OTHER INFORMATION: nanobody amino acid sequence

<400> SEQUENCE: 438

Gln Val Gln Leu Gln Glu Ser Gly Gly Gly Leu Val Gln Ala Gly Ala
1               5                   10                  15

Ser Leu Arg Leu Ser Cys Ala Ala Ser Val Arg Thr Phe Ser Ser Tyr
            20                  25                  30

Ala Val Gly Trp Phe Arg Gln Ala Pro Gly Lys Glu Arg Glu Phe Val
        35                  40                  45

Ala Gly Ile Thr Trp Ser Gly Gly Ser Lys Tyr Tyr Arg Asp Ala Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Val Tyr Ser Cys
                85                  90                  95

Ala Ala Thr Ser Ala Arg Tyr Thr Ser Gly Ala Leu Tyr Tyr Arg Asp
            100                 105                 110

Arg Gln Tyr Asn Tyr Trp Gly Gln Gly Thr Gln Val Thr Val Ser Ser
            115                 120                 125

Ala Ala Ala Tyr Pro Tyr Asp Val Pro Asp Tyr Gly Ser His His His
    130                 135                 140

His His His
145

<210> SEQ ID NO 439
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 439

Val Arg Thr Phe Ser Ser Tyr Ala
1               5

<210> SEQ ID NO 440
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 440

Ile Thr Trp Ser Gly Gly Ser Lys
1               5

```
<210> SEQ ID NO 441
<211> LENGTH: 21
<212> TYPE: PRT
<213> ORGANISM: Artificial sequence
<220> FEATURE:
<223> OTHER INFORMATION: Complementarity-determining region amino acid
      sequence

<400> SEQUENCE: 441

Ala Ala Thr Ser Ala Arg Tyr Thr Ser Gly Ala Leu Tyr Tyr Arg Asp
1               5                   10                  15

Arg Gln Tyr Asn Tyr
            20

<210> SEQ ID NO 442
<211> LENGTH: 145
<212> TYPE: PRT
<213> ORGANISM: Artificial sequence
<220> FEATURE:
<223> OTHER INFORMATION: nanobody amino acid sequence

<400> SEQUENCE: 442

Gln Val Gln Leu Gln Glu Ser Gly Gly Gly Leu Val Gln Ala Gly Gly
1               5                   10                  15

Ser Leu Arg Leu Ser Cys Ala Ala Ser Thr Arg Thr Phe Gly Asn Tyr
            20                  25                  30

Ala Met Gly Trp Phe Arg Gln Ala Pro Gly Lys Glu Arg Glu Phe Val
        35                  40                  45

Ala Ala Ile Asn Arg Arg Gly Thr Thr Thr Tyr Tyr Ala Asp Ser Val
    50                  55                  60

Lys Asp Arg Phe Thr Ile Ser Thr Asp Tyr Ala Lys Asn Thr Val Tyr
65                  70                  75                  80

Leu Glu Met Ile Ser Leu Lys Pro Glu Asp Thr Ala Val Tyr Tyr Cys
                85                  90                  95

Ala Val Asp Arg Ser Thr Gly Trp Gln Pro Ser Thr Ser Arg Tyr Asp
                100                 105                 110

Tyr Ala Ser Trp Gly Gln Gly Thr Gln Val Thr Val Ser Ser Ala Ala
        115                 120                 125

Ala Tyr Pro Tyr Asp Val Pro Asp Tyr Gly Ser His His His His His
    130                 135                 140

His
145

<210> SEQ ID NO 443
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 443

Thr Arg Thr Phe Gly Asn Tyr Ala
1               5

<210> SEQ ID NO 444
<211> LENGTH: 8
<212> TYPE: PRT
<213> ORGANISM: Artificial sequence
<220> FEATURE:
<223> OTHER INFORMATION: Complementarity-determining region amino acid
      sequence
```

-continued

<400> SEQUENCE: 444

Ile Asn Arg Arg Gly Thr Thr Thr
1               5

<210> SEQ ID NO 445
<211> LENGTH: 19
<212> TYPE: PRT
<213> ORGANISM: Artificial sequence
<220> FEATURE:
<223> OTHER INFORMATION: Complementarity-determining region amino acid
      sequence

<400> SEQUENCE: 445

Ala Val Asp Arg Ser Thr Gly Trp Gln Pro Ser Thr Ser Arg Tyr Asp
1               5                   10                  15

Tyr Ala Ser

<210> SEQ ID NO 446
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 446

Gln Val Gln Leu Gln Glu Ser Gly Gly Gly Leu Val Gln Ala Gly Ser
1               5                   10                  15

Ser Leu Arg Leu Ser Cys Ala Ala Ser Gly Arg Thr Phe Arg Tyr His
            20                  25                  30

Ala Met Gly Trp Phe Arg Gln Ala Pro Gly Lys Glu Arg Glu Phe Val
            35                  40                  45

Ala Gly Ile Ser Thr Ser Gly Gly Met Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Gly Asp Thr Ala Val Tyr Tyr Cys
                85                  90                  95

Ala Lys Phe His Gly Asp Lys Gly Tyr Gly Ser Ser Trp Tyr Tyr Asp
                100                 105                 110

Tyr Trp Gly Gln Gly Thr Gln Val Thr Val Ser Ser Ala Ala Ala Tyr
            115                 120                 125

Pro Tyr Asp Val Pro Asp Tyr Gly Ser His His His His His
        130                 135                 140

<210> SEQ ID NO 447
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 447

Gly Arg Thr Phe Arg Tyr His Ala
1               5

<210> SEQ ID NO 448
<211> LENGTH: 8
<212> TYPE: PRT
<213> ORGANISM: Artificial sequence
<220> FEATURE:
<223> OTHER INFORMATION: Complementarity-determining region amino acid -continued

```
    sequence

<400> SEQUENCE: 448

Ile Ser Thr Ser Gly Gly Met Thr
1               5

<210> SEQ ID NO 449
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 449

Ala Lys Phe His Gly Asp Lys Gly Tyr Gly Ser Ser Trp Tyr Tyr Asp
1               5                   10                  15

Tyr

<210> SEQ ID NO 450
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 450

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Arg Ile
        35                  40                  45

Ser Ile Ile Asn Ser Gly Gly Gly Ser Thr Ser Tyr Ala Asp Ser Val
    50                  55                  60

Lys Gly Arg Phe Thr Val Ser Arg Asp Asn Asn Lys Asn Thr Leu Tyr
65                  70                  75                  80

Leu Gln Met Asn Ser Leu Gln Pro Glu Asp Thr Ala Val Tyr Tyr Cys
                85                  90                  95

Gly Val Arg Arg Asn Trp Gly Leu Gly Thr His Ser Gly Glu Tyr Val
            100                 105                 110

Tyr Trp Gly Arg Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 451
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 451

Ile Asn Ser Gly Gly Gly Ser Thr
1               5

<210> SEQ ID NO 452
<211> LENGTH: 17
<212> TYPE: PRT
<213> ORGANISM: Artificial sequence
```

<220> FEATURE:
<223> OTHER INFORMATION: Complementarity-determining region amino acid
      sequence

<400> SEQUENCE: 452

Gly Val Arg Arg Asn Trp Gly Leu Gly Thr His Ser Gly Glu Tyr Val
1               5                   10                  15

Tyr

<210> SEQ ID NO 453
<211> LENGTH: 139
<212> TYPE: PRT
<213> ORGANISM: Artificial sequence
<220> FEATURE:
<223> OTHER INFORMATION: nanobody amino acid sequence

<400> SEQUENCE: 453

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Val Arg Glu Gly Val
        35                  40                  45

Ser Thr Ile Lys Ser Ser Asp Gly Ser Thr Tyr Tyr Ala Asp Ser Val
    50                  55                  60

Lys Gly Arg Phe Thr Ile Ser Leu Asp Asn Ala Lys Arg Thr Val Ser
65                  70                  75                  80

Leu Gln Met Asn Asn Leu Lys Pro Glu Asp Thr Ala Val Tyr Tyr Cys
                85                  90                  95

Ala Ala Gly Ala Arg Arg Trp Pro Tyr Asp Tyr Ile Tyr Trp Gly Arg
            100                 105                 110

Gly Thr Gln Val Thr Val Ser Ser Ala Ala Ala Tyr Pro Tyr Asp Val
        115                 120                 125

Pro Asp Tyr Gly Ser His His His His His His
    130                 135

<210> SEQ ID NO 454
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 454

Gly Phe Thr Phe Asp Asp Tyr Ala
1               5

<210> SEQ ID NO 455
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 455

Ile Lys Ser Ser Asp Gly Ser Thr
1               5

<210> SEQ ID NO 456
<211> LENGTH: 13

-continued

```
<212> TYPE: PRT
<213> ORGANISM: Artificial sequence
<220> FEATURE:
<223> OTHER INFORMATION: Complementarity-determining region amino acid
      sequence

<400> SEQUENCE: 456

Ala Ala Gly Ala Arg Arg Trp Pro Tyr Asp Tyr Ile Tyr
1               5                   10

<210> SEQ ID NO 457
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 457

Gln Val Gln Leu Gln Glu Ser Gly Gly Gly Val Val Gln Ala Gly Ala
1               5                   10                  15

Ser Leu Arg Leu Ser Cys Ala Ala Ser Glu Arg Ile Phe Leu Asn Tyr
            20                  25                  30

Asn Met Ala Trp Val Arg Gln Ala Pro Gly Lys Glu Arg Glu Phe Val
        35                  40                  45

Ala Ala Ile Thr Trp Ser Gly Ser Asn Ile Asp Tyr Ala Asp Thr Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Asp Pro Ser Tyr Trp Lys Ile Arg Thr Thr Leu Asn Gly Leu
            100                 105                 110

Asp Lys Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140

<210> SEQ ID NO 458
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 458

Glu Arg Ile Phe Leu Asn Tyr Asn
1               5

<210> SEQ ID NO 459
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 459

Ile Thr Trp Ser Gly Ser Asn Ile
1               5

<210> SEQ ID NO 460
<211> LENGTH: 18
```

<212> TYPE: PRT
<213> ORGANISM: Artificial sequence
<220> FEATURE:
<223> OTHER INFORMATION: Complementarity-determining region amino acid
      sequence

<400> SEQUENCE: 460

Ala Ala Asp Pro Ser Tyr Trp Lys Ile Arg Thr Thr Leu Asn Gly Leu
1               5                   10                  15

Asp Lys

<210> SEQ ID NO 461
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 461

Gln Val Gln Leu Gln Glu Ser Gly Gly Gly Phe Val Gln Ala Gly Asp
1               5                   10                  15

Ser Leu Arg Leu Ser Cys Ala Ala Ser Gly Arg Thr Phe Ser Arg Phe
            20                  25                  30

Pro Met Gly Trp Phe Arg Gln Ala Pro Gly Lys Glu Arg Glu Phe Val
            35                  40                  45

Ala Ala Ile Ser Trp Ser Gly Gly Ser Thr Leu Ile Thr Asp Ser Val
        50                  55                  60

Lys Asp Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Arg Arg Asp Ser Thr Thr Ser Tyr Val Thr Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 462
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 462

Gly Arg Thr Phe Ser Arg Phe Pro
1               5

<210> SEQ ID NO 463
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 463

Ile Ser Trp Ser Gly Gly Ser Thr
1               5

-continued

```
<210> SEQ ID NO 464
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 464

Ala Arg Arg Asp Ser Thr Thr Ser Tyr Val Thr
1               5                   10

<210> SEQ ID NO 465
<211> LENGTH: 137
<212> TYPE: PRT
<213> ORGANISM: Artificial sequence
<220> FEATURE:
<223> OTHER INFORMATION: nanobody amino acid sequence

<400> SEQUENCE: 465

Gln Val Gln Leu Gln Glu Ser Gly Gly Gly Leu Val Gln Ala Gly Gly
1               5                   10                  15

Ser Leu Arg Leu Ser Cys Thr Val Ser Gly Gly Thr Phe Thr Thr Tyr
            20                  25                  30

Thr Met Ala Trp Phe Arg Gln Ala Pro Gly Lys Glu Arg Glu Phe Val
            35                  40                  45

Ala Gln Ile Ser Trp Ser Gly Gly Ile Thr Ala Tyr Leu Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Arg Arg Gly Arg Lys Tyr Glu Asp Asp Tyr Trp Gly Gln Gly Thr
            100                 105                 110

Gln Val Thr Val Ser Ser Ala Ala Ala Tyr Pro Tyr Asp Val Pro Asp
        115                 120                 125

Tyr Gly Ser His His His His His His
    130                 135

<210> SEQ ID NO 466
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 466

Gly Gly Thr Phe Thr Thr Tyr Thr
1               5

<210> SEQ ID NO 467
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 467

Ile Ser Trp Ser Gly Gly Ile Thr
1               5
```

-continued

```
<210> SEQ ID NO 468
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 468

Ala Arg Arg Gly Arg Lys Tyr Glu Asp Asp Tyr
1               5                   10

<210> SEQ ID NO 469
<211> LENGTH: 136
<212> TYPE: PRT
<213> ORGANISM: Artificial sequence
<220> FEATURE:
<223> OTHER INFORMATION: nanobody amino acid sequence

<400> SEQUENCE: 469

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ile Met Gly Trp Phe Arg Gln Ala Pro Gly Lys Val Arg Glu Phe Val
            35                  40                  45

Ala Ser Ile Ser Trp Ser Gly Gly Phe Thr Tyr Tyr Ala Asp Ser Val
        50                  55                  60

Lys Gly Arg Ser Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Ala Asp Pro Gly Gln Gly Tyr Lys Tyr Trp Gly Gln Gly Thr Gln
                100                 105                 110

Val Thr Val Ser Ser Ala Ala Ala Tyr Pro Tyr Asp Val Pro Asp Tyr
            115                 120                 125

Gly Ser His His His His His His
    130                 135

<210> SEQ ID NO 470
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 470

Gly Arg Thr Phe Ser Ser Tyr Ile
1               5

<210> SEQ ID NO 471
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 471

Ile Ser Trp Ser Gly Gly Phe Thr
1               5
```

-continued

```
<210> SEQ ID NO 472
<211> LENGTH: 10
<212> TYPE: PRT
<213> ORGANISM: Artificial sequence
<220> FEATURE:
<223> OTHER INFORMATION: Complementarity-determining region amino acid
      sequence

<400> SEQUENCE: 472

Ala Ala Asp Pro Gly Gln Gly Tyr Lys Tyr
1               5                   10

<210> SEQ ID NO 473
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 473

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Ser Phe Arg Ser Tyr
            20                  25                  30

Thr Met Gly Trp Leu Arg Gln Ala Pro Gly Lys Glu Arg Glu Phe Val
        35                  40                  45

Ala Ala Ile Ser Met Ser Gly Val Val Thr Tyr Tyr Ala Asp Ser Val
    50                  55                  60

Lys Gly Arg Phe Thr Ile Ser Arg Asp Asn Ala Ala Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Pro Asp Arg Thr Gly Lys Ala Asp Tyr Ser Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 474
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 474

Gly Arg Ser Phe Arg Ser Tyr Thr
1               5

<210> SEQ ID NO 475
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 475

Ile Ser Met Ser Gly Val Val Thr
1               5
```

-continued

```
<210> SEQ ID NO 476
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 476

Ala Ala Arg Pro Asp Arg Thr Gly Lys Ala Asp Tyr
1               5                   10

<210> SEQ ID NO 477
<211> LENGTH: 137
<212> TYPE: PRT
<213> ORGANISM: Artificial sequence
<220> FEATURE:
<223> OTHER INFORMATION: nanobody amino acid sequence

<400> SEQUENCE: 477

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Thr Phe Ser Arg Ser
            20                  25                  30

Ile Met Gly Trp Phe Arg Gln Ala Pro Gly Lys Glu Arg Glu Arg Val
        35                  40                  45

Ala Ala Ile Ser Trp Ser Gly Ser Leu Thr Phe Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asp Ser Leu Lys Pro Glu Asp Thr Ala Val Tyr Tyr Cys
                85                  90                  95

Ala Ala Asp Lys Leu Gly Gly Thr Trp Asp Ser Trp Gly Pro Gly Thr
                100                 105                 110

Gln Val Thr Val Ser Ser Ala Ala Ala Tyr Pro Tyr Asp Val Pro Asp
        115                 120                 125

Tyr Gly Ser His His His His His His
    130                 135

<210> SEQ ID NO 478
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 478

Gly Gly Thr Phe Ser Arg Ser Ile
1               5

<210> SEQ ID NO 479
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 479

Ile Ser Trp Ser Gly Ser Leu Thr
1               5
```

<210> SEQ ID NO 480
<211> LENGTH: 11
<212> TYPE: PRT
<213> ORGANISM: Artificial sequence
<220> FEATURE:
<223> OTHER INFORMATION: Complementarity-determining region amino acid
      sequence

<400> SEQUENCE: 480

Ala Ala Asp Lys Leu Gly Gly Thr Trp Asp Ser
1               5                   10

<210> SEQ ID NO 481
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 481

Gln Val Gln Leu Gln Glu Ser Gly Gly Gly Leu Val Gln Ala Gly Gly
1               5                   10                  15

Ser Leu Arg Leu Ser Cys Thr Ala Ser Gly Arg Thr Phe Ser Ser Tyr
            20                  25                  30

Ser Met Ala Trp Phe Arg Gln Ala Ser Gly Lys Glu Arg Glu Ile Val
            35                  40                  45

Ala Ala Val Ser Arg Phe Gly Lys Phe Lys Tyr Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Thr Asp Gly Ser Ser Trp Tyr Leu Asp Tyr Trp Gly Gln Gly
            100                 105                 110

Thr Gln Val Thr Val Ser Ser Ala Ala Ala Tyr Pro Tyr Asp Val Pro
            115                 120                 125

Asp Tyr Gly Ser His His His His His His
    130                 135

<210> SEQ ID NO 482
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 482

Gly Arg Thr Phe Ser Ser Tyr Ser
1               5

<210> SEQ ID NO 483
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 483

Ala Lys Thr Asp Gly Ser Ser Trp Tyr Leu Asp Tyr
1               5                   10

<210> SEQ ID NO 484
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 484

Gln Val Gln Leu Gln Glu Ser Gly Gly Gly Leu Val Gln Ala Gly Asp
1               5                   10                  15

Ser Leu Arg Leu Ser Cys Thr Ala Ser Gly Arg Thr Phe Ser Ser Tyr
            20                  25                  30

Val Met Gly Trp Phe Arg Gln Ala Pro Gly Lys Glu Arg Glu Phe Val
        35                  40                  45

Ala Ala Ile Ser Arg Ser Gly Gly Asn Thr Tyr Phe Gly Asp Ser Ala
    50                  55                  60

Glu Ala Arg Phe Thr Ile Ser Arg Asp Asn Thr Lys Asn Thr Val Tyr
65                  70                  75                  80

Leu Gln Met Ser Ser Leu Arg Pro Asp Asp Thr Ala Val Tyr Tyr Cys
                85                  90                  95

Ala Arg Tyr Arg Leu Val Ala Gly Ser Thr Ser Arg Tyr Thr Tyr Asp
            100                 105                 110

Gln Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 485
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 485

Gly Arg Thr Phe Ser Ser Tyr Val
1               5

<210> SEQ ID NO 486
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 486

Ile Ser Arg Ser Gly Gly Asn Thr
1               5

<210> SEQ ID NO 487
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 487

Ala Arg Tyr Arg Leu Val Ala Gly Ser Thr Ser Arg Tyr Thr Tyr Asp
1               5                   10                  15

Gln

<210> SEQ ID NO 488
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 488

Gln Val Gln Leu Gln Glu Ser Gly Gly Gly Leu Val Gln Ala Gly Asp
1               5                   10                  15

Ser Leu Arg Leu Thr Cys Ala His Ser Gly Arg Pro Phe Ser Ser Ser
            20                  25                  30

Ala Met Gly Trp Phe Arg Gln Ala Pro Gly Lys Glu Arg Glu Phe Val
        35                  40                  45

Ala Ala Ile Ser Arg Gly Gly Leu Ser Lys Tyr Tyr Ala Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Ser Leu Arg Asp Arg Pro Thr Lys Asp Glu Tyr Val Val Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 489
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 489

Gly Arg Pro Phe Ser Ser Ser Ala
1               5

<210> SEQ ID NO 490
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 490

Ile Ser Arg Gly Gly Leu Ser Lys
1               5

<210> SEQ ID NO 491
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 491

Ala Gly Ser Leu Arg Asp Arg Pro Thr Lys Asp Glu Tyr Val Val
1               5                   10                  15

-continued

<210> SEQ ID NO 492
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 492

Gln Val Gln Leu Gln Glu Ser Gly Gly Gly Ser Val Gln Ala Gly Asp
1               5                   10                  15

Ser Leu Lys Leu Ser Cys Val Ala Ser Gly Arg Ser Arg Tyr Ala Leu
            20                  25                  30

Gly Trp Phe Arg Gln Ala Pro Gly Lys Ala Arg Glu Phe Val Gly Ala
        35                  40                  45

Ala Arg Gly Gly Ala Gly Asn Thr Tyr Tyr His Glu Ser Val Lys Gly
    50                  55                  60

Arg Phe Thr Ile Ser Arg Asp Asn Asp Lys Leu Thr Val Tyr Leu Gln
65                  70                  75                  80

Met Asn Asp Leu Lys Pro Glu Asp Thr Ala Val Tyr Thr Cys Ala Ala
                85                  90                  95

Gly Lys Asp Phe Gly Thr Ala Val Ser Trp Thr Ser Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 493
<211> LENGTH: 6
<212> TYPE: PRT
<213> ORGANISM: Artificial sequence
<220> FEATURE:
<223> OTHER INFORMATION: Complementarity-determining region amino acid
      sequence

<400> SEQUENCE: 493

Gly Arg Ser Arg Tyr Ala
1               5

<210> SEQ ID NO 494
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 494

Ala Arg Gly Gly Ala Gly Asn Thr
1               5

<210> SEQ ID NO 495
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 495

Ala Ala Gly Lys Asp Phe Gly Thr Ala Val Ser Trp Thr Ser
1               5                   10

<210> SEQ ID NO 496
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 496

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Thr Phe Ser Gly Leu
            20                  25                  30

Thr Met Gly Trp Phe Arg Gln Ala Pro Gly Lys Glu Arg Asp Phe Val
        35                  40                  45

Ala Ala Ile Ser Trp Asn Gly Arg Phe Thr Tyr Tyr Lys Asp Ser Val
    50                  55                  60

Lys Gly Arg Phe Ala Ile Ser Arg Asp Asn Ala Lys Ser Thr Val Tyr
65                  70                  75                  80

Leu Gln Met Thr Ser Leu Lys Pro Glu Asp Thr Ala Val Tyr Tyr Cys
                85                  90                  95

Gly Ala Asp Val Leu Ser Gly Arg Gly Tyr Arg Tyr Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 497
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 497

Ile Ser Trp Asn Gly Arg Phe Thr
1               5

<210> SEQ ID NO 498
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 498

Gly Ala Asp Val Leu Ser Gly Arg Gly Tyr Arg Tyr
1               5                   10

<210> SEQ ID NO 499
<211> LENGTH: 135
<212> TYPE: PRT
<213> ORGANISM: Artificial sequence
<220> FEATURE:
<223> OTHER INFORMATION: nanobody amino acid sequence

<400> SEQUENCE: 499

Gln Val Gln Leu Gln Glu Ser Gly Gly Gly Leu Val Gln Ala Gly Gly
1               5                   10                  15

-continued

```
Ser Leu Arg Leu Ser Cys Ala Val Ser Gly Arg Ala Phe Ser Thr Tyr
        20                  25                  30

Gly Met Gly Trp Phe Arg Gln Ala Pro Arg Lys Glu Arg Glu Phe Ile
        35                  40                  45

Thr Ala Ile Asn Arg Asn Gly Asp Arg Thr Trp Tyr Ala Asp Ser Val
        50                  55                  60

Thr Gly Arg Phe Thr Ile Ser Arg Asp Asn Asp Lys Asn Met Val Tyr
65                  70                  75                  80

Leu Gln Met Asp Ser Leu Lys Thr Glu Asp Thr Gly Ile Tyr Tyr Cys
                85                  90                  95

His Thr Arg Arg Phe Gly Tyr Asp Tyr Trp Gly Gln Gly Thr Gln Val
            100                 105                 110

Thr Val Ser Ser Ala Ala Ala Tyr Pro Tyr Asp Val Pro Asp Tyr Gly
        115                 120                 125

Ser His His His His His
    130                 135
```

<210> SEQ ID NO 500
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 500

```
Gly Arg Ala Phe Ser Thr Tyr Gly
1               5
```

<210> SEQ ID NO 501
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 501

```
Ile Asn Arg Asn Gly Asp Arg Thr
1               5
```

<210> SEQ ID NO 502
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 502

```
His Thr Arg Arg Phe Gly Tyr Asp Tyr
1               5
```

<210> SEQ ID NO 503
<211> LENGTH: 140
<212> TYPE: PRT
<213> ORGANISM: Artificial sequence
<220> FEATURE:
<223> OTHER INFORMATION: nanobody amino acid sequence

<400> SEQUENCE: 503

```
Gln Val Gln Leu Gln Glu Ser Gly Gly Gly Trp Val Gln Pro Gly Gly
1               5                   10                  15
```

-continued

Ser Leu Arg Leu Ser Cys Thr Ile Ser Gly Leu Ser Arg Tyr Tyr Ala
            20                  25                  30

Met Gly Trp Phe Arg Gln Val Pro Gly Lys Glu Arg Glu Ser Val Ala
        35                  40                  45

Thr Ile Ser Leu Arg Gly Gly Arg Thr Tyr Tyr Ala Asp Ser Val Glu
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Val
                85                  90                  95

Ala Asp Thr Thr Trp Gly Ala Pro Arg Ser Arg Tyr His Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His
    130                 135                 140

<210> SEQ ID NO 504
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 504

Gly Leu Ser Arg Tyr Tyr Ala
1               5

<210> SEQ ID NO 505
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 505

Ile Ser Leu Arg Gly Gly Arg Thr
1               5

<210> SEQ ID NO 506
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 506

Val Ala Asp Thr Thr Trp Gly Ala Pro Arg Ser Arg Tyr His Tyr
1               5                   10                  15

<210> SEQ ID NO 507
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 507

Gln Val Gln Leu Gln Glu Ser Gly Gly Gly Leu Val Gln Pro Gly Gly
1               5                   10                  15

```
Ser Leu Arg Leu Ser Cys Ala Ala Ser Gly Phe Thr Phe Arg Ser Tyr
        20                  25                  30

Ala Met Ser Trp Val Arg Gln Ala Pro Gly Gln Gly Leu Glu Trp Val
        35                  40                  45

Ser Ala Ile Asn Ser Gly Gly Gly Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Met Gly Ser Ser Ser Arg Gly Asn Arg Tyr Leu Glu Val Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140
```

```
<210> SEQ ID NO 508
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 508

Ala Lys Met Gly Ser Ser Ser Arg Gly Asn Arg Tyr Leu Glu Val
1               5                   10                  15
```

```
<210> SEQ ID NO 509
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 509

Ile Asn Ser Gly Gly Gly Ser Thr
1               5
```

```
<210> SEQ ID NO 510
<211> LENGTH: 15
<212> TYPE: PRT
<213> ORGANISM: Artificial sequence
<220> FEATURE:
<223> OTHER INFORMATION: Complementarity-determining region amino acid
      sequence

<400> SEQUENCE: 510

Ala Lys Met Gly Ser Ser Ser Arg Gly Asn Arg Tyr Leu Glu Val
1               5                   10                  15
```

```
<210> SEQ ID NO 511
<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 511

Gln Val Gln Leu Gln Glu Ser Gly Gly Gly Leu Val Gln Ala Gly Asp
1               5                   10                  15
```

-continued

```
Ser Leu Arg Leu Ser Cys Glu Ala Ser Ala Arg Thr Phe Ile Ala Tyr
        20                  25                  30

Ala Val Gly Trp Phe Arg Gln Ala Pro Gly Lys Glu Arg Glu Phe Val
        35                  40                  45

Ala Ala Ile Ser Trp Asn Gly Gly Met Thr Asp Tyr Ala Asp Phe Val
        50                  55                  60

Lys Gly Arg Phe Ala Ile Ser Arg Asp Asn Ala Lys Thr Val Ser Leu
65                  70                  75                  80

Gln Met Asn Asn Leu Lys Pro Glu Asp Thr Ala Leu Tyr Tyr Cys Thr
                85                  90                  95

Ala Gly Pro Ala Arg Arg Ser Tyr Ser Tyr Arg Asp Gly Tyr Asp Tyr
                100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140
```

<210> SEQ ID NO 512
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 512

```
Ala Arg Thr Phe Ile Ala Tyr Ala
1               5
```

<210> SEQ ID NO 513
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 513

```
Ile Ser Trp Asn Gly Gly Met Thr
1               5
```

<210> SEQ ID NO 514
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 514

```
Thr Ala Gly Pro Ala Arg Arg Ser Tyr Ser Tyr Arg Asp Gly Tyr Asp
1               5                   10                  15

Tyr
```

<210> SEQ ID NO 515
<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 515

```
Gln Val Gln Leu Gln Glu Ser Gly Gly Gly Leu Val Gln Thr Gly Gly
```

-continued

```
1              5              10             15

Ser Leu Arg Leu Ser Cys Glu Ala Ser Ala Arg Thr Phe Ile Ala Tyr
        20             25             30

Ala Val Gly Trp Phe Arg Gln Ala Pro Gly Lys Glu Arg Glu Phe Val
        35             40             45

Ala Ala Ile Ser Trp Asn Gly Gly Met Thr Asp Tyr Ala Asp Phe Val
        50             55             60

Lys Gly Arg Phe Ala Ile Ser Arg Asp Ser Ala Lys Thr Val Ser Leu
65             70             75             80

Gln Met Asn Asn Leu Lys Pro Glu Asp Thr Ala Leu Tyr Tyr Cys Thr
                85             90             95

Ala Gly Pro Ala Arg Arg Ser Tyr Ser Tyr Arg Asp Gly Tyr Asp Tyr
            100            105            110

Trp Gly Gln Gly Thr Gln Val Thr Val Ser Ser Ala Ala Ala Tyr Pro
            115            120            125

Tyr Asp Val Pro Asp Tyr Gly Ser His His His His His
    130            135            140
```

```
<210> SEQ ID NO 516
<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 516
```

```
Gln Val Gln Leu Gln Glu Ser Gly Gly Gly Leu Val Gln Val Gly Gly
1              5              10             15

Ser Leu Arg Ile Ser Cys Val Ala Ser Gly Arg Thr Gly Ser Tyr Tyr
        20             25             30

Ala Met Gly Trp Phe Arg Gln Ala Pro Gly Lys Glu Arg Glu Phe Val
        35             40             45

Ala Ala Ile Ser Trp Asn Gly Gly Met Thr Asp Tyr Ala Asp Phe Val
        50             55             60

Lys Gly Arg Phe Ala Ile Ser Arg Asp Asn Ala Lys Thr Val Ser Leu
65             70             75             80

Gln Met Asn Asn Leu Lys Pro Glu Asp Thr Ala Leu Tyr Tyr Cys Thr
                85             90             95

Ala Gly Pro Ala Arg Arg Ser Tyr Ser Tyr Arg Asp Gly Tyr Asp Tyr
            100            105            110

Trp Gly Gln Gly Thr Gln Val Thr Val Ser Ser Ala Ala Ala Tyr Pro
            115            120            125

Tyr Asp Val Pro Asp Tyr Gly Ser His His His His His
    130            135            140
```

```
<210> SEQ ID NO 517
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 517
```

```
Gly Arg Thr Gly Ser Tyr Tyr Ala
1              5
```

```
<210> SEQ ID NO 518
```

<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 518

Gln Val Gln Leu Gln Glu Ser Gly Gly Gly Leu Val Gln Pro Gly Arg
1               5                   10                  15

Ser Leu Arg Leu Ser Cys Glu Ala Ser Ala Arg Thr Phe Ile Ala Tyr
            20                  25                  30

Ala Val Gly Trp Phe Arg Gln Ala Pro Gly Lys Glu Arg Glu Phe Val
            35                  40                  45

Ala Ala Ile Ser Trp Asn Gly Gly Met Thr Asp Tyr Ala Asp Phe Val
        50                  55                  60

Lys Gly Arg Phe Ala Ile Ser Arg Asp Asn Ala Lys Thr Val Ser Leu
65                  70                  75                  80

Gln Met Asn Asn Leu Lys Pro Glu Asp Thr Ala Leu Tyr Tyr Cys Thr
                85                  90                  95

Ala Gly Pro Ala Arg Arg Ser Tyr Ser Tyr Arg Asp Gly Tyr Asp Tyr
            100                 105                 110

Trp Gly Gln Gly Thr Gln Val Thr Val Ser Ser Ala Ala Ala Tyr Pro
            115                 120                 125

Tyr Asp Val Pro Asp Tyr Gly Ser His His His His His His
        130                 135                 140

<210> SEQ ID NO 519
<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 519

Gln Val Gln Leu Gln Glu Ser Gly Gly Gly Leu Val Gln Ser Gly Gly
1               5                   10                  15

Ser Leu Thr Leu Ser Cys Ala Ala Ser Ala Arg Thr Phe Ile Ala Tyr
            20                  25                  30

Ala Val Gly Trp Phe Arg Gln Ala Pro Gly Lys Glu Arg Glu Phe Val
            35                  40                  45

Ala Ala Ile Ser Trp Asn Gly Gly Met Thr Asp Tyr Ala Asp Phe Val
        50                  55                  60

Lys Gly Arg Phe Ala Ile Ser Arg Asp Asn Ala Lys Thr Val Ser Leu
65                  70                  75                  80

Gln Met Asn Asn Leu Lys Pro Glu Asp Thr Ala Leu Tyr Tyr Cys Thr
                85                  90                  95

Ala Gly Pro Ala Arg Arg Ser Tyr Ser Tyr Arg Asp Gly Tyr Asp Tyr
            100                 105                 110

Trp Gly Gln Gly Thr Gln Val Thr Val Ser Ser Ala Ala Ala Tyr Pro
            115                 120                 125

Tyr Asp Val Pro Asp Tyr Gly Ser His His His His His His
        130                 135                 140

<210> SEQ ID NO 520
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 520

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Thr Asn
            20                  25                  30

Ala Met Gly Trp Tyr Arg Gln Ala Pro Asp Lys Gln Arg Glu Phe Leu
        35                  40                  45

Ala Val Ile Thr Pro Arg Gly Arg Thr Ala Tyr Ala Asp Ser Ala Lys
        50                  55                  60

Gly Arg Phe Thr Ile Ser Arg Asp Asn Ala Met Asn Ser Val Tyr Leu
65                  70                  75                  80

Gln Met Asn Ser Leu Lys Phe Glu Asp Thr Ala Val Tyr Tyr Cys Tyr
                85                  90                  95

Ala Gly Arg Tyr Arg Ser Tyr Asp Ala Arg Phe Ala Thr Asp Ile Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140
```

<210> SEQ ID NO 521
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 521

```
Gly Ser Ile Phe Ser Thr Asn Ala
1               5
```

<210> SEQ ID NO 522
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 522

```
Ile Thr Pro Arg Gly Arg Thr
1               5
```

<210> SEQ ID NO 523
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 523

```
Tyr Ala Gly Arg Tyr Arg Ser Tyr Asp Ala Arg Phe Ala Thr Asp Ile
1               5                   10                  15
```

<210> SEQ ID NO 524
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 524

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Thr Asn
                20                  25                  30

Ala Met Gly Trp Tyr Arg Gln Ala Pro Asp Lys Gln Arg Glu Phe Leu
            35                  40                  45

Ala Val Ile Thr Pro Arg Gly Arg Thr Ala Tyr Ala Asp Ser Ala Lys
        50                  55                  60

Gly Arg Phe Thr Ile Ser Arg Asp Asn Ala Met Asn Ser Val Tyr Leu
65                  70                  75                  80

Gln Met Asn Ser Leu Lys Phe Glu Asp Thr Ala Val Tyr Tyr Cys Tyr
                85                  90                  95

Ala Gly Arg Tyr Arg Ser Tyr Asp Ala Arg Phe Ala Thr Asp Ile Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 525
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 525

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Thr Asn
                20                  25                  30

Ala Met Gly Trp Tyr Arg Gln Ala Pro Asp Lys Gln Arg Glu Phe Leu
            35                  40                  45

Ala Val Ile Thr Pro Arg Gly Arg Thr Ala Tyr Ala Asp Ser Ala Lys
        50                  55                  60

Gly Arg Phe Thr Ile Ser Arg Asp Asn Ala Met Asn Ser Val Tyr Leu
65                  70                  75                  80

Gln Met Asn Ser Leu Lys Phe Glu Asp Thr Ala Val Tyr Tyr Cys Tyr
                85                  90                  95

Ala Gly Arg Tyr Arg Ser Phe Asp Ala Arg Phe Ala Thr Asp Ile Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 526
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 526

Tyr Ala Gly Arg Tyr Arg Ser Phe Asp Ala Arg Phe Ala Thr Asp Ile

```
1               5                   10                  15
```

<210> SEQ ID NO 527
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 527

```
Gln Val Gln Leu Gln Glu Ser Gly Gly Gly Leu Val Arg Ala Gly Gly
1               5                   10                  15

Ser Leu Arg Leu Ser Cys Ala Ala Ser Gly Ser Ile Phe Ser Thr Asn
            20                  25                  30

Ala Met Gly Trp Tyr Arg Gln Ala Pro Asp Lys Gln Arg Glu Phe Leu
        35                  40                  45

Ala Val Ile Thr Pro Arg Gly Arg Thr Ala Tyr Ala Asp Ser Ala Lys
    50                  55                  60

Gly Arg Phe Thr Ile Ser Arg Asp Asn Ala Met Asn Ser Val Tyr Leu
65                  70                  75                  80

Gln Met Asn Ser Leu Lys Phe Glu Asp Thr Ala Val Tyr Tyr Cys Tyr
                85                  90                  95

Ala Gly Arg Tyr Arg Ser Phe Asp Ala Arg Phe Ala Thr Asp Ile Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140
```

<210> SEQ ID NO 528
<211> LENGTH: 141
<212> TYPE: PRT
<213> ORGANISM: Artificial sequence
<220> FEATURE:
<223> OTHER INFORMATION: nanobody amino acid sequence

<400> SEQUENCE: 528

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Thr Asn
            20                  25                  30

Ala Met Gly Trp Tyr Arg Gln Ala Pro Asp Lys Gln Arg Glu Phe Leu
        35                  40                  45

Ala Val Ile Thr Pro Arg Gly Arg Thr Ala Tyr Ala Asp Ser Ala Lys
    50                  55                  60

Gly Arg Phe Thr Ile Ser Arg Asp Asn Ala Met Asn Ser Val Tyr Leu
65                  70                  75                  80

Gln Met Asn Ser Leu Lys Phe Glu Asp Thr Ala Val Tyr Tyr Cys Tyr
                85                  90                  95

Ala Gly Arg Tyr Arg Ser Phe Asp Ala Arg Phe Ala Thr Asp Ile Trp
            100                 105                 110

Ser Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140
```

<210> SEQ ID NO 529
<211> LENGTH: 141

<212> TYPE: PRT
<213> ORGANISM: Artificial sequence
<220> FEATURE:
<223> OTHER INFORMATION: nanobody amino acid sequence

<400> SEQUENCE: 529

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Thr Asn
            20                  25                  30

Ala Met Gly Trp Tyr Arg Gln Ala Pro Asp Lys Gln Arg Glu Phe Leu
            35                  40                  45

Ala Val Ile Thr Pro Arg Gly Arg Thr Ala Tyr Ala Asp Ser Ala Lys
        50                  55                  60

Gly Arg Phe Thr Ile Ser Arg Asp Asn Ala Val Asn Ser Val Tyr Leu
65                  70                  75                  80

Gln Met Asn Ser Leu Lys Phe Glu Asp Thr Ala Val Tyr Tyr Cys Tyr
                85                  90                  95

Ala Gly Arg Tyr Arg Ser Phe Asp Ala Arg Phe Ala Thr Asp Ile Trp
            100                 105                 110

Gly Gln Gly Thr Gln Val Thr Val Ser Ser Ala Ala Ala Tyr Pro Tyr
            115                 120                 125

Asp Val Pro Asp Tyr Gly Ser His His His His His His
    130                 135                 140
```

<210> SEQ ID NO 530
<211> LENGTH: 139
<212> TYPE: PRT
<213> ORGANISM: Artificial sequence
<220> FEATURE:
<223> OTHER INFORMATION: nanobody amino acid sequence

<400> SEQUENCE: 530

```
Gln Val Gln Leu Gln Glu Ser Gly Gly Gly Leu Val His Pro Gly Gly
1               5                   10                  15

Ser Leu Arg Leu Ser Cys Val Ala Ser Gly Ala Phe Leu Thr Gly Ala
            20                  25                  30

Thr Val Gly Trp Tyr Arg Gln Ala Pro Gly Lys Leu Arg Glu Leu Val
            35                  40                  45

Ala Ala Ile Ile Thr Gly Gly Thr Thr Thr Tyr Ala Asp Ser Val Lys
        50                  55                  60

Gly Arg Phe Ser Ile Ser Arg Asp Tyr Thr Lys Arg Ala Leu Ile Leu
65                  70                  75                  80

Gln Met Asp Ser Leu Arg Pro Asp Asp Thr Ala Val Tyr Phe Cys Ser
                85                  90                  95

Ile Arg Gly Phe Tyr Arg Gln Thr Gln Phe Arg Glu Ile Trp Gly Gln
            100                 105                 110

Gly Thr Gln Val Thr Val Ser Ser Ala Ala Ala Tyr Pro Tyr Asp Val
            115                 120                 125

Pro Asp Tyr Gly Ser His His His His His His
    130                 135
```

<210> SEQ ID NO 531
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 531

Gly Ala Phe Leu Thr Gly Ala Thr
1               5

<210> SEQ ID NO 532
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 532

Ile Ile Thr Gly Gly Thr Thr
1               5

<210> SEQ ID NO 533
<211> LENGTH: 14
<212> TYPE: PRT
<213> ORGANISM: Artificial sequence
<220> FEATURE:
<223> OTHER INFORMATION: Complementarity-determining region amino acid
      sequence

<400> SEQUENCE: 533

Ser Ile Arg Gly Phe Tyr Arg Gln Thr Gln Phe Arg Glu Ile
1               5                   10

<210> SEQ ID NO 534
<211> LENGTH: 139
<212> TYPE: PRT
<213> ORGANISM: Artificial sequence
<220> FEATURE:
<223> OTHER INFORMATION: nanobody amino acid sequence

<400> SEQUENCE: 534

Gln Val Gln Leu Gln Glu Ser Gly Gly Gly Leu Val Gln Pro Gly Glu
1               5                   10                  15

Ser Leu Arg Leu Ser Cys Val Ala Ser Gly Ala Phe Leu Thr Gly Ala
            20                  25                  30

Thr Val Gly Trp Tyr Arg Gln Ala Pro Gly Lys Leu Arg Glu Leu Val
            35                  40                  45

Ala Ala Ile Ile Thr Gly Gly Thr Thr Thr Tyr Ala Asp Ser Val Lys
    50                  55                  60

Gly Arg Phe Ser Ile Ser Arg Asp Tyr Thr Lys Arg Ala Leu Ile Leu
65                  70                  75                  80

Gln Met Asp Ser Leu Arg Pro Asp Asp Thr Ala Val Tyr Phe Cys Ser
                85                  90                  95

Ile Arg Gly Phe Tyr Arg Gln Thr Gln Phe Arg Glu Ile Trp Gly Gln
                100                 105                 110

Gly Thr Gln Val Thr Val Ser Ser Ala Ala Ala Tyr Pro Tyr Asp Val
            115                 120                 125

Pro Asp Tyr Gly Ser His His His His His
    130                 135

<210> SEQ ID NO 535
<211> LENGTH: 139
<212> TYPE: PRT
<213> ORGANISM: Artificial sequence
<220> FEATURE:
<223> OTHER INFORMATION: nanobody amino acid sequence

```
<400> SEQUENCE: 535

Gln Val Gln Leu Gln Glu Ser Gly Gly Gly Leu Val Gln Ala Gly Gly
1               5                   10                  15

Ser Leu Arg Leu Ser Cys Val Ala Ser Gly Ala Phe Leu Thr Gly Ala
            20                  25                  30

Thr Val Gly Trp Tyr Arg Gln Ala Pro Gly Lys Leu Arg Glu Leu Val
            35                  40                  45

Ala Ala Ile Ile Thr Gly Gly Thr Thr Thr Tyr Ala Asp Ser Val Lys
    50                  55                  60

Gly Arg Phe Ser Ile Ser Arg Asp Tyr Thr Lys Arg Ala Leu Ile Leu
65                  70                  75                  80

Gln Met Asp Ser Leu Arg Pro Asp Asp Thr Ala Val Tyr Phe Cys Ser
                85                  90                  95

Ile Arg Gly Phe Tyr Arg Gln Thr Gln Phe Arg Glu Ile Trp Gly Gln
            100                 105                 110

Gly Thr Gln Val Thr Val Ser Ser Ala Ala Ala Tyr Pro Tyr Asp Val
            115                 120                 125

Pro Asp Tyr Gly Ser His His His His His His
    130                 135

<210> SEQ ID NO 536
<211> LENGTH: 139
<212> TYPE: PRT
<213> ORGANISM: Artificial sequence
<220> FEATURE:
<223> OTHER INFORMATION: nanobody amino acid sequence

<400> SEQUENCE: 536

Gln Val Gln Leu Gln Glu Ser Gly Gly Gly Glu Val Gln Ala Gly Gly
1               5                   10                  15

Ser Leu Arg Leu Ser Cys Val Ala Ser Gly Ala Phe Leu Thr Gly Ala
            20                  25                  30

Thr Val Gly Trp Tyr Arg Gln Ala Pro Gly Lys Leu Arg Glu Leu Val
            35                  40                  45

Ala Ala Ile Ile Thr Gly Gly Thr Thr Thr Tyr Ala Asp Ser Val Lys
    50                  55                  60

Gly Arg Phe Ser Ile Ser Arg Asp Tyr Thr Lys Arg Ala Leu Ile Leu
65                  70                  75                  80

Gln Met Asp Ser Leu Arg Pro Asp Asp Thr Ala Val Tyr Phe Cys Ser
                85                  90                  95

Ile Arg Gly Phe Tyr Arg Gln Thr Gln Phe Arg Glu Ile Trp Gly Gln
            100                 105                 110

Gly Thr Gln Val Thr Val Ser Ser Ala Ala Ala Tyr Pro Tyr Asp Val
            115                 120                 125

Pro Asp Tyr Gly Ser His His His His His His
    130                 135

<210> SEQ ID NO 537
<211> LENGTH: 139
<212> TYPE: PRT
<213> ORGANISM: Artificial sequence
<220> FEATURE:
<223> OTHER INFORMATION: nanobody amino acid sequence

<400> SEQUENCE: 537

Gln Val Gln Leu Gln Glu Ser Gly Gly Gly Glu Val Gln Ala Gly Gly
1               5                   10                  15
```

-continued

```
Ser Leu Arg Leu Ser Cys Val Ala Ser Gly Ala Phe Leu Thr Gly Ala
        20                  25                  30

Thr Val Gly Trp Tyr Arg Gln Thr Pro Gly Asn Leu Arg Glu Leu Val
        35                  40                  45

Ala Ala Ile Ile Thr Gly Gly Thr Thr Thr Tyr Ala Asp Ser Val Lys
        50                  55                  60

Gly Arg Phe Ser Ile Ser Arg Asp Tyr Thr Lys Arg Ala Leu Ile Leu
65                  70                  75                  80

Gln Met Asp Ser Leu Arg Pro Asp Asp Thr Ala Val Tyr Phe Cys Ser
                85                  90                  95

Ile Arg Gly Phe Tyr Arg Gln Thr Gln Phe Arg Glu Ile Trp Gly Gln
            100                 105                 110

Gly Thr Gln Val Thr Val Ser Ser Ala Ala Ala Tyr Pro Tyr Asp Val
        115                 120                 125

Pro Asp Tyr Gly Ser His His His His His
    130                 135
```

```
<210> SEQ ID NO 538
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 538
```

```
Gln Val Gln Leu Gln Glu Ser Gly Gly Gly Leu Val Gln Thr Gly Gly
1               5                   10                  15

Ser Leu Arg Leu Ser Cys Ala Ala Ser Gly Arg Thr Phe Ser Asn Tyr
        20                  25                  30

Val Met Gly Trp Phe Arg Gln Ala Pro Gly Lys Glu Arg Glu Leu Ile
        35                  40                  45

Gly Ala Ile Asn Arg Ser Ser Thr Arg Leu Tyr Tyr Ala Asp Ser Val
        50                  55                  60

Lys Gly Arg Phe Ser Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Val Ser Ile Leu Gly Lys Gly Tyr Arg Asp Val Asp
            100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140
```

```
<210> SEQ ID NO 539
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 539
```

```
Gly Arg Thr Phe Ser Asn Tyr Val
1               5
```

```
<210> SEQ ID NO 540
<211> LENGTH: 8
<212> TYPE: PRT
```

-continued

```
<213> ORGANISM: Artificial sequence
<220> FEATURE:
<223> OTHER INFORMATION: Complementarity-determining region amino acid
      sequence

<400> SEQUENCE: 540

Ile Asn Arg Ser Ser Thr Arg Leu
1               5

<210> SEQ ID NO 541
<211> LENGTH: 17
<212> TYPE: PRT
<213> ORGANISM: Artificial sequence
<220> FEATURE:
<223> OTHER INFORMATION: Complementarity-determining region amino acid
      sequence

<400> SEQUENCE: 541

Ala Ala Asp Leu Val Ser Ile Leu Gly Lys Gly Tyr Arg Asp Val Asp
1               5                   10                  15

Tyr

<210> SEQ ID NO 542
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 542

Gln Val Gln Leu Gln Glu Ser Gly Gly Gly Ser Val Gln Ala Gly Gly
1               5                   10                  15

Ser Leu Arg Leu Ser Cys Ala Ala Ser Gly Arg Thr Phe Ser Asn Tyr
            20                  25                  30

Val Met Gly Trp Phe Arg Gln Ala Pro Gly Lys Glu Arg Glu Leu Ile
        35                  40                  45

Gly Ala Ile Asn Arg Ser Ser Thr Arg Leu Tyr Tyr Ala Asp Ser Val
    50                  55                  60

Lys Gly Arg Phe Ser Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Val Ser Ile Leu Gly Lys Gly Tyr Arg Asp Val Asp
            100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140

<210> SEQ ID NO 543
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 543

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30
```

```
Val Met Gly Trp Phe Arg Gln Ala Pro Gly Lys Glu Arg Glu Leu Ile
    35                  40                  45

Gly Ala Ile Asn Arg Ser Ser Thr Arg Leu Tyr Tyr Ala Asp Ser Val
    50                  55                  60

Lys Gly Arg Phe Ser Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Val Ser Ile Leu Gly Lys Gly Tyr Arg Asp Val Asp
                100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His
    130                 135                 140
```

<210> SEQ ID NO 544
<211> LENGTH: 143
<212> TYPE: PRT
<213> ORGANISM: Artificial sequence
<220> FEATURE:
<223> OTHER INFORMATION: nanobody amino acid sequence

<400> SEQUENCE: 544

```
Gln Val Gln Leu Gln Glu Ser Gly Gly Gly Leu Val Gln Pro Gly Gly
1                   5                   10                  15

Ser Leu Arg Val Ser Cys Ala Ala Ser Gly Phe Ser Phe Ser Asn Tyr
                20                  25                  30

Val Met Gly Trp Phe Arg Gln Ala Pro Gly Lys Glu Arg Glu Leu Ile
    35                  40                  45

Gly Ala Ile Asn Arg Ser Ser Thr Arg Leu Tyr Tyr Ala Asp Ser Val
    50                  55                  60

Lys Gly Arg Phe Ser Ile Ser Arg Asp Asn Ala Lys Ser Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Val Ser Ile Leu Gly Lys Gly Tyr Arg Asp Val Asp
                100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His
    130                 135                 140
```

<210> SEQ ID NO 545
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 545

```
Gly Phe Ser Phe Ser Asn Tyr Val
1                   5
```

<210> SEQ ID NO 546
<211> LENGTH: 144
<212> TYPE: PRT
<213> ORGANISM: Artificial sequence
<220> FEATURE:
<223> OTHER INFORMATION: nanobody amino acid sequence -continued

<400> SEQUENCE: 546

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Phe Ser Pro Tyr
            20                  25                  30

Thr Met Gly Trp Phe Arg Arg Ala Pro Gly Lys Glu Arg Glu Phe Val
        35                  40                  45

Ala Ala Ile Ser Trp Gly Ala Gly Val Lys Ser Tyr Ala Asp Ser Val
        50                  55                  60

Lys Gly Arg Phe Thr Ile Ser Arg Asp Asn Ala Glu Asn Thr Val Tyr
65                  70                  75                  80

Leu Gln Met Asn Met Leu Lys Pro Asp Asp Thr Ala Leu Tyr Tyr Cys
                85                  90                  95

Ala Ala Lys Arg Pro Ile Ser Gly Ser Tyr Ser Asn Glu Arg Asp Tyr
            100                 105                 110

Ala Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140

<210> SEQ ID NO 547
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 547

Gly Arg Thr Phe Ser Pro Tyr Thr
1               5

<210> SEQ ID NO 548
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 548

Ile Ser Trp Gly Ala Gly Val Lys
1               5

<210> SEQ ID NO 549
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 549

Ala Ala Lys Arg Pro Ile Ser Gly Ser Tyr Ser Asn Glu Arg Asp Tyr
1               5                   10                  15

Ala Tyr

<210> SEQ ID NO 550
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 550

Gln Val Gln Leu Gln Glu Ser Gly Gly Gly Leu Val Gln Pro Gly Gly
1               5                   10                  15

Ser Leu Arg Leu Ser Cys Val Ala Ser Gly Arg Thr Phe Ser Pro Tyr
            20                  25                  30

Thr Met Gly Trp Phe Arg Arg Ala Pro Gly Lys Glu Arg Glu Phe Val
        35                  40                  45

Ala Ala Ile Ser Trp Gly Ala Gly Val Lys Ser Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Met Leu Lys Pro Asp Asp Thr Ala Leu Tyr Tyr Cys
                85                  90                  95

Ala Ala Lys Arg Pro Ile Ser Gly Ser Tyr Ser Asn Glu Arg Asp Tyr
            100                 105                 110

Ala Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His His
    130                 135                 140

<210> SEQ ID NO 551
<211> LENGTH: 134
<212> TYPE: PRT
<213> ORGANISM: Artificial sequence
<220> FEATURE:
<223> OTHER INFORMATION: nanobody amino acid sequence

<400> SEQUENCE: 551

Gln Val Gln Leu Gln Glu Ser Gly Gly Gly Leu Val Gln Thr Gly Glu
1               5                   10                  15

Ser Leu Arg Leu Ser Cys Ala Gly Thr Asn Phe Leu Ser Ser Arg Phe
            20                  25                  30

Glu Met Gly Trp Tyr Arg Gln Ile Pro Gly Lys Gln Arg Glu Leu Val
        35                  40                  45

Ala Arg Ile Phe Arg Asp Gly Asn Thr Asp Tyr Val Asp Ser Val Lys
    50                  55                  60

Gly Arg Phe Thr Ile Ser Arg Asp Thr Ala Lys Asn Thr Ile Asp Leu
65                  70                  75                  80

Gln Met Asn Asn Leu Lys Pro Glu Asp Thr Ala Gly Tyr Phe Cys His
                85                  90                  95

Val His Ile Leu Gly Arg Asp Tyr Trp Gly Gln Gly Thr Gln Val Thr
            100                 105                 110

Val Ser Ser Ala Ala Ala Tyr Pro Tyr Asp Val Pro Asp Tyr Gly Ser
        115                 120                 125

His His His His His His
    130

<210> SEQ ID NO 552
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 552

Asn Phe Leu Ser Ser Arg Phe Glu
1               5

<210> SEQ ID NO 553
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 553

Ile Phe Arg Asp Gly Asn Thr
1               5

<210> SEQ ID NO 554
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 554

His Val His Ile Leu Gly Arg Asp Tyr
1               5

<210> SEQ ID NO 555
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 555

Gln Val Gln Leu Gln Glu Ser Gly Gly Gly Leu Val Gln Ala Gly Asp
1               5                   10                  15

Ser Leu Arg Ile Ser Cys Lys Ala Ser Gly Arg Thr Phe Ser Ser Tyr
            20                  25                  30

Pro Ile Gly Trp Phe Arg Gln Ala Pro Gly Lys Glu Arg Glu Phe Val
        35                  40                  45

Ala Ala Ile Ser Arg Ser Gly Gly Arg Thr Tyr Tyr Ala Asp Ser Val
    50                  55                  60

Lys Gly Arg Leu Thr Ile Ser Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Lys Thr Thr Met Gly Leu Pro Val Gly Gly Thr Tyr Glu Tyr
            100                 105                 110

Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His
    130                 135                 140

<210> SEQ ID NO 556
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 556

-continued

```
Gly Arg Thr Phe Ser Ser Tyr Pro
1               5
```

<210> SEQ ID NO 557
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 557

```
Ile Ser Arg Ser Gly Gly Arg Thr
1               5
```

<210> SEQ ID NO 558
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 558

```
Ala Ala Lys Thr Thr Met Gly Leu Pro Val Gly Gly Thr Tyr Glu Tyr
1               5                   10                  15

Asp Tyr
```

<210> SEQ ID NO 559
<211> LENGTH: 144
<212> TYPE: PRT
<213> ORGANISM: Artificial sequence
<220> FEATURE:
<223> OTHER INFORMATION: nanobody amino acid sequence

<400> SEQUENCE: 559

```
Gln Val Gln Leu Gln Glu Ser Gly Gly Gly Leu Val Gln Ala Gly Asp
1               5                   10                  15

Ser Leu Arg Ile Ser Cys Lys Ala Ser Gly Arg Thr Phe Ser Ser Tyr
                20                  25                  30

Pro Ile Gly Trp Phe Arg Gln Ala Pro Gly Lys Glu Arg Glu Phe Val
                35                  40                  45

Ala Ala Ile Ser Arg Ser Gly Gly Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Lys Thr Thr Met Gly Leu Pro Val Gly Gly Thr Tyr Glu Tyr
                100                 105                 110

Asp Tyr Trp Gly Gln Gly Thr Gln Val Thr Val Ser Ser Ala Ala Ala
        115                 120                 125

Tyr Pro Tyr Asp Val Pro Asp Tyr Gly Ser His His His His His
        130                 135                 140
```

<210> SEQ ID NO 560
<211> LENGTH: 142
<212> TYPE: PRT
<213> ORGANISM: Artificial sequence
<220> FEATURE:
<223> OTHER INFORMATION: nanobody amino acid sequence

```
<400> SEQUENCE: 560

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Ser Phe Val
        35                  40                  45

Ala Ala Ile Asp Ser Asn Gly Ser Asn Thr Tyr Tyr Ala Asp Ser Leu
    50                  55                  60

Lys Gly Arg Phe Thr Ile Ala Arg Asp Asn Ala Lys Ser Met Val Phe
65                  70                  75                  80

Leu Arg Met Asn Asn Leu Glu Pro Glu Asp Thr Ala Val Tyr Tyr Cys
                85                  90                  95

Ala Ala Gly Gln Asn Phe Trp Thr Phe Thr Thr Thr Pro Pro Pro Tyr
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His
    130                 135                 140

<210> SEQ ID NO 561
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 561

Gly Phe Thr Leu Asp Asp Tyr Ala
1               5

<210> SEQ ID NO 562
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 562

Ile Asp Ser Asn Gly Ser Asn Thr
1               5

<210> SEQ ID NO 563
<211> LENGTH: 16
<212> TYPE: PRT
<213> ORGANISM: Artificial sequence
<220> FEATURE:
<223> OTHER INFORMATION: Complementarity-determining region amino acid
      sequence

<400> SEQUENCE: 563

Ala Ala Gly Gln Asn Phe Trp Thr Phe Thr Thr Thr Pro Pro Pro Tyr
1               5                   10                  15

<210> SEQ ID NO 564
<211> LENGTH: 145
<212> TYPE: PRT
<213> ORGANISM: Artificial sequence
<220> FEATURE:
<223> OTHER INFORMATION: nanobody amino acid sequence
```

<400> SEQUENCE: 564

Gln Val Gln Leu Gln Glu Ser Gly Gly Gly Leu Val Gln Ala Gly Asp
1               5                   10                  15

Ser Leu Arg Ile Ser Cys Lys Ala Ser Gly Arg Thr Phe Ser Asn Tyr
            20                  25                  30

Pro Ile Gly Trp Phe Arg Gln Ala Pro Gly Lys Glu Arg Glu Phe Val
        35                  40                  45

Ala Ala Ile Ser Arg Ser Gly Gly Gly Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Arg Asp Asp Thr Ala Val Tyr Tyr Cys
                85                  90                  95

Ala Ala Tyr Phe Gly Asn Leu Gly Gly Gly Val Gly Arg Ser Ser Asp
            100                 105                 110

Tyr Asp Tyr Trp Gly Gln Gly Thr Gln Val Thr Val Ser Ser Ala Ala
        115                 120                 125

Ala Tyr Pro Tyr Asp Val Pro Asp Tyr Gly Ser His His His His
    130                 135                 140

His
145

<210> SEQ ID NO 565
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 565

Gly Arg Thr Phe Ser Asn Tyr Pro
1               5

<210> SEQ ID NO 566
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 566

Ile Ser Arg Ser Gly Gly Gly Thr
1               5

<210> SEQ ID NO 567
<211> LENGTH: 19
<212> TYPE: PRT
<213> ORGANISM: Artificial sequence
<220> FEATURE:
<223> OTHER INFORMATION: Complementarity-determining region amino acid
      sequence

<400> SEQUENCE: 567

Ala Ala Tyr Phe Gly Asn Leu Gly Gly Gly Val Gly Arg Ser Ser Asp
1               5                   10                  15

Tyr Asp Tyr

<210> SEQ ID NO 568
<211> LENGTH: 134

```
<212> TYPE: PRT
<213> ORGANISM: Artificial sequence
<220> FEATURE:
<223> OTHER INFORMATION: nanobody amino acid sequence

<400> SEQUENCE: 568

Gln Val Gln Leu Gln Glu Ser Gly Gly Gly Ser Val Gln Ala Gly Glu
1               5                   10                  15

Ser Leu Thr Leu Ser Cys Ala Ala Ser Asn Val Leu Val Ser Lys Phe
            20                  25                  30

Thr Val Ala Trp Phe Arg Gln Ala Pro Gly Lys Gln Arg Glu Leu Val
        35                  40                  45

Ala Asp Ile Ala Arg Ala Gly Phe Thr Ser Tyr Ala Asp Phe Val Arg
    50                  55                  60

Gly Arg Phe Ser Ile Ser Arg Asp Asn Ala Gln Asn Thr Val Thr Leu
65                  70                  75                  80

Gln Met Asn Ser Leu Thr Pro Glu Asp Thr Ala Val Tyr Tyr Cys Asn
                85                  90                  95

Cys His Val Leu Gly Arg Asp Tyr Trp Gly Gln Gly Thr Gln Val Thr
            100                 105                 110

Val Ser Ser Ala Ala Ala Tyr Pro Tyr Asp Val Pro Asp Tyr Gly Ser
            115                 120                 125

His His His His His His
    130

<210> SEQ ID NO 569
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 569

Asn Val Leu Val Ser Lys Phe Thr
1               5

<210> SEQ ID NO 570
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 570

Ile Ala Arg Ala Gly Phe Thr
1               5

<210> SEQ ID NO 571
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 571

Asn Cys His Val Leu Gly Arg Asp Tyr
1               5

<210> SEQ ID NO 572
<211> LENGTH: 134
```

```
<212> TYPE: PRT
<213> ORGANISM: Artificial sequence
<220> FEATURE:
<223> OTHER INFORMATION: nanobody amino acid sequence

<400> SEQUENCE: 572

Gln Val Gln Leu Gln Glu Ser Gly Gly Gly Ser Val Gln Pro Gly Gly
1               5                   10                  15

Ser Leu Arg Leu Ser Cys Ala Ala Ser Ile Arg Thr Phe Ser Thr Tyr
            20                  25                  30

Ala Phe Ala Trp Tyr Arg Gln Ala Pro Gly Lys Gln Arg Glu Leu Val
            35                  40                  45

Ala Gly Ile Ser Ser Gly Ser Arg Thr Asn Tyr Ala Asp Ser Val Lys
        50                  55                  60

Gly Arg Phe Thr Ile Ser Arg Asp Asn Ala Lys Lys Thr Val Tyr Leu
65                  70                  75                  80

Gln Met Asn Asn Leu Gln Pro Glu Asp Thr Ala Val Tyr Tyr Cys Thr
                85                  90                  95

Lys Gly Arg Thr Asn Ile Asp Tyr Trp Gly Gln Gly Thr Gln Val Thr
                100                 105                 110

Val Ser Ser Ala Ala Ala Tyr Pro Tyr Asp Val Pro Asp Tyr Gly Ser
            115                 120                 125

His His His His His His
        130

<210> SEQ ID NO 573
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 573

Ile Arg Thr Phe Ser Thr Tyr Ala
1               5

<210> SEQ ID NO 574
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 574

Ile Ser Ser Gly Ser Arg Thr
1               5

<210> SEQ ID NO 575
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 575

Thr Lys Gly Arg Thr Asn Ile Asp Tyr
1               5

<210> SEQ ID NO 576
<211> LENGTH: 144
```

```
<212> TYPE: PRT
<213> ORGANISM: Artificial sequence
<220> FEATURE:
<223> OTHER INFORMATION: nanobody amino acid sequence

<400> SEQUENCE: 576

Gln Val Gln Leu Gln Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
            35                  40                  45

Ala Thr Ile Ser Thr Gly Gly Thr Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Gly Leu Lys Pro Glu Asp Thr Ala Val Tyr Tyr Cys
                85                  90                  95

Ala Ala Lys Met Ala Thr Gly Thr Ala Ser Ile Arg Thr Tyr Glu Tyr
            100                 105                 110

Ala Tyr Trp Gly Gln Gly Thr Gln Val Thr Val Ser Ser Ala Ala Ala
            115                 120                 125

Tyr Pro Tyr Asp Val Pro Asp Tyr Gly Ser His His His His His His
    130                 135                 140

<210> SEQ ID NO 577
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 577

Ile Ser Thr Gly Gly Gly Thr Thr
1               5

<210> SEQ ID NO 578
<211> LENGTH: 18
<212> TYPE: PRT
<213> ORGANISM: Artificial sequence
<220> FEATURE:
<223> OTHER INFORMATION: Complementarity-determining region amino acid
      sequence

<400> SEQUENCE: 578

Ala Ala Lys Met Ala Thr Gly Thr Ala Ser Ile Arg Thr Tyr Glu Tyr
1               5                   10                  15

Ala Tyr

<210> SEQ ID NO 579
<211> LENGTH: 142
<212> TYPE: PRT
<213> ORGANISM: Artificial sequence
<220> FEATURE:
<223> OTHER INFORMATION: nanobody amino acid sequence

<400> SEQUENCE: 579

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

```
Ala Met Gly Trp Phe Arg Gln Thr Pro Gly Lys Glu Arg Glu Phe Val
        35                  40                  45

Ala Ala Ile Leu Trp Gly Gly Val Ile Ala Asp Ser Val Lys Gly Arg
        50                  55                  60

Phe Thr Ile Ser Arg Asp Asn Ala Lys Asn Thr Val Asp Leu Gln Met
65                  70                  75                  80

Phe Ser Leu Lys Pro Glu Asp Thr Ala Val Tyr Tyr Cys Ala Arg Arg
                85                  90                  95

Arg Gly Gly Leu Asn Asn His Leu Gly Ser Val Gly Asn Tyr Asp Tyr
                100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His
    130                 135                 140
```

```
<210> SEQ ID NO 580
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 580

Gly Phe Thr Phe Ser Arg Tyr Ala
1               5
```

```
<210> SEQ ID NO 581
<211> LENGTH: 6
<212> TYPE: PRT
<213> ORGANISM: Artificial sequence
<220> FEATURE:
<223> OTHER INFORMATION: Complementarity-determining region amino acid
      sequence

<400> SEQUENCE: 581

Ile Leu Trp Gly Gly Val
1               5
```

```
<210> SEQ ID NO 582
<211> LENGTH: 19
<212> TYPE: PRT
<213> ORGANISM: Artificial sequence
<220> FEATURE:
<223> OTHER INFORMATION: Complementarity-determining region amino acid
      sequence

<400> SEQUENCE: 582

Ala Arg Arg Arg Gly Gly Leu Asn Asn His Leu Gly Ser Val Gly Asn
1               5                   10                  15

Tyr Asp Tyr
```

```
<210> SEQ ID NO 583
<211> LENGTH: 134
<212> TYPE: PRT
<213> ORGANISM: Artificial sequence
<220> FEATURE:
<223> OTHER INFORMATION: nanobody amino acid sequence

<400> SEQUENCE: 583

Gln Val Gln Leu Gln Glu Ser Gly Gly Gly Ser Val Gln Pro Gly Gly
1               5                   10                  15
```

```
Ser Leu Arg Leu Ser Cys Glu Ile Ile Gly Ala Thr Val Ser Ser Ser
        20                  25                  30

Ser Met Ala Trp Tyr Arg Gln Ala Pro Gly Leu Gln Arg Glu Leu Val
        35                  40                  45

Ala Gly Ile Thr Thr Pro Ser Asn Pro His Tyr Ala Ala Ser Val Arg
    50                  55                  60

Gly Arg Phe Thr Ile Ser Arg Asp Gly Ala Arg Asn Leu Asn Tyr Leu
65                  70                  75                  80

Gln Ile Asp Ser Ala Lys Pro Glu Asp Thr Ala Val Tyr Tyr Cys His
                85                  90                  95

Ala Ala Ile Arg Gly Ser Ile Tyr Arg Gly Gln Gly Thr Gln Val Thr
            100                 105                 110

Val Ser Ser Ala Ala Ala Tyr Pro Tyr Asp Val Pro Asp Tyr Gly Ser
        115                 120                 125

His His His His His His
    130
```

```
<210> SEQ ID NO 584
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 584

Gly Ala Thr Val Ser Ser Ser Ser
1               5
```

```
<210> SEQ ID NO 585
<211> LENGTH: 7
<212> TYPE: PRT
<213> ORGANISM: Artificial sequence
<220> FEATURE:
<223> OTHER INFORMATION: Complementarity-determining region amino acid
      sequence

<400> SEQUENCE: 585

Ile Thr Thr Pro Ser Asn Pro
1               5
```

```
<210> SEQ ID NO 586
<211> LENGTH: 9
<212> TYPE: PRT
<213> ORGANISM: Artificial sequence
<220> FEATURE:
<223> OTHER INFORMATION: Complementarity-determining region amino acid
      sequence

<400> SEQUENCE: 586

His Ala Ala Ile Arg Gly Ser Ile Tyr
1               5
```

```
<210> SEQ ID NO 587
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 587

Gln Val Gln Leu Gln Glu Ser Gly Gly Gly Leu Val Gln Ala Gly Gly
1               5                   10                  15
```

-continued

```
Ser Leu Arg Leu Ser Cys Ala Thr Ser Gly Arg Ala Phe Thr Asn Tyr
        20                  25                  30

His Met Gly Trp Phe Arg Gln Thr Pro Gly Lys Glu Arg Glu Phe Val
        35                  40                  45

Ala Leu Ile Ser Trp Ser Gly Asp Ser Thr Arg Tyr Ala Asp Ser Val
        50                  55                  60

Lys Gly Arg Phe Thr Ile Ser Arg Asp Asn Ala Lys Arg Thr Val Ala
65                  70                  75                  80

Leu Gln Met Asp Ser Leu Lys Pro Glu Asp Ser Ala Val Tyr Tyr Cys
                85                  90                  95

Ala Ser Arg Leu Val Gly Gln Ser Gln Tyr Glu Val Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
        130                 135
```

<210> SEQ ID NO 588
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 588

```
Gly Arg Ala Phe Thr Asn Tyr His
1               5
```

<210> SEQ ID NO 589
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 589

```
Ile Ser Trp Ser Gly Asp Ser Thr
1               5
```

<210> SEQ ID NO 590
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 590

```
Ala Ser Arg Leu Val Gly Gln Ser Gln Tyr Glu Val
1               5                   10
```

<210> SEQ ID NO 591
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 591

```
Gln Val Gln Leu Gln Glu Ser Gly Gly Gly Leu Val Gln Ala Gly Gly
1               5                   10                  15
```

Ser Leu Arg Leu Ser Cys Ala Ala Ser Gly Arg Ala Phe Thr Asn Tyr
        20                  25                  30

His Met Gly Trp Phe Arg Gln Thr Pro Gly Lys Glu Arg Glu Phe Val
        35                  40                  45

Ala Leu Ile Ser Trp Ser Gly Asp Ser Thr Arg Tyr Ala Asp Ser Val
    50                  55                  60

Lys Gly Arg Phe Thr Ile Ser Arg Asp Asn Ala Lys Arg Thr Val Ala
65                  70                  75                  80

Leu Gln Met Asp Ser Leu Lys Pro Glu Asp Ser Ala Val Tyr Tyr Cys
                85                  90                  95

Ala Ser Arg Leu Val Gly Gln Ser Gln Tyr Glu Ile Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 592
<211> LENGTH: 12
<212> TYPE: PRT
<213> ORGANISM: Artificial sequence
<220> FEATURE:
<223> OTHER INFORMATION: Complementarity-determining region amino acid
      sequence

<400> SEQUENCE: 592

Ala Ser Arg Leu Val Gly Gln Ser Gln Tyr Glu Ile
1               5                   10

<210> SEQ ID NO 593
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 593

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ala Phe Thr Asn Tyr
        20                  25                  30

His Met Gly Trp Phe Arg Gln Thr Pro Gly Lys Glu Arg Glu Phe Val
        35                  40                  45

Ala Leu Ile Ser Trp Ser Gly Asp Ser Thr Arg Tyr Ala Asp Ser Val
    50                  55                  60

Lys Gly Arg Phe Thr Ile Ser Arg Asp Asn Ala Lys Arg Thr Val Ala
65                  70                  75                  80

Leu Gln Met Asp Ser Leu Lys Pro Glu Asp Ser Ala Val Tyr Tyr Cys
                85                  90                  95

Ala Ser Arg Leu Val Gly Gln Ser Gln Tyr Glu Val Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 594
<211> LENGTH: 138
<212> TYPE: PRT

<213> ORGANISM: Artificial sequence
<220> FEATURE:
<223> OTHER INFORMATION: nanobody amino acid sequence

<400> SEQUENCE: 594

Gln Val Gln Leu Gln Glu Ser Gly Gly Gly Leu Val Gln Ala Gly Gly
1               5                   10                  15

Ser Leu Arg Leu Ser Cys Ala Ala Ser Thr Arg Ala Phe Thr Asn Tyr
            20                  25                  30

His Met Gly Trp Phe Arg Gln Thr Pro Gly Lys Glu Arg Glu Phe Val
        35                  40                  45

Ala Leu Ile Ser Trp Ser Gly Asp Ser Thr Arg Tyr Ala Asp Ser Val
    50                  55                  60

Lys Gly Arg Phe Thr Ile Ser Arg Asp Asn Ala Lys Arg Thr Val Ala
65                  70                  75                  80

Leu Gln Met Asp Ser Leu Lys Pro Glu Asp Ser Ala Val Tyr Tyr Cys
                85                  90                  95

Ala Ser Arg Leu Val Gly Gln Ser Gln Tyr Glu Ile Trp Gly Gln Gly
            100                 105                 110

Thr Gln Val Thr Val Ser Ser Ala Ala Ala Tyr Pro Tyr Asp Val Pro
        115                 120                 125

Asp Tyr Gly Ser His His His His His His
    130                 135

<210> SEQ ID NO 595
<211> LENGTH: 8
<212> TYPE: PRT
<213> ORGANISM: Artificial sequence
<220> FEATURE:
<223> OTHER INFORMATION: Complementarity-determining region amino acid
      sequence

<400> SEQUENCE: 595

Thr Arg Ala Phe Thr Asn Tyr His
1               5

<210> SEQ ID NO 596
<211> LENGTH: 138
<212> TYPE: PRT
<213> ORGANISM: Artificial sequence
<220> FEATURE:
<223> OTHER INFORMATION: nanobody amino acid sequence

<400> SEQUENCE: 596

Gln Val Gln Leu Gln Glu Ser Gly Gly Gly Leu Val Gln Thr Gly Gly
1               5                   10                  15

Ser Leu Arg Leu Ser Cys Ala Ala Ser Gly Arg Ala Phe Thr Asn Tyr
            20                  25                  30

His Met Gly Trp Phe Arg Gln Thr Pro Gly Lys Glu Arg Glu Phe Val
        35                  40                  45

Ala Leu Ile Ser Trp Ser Gly Asp Ser Thr Arg Tyr Ala Asp Ser Val
    50                  55                  60

Lys Gly Arg Phe Thr Ile Ser Arg Asp Asn Ala Lys Arg Thr Val Ala
65                  70                  75                  80

Leu Gln Met Asp Ser Leu Lys Pro Glu Asp Ser Ala Val Tyr Tyr Cys
                85                  90                  95

Ala Ser Arg Leu Val Gly Gln Ser Gln Tyr Glu Val Trp Gly Gln Gly
            100                 105                 110

Thr Gln Val Thr Val Ser Ser Ala Ala Ala Tyr Pro Tyr Asp Val Pro

-continued

```
        115                 120                 125

Asp Tyr Gly Ser His His His His His His
    130                 135
```

INSECT CONTROL NANOBODIES AND USES THEREOF

RELATED APPLICATIONS

This application is a National Phase of PCT Patent Application No. PCT/IL2020/051170 having the International filing date of Nov. 11, 2020, which claims the benefit of priority under 35 USC § 119(e) of U.S. Provisional Patent Application No. 62/933,533 filed on Nov. 11, 2019. The contents of the above applications are all incorporated by reference as if fully set forth herein in their entirety.

SEQUENCE LISTING STATEMENT

The ASCII file, entitled 92382SequenceListing.txt, created on 2022, 10 May, comprising 387,592 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to insect control nanobodies and uses thereof.

Management of insect pests in the past 70 years has been achieved mainly through application of synthetic pesticides. Since the discovery of the insecticidal properties of DDT by Paul Müller in 1939, hundreds of insecticidal compounds have been developed, accompanied by a relatively steady increase in insecticide use. Most of the currently used chemical insecticides have a high potential for damaging the ecosystem, they are toxic to humans directly or through the food chain and their use is also impeded by development of genetic insect resistance. The most prominent biological solutions currently in use include beneficial organisms or natural enemies that reduce harm caused by insects, pheromones that act as bait or harm reproduction, release of sterile males, spraying with *Bacillus thuringiensis* toxin or genetically modified crops containing a gene for *Bacillus thuringiensis* toxin that is lethal to the insects but not to humans. However, these biological solutions also have disadvantage, including low efficiency, danger of violating the natural ecological balance and development genetic insect resistance (e.g. in the case of the use of *Bacillus* toxin).

Nanobodies, also known as VHH antibodies, are single domain antibodies which practically contain the heavy chain of an antibody (HCAb) and completely lack the light chain. They were discovered in the blood of camels by Raymond Hamers who was credited with this discovery in 1989 at Vrije Universiteit Brussel. Nanobodies are the smallest available intact antigen binding fragment (Cortez-Retamozo et al., 2004; Revets et al., 2005) with a size of approximately 15 kDa. The nanobodies have significant advantages including high production yield in a broad variety of expression systems, their minimal size allows high accessibility to their epitopes, high physical-chemical stability, reversible refolding and high solubility in aqueous solutions, highly homogenous showing no signs of spontaneous dimerization and ability to specifically recognize unique epitopes with sub-nanomolar affinities. The use of nanobodies as insecticides has been previously suggested (see e.g. EP Patent Application Publication Nos: EP3415010 and EP2609116; US Patent Publication No: U.S. Pat. No. 9,516,879; US Patent Application Publication No: U.S. Pat. No. 9,803,003B2; and International Patent Application Publication No. WO2014191146).

SUMMARY OF THE INVENTION

According to an aspect of some embodiments of the present invention there is provided a nanobody which specifically binds to an insect polypeptide selected from the group consisting of:

(i) a polypeptide comprising a chitin binding domain (CBD), wherein the nanobody binds the CBD;

(ii) V-ATPase subunit c, wherein the nanobody comprises complementarity determining regions (CDRs) as set forth in SEQ ID NOs: 167-169; 171 and 168-169; 174 and 168-169; 167, 178 and 169; or 180-182 arranged in a sequential order from N to C on the nanobody;

(iii) trehalase;

(iv) cytochrome p450 monooxygenase;

(v) chitin deacetylase;

(vi) chitin synthase; and (vii) NPC1 sterol transporter, wherein binding of the nanobody to the insect polypeptide confers an insect control activity to the nanobody.

According to an aspect of some embodiments of the present invention there is provided a composition comprising a nanobody which specifically binds to an insect polypeptide selected from the group consisting of:

(i) a polypeptide comprising a chitin binding domain (CBD), wherein the nanobody binds the CBD;

(ii) V-ATPase subunit c, wherein the nanobody comprises complementarity determining regions (CDRs) as set forth in SEQ ID NOs: 167-169; 171 and 168-169; 174 and 168-169; 167, 178 and 169; 180-182; 187-189; or 191-193 arranged in a sequential order from N to C on the nanobody;

(iii) trehalase;

(iv) cytochrome p450 monooxygenase;

(v) chitin deacetylase;

(vi) chitin synthase; and (vii) NPC1 sterol transporter, and a toxin moiety having an insect control activity.

According to some embodiments of the invention, the binding of the nanobody to the insect polypeptide confers an insect control activity to the nanobody.

According to some embodiments of the invention, the nanobody downregulates activity of the insect polypeptide.

According to some embodiments of the invention, the nanobody or the composition being formulated for delivery by spraying, irrigation and/or fumigation.

According to some embodiments of the invention, the CBD is type 2 chitin-binding domain (ChtBD2).

According to some embodiments of the invention, the CBD comprises an amino acid sequence selected form the group consisting of SEQ ID NO: 3-7.

According to some embodiments of the invention, the nanobody specifically binds the CBD and comprises complementarity determining regions (CDRs) as set forth in SEQ ID NOs: 15-17; 19-21; 23-25; or 15 and 28-29 arranged in a sequential order from N to C on the nanobody.

According to some embodiments of the invention, the nanobody specifically binds the CBD and comprises complementarity determining regions (CDRs) as set forth in SEQ ID NOs: 15-17; 19-21; 23-25; 15 and 28-29; 31-33; 35-37; 39-41; 43-45; 47-49; 51-53; 55-57; 59-61; 63-65; 67-69; 71-73; 75-77; 79-81; 83-85; 87-89; 91, 80 and 93; 95-97; 99-101; 103-105; 107-109; 111-113; 115-117; 119-

121; 123-125; 127-129; 131-133; 135-137; 139-141; 143-145; 147-149; 151-153; 15 and 156-157; 159-161; or 163-165 arranged in a sequential order from N to C on the nanobody.

According to some embodiments of the invention, the nanobody specifically binds the V-ATPase subunit c and comprises complementarity determining regions (CDRs) as set forth in SEQ ID NOs: 167-169; 171 and 168-169; 174 and 168-169; 167, 178 and 169; or 180-182 arranged in a sequential order from N to C on the nanobody.

According to some embodiments of the invention, the nanobody specifically binds the trehalase and comprises complementarity determining regions (CDRs) as set forth in SEQ ID NOs: 195-197; 199 and 196-197; 201-203; 201 and 205-206; 208-210; 212 and 209-210; 215-217; 219-221; 223-225; 227-229; 231, 228 and 232; 234-236; 238-240; 242-244; 246-248; 250-252; 254-256; 258-260; 588-590; 5889-589 and 592; or 595, 589 and 592 arranged in a sequential order from N to C on the nanobody.

According to some embodiments of the invention, the nanobody specifically binds the trehalase and comprises complementarity determining regions (CDRs) as set forth in SEQ ID NOs: 195-197; 199 and 196-197; 201-203; 201 and 205-206; 208-210; 212 and 209-210; 215-217; 219-221; 223-225; 227-229; 231, 228 and 232; 234-236; 238-240; 242-244; 246-248; 250-252; 254-256; or 258-260 arranged in a sequential order from N to C on the nanobody.

According to some embodiments of the invention, the nanobody specifically binds the trehalase and comprises complementarity determining regions (CDRs) as set forth in SEQ ID NOs: 201 and 205-206; 208-210; 212 and 209-210; 223-225; 238-240; 242-244; 246-248; 588-590; or 595, 589 and 592 arranged in a sequential order from N to C on the nanobody.

According to some embodiments of the invention, the nanobody specifically binds the cytochrome p450 monooxygenase and comprises complementarity determining regions (CDRs) as set forth in SEQ ID NOs: 262-264; 262-263 and 266; 262, 270 and 264; 274-276; 280 and 275-276; 282 and 275-276; 282, 275 and 285; 287, 220 and 289; 291, 220 and 289; 239-294 and 289; 296-298; 300-302; 304-306; 308-310; 312-314; or 316-318 arranged in a sequential order from N to C on the nanobody.

According to some embodiments of the invention, the nanobody specifically binds the cytochrome p450 monooxygenase and comprises complementarity determining regions (CDRs) as set forth in SEQ ID NOs: 262-264; 287, 220 and 289; 296-298; 300-302; 304-306; or 312-314 arranged in a sequential order from N to C on the nanobody.

According to some embodiments of the invention, the nanobody specifically binds the chitin deacetylase and comprises complementarity determining regions (CDRs) as set forth in SEQ ID NOs: 320-322; 320 and 324-325; 327, 321 and 328; 320-321 and 332; 208 and 336-337; 320, 324 and 339; 343-345; 347-349; 351-353; 351, 347 and 356; 358-360; 358-359 and 362; 365, 359 and 366; 368-370; 372 and 369-370; 374, 369 and 375; 377-379; 381-383; 385 and 382-383; 387-389; 387, 391 and 389; 394-396; 398-400; 402-404; or 406-408 arranged in a sequential order from N to C on the nanobody.

According to some embodiments of the invention, the nanobody specifically binds the chitin deacetylase and comprises complementarity determining regions (CDRs) as set forth in SEQ ID NOs: 320-322; 320 and 324-325; 372 and 369-370; 374, 369 and 375; 377-379; 387-389; or 398-400 arranged in a sequential order from N to C on the nanobody.

According to some embodiments of the invention, the nanobody specifically binds the chitin synthase and comprises complementarity determining regions (CDRs) as set forth in SEQ ID NOs: 412-414; 418-420; 422-424; 426-428; 426-427 and 430; 432-434; 436, 140 and 437; 439-441; 443-445; 447-449; 356 and 451-452; 454-456; 458-460; 462-464; 466-468; 470-472; 474-476; 478-480; 482, 479 and 483; 485-487; 489-491; 493-495; 426 and 497-498; 500-502; 504-506; or 508-510 arranged in a sequential order from N to C on the nanobody.

According to some embodiments of the invention, the nanobody specifically binds the chitin synthase and comprises complementarity determining regions (CDRs) as set forth in SEQ ID NOs: 412-414; 418-420; 426-428; 432-434; 443-445; 447-449; 466-468; 482, 479 and 483; 426 and 497-498; or 504-506 arranged in a sequential order from N to C on the nanobody.

According to some embodiments of the invention, the nanobody specifically binds the NPC1 sterol transporter and comprises complementarity determining regions (CDRs) as set forth in SEQ ID NOs: 512-514; 517 and 513-514; 521-523; 521-522 and 526; 531-533; 539-541; 485 and 540-541; 545 and 540-451; 547-549; 552-554; 556-558; 561-563; 565-567; 569-571; 573-575; 485 and 577-578; 580-582; or 584-586 arranged in a sequential order from N to C on the nanobody.

According to some embodiments of the invention, the nanobody specifically binds the NPC1 sterol transporter and comprises complementarity determining regions (CDRs) as set forth in SEQ ID NOs: 517 and 513-514; 485 and 540-541; 545 and 540-541; 556-558; 565-567; 573-575; 485 and 577-578; or 580-582 arranged in a sequential order from N to C on the nanobody.

According to an aspect of some embodiments of the present invention there is provided a polynucleotide encoding the nanobody or the composition.

According to an aspect of some embodiments of the present invention there is provided a nucleic acid construct comprising the polynucleotide and a cis-acting regulatory element for directing expression of the polynucleotide.

According to an aspect of some embodiments of the present invention there is provided a host cell comprising the nanobody or the composition or a polynucleotide or a nucleic acid construct encoding it.

According to an aspect of some embodiments of the present invention there is provided a method of producing an insect control nanobody, the method comprising expressing in a host cell the polynucleotide or the nucleic acid construct.

According to some embodiments of the invention, the method comprising isolating the nanobody.

According to an aspect of some embodiments of the present invention there is provided a method of insect control, the method comprising contacting the insect with the nanobody or the composition, a polynucleotide or a nucleic acid construct encoding same or a host cell expressing same.

According to some embodiments of the invention, the contacting comprises applying the nanobody or the composition directly to the insect.

According to some embodiments of the invention, the contacting comprises applying the nanobody or the composition to an organism or a surface, which may be in contact with the insect.

According to some embodiments of the invention, the nanobody or the composition is formulated as a liquid formulation.

According to some embodiments of the invention, the nanobody or the composition is formulated as a dry formulation.

According to an aspect of some embodiments of the present invention there is provided a plant comprising the nanobody or the composition or a polynucleotide or a nucleic acid construct encoding it.

According to some embodiments of the invention, the plant being a transgenic plant.

According to an aspect of some embodiments of the present invention there is provided a commodity product comprising the nanobody or the composition.

According to some embodiments of the invention, the commodity product is produced from the plant.

According to an aspect of some embodiments of the present invention there is provided a method of producing a nanobody, the method comprising immunizing a camelid with a recombinant or purified insect polypeptide selected from the group consisting of:

(i) a polypeptide comprising a chitin binding domain (CBD);
    (ii) V-ATPase subunit c;
    (iii) trehalase;
    (iv) cytochrome p450 monooxygenase;
    (v) chitin deacetylase;
    (vi) chitin synthase; and
    (vii) NPC1 sterol transporter,
    wherein purity of the insect polypeptide in an insect polypeptide preparation is at least 80%.

According to some embodiments of the invention, the method comprising isolating the antibody following the immunizing.

According to some embodiments of the invention, the camelid is a llama.

According to some embodiments of the invention, the insect is selected from the group consisting of moth, stinkbug, hopper, beetle, aphid and honeybee.

According to some embodiments of the invention, the insect is a moth.

According to some embodiments of the invention, the moth is selected from the group consisting of *Helicoverpa armigera* and *Spodoptera frugiperda*.

According to some embodiments of the invention, the moth is *Helicoverpa armigera*.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A demonstrates fluorescently labeled nanobody tracked in larvae food following 48 hours and 6 days of incubation with larvae. The upper panel shows bright field images and the lower panel shows images reflecting the Cy3 signal of food fed to larvae. In addition, the yellow dashed line represents two different areas, the right side of the dashed line signals intact food, while the left side of the dashed line signals larvae feces. Differences in fluorescents intensity between food and feces represent uptake by larvae's gut. FIG. 5B demonstrates presence of the Cy5-labeled CB20901 nanobody throughout the intestinal track of live larvae following 48 hours of incubation with food containing the Cy3-labeled nanobody or following 36 hours of incubation with food containing the Cy3-labeled nanobody followed by 12 hours incubation with food not containing the nanobody, as indicated. FIG. 5C demonstrates presence of the Cy5-labeled CB20901 nanobody in larvae gut and specifically the peritrophic membrane following 36 hours of incubation with food containing the Cy3-labeled nanobody followed by 12 hours incubation with food not containing the nanobody as compared to larvae fed with food not containing the nanobody for 48 hours, as indicated. The upper panel shows bright field images and the lower panel shows images reflecting the Cy3 signal.

(FIG. 11B), as compared to room temperature (RT) control, as determined by ELISA. Each treatment included three repetitions; data is presented as average ±SE.

(FIG. 16B), as compared to room temperature (RT) control, as determined by ELISA. Each treatment included three repetitions; data is presented as average ±SE.

(FIG. 19B), as compared to room temperature (RT) control, as determined by ELISA. Each treatment included three repetitions; data is presented as average ±SE.

DESCRIPTION OF SPECIFIC EMBODIMENTS OF THE INVENTION

Figure 1:
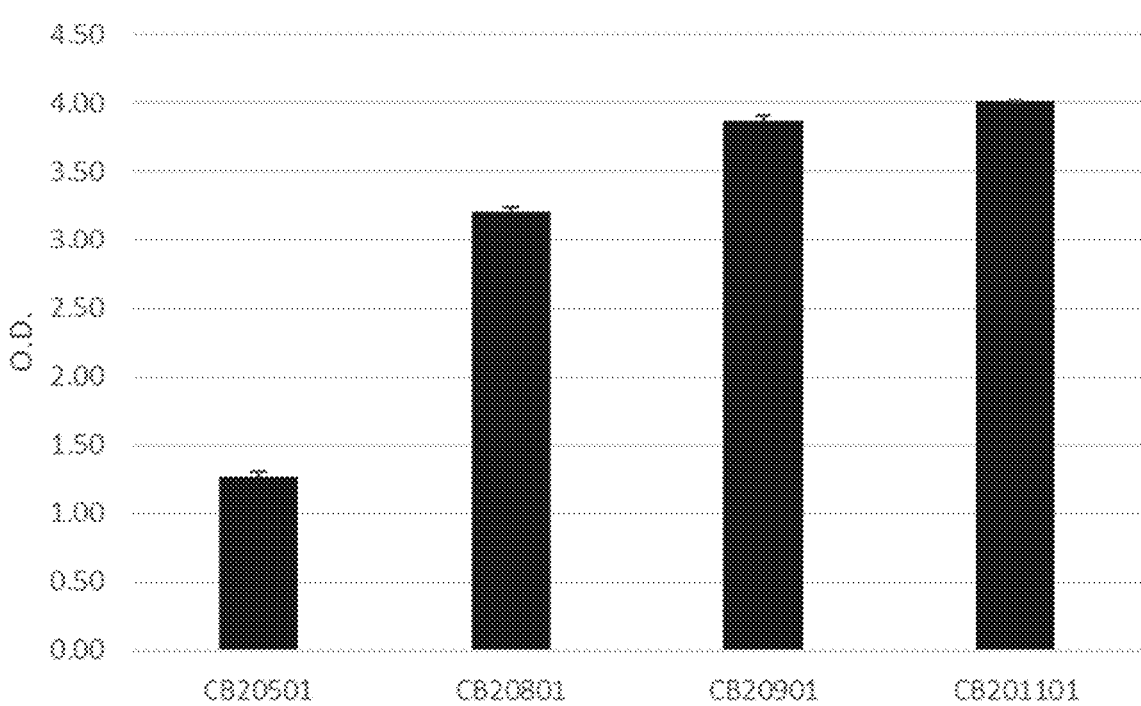
FIG. 1 is a graph demonstrating specific binding of the generated anti-CBD nanobodies referred to herein as CB20501, CB20801, CB20901 and CB201101 to the target CBD antigen, as determined by ELISA. Each experiment was performed five times; data is presented as average ±SE.

The present invention, in some embodiments thereof, relates to insect control nanobodies and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Management of insect pests in the past 70 years has been achieved mainly through application of synthetic pesticides, most of them have a high potential for damaging the ecosystem, they are toxic to humans directly or through the food chain and their use is also impeded by development of genetic insect resistance. The most prominent biological solutions currently in use also have many disadvantages, including low efficiency, danger of violating the natural ecological balance and development genetic insect resistance.

Whilst reducing the present invention to practice, the present inventors have now developed nanobodies targeting several insect polypeptides having insect control activities. Consequently, specific embodiments of the present teachings suggest their use as insecticides.

Thus, according to a first aspect of the present invention, there is provided a nanobody which specifically binds to an insect polypeptide selected from the group consisting of:

(i) a polypeptide comprising a chitin binding domain (CBD), wherein said nanobody binds said CBD;

(ii) V-ATPase subunit c, wherein said nanobody comprises complementarity determining regions (CDRs) as set forth in SEQ ID NOs: 167-169; 171 and 168-169; 174 and 168-169; 167, 178 and 169; or 180-182 arranged in a sequential order from N to C on said nanobody;

(iii) trehalase;

(iv) cytochrome p450 monooxygenase;

(v) chitin deacetylase;

(vi) chitin synthase; and (vii) NPC1 sterol transporter, wherein binding of said nanobody to said insect polypeptide confers an insect control activity to said nanobody.

According to an additional or an alternative aspect of the present invention, there is provided a composition comprising a nanobody, which specifically binds to an insect polypeptide selected from the group consisting of:

(i) a polypeptide comprising a chitin binding domain (CBD), wherein said nanobody binds said CBD;

(ii) V-ATPase subunit c, wherein said nanobody comprises complementarity determining regions (CDRs) as set forth in SEQ ID NOs: 167-169; 171 and 168-169; 174 and 168-169; 167, 178 and 169; 180-182; 187-189; or 191-193 arranged in a sequential order from N to C on said nanobody;

(iii) trehalase;

(iv) cytochrome p450 monooxygenase;

(v) chitin deacetylase;

(vi) chitin synthase; and (vii) NPC1 sterol transporter, and a toxin moiety having an insect control activity.

As used herein, the term "nanobody" refers to a single-domain antigen binding fragment.

According to a specific embodiment, the nanobody is a single variable domain derived from naturally occurring heavy chain of an antibody. Nanobodies are usually derived from heavy chain only antibodies (devoid of light chains) seen in camelids (Hamers-Casterman et al., 1993, Nature 363: 446-448; Desmyter et al., 1996, Nat. Struct. Biol. 803-811) and consequently are often referred to as VHH antibody or VHH sequence. Camelids comprise old world camelids (*Camelus bactrianus* and *Camelus dromedarius*) and new world camelids (for example, *Lama paccos, Lama glama, Lama guanicoe* and *Lama vicugna*). Non-limiting examples of camelids include dromedary camels, Bactrian camels, wild Bactrian camels, llamas, alpacas, vicunas, and guanacos. According to specific embodiments, the camelid is a llama.

NANOBODY® and NANOBODIES® are registered trademarks of Ablynx NV (Belgium).

For a further description of VHH's or Nanobodies, reference is made to the book "Single domain antibodies," Methods in Molecular Biology, Eds. Saerens and Muyldermans, 2012, Vol. 911, in particular to the Chapter by Vincke and Muyldermans (2012), as well as to a non-limiting list of patent applications, which are mentioned as general background art, and include: WO 94/04678, WO 95/04079, WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever, WO 97/49805, WO 01/21817, WO 03/035694, WO 03/054016 and WO 03/055527 of the Vlaams Instituut voor Biotechnologie (VIB); WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. As will be known by the person skilled in the art, the nanobodies are particularly characterized by the presence of one or more Camelidae "hallmark residues" in one or more of the framework sequences (according to Kabat numbering), as described, for example, in WO 08/020079, on page 75, Table A-3, incorporated herein by reference.

According to a specific embodiment, the nanobody refers to an intact molecule (i.e. comprising 4 frameworks regions and 3 complementarity-determining regions) or a functional fragment thereof capable of binding to an epitope of the antigen to which the intact molecule binds.

As used herein, the term "epitope" refers to any antigenic determinant on an antigen to which the paratope of a nanobody binds. Epitopic determinants usually consist of chemically active surface groupings of molecules such as amino acids or carbohydrate side chains and usually have specific three dimensional structural characteristics, as well as specific charge characteristics.

According to specific embodiments, the nanobody is a whole or intact nanobody.

According to specific embodiments, the nanobody is a nanobody fragment.

According to specific embodiments, the size of the nanobody is 5-30 kDa, 10-30 Kda or 10-20 Kda.

According to specific embodiments, the size of the nanobody is about 15 kDa.

The term "nanobody" also encompasses natural or synthetic analogs, homologous, mutants and variants of a nanobody.

Generally, intact nanobodies comprise three complementarity-determining region (CDRs) (CDR1; CDR2; and CDR3).

As used herein, the terms "complementarity-determining region" or "CDR" are used interchangeably to refer to the antigen binding regions found within the variable region of the heavy chain polypeptide. The identity of the amino acid residues in a particular nanobody that make up a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), as applied to $V_{HH}$ domains from Camelids in the article of Riechmann and Muyldermans (1999), location of the structural loop regions as defined by Chothia et al. (see, e.g., Chothia et al., Nature 342:877-883, 1989), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "CDRs" may refer to CDRs defined by any approach known in the art, including combinations of approaches.

According to specific embodiments, the CDR is as defined by Kabat et al. as applied to $V_{HH}$ domains from Camelids in the article of Riechmann and Muyldermans (1999).

The nanobody may be mono-specific (capable of recognizing one epitope or protein), bi-specific (capable of binding two epitopes or proteins) or multi-specific (capable of recognizing multiple epitopes or proteins).

According to specific embodiments, the nanobody is a mono-specific nanobody.

According to specific embodiments, the nanobody is a multi-specific e.g. bi-specific, tri-specific, tetra-specific.

According to specific embodiments, the nanobody is a bi-specific nanobody. Methods of generating bi-specific nanobodies are known in the art and disclosed e.g., in Deffar K, Shi H, Li L, Wang X, Zhu X (2009) Afr J Biotechnol 8(12):2645-2652); and Zhu, Y. et al. (2017). *Scientific reports*, 7(1), 2602; the contents of which are fully incorporated herein by reference.

The nanobodies disclosed herein specifically bind an insect polypeptide described herein.

Preferably, the nanobody specifically binds at least one epitope of an insect polypeptide described herein.

Assays for testing binding are well known in the art and include, but not limited to ELISA, radioimmunoassays (RIA), flow cytometry, BiaCore, bio-layer interferometry Blitz® assay, HPLC.

According to specific embodiments, the nanobody binds the insect polypeptide with a Kd $\leq 10^{-6}$ M, $\leq 10^{-7}$ M, $\leq 10^{-8}$ M, $\leq 10^{-9}$ M, each possibility represents a separate embodiment of the present invention.

According to specific embodiments, the nanobody is capable of binding to the insect polypeptide under open field or controlled conditions, e.g., greenhouse.

The term "insect" is used herein in the broad popular sense and includes all species of the superphylum Panarthropoda (classification Systema Naturae, Brands, S. J. (comp.) 1989-2005. Systema Naturae 2000. Amsterdam, The Netherlands, [www(dot)sn2000(dot)taxonomy(dot) n1/]), including the phyla Arthropoda, Tardigrada and Onychophora; and includes all the different phases of the life cycle, such as, but not limited to eggs, larvae, nymphs, pupae and adults. According to specific embodiments, the insect belongs to the phylum Arthropoda (including, but not limited to the orders Archaeognatha, Thysanura, Paleoptera and Neoptera, also ticks, mites and spiders), even more preferably to the epiclass Hexapoda, most preferably to the class Insecta. According to specific embodiments, the insect belongs to the order Lepidoptera. Non-limiting examples of insects include bedbugs, house flies, moths, beetles, grasshoppers, caterpillars, aphids, mosquitos, fleas, horseflies, hornets, cockroaches and ants, such as, but not limited to:

from the order Lepidoptera, for example: *Acleris* spp., *Adoxophyes* spp., *Agrotis* spp., *Alabama argillacea*, *Amyelois* spp., *Anticarsia gemmatalis*, *Archips* spp., *Argyrotaenia* spp., *Autographa* spp., *Busseola fusca*, *Cadra cautella*, *Carposina nipponensis*, *Chilo suppressalis*, *Chilo* spp., *Choristoneura conflictana*, *Choristoneura fumiferana*, *Choristoneura occidentalis*, *Choristoneura rosaceana*, *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydalima perspectalis*, *Cydia inopinata*, *Cydia* spp., *Diatraea* spp., *Diparopsis castanea*, *Earias* spp., *Ephestia* spp., *Eucosma* spp., *Eupoecilia ambiguella*, *Euproctis* spp., *Euxoa* spp., *Grapholita prunivora*, *Grapholita* spp., *Hedya nubiferanal*, *Helicoverpa armigera*, *Helicoverpa zea*, *Helicoverpa* spp., *Heliothis* spp., *Hellula undalis*, *Hyphantria cunea*, *Keiferia lycopersicella*, *Leucoptera scitella*, *Lithocolletis* spp., *Lobesia botrana*, *Lymantria* spp., *Lyonetia* spp., *Malacosoma* spp., *Mamestra brassicae*, *Manduca sexta*, *Numonia pyrivorella*, *Operophtera* spp., *Opogona sacchari*, *Ostrinia nubilalis*, *Pammene* spp., *Pandemis* spp., *Panolis flammea*, *Paysandisia archon*, *Pectinophora gossypiella*, *Phthorimaea operculella*, *Phyllonorycter* spp., *Pieris rapae*, *Pieris* spp., *Platynota rostrana*, *Plutella xylostella*, *Prays* spp., *Scirpophaga* spp., *Sesamia* spp., *Sesia* spp., *Sparganothis* spp., *Spodoptera dolichos*, *Spodoptera eridania*, *Spodoptera exigua*, *Spodoptera frugiperda*, *Spodoptera littoralis*, *Spodoptera litura*, *Spodoptera* spp., *Synanthedon* spp., *Tecia solanivora*, *Thaumatotibia leucotreta*, *Thaumetopoea processionea*, *Thaumetopoea* spp., *Tortrix* spp., *Trichoplusia ni*, and *Yponomeuta* spp.;

from the order Coleoptera, for example, *Agrilus anxius*, *Agrilus planipennis*, *Agriotes* spp., *Anomala orientalis*, Anoplophora chinensis, Anoplophora glabripennis, Anoplophora spp., Anthonomus bisignifer, Anthonomus eugenii, Anthonomus grandis, Anthonomus quadrigibbus, Anthonomus signatus, Anthonomus spp., Apriona spp., Arrhenodes minutus, Atomaria linearis, Chaetocnema tibialis, Conotrachelus nenuphar, Cosmopolites spp., Curculio spp., Dendroctonus micans, Dendrolimus sibiricus, Dermestes spp., Diabrotica virgifera, Diabrotica virgifera zeae, Diabrotica virgifera, Diabrotica balteata, Diabrotica barberi, Diabrotica undecimpunctata howardi, Diabrotica undecimpunctata tenella, Diabrotica undecimpunctata, Diabrotica undecimpunctata, Diabrotica spp., Epilachna varivestis, Epilachna spp., Epitrix cucumeris, Eremnus cerealis, Eremnus spp., Gonipterus scutellatus, Ips amitinus, Ips cembrae, Ips duplicatus, Ips sexdentatus, Ips typographus, Ips spp., Leptinotarsa decemlineata, Leptinotarsa juncta, Leptinotarsa texana, Lissorhoptrus spp., Listronotus bonariensis, Melolontha spp., Monochamus spp., Naupactus leucoloma, Oryzaephilus spp., Otiorhynchus spp., Phlyctinus spp., Pissodes nemorensis, Pissodes strobi, Pissodes terminalis, Pissodes spp., Popilia japonica, Popilia spp., Premnotrypes spp., Pseudopityophthorus minutissimus, Pseudopityophthorus pruinosus, Psylliodes spp., Rhizopertha spp., Rhynchophorus ferrugineus, Rhynchophorus palmarum, Scarabaeidae family spp., Scolytidae family spp., Sitophilus spp., Sitotroga spp., Sternochetus mangiferae, Tenebrio spp., Tribolium castaneum, Tribolium spp. and Trogoderma spp.;

from the order Orthoptera, for example, Gryllotalpa spp., Locusta spp., and Schistocerca spp.;

from the order Blattaria, from example, Blatta spp., Blattella spp., Periplaneta spp., and Leucophaea maderae, from the order Isoptera, for example, Coptotermes spp. and Reticulitermes spp.;

from the order Psocoptera, for example, Liposcelis spp.;

from the order Phthiraptera, suborder Anoplura, for example, Haematopinus spp., Linognathus spp., and Pediculus spp., and Trichodectes spp.;

from the order Phthiraptera, suborder Ischnocera, for example, Damalinia spp.;

from the order Thysanoptera, for example, Frankliniella occidentalis, Frankliniella platensis, Frankliniella spp., Hercinothrips spp., Taeniothrips spp., Thrips palmi, Thrips tabaci, Scirtothrips aurantii, Scirtothrips citri, Scirtothrips dorsalis, and Scirtothrips spp.;

from the order Hemiptera, suborder Heteroptera, for example, Cimex spp., Distantiella theobroma, Dysdercus spp., Euschistus spp., Eurygaster spp., Leptocorisa spp., Nezara spp., Piesma spp., Rhodnius spp., Sahlbergella singularis, Scotinophara spp., Triatoma spp., Miridae family spp. such as Lygus hesperus and Lygus lineoloris, Lygaeidae family spp. such as Blissus leucopterus, and Pentatomidae family spp.;

from the order Hemiptera, suborder Sternorrhyncha, for example, Aleurocanthus spiniferus, Aleurocanthus woglumi, Aleurocanthus spp., Aleurothrixus floccosus, Aleyrodes brassicae, Aonidella citrina, Aonidiella spp., Aphididae family spp., Acyrthosiphon spp., Aphis fabae, Aphis glycines, Aphis gossypii, Aphis spp., Aspidiotus spp., Bemisia tabaci, Ceroplastes spp., Chrysomphalus aonidium, Chrysomphalus dictyospermi, Coccus hesperidum, Daktulosphaira vitifoliae, Diaphorina citri, Eriosoma larigerum, Gascardia spp., Lacanium corni, Lepidosaphes spp., Lopholeucaspis japonica, Macrosiphus spp., Margarodes prieskaensis, Margarodes vitis, Margarodes vredendalensis, Myzus persicae, Myzus spp., Parasaissetia nigra, Pemphigus spp., Phylloxera spp., Planococcus spp., Pseudaulacaspis spp., Pseudococcus spp., Psylla spp., Pulvinaria aethiopica, Quadraspidiotus spp., Rhopalosiphum spp., Ripersiella hibisci, Saissetia spp., Schizaphis spp., Sitobion spp., Toxoptera citricida, Trialeurodes vaporariorum, Trioza erytreae, and Unaspis citri;

from the order Hemiptera, suborder Auchenorrhyncha, for example, Circulifer haematoceps, Circulifer tenellus, Draeculacephala minerva, Empoasca spp., Erythroneura spp., Graphocephala atropunctata, Hishimonus phycitis, Myndus crudus, Laodelphax spp., Nephotettix spp., Nilaparvata spp., Scaphoideus luteolus, Scaphoideus spp., and Xyphon fulgida;

from the order Hymenoptera, for example, Acromyrmex, Atta spp., Cephus spp., Diprionidae family spp. such as Diprion spp. and Gilpinia polytoma, Hoplocampa spp., Lasius spp., Monomorium pharaonis, Neodiprion spp., Formicidae family spp. such as Solenopsis spp., and Vespa spp.;

from the order Diptera, for example, Aedes albopictus, Aedes cinereus, Aedes polynesiensis, Aedes spp., Amauromyza maculosa, Anastrepha fraterculus, Anastrepha ludens, Anastrepha obliqua, Anastrepha suspensa, Anastrepha spp., Anopheles gambiae, Anopheles spp., Aschistonyx eppoi, Atherigona soccata, Bactrocera spp., Bibio hortulanus, Calliphora erythrocephala, Cephalcia lariciphila, Ceratitis rosa, Ceratitis spp., Chrysomyia spp., Culex spp., Cuterebra spp., Dacus spp., Drosophila melanogaster, Dryocosmus kuriphilus, Euphranta canadensis, Euphranta japonica, Fannia spp., Gastrophilus spp., Gilpinia hercyniae, Glossina spp., Hypoderma spp., Hippobosca spp., Liriomyza bryoniae, Liriomyza huidobrensis, Liriomyza sativae, Liriomyza trifolii, Liriomyza spp., Lucilia spp., Melanagromyza spp., Musca spp., Oestrus spp., Orseolia spp., Oscinella frit, Pardalaspis cyanescens, Pardalaspis quinaria, Pegomyia hyoscyami, Phorbia spp., Rhagoletis pomonella, Rhagoletis spp., Sciara spp., Stomoxys spp., Tabanus spp., and Tipula spp.;

from the order Siphonaptera, for example, Ceratophyllus spp. and Xenopsylla cheopis; and from the infraclass Thysanura, order Zygentoma, for example, Lepisma saccharina.

According to specific embodiments, the insect is considered as a pest. As used herein, the term "pest" refers to an agricultural pest organisms, including but not limited to aphids, grasshoppers, caterpillars, beetles, moths, stinkbugs, Thrips, white flied, household pest organisms, such as cockroaches, ants, wasps, flies, house crickets, bed bugs, wood worms, mealworm beetles, earwigs, silverfish, termites, blood-feeding pest insects such as mosquitos, fleas and lice etc. According to specific embodiments, the insect is an agricultural pest organism.

According to specific embodiments, the insect is selected from the group consisting of moth, stinkbug, hopper, beetle, aphid and honeybee.

According to specific embodiments, the insect is a moth.

According to specific embodiments, the insect is a Noctuid.

Non-limiting Examples of moths include Helicoverpa armigera, Cydia pomonella and Spodoptera frugiperda.

According to specific embodiments, the moth is Helicoverpa armigera and/or, Spodoptera frugiperda.

According to specific embodiments, the moth is *Helicoverpa armigera*.

According to specific embodiments, the insect is selected from the group consisting of *Helicoverpa armigera, Spodoptera frugiperda, Nezara viridula, Nilaraparvata lugens, Aphis gossypii, Cydia pomonella*, Leaf Feeding beetles (e.g. *Leptinotarsa decemlineata* or *Phaedon cochleariae*) and honeybee.

According to specific embodiments, the nanobody binds an insect polypeptide selected from the group consisting of:

(i) a polypeptide comprising a chitin binding domain (CBD), wherein said nanobody binds said CBD;

(ii) V-ATPase subunit c, wherein said nanobody comprises complementarity determining regions (CDRs) as set forth in SEQ ID NOs: 167-169; 171 and 168-169; 174 and 168-169; 167, 178 and 169; 180-182; 187-189; or 191-193 arranged in a sequential order from N to C on said nanobody;

(iii) trehalase;

(iv) cytochrome p450 monooxygenase;

(v) chitin deacetylase;

(vi) chitin synthase; and (vii) NPC1 sterol transporter.

As used herein, the term "specifically bind" refers to the ability of the nanobody to bind a target insect polypeptide in a physiological environment e.g., in the insect under physiological conditions at a higher affinity compared to other polypeptides in said environment.

According to specific embodiments, the nanobody binds an insect polypeptide with no cross reactivity with non-insect (e.g. plant, human) polypeptides.

According to specific embodiments, the nanobody specifically binds one of the insect polypeptides (i)-(vii) with no cross reactivity with the other insect polypeptides.

According to specific embodiments, the nanobody binds at least two of the insect polypeptides (i)-(vii). e.g., by way of multi-specificities such as a bi-specific nanobody.

According to specific embodiments, the nanobody is a nanobody combination comprising at least two nanobodies each binding distinct insect polypeptides selected from the group consisting of insect polypeptides (i)-(vii).

According to specific embodiments, the nanobody or the nanobody combination binds (i)+(ii), (i)+(iii), (i)+(iv), (i)+(v), (i)+(vi), (i)+(vii), (ii)+(iii), (ii)+(iv), (ii)+(v), (ii)+(vi), (ii)+(vii), (iii)+(iv), (iii)+(v), (iii)+(vi), (iii)+(vii), (iv)+(v), (iv)+(vi), (iv)+(vii), (v)+(vi), (v)+(vii), (vi)+(vii).

According to specific embodiments, the nanobody binds a polypeptide comprising a chitin binding domain (CBD), wherein said nanobody binds said CBD.

As used herein the term "chitin binding domain (CBD)" refers to an insect amino acid domain capable of binding an insect chitin (a linear polysaccharide consisting of (1->4)-beta-linked D-glucosamine residues, most of which are N-acetylated), or to antigenic fragments thereof capable of eliciting a specific immune response against said fragment. Non-limiting examples of CBDs include type 2 chitin-binding domain (ChtBD2) and Rebers and Riddiform consensus sequence. According to other specific embodiments, the CBD comprises the Rebers and Riddiford consensus sequence.

As used herein the term "Rebers and Riddiford consensus sequence" refers to a consensus sequence as described by Pfam database entry pfam00379 (see Rebers and Riddiford, 1988; Anderson, 2010; Karouzou et al., 2007; Willis, 2010, the content of which are incorporated herein by reference in their entirety).

According to specific embodiments, the CBD is type 2 chitin-binding domain (ChtBD2).

As used herein, the term "type 2 chitin-binding domain (ChtBD2)", also referred to as the peritrophin A domain refers to a an amino acid sequence having six cysteines that form three disulphide bridges. Such CBDs are known in the art and disclosed e.g. in Tetreau, Guillaume, et al. *Insect biochemistry and molecular biology* 62 (2015): 127-141). According to specific embodiments, the ChtBD2 has a consensus sequence of: CX11-30CX5-6CX9-24CX12-17CX6-12C (SEQ ID NO: 409).

According to specific embodiments, the ChtBD2 comprises an amino acid sequence having at least 60%, at least 70%, at least 75%, at least 80%, at least 85%, at least 90%, at least 95%, at least 96%, at least 97%, at least 98%, at least 99%, or 100% identity to an amino acid sequence selected form the group consisting of SEQ ID NO: 3-7.

According to specific embodiments, the ChtBD2 comprises an amino acid sequence having at least 60%, at least 70%, at least 75%, at least 80%, at least 85%, at least 90%, at least 95%, at least 96%, at least 97%, at least 98%, at least 99%, or 100% identity to an amino acid sequence provided in GeneBank Accession No XP_021181774 (SEQ ID NO: 410).

Sequence identity or homology can be determined using any protein or nucleic acid sequence alignment algorithm such as Blast, ClustalW, and MUSCLE.

According to specific embodiments, the ChtBD2 comprises an amino acid sequence selected form the group consisting of SEQ ID NO: 3-7.

Non-limiting examples of polypeptides comprising ChtBD2 include Peritrophic Matrix Proteins (PMPs) such as TcPMP5-B, HaIIM86; and Cuticle Proteins Analogous to Peritrophins (CPAPs) such as BmCPAP3-A1, BmCPAP3-A2, BmCPAP3-B, BmCPAP3-C, BmCPAP3-D1 and BmCPAP3-D2.

According to specific embodiments, the polypeptide comprising ChtBD2 is a PMP protein.

According to specific embodiments, the polypeptide comprising ChtBD2 is TcPMP5-B (PMP5-B of *Tribolium castaneum*).

According to specific embodiments, the polypeptide comprising ChtBD2 comprises an amino acid sequence selected from the group consisting of SEQ ID NO: 1-2.

According to specific embodiments, the polypeptide comprising ChtBD2 consists of an amino acid sequence selected from the group consisting of SEQ ID NO: 1-2.

Non-limiting examples of nanobodies specifically binding ChtBD2 and their respective CDRs are shown in Tables 2A-B hereinbelow.

According to specific embodiments, the nanobody specifically binds ChtBD2 and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 15-17; 19-21; 23-25; 15 and 28-29; 31-33; 35-37; 39-41; 43-45; 47-49; 51-53; 55-57; 59-61; 63-65; 67-69; 71-73; 75-77; 79-81; 83-85; 87-89; 91, 80 and 93; 95-97; 99-101; 103-105; 107-109; 111-113; 115-117; 119-121; 123-125; 127-129; 131-133; 135-137; 139-141; 143-145; 147-149; 151-153; 15 and 156-157; 159-161; or 163-165 arranged in a sequential order from N to C on said nanobody.

According to specific embodiments, the nanobody specifically binds ChtBD2 and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 15-17; 19-21; 23-25; or 15 and 28-29 arranged in a sequential order from N to C on said nanobody.

According to specific embodiments, the nanobody specifically binds ChtBD2 and comprises CDRs as set forth in SEQ ID NOs: 15-17; 19-21; 23-25; 15 and 28-29; 31-33; 35-37; 39-41; 43-45; 47-49; 51-53; 55-57; 59-61; 63-65; 67-69; 71-73; 75-77; 79-81; 83-85; 87-89; 91, 80 and 93; 95-97; 99-101; 103-105; 107-109; 111-113; 115-117; 119-121; 123-125; 127-129; 131-133; 135-137; 139-141; 143-145; 147-149; 151-153; 15 and 156-157; 159-161; or 163-165 arranged in a sequential order from N to C on said nanobody.

According to specific embodiments, the nanobody specifically binds ChtBD2 and comprises CDRs as set forth in SEQ ID NOs: 15-17; 19-21; 23-25; or 15 and 28-29 arranged in a sequential order from N to C on said nanobody.

According to specific embodiments, the nanobody specifically binds ChtBD2 and comprises CDRs as set forth in SEQ ID NOs: 15-17 arranged in a sequential order from N to C on said nanobody.

According to specific embodiments, the nanobody specifically binds ChtBD2 and comprises CDRs as set forth in SEQ ID NOs: 19-21 arranged in a sequential order from N to C on said nanobody.

According to specific embodiments, the nanobody specifically binds ChtBD2 and comprises CDRs as set forth in SEQ ID NOs: 23-25 arranged in a sequential order from N to C on said nanobody.

According to specific embodiments, the nanobody specifically binds ChtBD2 and comprises CDRs as set forth in SEQ ID NOs: 15 and 28-29 arranged in a sequential order from N to C on said nanobody.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158 and 162 each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 14, 18, 22 and 26.

According to specific embodiments, the nanobody comprises an amino acid sequence selected from the group consisting of SEQ ID NOs: 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158 and 162.

According to specific embodiments, the nanobody comprises an amino acid sequence selected from the group consisting of SEQ ID NOs: 14, 18, 22 and 26.

According to specific embodiments, the nanobody comprises SEQ ID NO: 14.

According to specific embodiments, the nanobody comprises SEQ ID NO: 18.

According to specific embodiments, the nanobody comprises SEQ ID NO: 22.

According to specific embodiments, the nanobody comprises SEQ ID NO: 26.

According to specific embodiments, the nanobody consists of an amino acid sequence selected from the group consisting of SEQ ID NOs: 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158 and 162.

According to specific embodiments, the nanobody consists of SEQ ID NOs: 14, 18, 22 or 26.

According to specific embodiments, the nanobody consists of SEQ ID NO: 14.

According to specific embodiments, the nanobody consists of SEQ ID NO: 18.

According to specific embodiments, the nanobody consists of SEQ ID NO: 22.

According to specific embodiments, the nanobody consists of SEQ ID NO: 26.

According to specific embodiments, the nanobody binds a V-ATPase subunit c.

Non-limiting examples of nanobodies specifically binding V-ATPase subunit c and their respective CDRs are shown in Tables 3A-B hereinbelow.

According to specific embodiments, the nanobody binds a V-ATPase subunit c, wherein said nanobody comprises complementarity determining regions (CDRs) as set forth in SEQ ID NOs: 167-169; 171 and 168-169; 174 and 168-169; 167, 178 and 169; 180-182; 187-189; or 191-193 arranged in a sequential order from N to C on said nanobody.

According to specific embodiments, the nanobody binds a V-ATPase subunit c, wherein said nanobody comprises complementarity determining regions (CDRs) as set forth in SEQ ID NOs: 167-169; 171 and 168-169; 174 and 168-169; 167, 178 and 169; or 180-182 arranged in a sequential order from N to C on said nanobody.

According to specific embodiments, the nanobody binds a V-ATPase subunit c, wherein said nanobody comprises complementarity determining regions (CDRs) as set forth in SEQ ID NOs: 167-169; or 167, 178 and 169 arranged in a sequential order from N to C on said nanobody.

According to specific embodiments, the nanobody binds a V-ATPase subunit c, wherein said nanobody comprises complementarity determining regions (CDRs) as set forth in SEQ ID NOs: 167-169 arranged in a sequential order from N to C on said nanobody.

According to specific embodiments, the nanobody binds a V-ATPase subunit c, wherein said nanobody comprises complementarity determining regions (CDRs) as set forth in SEQ ID NOs: 171 and 168-169 arranged in a sequential order from N to C on said nanobody.

According to specific embodiments, the nanobody binds a V-ATPase subunit c, wherein said nanobody comprises complementarity determining regions (CDRs) as set forth in SEQ ID NOs: 174 and 168-169 arranged in a sequential order from N to C on said nanobody.

According to specific embodiments, the nanobody binds a V-ATPase subunit c, wherein said nanobody comprises complementarity determining regions (CDRs) as set forth in SEQ ID NOs: 167, 178 and 169 arranged in a sequential order from N to C on said nanobody.

According to specific embodiments, the nanobody binds a V-ATPase subunit c, wherein said nanobody comprises complementarity determining regions (CDRs) as set forth in SEQ ID NOs: 180-182 arranged in a sequential order from N to C on said nanobody.

As used herein, the term "V-ATPase subunit c" refer to the amino acid sequence of the insect enzyme Pfam PF03223, an enzyme that catalyzes proton electrochemical potential gradient, or to antigenic fragments thereof capable of eliciting a specific immune response against said fragment.

According to specific embodiments, the V-ATPase subunit c is the *Helicoverpa armigera* V-ATPase subunit c, such as provided in GeneBank Accession No. XP_021198264.

According to specific embodiments, the V-ATPase subunit c comprises SEQ ID NO: 8.

According to specific embodiments, the V-ATPase subunit c consists of SEQ ID NO: 8.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 166, 170, 172, 173, 175, 176, 177, 179, 183, 185, 186 and 190, each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 166, 170, 172, 173, 175, 176, 177 and 179.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 176 and 177.

According to specific embodiments, the nanobody comprises an amino acid sequence selected from the group consisting of SEQ ID NOs: 166, 170, 172, 173, 175, 176, 177, 179, 183, 185, 186 and 190.

According to specific embodiments, the nanobody comprises an amino acid sequence selected from the group consisting of SEQ ID NOs: 166, 170, 172, 173, 175, 176, 177 and 179.

According to specific embodiments, the nanobody comprises an amino acid sequence selected from the group consisting of SEQ ID NOs: 176 and 177.

According to specific embodiments, the nanobody comprises SEQ ID NO: 166.

According to specific embodiments, the nanobody comprises SEQ ID NO: 170.

According to specific embodiments, the nanobody comprises SEQ ID NO: 172.

According to specific embodiments, the nanobody comprises SEQ ID NO: 173.

According to specific embodiments, the nanobody comprises SEQ ID NO: 175.

According to specific embodiments, the nanobody comprises SEQ ID NO: 176.

According to specific embodiments, the nanobody comprises SEQ ID NO: 177.

According to specific embodiments, the nanobody comprises SEQ ID NO: 179.

According to specific embodiments, the nanobody consists of an amino acid sequence selected from the group consisting of SEQ ID NOs: 166, 170, 172, 173, 175, 176, 177, 179, 183, 185, 186 and 190.

According to specific embodiments, the nanobody consists of an amino acid sequence selected from the group consisting of SEQ ID NOs: 166, 170, 172, 173, 175, 176, 177 and 179.

According to specific embodiments, the nanobody consists of an amino acid sequence selected from the group consisting of SEQ ID NOs: 176 and 177.

According to specific embodiments, the nanobody consists of SEQ ID NO: 166.

According to specific embodiments, the nanobody consists of SEQ ID NO: 170.

According to specific embodiments, the nanobody consists of SEQ ID NO: 172.

According to specific embodiments, the nanobody consists of SEQ ID NO: 173.

According to specific embodiments, the nanobody consists of SEQ ID NO: 175.

According to specific embodiments, the nanobody consists of SEQ ID NO: 176.

According to specific embodiments, the nanobody consists of SEQ ID NO: 177.

According to specific embodiments, the nanobody consists of SEQ ID NO: 179.

According to specific embodiments, the nanobody binds a trehalase.

As used herein, the term "trehalase" refer to the amino acid sequence of the insect enzyme E.C. No. 3.2.1.2, an enzyme which catalyzes the conversion of trehalose to glucose, or to antigenic fragments thereof capable of eliciting a specific immune response against said fragment.

According to specific embodiments, the trehalase is the *Helicoverpa armigera* trehalase, such as provided in GeneBank Accession No. AJK29979.

According to specific embodiments, the trehalase comprises SEQ ID NO: 10.

According to specific embodiments, the trehalase consists of SEQ ID NO: 10.

Non-limiting examples of nanobodies specifically binding trehalase and their respective CDRs are shown in Table 4 hereinbelow.

According to specific embodiments, the nanobody specifically binds trehalase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 195-197; 199 and 196-197; 201-203; 201 and 205-206; 208-210; 212 and 209-210; 215-217; 219-221; 223-225; 227-229; 231, 228 and 232; 234-236; 238-240; 242-244; 246-248; 250-252; 254-256; 258-260; 588-590; 5889-589 and 592; or 595, 589 and 592 arranged in a sequential order from N to C on said nanobody.

According to specific embodiments, the nanobody specifically binds trehalase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 195-197; 199 and 196-197; 201-203; 201 and 205-206; 208-210; 212 and 209-210; 215-217; 219-221; 223-225; 227-229; 231, 228 and 232; 234-236; 238-240; 242-244; 246-248; 250-252; 254-256; or 258-260 arranged in a sequential order from N to C on said nanobody.

According to specific embodiments, the nanobody specifically binds trehalase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 201 and 205-206; 208-210; 212 and 209-210; 223-225;

238-240; 242-244; 246-248; 588-590; or 595, 589 and 592 arranged in a sequential order from N to C on said nanobody.

According to specific embodiments, the nanobody specifically binds trehalase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 201 and 205-206; 208-210; 212 and 209-210; 223-225; 588-590; or 595, 589 and 592; arranged in a sequential order from N to C on said nanobody.

According to specific embodiments, the nanobody specifically binds trehalase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 201 and 205-206; 208-210; 223-225; or 588-590; arranged in a sequential order from N to C on said nanobody.

According to specific embodiments, the nanobody specifically binds trehalase and comprises CDRs as set forth in SEQ ID NOs: 195-197; 199 and 196-197; 201-203; 201 and 205-206; 208-210; 212 and 209-210; 215-217; 219-221; 223-225; 227-229; 231, 228 and 232; 234-236; 238-240; 242-244; 246-248; 250-252; 254-256; 258-260; 588-590; 5889-589 and 592; or 595, 589 and 592 arranged in a sequential order from N to C on said nanobody.

According to specific embodiments, the nanobody specifically binds trehalase and comprises CDRs as set forth in SEQ ID NOs: 195-197; 199 and 196-197; 201-203; 201 and 205-206; 208-210; 212 and 209-210; 215-217; 219-221; 223-225; 227-229; 231, 228 and 232; 234-236; 238-240; 242-244; 246-248; 250-252; 254-256; or 258-260 arranged in a sequential order from N to C on said nanobody.

According to specific embodiments, the nanobody specifically binds trehalase and comprises CDRs as set forth in SEQ ID NOs: 201 and 205-206; 208-210; 212 and 209-210; 223-225; 238-240; 242-244; 246-248; 588-590; or 595, 589 and 592 arranged in a sequential order from N to C on said nanobody.

According to specific embodiments, the nanobody specifically binds trehalase and comprises CDRs as set forth in SEQ ID NOs: 201 and 205-206; 208-210; 212 and 209-210; 223-225; 588-590; or 595, 589 and 592 arranged in a sequential order from N to C on said nanobody.

According to specific embodiments, the nanobody specifically binds trehalase and comprises CDRs as set forth in SEQ ID NOs: 201 and 205-206; 208-210; 223-225; or 588-590; arranged in a sequential order from N to C on said nanobody.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 194, 198, 200, 204, 207, 211, 213, 214, 218, 222, 226, 230, 233, 237, 241, 245, 249, 253, 257, 587, 591, 593, 594 and 596 each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 194, 198, 200, 204, 207, 211, 213, 214, 218, 222, 226, 230, 233, 237, 241, 245, 249, 253 and 257, each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 204, 207, 211, 213, 222, 237, 241, 245, 587 and 594.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 204, 207, 211, 213, 222, 587 and 594.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 204, 207, 222 and 587.

According to specific embodiments, the nanobody comprises an amino acid sequence selected from the group consisting of SEQ ID NOs: 194, 198, 200, 204, 207, 211, 213, 214, 218, 222, 226, 230, 233, 237, 241, 245, 249, 253, 257, 587, 591, 593, 594 and 596. According to specific embodiments, the nanobody comprises an amino acid sequence selected from the group consisting of SEQ ID NOs: 194, 198, 200, 204, 207, 211, 213, 214, 218, 222, 226, 230, 233, 237, 241, 245, 249, 253 and 257.

According to specific embodiments, the nanobody comprises an amino acid sequence selected from the group consisting of SEQ ID NOs: 204, 207, 211, 213, 222, 237, 241, 245, 587 and 594.

According to specific embodiments, the nanobody comprises an amino acid sequence selected from the group consisting of SEQ ID NOs: 204, 207, 211, 213, 222, 587 and 594.

According to specific embodiments, the nanobody comprises an amino acid sequence selected from the group consisting of SEQ ID NOs: 204, 207, 222 and 587.

According to specific embodiments, the nanobody comprises SEQ ID NO: 204.

According to specific embodiments, the nanobody comprises SEQ ID NO: 207.

According to specific embodiments, the nanobody comprises SEQ ID NO: 211.

According to specific embodiments, the nanobody comprises SEQ ID NO: 213.

According to specific embodiments, the nanobody comprises SEQ ID NO: 222.

According to specific embodiments, the nanobody comprises SEQ ID NO: 587.

According to specific embodiments, the nanobody comprises SEQ ID NO: 594.

According to specific embodiments, the nanobody consists of an amino acid sequence selected from the group consisting of SEQ ID NOs: 194, 198, 200, 204, 207, 211, 213, 214, 218, 222, 226, 230, 233, 237, 241, 245, 249, 253, 257, 587, 591, 593, 594 and 596.

According to specific embodiments, the nanobody consists of an amino acid sequence selected from the group consisting of SEQ ID NOs: 194, 198, 200, 204, 207, 211, 213, 214, 218, 222, 226, 230, 233, 237, 241, 245, 249, 253 and 257.

According to specific embodiments, the nanobody consists of an amino acid sequence selected from the group consisting of SEQ ID NOs: 204, 207, 211, 213, 222, 237, 241, 245, 587 and 594.

According to specific embodiments, the nanobody consists of an amino acid sequence selected from the group consisting of SEQ ID NOs: 204, 207, 211, 213, 222, 587 and 594.

According to specific embodiments, the nanobody consists of an amino acid sequence selected from the group consisting of SEQ ID NOs: 204, 207, 222 and 587.

According to specific embodiments, the nanobody consists of SEQ ID NO: 204.

According to specific embodiments, the nanobody consists of SEQ ID NO: 207.

According to specific embodiments, the nanobody consists of SEQ ID NO: 211.

According to specific embodiments, the nanobody consists of SEQ ID NO: 213.

According to specific embodiments, the nanobody consists of SEQ ID NO: 222.

According to specific embodiments, the nanobody consists of SEQ ID NO: 587.

According to specific embodiments, the nanobody consists of SEQ ID NO: 594.

According to specific embodiments, the nanobody binds a cytochrome p450 monooxygenase.

As used herein, the term "cytochrome p450 monooxygenase", refer to the amino acid sequence of the insect enzyme E.C. No. 1.14, an enzyme containing heme as a cofactor that incorporates one hydroxyl group into a substrate leading to reduction of two atoms of dioxygen to one hydroxyl group and one $H_2O$ molecule by the concomitant oxidation of NAD(P)H, or to antigenic fragments thereof capable of eliciting a specific immune response against said fragment.

According to specific embodiments, the cytochrome p450 monooxygenase is the *Helicoverpa armigera* cytochrome p450 monooxygenase, such as provided in GeneBank Accession No. AKS48889.

According to specific embodiments, the cytochrome p450 monooxygenase comprises SEQ ID NO: 11.

According to specific embodiments, the cytochrome p450 monooxygenase consists of SEQ ID NO: 11.

Non-limiting examples of nanobodies specifically binding cytochrome p450 monooxygenase and their respective CDRs are shown in Table 5 hereinbelow.

According to specific embodiments, the nanobody specifically binds cytochrome p450 monooxygenase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 262-264; 262-263 and 266; 262, 270 and 264; 274-276; 280 and 275-276; 282 and 275-276; 282, 275 and 285; 287, 220 and 289; 291, 220 and 289; 239-294 and 289; 296-298; 300-302; 304-306; 308-310; 312-314; or 316-318 arranged in a sequential order from N to C on said nanobody.

According to specific embodiments, the nanobody specifically binds cytochrome p450 monooxygenase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 262-264; 287, 220 and 289; 296-298;

300-302; 304-306; or 312-314 arranged in a sequential order from N to C on said nanobody.

According to specific embodiments, the nanobody specifically binds cytochrome p450 monooxygenase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 300-302; or 312-314 arranged in a sequential order from N to C on said nanobody.

According to specific embodiments, the nanobody specifically binds cytochrome p450 monooxygenase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 312-314 arranged in a sequential order from N to C on said nanobody.

According to specific embodiments, the nanobody specifically binds cytochrome p450 monooxygenase and comprises CDRs as set forth in SEQ ID NOs: 262-264; 262-263 and 266; 262, 270 and 264; 274-276; 280 and 275-276; 282 and 275-276; 282, 275 and 285; 287, 220 and 289; 291, 220 and 289; 239-294 and 289; 296-298; 300-302; 304-306; 308-310; 312-314; or 316-318 arranged in a sequential order from N to C on said nanobody.

According to specific embodiments, the nanobody specifically binds cytochrome p450 monooxygenase and comprises CDRs as set forth in SEQ ID NOs: 262-264; 287, 220 and 289; 296-298; 300-302; 304-306; or 312-314 arranged in a sequential order from N to C on said nanobody.

According to specific embodiments, the nanobody specifically binds cytochrome p450 monooxygenase and comprises CDRs as set forth in SEQ ID NOs: 300-302; or 312-314 arranged in a sequential order from N to C on said nanobody.

According to specific embodiments, the nanobody specifically binds cytochrome p450 monooxygenase and comprises CDRs as set forth in SEQ ID NOs: 312-314 arranged in a sequential order from N to C on said nanobody.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 261, 265, 267, 268, 269, 271, 272, 273, 277, 278, 279, 281, 283, 284, 286, 29, 292, 295, 299, 303, 307, 311 and 315, each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 261, 286, 295, 299, 303 and 311.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 299 and 311.

According to specific embodiments, the nanobody comprises an amino acid sequence selected from the group consisting of SEQ ID NOs: 261, 265, 267, 268, 269, 271, 272, 273, 277, 278, 279, 281, 283, 284, 286, 29, 292, 295, 299, 303, 307, 311 and 315.

According to specific embodiments, the nanobody comprises an amino acid sequence selected from the group consisting of SEQ ID NOs: 261, 286, 295, 299, 303 and 311.

According to specific embodiments, the nanobody comprises an amino acid sequence selected from the group consisting of SEQ ID NOs: 299 and 311.

According to specific embodiments, the nanobody comprises SEQ ID NO: 311.

According to specific embodiments, the nanobody comprises SEQ ID NO: 299.

According to specific embodiments, the nanobody consists of an amino acid sequence selected from the group consisting of SEQ ID NOs: 261, 265, 267, 268, 269, 271, 272, 273, 277, 278, 279, 281, 283, 284, 286, 29, 292, 295, 299, 303, 307, 311 and 315.

According to specific embodiments, the nanobody consists of an amino acid sequence selected from the group consisting of SEQ ID NOs: 261, 286, 295, 299, 303 and 311.

According to specific embodiments, the nanobody consists of an amino acid sequence selected from the group consisting of SEQ ID NOs: 299 and 311.

According to specific embodiments, the nanobody consists of SEQ ID NO: 311.

According to specific embodiments, the nanobody consists of SEQ ID NO: 299.

According to specific embodiments, the nanobody binds a chitin deacetylase.

As used herein, the term "chitin deacetylase" refers to the amino acid sequence of the insect enzyme E.C. No. 3.5.1.41, an enzyme that catalyzes the conversion of chitin and $H_2O$ to chitosan and acetate, or to antigenic fragments thereof capable of eliciting a specific immune response against said fragment.

According to specific embodiments, the chitin deacetylase is the *Helicoverpa armigera* chitin deacetylase, such as provided in GeneBank Accession No. AJA30435.

According to specific embodiments, the chitin deacetylase comprises SEQ ID NO: 9.

According to specific embodiments, the chitin deacetylase consists of SEQ ID NO: 9.

Non-limiting examples of nanobodies specifically binding chitin deacetylase and their respective CDRs are shown in Table 6 hereinbelow.

According to specific embodiments, the nanobody specifically binds chitin deacetylase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 320-322; 320 and 324-325; 327, 321 and 328; 320-321 and 332; 208 and 336-337; 320, 324 and 339; 343-345; 347-349; 351-353; 351, 347 and 356; 358-360; 358-359 and 362; 365, 359 and 366; 368-370; 372 and 369-370; 374, 369 and 375; 377-379; 381-383; 385 and 382-383; 387-389; 387, 391 and 389; 394-396; 398-400; 402-404; or 406-408 arranged in a sequential order from N to C on said nanobody.

According to specific embodiments, the nanobody specifically binds chitin deacetylase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 320-322; 320 and 324-325; 372 and 369-370; 374, 369 and 375; 377-379; 387-389; or 398-400 arranged in a sequential order from N to C on said nanobody.

According to specific embodiments, the nanobody specifically binds chitin deacetylase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 320 and 324-325; 372 and 369-370; 374, 369 and 375; or 387-389 arranged in a sequential order from N to C on said nanobody.

According to specific embodiments, the nanobody specifically binds chitin deacetylase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 320 and 324-325; 374, 369 and 375; or 387-389 arranged in a sequential order from N to C on said nanobody.

According to specific embodiments, the nanobody specifically binds chitin deacetylase and comprises CDRs as set forth in SEQ ID NOs: 320-322; 320 and 324-325; 327, 321 and 328; 320-321 and 332; 208 and 336-337; 320, 324 and 339; 343-345; 347-349; 351-353; 351, 347 and 356; 358-360; 358-359 and 362; 365, 359 and 366; 368-370; 372 and 369-370; 374, 369 and 375; 377-379; 381-383; 385 and 382-383; 387-389; 387, 391 and 389; 394-396; 398-400; 402-404; or 406-408 arranged in a sequential order from N to C on said nanobody.

According to specific embodiments, the nanobody specifically binds chitin deacetylase and comprises CDRs as set forth in SEQ ID NOs: 320-322; 320 and 324-325; 372 and 369-370; 374, 369 and 375; 377-379; 387-389; or 398-400 arranged in a sequential order from N to C on said nanobody.

According to specific embodiments, the nanobody specifically binds chitin deacetylase and comprises CDRs as set forth in SEQ ID NOs: 320 and 324-325; 372 and 369-370; 374, 369 and 375; or 387-389 arranged in a sequential order from N to C on said nanobody.

According to specific embodiments, the nanobody specifically binds chitin deacetylase and comprises CDRs as set forth in SEQ ID NOs: 320 and 324-325; 374, 369 and 375; or 387-389 arranged in a sequential order from N to C on said nanobody.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 319, 323, 326, 329, 331, 333, 334, 338, 340, 341, 342, 346, 350, 354, 355, 357, 361, 363, 364, 367, 371, 373, 376, 380, 384, 386, 390, 392, 393, 397, 401 and 405, each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 319, 323, 371, 373, 376, 386 and 397.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 323, 371, 373 and 386.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 323, 373 and 386.

According to specific embodiments, the nanobody comprises an amino acid sequence selected from the group consisting of SEQ ID NOs: 319, 323, 326, 329, 331, 333, 334, 338, 340, 341, 342, 346, 350, 354, 355, 357, 361, 363, 364, 367, 371, 373, 376, 380, 384, 386, 390, 392, 393, 397, 401 and 405.

According to specific embodiments, the nanobody comprises an amino acid sequence selected from the group consisting of SEQ ID NOs: 319, 323, 371, 373, 376, 386 and 397.

According to specific embodiments, the nanobody comprises an amino acid sequence selected from the group consisting of SEQ ID NOs: 323, 371, 373 and 386.

According to specific embodiments, the nanobody comprises an amino acid sequence selected from the group consisting of SEQ ID NOs: 323, 373 and 386.

According to specific embodiments, the nanobody comprises SEQ ID NO: 323.

According to specific embodiments, the nanobody comprises SEQ ID NO: 371 According to specific embodiments, the nanobody comprises SEQ ID NO: 373.

According to specific embodiments, the nanobody comprises SEQ ID NO: 386.

According to specific embodiments, the nanobody consists of an amino acid sequence selected from the group consisting of SEQ ID NOs: 319, 323, 326, 329, 331, 333, 334, 338, 340, 341, 342, 346, 350, 354, 355, 357, 361, 363, 364, 367, 371, 373, 376, 380, 384, 386, 390, 392, 393, 397, 401 and 405.

According to specific embodiments, the nanobody consists of an amino acid sequence selected from the group consisting of SEQ ID NOs: 319, 323, 371, 373, 376, 386 and 397.

According to specific embodiments, the nanobody consists of an amino acid sequence selected from the group consisting of SEQ ID NOs: 323, 371, 373 and 386.

According to specific embodiments, the nanobody consists of SEQ ID NO: 323.

According to specific embodiments, the nanobody consists of SEQ ID NO: 371

According to specific embodiments, the nanobody consists of SEQ ID NO: 373.

According to specific embodiments, the nanobody consists of SEQ ID NO: 386.

According to specific embodiments, the nanobody binds a chitin synthase.

As used herein, the term "chitin synthase" refers to the amino acid sequence of the insect enzyme E.C. No. EC 2.4.1.16, an enzyme which catalyzes the conversion of UDP-N-acetyl-D-glucosamine and [1,4-(N-acetyl-beta-D-glucosaminyl)]n to UDP+[1,4-(N-acetyl-beta-D-glucosaminyl)]n$^+$1, or to antigenic fragments thereof capable of eliciting a specific immune response against said fragment.

According to specific embodiments, the chitin synthase is the *Helicoverpa armigera* chitin synthase, such as provided in GeneBank Accession No. AKZ08594.

According to specific embodiments, the chitin synthase comprises SEQ ID NO: 12.

According to specific embodiments, the chitin synthase consists of an amino acid sequence selected from the group consisting of SEQ ID NO: 12.

Non-limiting examples of nanobodies specifically binding chitin synthase and their respective CDRs are shown in Table 7 hereinbelow.

According to specific embodiments, the nanobody specifically binds chitin synthase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 412-414; 418-420; 422-424; 426-428; 426-427 and 430; 432-434; 436, 140 and 437; 439-441; 443-445; 447-449; 356 and 451-452; 454-456; 458-460; 462-464; 466-468; 470-472; 474-476; 478-480; 482, 479 and 483; 485-487; 489-491; 493-495; 426 and 497-498; 500-502; 504-506; or 508-510 arranged in a sequential order from N to C on said nanobody.

According to specific embodiments, the nanobody specifically binds chitin synthase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 412-414; 418-420; 426-428; 432-434; 443-445; 447-449; 466-468; 482, 479 and 483; 426 and 497-498; or 504-506 arranged in a sequential order from N to C on said nanobody.

According to specific embodiments, the nanobody specifically binds chitin synthase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 426-428; 432-434; or 443-445 arranged in a sequential order from N to C on said nanobody.

According to specific embodiments, the nanobody specifically binds chitin synthase and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 426-428; or 443-445 arranged in a sequential order from N to C on said nanobody.

According to specific embodiments, the nanobody specifically binds chitin synthase and comprises CDRs as set forth in SEQ ID NOs: 412-414; 418-420; 422-424; 426-428; 426-427 and 430; 432-434; 436, 140 and 437; 439-441; 443-445; 447-449; 356 and 451-452; 454-456; 458-460; 462-464; 466-468; 470-472; 474-476; 478-480; 482, 479 and 483; 485-487; 489-491; 493-495; 426 and 497-498; 500-502; 504-506; or 508-510 arranged in a sequential order from N to C on said nanobody.

According to specific embodiments, the nanobody specifically binds chitin synthase and comprises CDRs as set forth in SEQ ID NOs: 412-414; 418-420; 426-428; 432-434; 443-445; 447-449; 466-468; 482, 479 and 483; 426 and 497-498; or 504-506 arranged in a sequential order from N to C on said nanobody.

According to specific embodiments, the nanobody specifically binds chitin synthase and comprises CDRs as set forth in SEQ ID NOs: 426-428; 432-434; or 443-445 arranged in a sequential order from N to C on said nanobody.

According to specific embodiments, the nanobody specifically binds chitin synthase and comprises CDRs as set forth in SEQ ID NOs: 426-428; or 443-445 arranged in a sequential order from N to C on said nanobody.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 411, 415, 416, 417, 421, 425, 429, 431, 435, 438, 442, 446, 450, 453, 457, 461, 465, 469, 473, 477, 481, 484, 488, 492, 496, 499, 503 and 507, each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 411, 417, 425, 431, 442, 446, 465, 481, 496 and 503.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 425, 431 and 442.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 425 and 442.

According to specific embodiments, the nanobody comprises an amino acid sequence selected from the group consisting of SEQ ID NOs: 411, 415, 416, 417, 421, 425, 429, 431, 435, 438, 442, 446, 450, 453, 457, 461, 465, 469, 473, 477, 481, 484, 488, 492, 496, 499, 503 and 507.

According to specific embodiments, the nanobody comprises an amino acid sequence selected from the group consisting of SEQ ID NOs: 411, 417, 425, 431, 442, 446, 465, 481, 496 and 503.

According to specific embodiments, the nanobody comprises an amino acid sequence selected from the group consisting of SEQ ID NOs: 425, 431 and 442.

According to specific embodiments, the nanobody comprises an amino acid sequence selected from the group consisting of SEQ ID NOs: 425 and 442.

According to specific embodiments, the nanobody comprises SEQ ID NO: 425.

According to specific embodiments, the nanobody comprises SEQ ID NO: 431.

According to specific embodiments, the nanobody comprises SEQ ID NO: 442.

According to specific embodiments, the nanobody consists of an amino acid sequence selected from the group consisting of SEQ ID NOs: 411, 415, 416, 417, 421, 425, 429, 431, 435, 438, 442, 446, 450, 453, 457, 461, 465, 469, 473, 477, 481, 484, 488, 492, 496, 499, 503 and 507.

According to specific embodiments, the nanobody consists of an amino acid sequence selected from the group consisting of SEQ ID NOs: 411, 417, 425, 431, 442, 446, 465, 481, 496 and 503.

According to specific embodiments, the nanobody consists of an amino acid sequence selected from the group consisting of SEQ ID NOs: 425, 431 and 442.

According to specific embodiments, the nanobody consists of an amino acid sequence selected from the group consisting of SEQ ID NOs: 425 and 442.

According to specific embodiments, the nanobody consists of SEQ ID NO: 425.

According to specific embodiments, the nanobody consists of SEQ ID NO: 431.

According to specific embodiments, the nanobody consists of SEQ ID NO: 442.

According to specific embodiments, the nanobody binds a NPC1 sterol transporter.

As used herein, the term "NPC1 sterol transporter" refers to the amino acid sequence of the insect protein encoded by the NPC1 gene (Gene ID: 4864, or to antigenic fragments thereof capable of eliciting a specific immune response against said fragment.

According to specific embodiments, the NPC1 sterol transporter is the *Helicoverpa armigera* NPC1 sterol transporter, such as provided in GeneBank Accession No. XP_021186115.

According to specific embodiments, the NPC1 sterol transporter comprises SEQ ID NO: 13.

According to specific embodiments, the NPC1 sterol transporter consists of SEQ ID NO: 13.

Non-limiting examples of nanobodies specifically binding NPC1 sterol transporter and their respective CDRs are shown in Table 8 hereinbelow.

According to specific embodiments, the nanobody specifically binds NPC1 sterol transporter and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 512-514; 517 and 513-514; 521-523; 521-522 and 526; 531-533; 539-541; 485 and 540-541; 545 and 540-451; 547-549; 552-554; 556-558; 561-563; 565-567; 569-571; 573-575; 485 and 577-578; 580-582; or 584-586 arranged in a sequential order from N to C on said nanobody.

According to specific embodiments, the nanobody specifically binds NPC1 sterol transporter and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 517 and 513-514; 485 and 540-541; 545 and 540-541; 556-558; 565-567; 573-575; 485 and 577-578; or 580-582 arranged in a sequential order from N to C on said nanobody.

According to specific embodiments, the nanobody specifically binds NPC1 sterol transporter and comprises CDRs having an amino acid sequence having at least 70%, at least 75%, at least 80%, at least 85%, at least 90%, at least 95%, at least 96%, at least 97%, at least 98%, at least 99%, or 100% identity to amino acid sequences as set forth in SEQ ID NOs: 485 and 540-541; or 545 and 540-541 arranged in a sequential order from N to C on said nanobody.

According to specific embodiments, the nanobody specifically binds NPC1 sterol transporter e and comprises CDRs as set forth in SEQ ID NOs: 512-514; 517 and 513-514; 521-523; 521-522 and 526; 531-533; 539-541; 485 and 540-541; 545 and 540-451; 547-549; 552-554; 556-558; 561-563; 565-567; 569-571; 573-575; 485 and 577-578; 580-582; or 584-586 arranged in a sequential order from N to C on said nanobody.

According to specific embodiments, the nanobody specifically binds NPC1 sterol transporter and comprises CDRs as set forth in SEQ ID NOs: 517 and 513-514; 485 and 540-541; 545 and 540-541; 556-558; 565-567; 573-575; 485 and 577-578; or 580-582 arranged in a sequential order from N to C on said nanobody.

According to specific embodiments, the nanobody specifically binds NPC1 sterol transporter and comprises CDRs as set forth in SEQ ID NOs: 485 and 540-541; or 545 and 540-541 arranged in a sequential order from N to C on said nanobody.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 511, 515, 516, 518, 519, 520, 524, 525, 527, 528, 529, 530, 534, 535, 536, 537, 538, 542, 543, 544, 546, 550, 551, 555, 559, 560, 564, 568, 572, 576, 579 and 583, each possibility represents a separate embodiment of the present invention.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 516, 543, 544, 555, 564, 572, 576 and 579.

According to specific embodiments, the nanobody comprises an amino acid sequence having at least 70%, at least 75%, at least 80%, at least 85%, at least 90%, at least 95%, at least 96%, at least 97%, at least 98%, at least 99% or 100% identity to an amino acid sequence selected from the group consisting of SEQ ID NOs: 543 and 544.

According to specific embodiments, the nanobody comprises an amino acid sequence selected from the group consisting of SEQ ID NOs: 511, 515, 516, 518, 519, 520, 524, 525, 527, 528, 529, 530, 534, 535, 536, 537, 538, 542, 543, 544, 546, 550, 551, 555, 559, 560, 564, 568, 572, 576, 579 and 583.

According to specific embodiments, the nanobody comprises an amino acid sequence selected from the group consisting of SEQ ID NOs: 516, 543, 544, 555, 564, 572, 576 and 579.

According to specific embodiments, the nanobody comprises an amino acid sequence selected from the group consisting of SEQ ID NOs: 543 and 544.

According to specific embodiments, the nanobody comprises SEQ ID NO: 543.

According to specific embodiments, the nanobody comprises SEQ ID NO: 544.

According to specific embodiments, the nanobody consists of an amino acid sequence selected from the group consisting of SEQ ID NOs: 511, 515, 516, 518, 519, 520, 524, 525, 527, 528, 529, 530, 534, 535, 536, 537, 538, 542, 543, 544, 546, 550, 551, 555, 559, 560, 564, 568, 572, 576, 579 and 583.

According to specific embodiments, the nanobody consists of an amino acid sequence selected from the group consisting of SEQ ID NOs: 516, 543, 544, 555, 564, 572, 576 and 579.

According to specific embodiments, the nanobody consists of an amino acid sequence selected from the group consisting of SEQ ID NOs: 543 and 544.

According to specific embodiments, the nanobody consists of SEQ ID NO: 543.

According to specific embodiments, the nanobody consists of SEQ ID NO: 544.

It should be noted that the nanobodies of some embodiments of the present invention in their broadest sense are not limited to a specific biological source or to a specific method of preparation. For example, nanobodies, can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab," as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a nanobody using techniques for nucleic acid synthesis known per se, followed by expression of the nucleic acid thus obtained; and/or (8) by any combination of one or more of the foregoing. A further description of nanobodies, including humanization and/or camelization of nanobodies, can be found, e.g., in WO 08/101985 and WO 08/142164, as well as further herein. A recently reported fully in vitro platform based on yeast surface display for nanobody discovery is disclosed in McMahon, Conor, et al. "*Nature structural & molecular biology* 25.3 (2018): 289.

According to specific embodiments, the nanobody is "camelized." For example, "camelization" can be performed by providing a nucleotide sequence that encodes a naturally occurring VH domain and then changing, in a manner known per se, one or more codons in the nucleotide sequence in such a way that the new nucleotide sequence encodes a "camelized" nanobody, respectively. This nucleic acid can then be expressed in a manner known per se, so as to provide the desired nanobody.

Other suitable methods and techniques for obtaining the nanobody and/or nucleic acid sequence encoding same, starting from naturally occurring VH sequences or preferably $V_HH$ sequences, will be clear from the skilled person, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide the nanobody or a nucleic acid sequence encoding same.

A specific method of generating nanobodies is described herein.

According to an aspect of the present invention there is provided a method of producing a nanobody, the method comprising immunizing a camelid with a recombinant or purified insect polypeptide selected from the group consisting of:

(i) a polypeptide comprising a chitin binding domain (CBD);
(ii) V-ATPase subunit c;
(iii) trehalase;
(iv) cytochrome p450 monooxygenase;
(v) chitin deacetylase;
(vi) chitin synthase; and
(vii) NPC1 sterol transporter, wherein purity of said insect polypeptide in an insect polypeptide preparation is at least 80%.

As used herein, the phrase "purified insect polypeptide" refers to a polypeptide purified from an insect such that its purity compared to other polypeptides present in the protein preparation is at least 80%.

According to specific embodiments, the purity of the insect polypeptide in the purified insect protein preparation is at least 85%, at least 90%, at least 95%, at least 96%, at least 97%, at least 98%, at least 99% or 100%, each possibility represents a separate embodiment of the present invention.

According to specific embodiments, the method further comprising isolating the nanobody.

Methods of isolating nanobodies are well known and are disclosed e.g. in Pardon et al. Nat Protoc. 2014 March; 9(3): 674-693, the contents of which are fully incorporated herein by reference, and in the Examples section that follows.

Once nanobodies are obtained, the binding and/or the biological activity (e.g. insect control activity) of the nanobody can be assayed either in vivo or in vitro. Such methods are known in the art and are further disclosed hereinabove and below.

Thus, according to specific embodiments, the method further comprises selecting a nanobody demonstrating an insect control activity in a biological assay. Such assays are known in the art and are further described hereinbelow.

According to specific embodiments, the nanobody is a naked nanobody.

As used herein, the term "naked nanobody" refers to a nanobody which does not comprise a heterologous effector moiety e.g. toxin moiety, detectable moiety.

According to specific embodiments, the nanobody comprises a heterologous effector moiety e.g. toxin moiety, detectable moiety. The effector moiety can be proteinaceous or non-proteinaceous (e.g. small molecule chemical compounds); the latter generally being generated using functional groups on the nanobody and on the conjugate partner.

Thus, for example, various types of detectable or reporter moieties may be conjugated to the nanobody of the invention. These include, but not are limited to, a radioactive isotope (such as [125]iodine), a phosphorescent chemical, a chemiluminescent chemical, a fluorescent chemical or polypeptide (e.g. phycoerythrin (PE), fluorescein isothiocyanate (FITC), Cy-chrome, rhodamine, green fluorescent protein (GFP), blue fluorescent protein (BFP), Texas red, Cy5, PE-Cy5, and the like), an enzyme (e.g. e.g., horseradish peroxidase (HPR), beta-galactosidase, and alkaline phosphatase (AP), an affinity tag [e.g. an antigen identifiable by a corresponding antibody (e.g., digoxigenin (DIG) which is identified by an anti-DIG antibody) or a molecule having a high affinity towards the tag (e.g., streptavidin and biotin)], and molecules (contrast agents) detectable by Positron Emission Tomography (PET) or Magnetic Resonance Imaging (MRI).

According to specific embodiments, the nanobody comprises a toxin.

As used herein, the term "toxin" or "toxin moiety" refers to a compound having an insect control activity (as defined hereinbelow) including, but not limited to, a polypeptide, a polynucleotide, a small molecule, etc.

Non-limiting Examples of toxin moieties include δ-endotoxins [such as Cry1A, Cry1B, Cry1C, Cry1D, Cry1E, Cry1F, Cry1G, Cry1H, Cry1I, Cry1J, Cry1K, Cry2A, Cry7B, Cry8D, Cry9A, Cry9B, Cry9C, Cry9D, Cry9E, Cry15A, Cry22A, Cry32A, Cry51A, Cyt1A (Crickmore et al., 1998; van Frankenhuyzen, 2009], colicins (such as colicin E1, colicin 1a, colicin A, colicin N), actinoporins (such as equinatoxin II, sticholysin II, fragaceatoxin C), ClyA family toxins (such as cytolysin A, non-haemolytic tripartite enterotoxin, haemolysin BL), haemolysins (such as α-haemolysin, γ-haemolysin, leukocidins, nectrotic enteritis toxin B, δ-toxin, *Vibrio cholerae* cytolysin, *Vibrio vulnificus* haemolysin), aerolysin family toxins (such as aerolysin, α-toxin, hydralysin, ε-toxin, enterotoxin, haemolytic lectin, kysenin), cholesterol-dependent cytolysins (such as perfringolysin, suilysin, intermedilysin, listeriolysin O, lectinolysin, anthrolysin, streptolysin), membrane attack complex components/perforins (such as Plu-MACPF, Bth-MACPF), repeats-in-toxins (such as HlyA, bifunctional haemolysin-adenylyl cyclase toxin, MARTX) (Dal Peraro and van der Goot, 2016), spider toxins, scorpion toxins, patatin, a *Bacillus thuringiensis* insecticidal protein, a Xenorhabdus insecticidal protein, a *Photorhabdus* insecticidal protein, a *Bacillus laterosporous* insecticidal protein, a *Bacillus bombysepticus* insecticidal protein, a *Bacillus sphaericus* insecticidal protein, and insect-controlling double-stranded RNAs The effector moiety e.g. toxin moiety, detectable moiety may be attached or conjugated to the nanobody of the invention in various ways, depending on the context, application and purpose.

The effector moiety may be coupled directly or indirectly (e.g. when comprised in a carrier) to the nanobody. The coupling can be a covalent or non-covalent binding.

When the effector moiety is a polypeptide, the immunoconjugate may be produced by recombinant means. For example, the nucleic acid sequence encoding a toxin or a fluorescent protein may be ligated in-frame with the nucleic acid sequence encoding the nanobody and be expressed in a host cell to produce a recombinant conjugated antibody. Alternatively, the effector moiety may be chemically synthesized by, for example, the stepwise addition of one or more amino acid residues in defined order such as solid phase peptide synthetic techniques.

An effector moiety may also be attached to the nanobody using standard chemical synthesis techniques widely practiced in the art [see e.g., worldwideweb (dot) chemistry (dot) org/portal/Chemistry)], such as using any suitable chemical linkage, direct or indirect, as via a peptide bond (when the effector moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling is provided in details in U.S. Pat. Nos. 3,940,475, 4,289,747, and 4,376,110.

Exemplary methods for conjugating peptide moieties to the nanobody include, but not limited to SPDP conjugation, Glutaraldehyde conjugation and Carbodiimide conjugation.

The nanobody can also be attached to particles or carriers, which comprise the effector moiety. Methods of covalently binding a nanobody to an encapsulating particle are known in the art and disclosed for example in U.S. Pat. Nos. 5,171,578, 5,204,096 and 5,258,499.

Any of the polypeptides (e.g. nanobodies and proteinaceous compositions) described herein can be encoded from a polynucleotide. These polynucleotides can be used per se or in the recombinant production of the polypeptides disclosed herein.

Thus, according to an aspect of the present invention there is provided a polynucleotide encoding the nanobody or the composition comprising the nanobody and the toxin.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

According to specific embodiments, any of the polynucleotides and nucleic acid sequences disclosed herein may comprise conservative nucleic acid substitutions. Conservatively modified polynucleotides refer to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified polynucleotides. According to specific embodiments, any polynucleotide and nucleic acid sequence described herein, which, encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a polynucleotide which encodes a polypeptide is implicit in a described sequence with respect to the expression product.

According to specific embodiments, the nucleic acid sequences disclosed herein are codon optimized for e.g. mammalian or plan expression.

Methods of codon optimization are known in the art and disclosed e.g. in the Codon Usage Database through the NIAS (National Institute of Agrobiological Sciences) DNA bank in Japan (www(dot)kazusa(dot)or(dot)jp/codon/); International Patent Application on. 93/07278; and Grote et al. Nucleic Acid Res. Nucleic Acids Res. (2005) Jul. 1; 33(Web Server issue): W526-W531).

Thus, some embodiments of the invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

To express an exogenous polypeptide in a cell, a polynucleotide sequence encoding the polypeptide is preferably ligated into a nucleic acid construct suitable for expression in the cell. Such a nucleic acid construct includes a promoter sequence for directing transcription of the polynucleotide sequence in the cell in a constitutive or inducible manner.

Hence, according to an aspect of the present invention there is provided a nucleic acid construct comprising the polynucleotide and a cis-acting regulatory element for directing expression of said polynucleotide.

According to specific embodiments, the regulatory element is a heterologous regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the polypeptide from a cell in which it is placed. According to specific embodiments, the signal sequence is the native signal sequence of the polypeptide (e.g. nanobody) of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], pancreas-specific promoters [Edlunch et al. (1985) Science 230:912-916] or mammary gland-specific promoters such as the milk whey promoter (U.S. Pat. No. 4,873,316 and European Application Publication No. 264,166).

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843], include AlcR/AlcA (ethanol inducible); GR fusions, GVG, and pOp/LhGR (dexamethasone inducible); XVE/OlexA (beta-estradiol inducible); or heat shock promoters, e.g., soybean hsp17.5-E or hsp17.3-B [Gurley et al. (1986) Mol. Cell. Biol. 6:559-565] can be used.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long terminal repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference. Enhancers specific for distinct neuronal cell types that can be included in AAV expression vectors to gain specificity without a Cre-driver line have also been described in the arts and described e.g. in Hrvatin et al. (doi: www(dot)doi(dot)org/10.1101/570895), which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding the polypeptide can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMTO10/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such, no general description of selection consideration is provided herein.

The cells may be transformed stably or transiently with the nucleic acid constructs of some embodiments of the invention. In stable transformation, the nucleic acid molecule of some embodiments of the invention is integrated into the cell genome and as such it represents a stable and inherited trait. In transient transformation, the nucleic acid molecule is expressed by the cell transformed but it is not integrated into the genome and as such, it represents a transient trait.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In cases where plant expression vectors are used, the constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the polypeptide of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the polypeptide and the heterologous protein, the polypeptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

The present invention also contemplates cells comprising the polypeptides, polynucleotides and nucleic acid constructs described herein.

Thus, according to an aspect of the present invention there is provided a host cell comprising the nanobody or the composition comprising the nanobody and the toxin or a polynucleotide or a nucleic acid construct encoding same.

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

According to specific embodiments, the cell is a mammalian cell.

According to specific embodiments, the cell is a camelid cell.

Suitable mammalian cells include primary cells and immortalized cell lines.

According to other specific embodiments, the mammalian cell is an immortalized cell line.

Suitable mammalian cell lines include, but are not limited to, HeLa cells (e.g., American Type Culture Collection (ATCC) No. CCL-2), CHO cells (e.g., ATCC Nos.

CRL9618, CCL61, CRL9096), HEK293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, NS0, Sp2/0, BHK, Namalwa, and the like.

According to specific embodiments, the cell is E. coli e.g. SHuffle T7 Express & BL21.

According to specific embodiments, the cell is a plant cell.

According to an aspect of the present invention there is provided a method of producing an insect control nanobody, the method comprising expressing in a host cell the polynucleotide or the nucleic acid construct disclosed herein.

According to specific embodiments, the method further comprising isolating the nanobody.

Isolation or recovery of any of the recombinant polypeptides (e.g. nanobody) may be effected by any method known in the art. According to specific embodiments, recovery or isolation of the recombinant polypeptide is effected following an appropriate time in culture. The phrase "recovering the recombinant polypeptide" or "isolating the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, mix mode chromatography, metal affinity chromatography, Lectins affinity chromatography chromatofocusing and differential solubilization.

According to specific embodiments, following synthesis and purification, the binding and/or the insect control activity of the nanobody can be assayed either in vivo or in vitro. Such methods are known in the art and are further disclosed hereinabove and below.

The compositions disclosed herein (e.g. the nanobodies, the composition comprising the nanobody and the toxin, polynucleotides and nucleic acid constructs encoding same and host cells expressing same) may be formulated in an appropriate means such as lyophilized, freeze-dried, desiccated, or in an aqueous carrier, medium or suitable diluent, such as saline or other buffer. According to specific embodiments, the formulated compositions may be in the form of a dust or granular material, powder, gel, cream, paste, pellet, tablet or a suspension in oil (vegetable or mineral), or water or oil/water emulsions, capsule suspension, emulsifiable concentrate, or as a wettable powder, wettable granules, water dispersible granules, aerosols, foam, slurries or flowable concentrates.

According to specific embodiments, the composition is formulated as a liquid concentrate, dry powder, tablet, capsule suspension, slurry or "wet cake", which can be suitably diluted, dispersed, suspended, emulsified or otherwise suitably reconstituted by the end user prior to final use.

According to specific embodiments, the composition is formulated as a liquid formulation.

According to specific embodiments, the composition is formulated as a dry formulation.

According to specific embodiments, the composition is formulated for delivery by spraying, irrigation and/or fumigation.

According to specific embodiments, the compositions disclosed herein (e.g. the nanobodies, the composition comprising the nanobody and the toxin, polynucleotides and nucleic acid constructs encoding same and host cells expressing same) are stable, both during storage and during utilization, meaning that the integrity of the composition is maintained under storage and/or utilization conditions of the composition, which may include elevated temperatures, freeze-thaw cycles, changes in pH or in ionic strength, UV-irradiation, presence of harmful chemicals and the like.

According to specific embodiments, the integrity and activity of the composition is maintained under storage and/or utilization conditions of the composition, which may include elevated temperatures, freeze-thaw cycles, changes in pH or in ionic strength, UV-irradiation, presence of harmful chemicals and the like.

According to specific embodiments, the integrity and activity of the composition is maintained under open field or controlled conditions, e.g., greenhouse.

It should be noted that the compositions disclosed herein can be formulated with various carriers designed to increase e.g. delivery, stability, permeability and the like.

A "carrier", as used herein, means any solid, semi-solid or liquid carrier in or on(to) which a compound (e.g. nanobody and/or toxin, composition comprising same) can be suitably incorporated, included, immobilized, adsorbed, absorbed, bound, encapsulated, embedded, attached, or comprised. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, bucky-balls, water droplets that are part of an water-in-oil emulsion, oil droplets that are part of an oil-in-water emulsion, organic materials such as cork, wood or other plant-derived materials (e.g. in the form of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof.

According to specific embodiments, the carriers are such that they have immediate or gradual or slow release characteristics, for example over several minutes, several hours, several days or several weeks. Also, the carriers may be made of materials (e.g. polymers) that rupture or slowly degrade (for example, due to prolonged exposure to high or low temperature, sunlight, high or low humidity or other environmental factors or conditions) over time (e.g. over minutes, hours, days or weeks) and so release the compound (e.g. nanobody and/or toxin, composition comprising same) from the carrier. According to specific embodiments, the carrier is coupled, bound, linked or otherwise attached to or associated with the compound. According to specific embodiments, the carrier is covalently coupled to the compound.

The compositions disclosed herein (e.g. the nanobodies, the composition comprising the nanobody and the toxin, polynucleotides and nucleic acid constructs encoding same and host cells expressing same) may be formulated in a composition such as an agrochemical or insecticidal composition where is mixed with suitable physiologically acceptable carriers or excipients.

Herein the term "active ingredient" refers to the nanobodies, the composition comprising the nanobody and the toxin, the polynucleotides and nucleic acid constructs encoding same and the host cells expressing same accountable for the biological effect.

An "agrochemical formulation" as used herein means a composition for agricultural use, comprising one or more of the active ingredients described with other chemical components such as agriculturally acceptable carriers and excipients.

Hereinafter, the phrases "physiologically acceptable carrier" refer to a carrier or a diluent that does not cause significant irritation to an organism and does not abrogate the biological activity and properties of the administered compound. An adjuvant is included under these phrases.

According to specific embodiments, the composition is formulated with an agriculturally acceptable carrier. Suitable agricultural carriers can be solid or liquid and are well known in the art. The term "agriculturally acceptable carrier" covers all adjuvants, e.g., inert components, dispersants, surfactants, tackifiers, binders, etc. that are ordinarily used in insecticide formulation technology and are well known to the skilled artisan.

Herein the term "excipient" refers to an inert substance added to a composition to further facilitate administration of an active ingredient. Examples, without limitation, of excipients include calcium carbonate, calcium phosphate, various sugars and types of starch, cellulose derivatives, surfactant, gelatin, vegetable oils, polyethylene glycols, wetting agents, spreading agents, buffering agents, acidifiers and the like.

According to specific embodiments, the compositions disclosed herein (e.g. the nanobodies, the composition comprising the nanobody and the toxin, polynucleotides and nucleic acid constructs encoding same and host cells expressing same) may be the only active substance in the composition.

According to other specific embodiments, the composition comprises one or more additional active agents in addition to the compositions disclosed herein (e.g. the nanobodies, the composition comprising the nanobody and the toxin, polynucleotides and nucleic acid constructs encoding it and host cells expressing it). Non-limiting examples of such agents include herbicides, insecticides, plant growth regulators, safeners and the like.

According to specific embodiments, the composition disclosed herein and the additional active agent are in a co-formulation.

According to specific embodiments, the composition disclosed herein and the additional active agent are in separate containers.

According to other specific embodiments, the composition may comprise an insect attractant. The attractant may be a pheromone, such as a male or female pheromone for example. As an example, the pheromones referred to in the book "Insect Pheromones and their use in Pest Management" (Howse et al, Chapman and Hall, 1998) may be used in the invention.

The attractant may be present in the formulation or it may be applied separately from the formulation, to ensure that the insects are attracted to the site where the formulation is applied.

The nanobody and the compositions comprising the nanobody and the toxin of some embodiments of the invention are endowed with an insect control activity.

As used herein, the term "insect control" refers to preventing, inhibiting or reducing the ability of an insect to feed, grow, move, spread, develop, survive, and/or reproduce, and/or to limit insect-related damage, which may be manifested by e.g. killing of the insect, decreasing insect survival or longevity, decreasing insect's fecundity and/or fertility, decreasing or arresting insect's feeding, decreasing or arresting insect's growth, decreasing or arresting insect's development, decreasing or arresting insect's mobility and/ or preventing infestation by an insect. According to specific embodiments, the insect control activity is manifested by killing of the insect.

Methods of determining insect control activity are well known to the skilled in the art and are also disclosed in the Examples section which follows and include, but are not limited to in-vitro growing a larva in the presence of the nanobody or the composition and determining mortality, weight, length, pupation and adult emerged timing as compared to same in the absence of the nanobody or the composition.

The nanobody disclosed herein may have an insect control activity by itself or it may exert its insect control activity by delivering a toxin to an insect.

Thus, according to specific embodiments, binding of the nanobody to the insect polypeptide confers an insect control activity to the nanobody.

According to specific embodiments, the nanobody down-regulates activity of the insect polypeptide it binds.

As used herein, "downregulates activity" refers to a decrease of at least 5% in biological function of the insect polypeptide in the presence of the nanobody in comparison to it in the absence of the nanobody, as determined by a method suitable for determining activity of the insect polypeptide. Thus, for example determining the activity of a polypeptide comprising CBD may be effected by e.g. ELISA, Western blot analysis, immunoprecipitation or flow cytometry; determining the activity of V-ATPase subunit c may be effected by e.g. ATPase activity assays and/or ATP dependent proton transporter assays, determining activity of trehalase may be effected by e.g. ferric-ferrocyanide reaction for determining reducing sugars or quantitation of released glucose using glucose oxidase-peroxidase following incubation with trehalase; determining activity of cytochrome p450 monooxygenase may be effected by e.g. measurements of the oxidation of drugs or surrogate compounds, heme assay or the P450-Glo luminescent assay; determining the activity of chitin deacetylase may be effected by e.g. radiometric assay using as substrate partially O-hydroxyethylated chitin (glycol chitin), radiolabeled in N-acetyl groups or the Bergmeyer enzymatic assay determining acetate released by the action of chitin deacetylase on various chitinous substrates; determining the activity of chitin synthase may be effected by e.g. a radioactive assay using [$^{14}$C] UDP-N-acetyl-D-glucosamine (GlcNAc) as a substrate followed by quantization of insoluble $^{14}$C-labeled chitin after acid precipitation; and determining the activity of NPC1 sterol transporter may be effected by e.g. cholesterol absorption assay, sterol quantitation assay.

According to other specific embodiments the decrease is by at least a 10%, at least 20%, at least 30%, at least 40%, at least 50%, at least 60%, at least 70%, at least 80%, at least 90%, at least 95%, at least 99% or 100% as compared to same in the absence of the nanobody, as may be determined by e.g. any of the methods described hereinabove.

According to additional or alternative embodiments, the nanobody is a targeting agent, which serves to provide specific delivery of e.g. a toxin having an insect control activity to the insect.

Non-limiting examples of toxins and methods of coupling them to the nanobody are further described hereinabove.

As the nanobodies and compositions comprising the nanobody and the toxin of some embodiments of the invention are endowed with insect control activity, the present invention also encompasses methods of insect control.

Thus, according to an aspect of the present invention there is provided a method of insect control, the method comprising contacting the insect with the nanobody or the composition comprising the nanobody and the toxin, a polynucleotide or a nucleic acid construct encoding same or a host cell expressing same.

According to specific embodiments, the contacting comprises applying the nanobody or the composition comprising the nanobody and the toxin the directly to the insect.

According to specific embodiments, the contacting comprises applying the nanobody or the composition comprising the nanobody and the toxin to an organism or a surface, which may be in contact with said insect.

According to another aspect of the present invention, there is provided a method of preventing insect infestation of a commodity product, the method comprising adding to the product the nanobody or the composition comprising the nanobody and the toxin.

According to another aspect of the present invention, there is provided a method of preventing insect infestation of a commodity product, the method comprising packaging the product in a packaging material comprising the nanobody or the composition comprising the nanobody and the toxin.

The contacting or the adding may be effected using any suitable method known in the art, including, but not limited to spraying (including high volume (HV), low volume (LV) and ultra low volume (ULV) spraying), atomizing, brushing, dressing, dripping, coating, dipping, immersing, submerging, encrusting, spreading, foaming, fogging, injecting, adding to a culture, irrigating, applying as small droplets, a mist or an aerosol, recombinantly expressing the nucleic acid construct in a cell of an organism (as further disclosed hereinabove).

According to specific embodiments, contacting or adding is effected by spraying, irrigating and/or fumigation.

According to specific embodiments, contacting or adding is effected by introducing the polynucleotide or the nucleic acid construct into a cell of the organism.

According to specific embodiments, the organism is a plant.

As used herein, the term "surface" refers to any object, which may be in contact with an insect. Non-limiting surfaces include nets (e.g. mosquito nets), a light source, a colored object, a shape or silhouette that stand out of a contrasting background greenhouses, outdoor camping facilities, soil and the like.

According to specific embodiments, the commodity product is produced from a plant.

The term "plant" as used herein encompasses whole plants, a grafted plant, ancestors and progeny of the plants and plant parts, including seeds, shoots, stems, roots (including tubers), rootstock, scion, fruits, vegetables, flowers and plant cells, tissues and organs. The plant may be in any form including suspension cultures, embryos, meristematic regions, callus tissue, leaves, gametophytes, sporophytes, pollen, and microspores.

According to specific embodiments, the plant is a crop. "Crop" as used herein means a plant species or variety that is grown to be harvested as food, livestock fodder, fuel raw material, or for any other economic purpose. As a non-limiting example, the crops can be maize, cereals, such as wheat, rye, barley and oats, sorghum, rice, sugar beet and fodder beet, fruit, such as pome fruit (e.g., apples and pears), citrus fruit (e.g., oranges, lemons, limes, grapefruit, or mandarins), stone fruit (e.g., peaches, nectarines or plums), nuts (e.g., almonds or walnuts), soft fruit (e.g., cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fiber plants, such as cotton, flax or hemp, fuel crops, such as sugarcane, miscanthus or switchgrass, vegetables, such as potatoes, tomatoes, peppers, lettuce, spinach, onions, carrots, eggplants, asparagus or cabbage, ornamentals, such as flowers (e.g., petunias, pelargoniums, roses, tulips, lilies, or chrysanthemums), shrubs, broad-leaved trees (e.g., poplars or willows) and evergreens (e.g., conifers), grasses, such as lawn, turf or forage grass or other useful plants, such as coffee, tea, tobacco, hops, pepper, rubber or latex plants.

According to specific embodiments, the plant may be selected from the group consisting of maize, soybean, alfalfa, cotton, sunflower, *Brassica* oil seeds such as *Brassica napus* (e.g. canola, rape-seed), *Brassica rapa, Brassica juncea* (e.g. (field) mustard) and *Brassica carinata*, Arecaceae sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); Solanaceae sp. (e.g. tomatoes, potatoes, peppers, *capsicum*, aubergines, tobacco), *Liliaceae* sp., *Compositae* sp. (e.g. lettuce, artichokes and chicory—including root chicory, endive or common chicory), *Umbellhferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and Chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. *cannabis*), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*, and genetically modified types of these plants.

According to specific embodiments, the plant may be a harvestable part of the plant selected from the group consisting of a fruit, a flower, a nut, a vegetable, a fruit or vegetable with inedible peel, such as avocados, bananas, plantains, lemons, grapefruits, melons, oranges, pineapples, kiwi fruits, guavas, mandarins, mangoes and pumpkin.

According to specific embodiments, the plant is forest plant, such as described in e.g. www(dot)fao(dot)org/3/i0640e/i0640e13.pdf.

According to specific embodiments, the plant is an ornamental plant.

According to specific embodiments, the plant may be a cut flower of ornamental plants, preferably selected from *Alstroemeria*, carnation, *Chrysanthemum, Freesia, Gerbera, Gladiolus*, baby's breath (*Gypsophila* spp.), *Helianthus, Hydrangea, Lilium, Lisianthus*, roses and summer flowers.

According to specific embodiments, the plant is a cut grass or wood.

According to specific embodiments, the plant is cotton.

According to specific embodiments, the plant is a transgenic plant.

According to specific embodiments, the plant is a transgenic plant recombinantly expressing the nanobody or the composition comprising the nanobody and the toxin.

Methods of generating a transgenic plant are well known in the art and are also described hereinabove.

Following, the present invention also encompasses products comprising the nanobody or the composition comprising the nanobody and the toxin, polynucleotides or nucleic acid constructs encoding same or host cells expressing same.

According to specific embodiments, such products are more resistant to insect infestation or damage as compared to products not comprising the nanobody or the composition comprising the nanobody and the toxin, polynucleotides or nucleic acid constructs encoding same or host cells expressing same.

Thus, according to an aspect of the present invention, there is provided a plant comprising the nanobody or the composition comprising the nanobody and the toxin, or a polynucleotide or a nucleic acid construct encoding same.

According to another aspect of the present invention, there is provided a commodity product comprising the nanobody or the composition comprising the nanobody and the toxin.

According to another aspect of the present invention, there is provided a surface covered with the nanobody or the composition comprising the nanobody and the toxin.

According to another aspect of the present invention, there is provided a packaged product comprising a commodity product contained within a packaging material comprising the nanobody or the composition comprising the nanobody and the toxin.

Tables 1-8 hereinbelow list polypeptides and nanobodies that can be used with specific embodiments of the present invention.

TABLE 1

| Target proteins Amino Acid Sequences | | |
|---|---|---|
| SEQ ID NO: | Target | Amino Acid Sequence |
| 1 | A polypeptide comprising Chitin binding domain CBD-HaPMP5B1 | MGSSHHHHHHSSGLVPRGSHMGDRGISEPGNDQGNDNDSN DNNSSNEQGGVCNCNPEEAPAICASPGSEGVLVAHENCEK YYICNHGRPVVASCSGNLLFNPYTNECGWPRDVDCGDRI EPGCTGCNDNNNNDDDDSDCDGDDPVPPPADNDDSESADI DDLPPPGDDASVRPPVDEGTCNCNPEQAPSICAEDDSDGVL |

TABLE 1-continued

| SEQ ID NO: | Target | Amino Acid Sequence |
|---|---|---|
| | (The CBDs are marked in bold, SEQ ID Nos: 3-7) | VAHEDCNKFYKCHNGKPVALYCPGNLLYNPNTEQCDW PEKVDCGDRVIPDPEDNTVGGNNDGEDDSEGVLVAHENC NQFYKCSGGKPVALLCPGNLLFNPNTDQCDWPWEVDC GDRIIPDPDRTHCGSHCSTHCSTHCGSLLRLPLRLHCGSHCG SHCCTNTATNRRRNMQLQSWSTFHLCSRRLLIAHEDCNKF YICDHGKPVALSCPGNLLYNPYTEKCDWPENVECGDRAP DPDASQAPAICADSGSEGVLVAHENCDQYYICDGGRPVA RPCQGGLLYNPLTQYCDGQEMSTAVTGLSLMTAPVIPEM RPDCAVSQTPKEAW |
| 2 | A polypeptide comprising Chitin binding domain CBD-HaPMP5B2 (The CBDs are marked in bold, SEQ ID Nos: 5 and 7) | MGSSHHHHHHSSGLVPRGSHMDRVIPDPEDNTVGGNNDGE DDSEGVLVAHENCNQFYKCSGGKPVALLCPGNLLFNPN TDQCDWPWEVDCGDRIIPDPDRTHCGSHCSTHCSTHCGSL LRLPLRLHCGSHCGSHCCTNTATNRRRNMQLQSWSTFHLC SRRLLIAHEDCNKFYICDHGKPVALSCPGNLLYNPYTEKC DWPENVECGDRAPDPDASQAPA |
| 8 | V-ATPase sub unit c | MHHHHHHMSEYWVISAPGDKTCQQTWDTLNNATKSGNLS ANYKFPIPDLKVGTLDQLVGLSDDLGKLDTFVESVTRKVAQ YLGEVLEDQRDKLHENLMANNSDMPSYLTRFQWDMAKYP IKQSLRNIADIISKQVGQIDSDLKQKSAAYNALKGNLQNLEK KQTGSLLTRNLADLVKREHFILDSEYLTTLLVIVPKSMFND WTANYEKITDMIVPRSSQLIHQDNDYGLFNVTLFKKVVEEF KHHARERKFVVREFSYNEADMAAARTRSPSSSPTRRSSSILR KFINFLGPLVRWLKVNFSECFCAWIHVKALRVFVESVLRYG LPVNFQAVVMVPSRKNTKKLREVLQTLYAHLDHSAHQHTS SAQDNAELAGLGFGSSEYFPYVFYKINVDMLDKN |
| 9 | Chitin deacetylase | METRVKRQEEDGGDEVNAEQLCDGRPADEYFRLTTEGDCR DVVRCTRSGLKQITCPSGLAFDLDKQTCDWKGKVTNCDKL EKPRKVLPILKTDEPICPEGKLACGSGDCIEKELFCNGKPDC KDESDENACTVDVDPNRAPDCDPNQCALPDCFCSADGTRIP GGIEVNQVPQMITITFNGAVNVDNIDLYEQIFNGNRHNPNG CQIRGTFFVSHKYTNYAAVQELHRKGHEISVFSITHKDDPQ YWSSGSYDDWLAEMAGARLIVERFANITDSSIIGVRAPYLR VGGNKQFEMMADQYFVYDASITAPLGRVPIWPYTLYFRMP HKCNGNAHNCPSRSHPVWEMVMNELDRRDDPTFDESLPG CHVVDSCSNIQTGEQFARLLRHNSNRHYSTNRAPLGFHFHA SWLKSKKEFRDELIKFIEEMLEKNDVYFTSLIQVIQWMQNP TELTSLRDFQEWKQDKCDVKGQPFCSLPNACPLTTRELPGE TLRLFTCMECPNNYPWILDPTGEGFNVK |
| 10 | Trehalase | MDLPLTCTKPVYCNSNLLHQIQMARLYNDSKTFVDLQMNF DENKTLTDFETFFNLHNKNPTKEQLMBFVNEYFSNDNELEP WQPKDFSDNPAFLAKIKDDALREFGKGINNIWPLLARKVKA EVFQKPDQFSLVPLTHGFIIPGGRFKEIYYWDTFWIIEGLLIS GMQETAKGMIENLIELLNLFGHIPNGSRGYYQQRSQPPMLN AMVATYYMYTKDLEFLRNNIAYLEKELDFWMDNRVVSVN RGGKNYTLLRYYAPSKGPRPESYYEDYSNTEGFSEEDSTNF CIDIKSAAESGWDFSTRWFLMPDGSNNGTLTDLHTRYIIPVD LNAIFAGAAQYVSNFHALLKNPQKAARYGQLAQTWRDNIQ AVLWNDQDAMWYDFNIRDNLHRRYYYSSNAAPLWQNAV NPDFLKLNADRILKAITESGGVDFPGGVPTSLIRSGEQWDFP NVWPPEVSIEVAAIENIGTPEAITLAQEVAQTFVRSCHWGFQ KYKQMFEKYDAETPGRFGGGGEYNVQFGFGWSNGVVLEF LNKYGSQLTADDSNNTNNS |
| 11 | cytochrome p450 monooxygenase | MRTFNYWKKRNVRGPEPVVFFGNLKDSALRKKNMGVVM EELYNMFPEEKVIGIYRMTSPCLLVRDLDVIKHIMIKDFEVF SDRGVEFSKEGLGSNLFHADGETWRALGNRFTPIFTSGKLK NMFYLMHEGADNFIDHVSAECEKNQEFEVHSLLQTYTMSTI AACAFGISYDSIGDKVKALDIVDKIISEPSYAIELDMMYPGL LSKLNLSIFPTVVKNFFKSLVDNIVAQRNGKPSGRNDFMDLI LELRQLGEVTSNKYGSSASSLEITDEVICAQAFVFYIAGYET SATTMAYMIYQLALNPDIQNKLIAEVDEVLKANDGKVTYD TVKEMKYLNKAFDETLRMYSIVEPLQRKATRDYKIPGTDV VIEKDTIVLISPRGIHYDPKYYDNPKQFNPDRFDAEEVGKRH PCAYLPFGLGQRNCIGMRFGRLQSLLCITKILSKFRIEPSKNT DRNLQVEPHRGLIGPKGGIRVNAIPRKLVS |

TABLE 1-continued

| | Target proteins Amino Acid Sequences | |
|---|---|---|
| SEQ ID NO: | Target | Amino Acid Sequence |
| 12 | Chitin synthase | NCYFHGTVPDYLYFESPPVFTLSDFISRQMAWICRTFGLNEK LFVMPMYNGLLIDQSMALNRKRNDQRDVKTEDLAEIEKEK GDEYYETISVHTDNTGSSPKAIKSSDQITRIYACATMWHETK DEMMEFLKSILRLDEDQCARRVAQKYLRVVDPDYYEFETH IFLDDAFEISDHSDDDSQVNRFVKLLVDTIDEAASEVHQTNI RDVHVLPSRSSFNGTADILDRKEVMAENTYLLTLDGDIDFQ PHAVRLLIDLMKKNKNLGAACGRIHPVGSGPMVWYQMFE YAIGHWLQKATEHMIGCVLCSPGCFSLFRGKALMDDNVM KKYTLRSDEARHYVHTIRGRSMVMYAITATWLSCRILSCLR CYTHCPEGFNEFYNRRRWVPSTIANIMDLLADCKHTIKIND NISSPYIA |
| 13 | NPC1-sterol transporter | DSFQTKYFQYLNRYLNIGPPVYFVVTEGLNYSDMDTQNMI CGTRFCRPDSLSMQLYAAYRNPNETYIAQPPNSWLDDYFD WSALPNCCKYFPSNSSFCPNDRGAPCKACGIALEGDEQRPN STEFERYVPFFLQDIPDTSGSGCVKGGHAAYGQAVNYKMF NKTQAHVGATYYQGYHTVLKTSLDYYSALKGAREVAANL TETLNRNLKHQLNGTTINVFPYSVFYVFYEQYLTMWPDTL |

TABLE 2A

| | Amino acid sequences of anti-CBD Nanobodies | |
|---|---|---|
| SEQ ID NO: | Nanobody name | Amino Acid Sequence |
| 14 (The CDRs are marked in bold, SEQ ID Nos: 15-17) | CB20501 | MQVQLQESGGGLVQAGDSLRLSCAASG RSFSIYTMGWFRQAPGNEREFVTAISP SGGSTHYADFVKGRFTISRDNTKNTMY LQMNSLKPEDTAVYFCASTSSQHYEDT EESYKYWGQGTQVTVSSAAAYPYDVPD YGSHHHHHH |
| 18 (The CDRs are marked in bold, SEQ ID Nos: 19-21) | CB20801 | MQVQLQESGGGLVEAAGSLRLSCAALG SNLRINTMGWYRQAPGKQRELVATITN GGRKNYADSVKGRFTIFRGNANTVYLQ MNSLKPEDTAVYYCNAGLLDPPYSAPG DYWGEGTQVTVSSAAAYPYDVPDYGSH HHHHH |

TABLE 2A-continued

| | Amino acid sequences of anti-CBD Nanobodies | |
|---|---|---|
| SEQ ID NO: | Nanobody name | Amino Acid Sequence |
| 22 (The CDRs are marked in bold, SEQ ID Nos: 23-25) | CB20901 | MQVQLQESGGGLVQAGGSLTLSCAASG RSFSTYAMGWSRQAPGKEREFLAGISR GGGTTVYADSVKGRFTISRDNVKNTVY LQMNSLKPEDAAVYYCAALRPFDGSG ERRYDYWGQGTQVTVSSAAAYPYDVPD YGSHHHHHH |
| 26 (The CDRs are marked in bold, SEQ ID Nos: 15, 28-29) | CB201101 | MQVQLQESGGGLVQAGDSLRLSCAASG RSFSIYTMGWFRQAPGKEREFVAAISP SGVSTDYADSVRGRFTISRDNAKNTMY LQMNSLKPEDTAVYYCAAGGRHYTRHP YDYDYWGQGTQVTVSSAAAYPYDVPDY GSHHHHHH |

TABLE 2B

| | Amino acid sequences of anti-CBD Nanobodies | |
|---|---|---|
| SEQ ID NO: | Nanobody name | Amino Acid Sequence |
| 30 (The CDRs are marked in bold, SEQ ID Nos: 31-33) | CB10101 | MQVQLQESGGGLVQTGGSLRLSCAASGRSF SSYSMGWFRQGPGKGREWVADINESGSSTS YYDPVKGRFTISRDNSKNTVYLQMNDLKPE DTADYYCAALVTGGDTDLGEWDFWGPGTQV TVSSAAAYPYDVPDYGSHHHHHH |
| 34 (The CDRs are marked in bold, SEQ ID Nos: 35-37) | CB10201 | MQVQLQESGGGLVQAGDSLKLSCAASGGTF SSYVMGWFRQAPGKEREFVARIGVSEGYLY YADSVKDRFTISRDSAKNTGYLQMNALKPE DTAVYYCAAGPRRYWTREPDAYDYWGQGTQ VTVSSAAAYPYDVPDYGSHHHHHH |
| 38 (The CDRs are marked in bold, SEQ ID Nos: 39-41) | CB10301 | MQVQLQESGGGLVQAGGSLKLSCGASGRTF STNAMGWFRQAPGKEREFVATISAGGSLTY YADSVKGRFTISRDNAKNTVYLRMNSLKPD DTAVYYCAADQDSGRLPLINSGYEYWGQGT QVTVSSAAAYPYDVPDYGSHHHHHH |

TABLE 2B-continued

Amino acid sequences of anti-CBD Nanobodies

| SEQ ID NO: | Nanobody name | Amino Acid Sequence |
|---|---|---|
| 42 (The CDRs are marked in bold, SEQ ID Nos: 43-45) | CB10401 | MQVQLQESGGGLVQAGASLRLSCAASGRTF SSYGTAMGWFRQAPGKEREFVAAILWTGSS SYDSVKGRFTISRDNAKNTVYLQMISLNPE DTAVYYCAARSRYTGSYYEESTYNYWGQGT QVTVSSAAAYPYDVPDYGSHHHHHH |
| 46 (The CDRs are marked in bold, SEQ ID Nos: 47-49) | CB10501 | MQVQLQESGGGVVQPGGSLRLSCAASGRDF SNYNMAWFRQAPGKERDVVATIRRSGDITS YTDSVKGRFTISRDNAKNTVYLQMNSLKPE DTAAYYCAARTGSFLTVLITTPGNYNYWGQ GTQVTVSSAAAYPYDVPDYGSHHHHHH |
| 50 (The CDRs are marked in bold, SEQ ID Nos: 51-53) | CB10701 | MQVQLQESGGGLVQAGDSLRLSCAASGRTF SAFRMAWFRQAPGKERALVADISRLSTRTY YADSVKGRFTISRDNAKNTVYLQMNSLKPE DTAVYYCAADLEGVGPMWEYWVQGTQVIVS SAAAYPYDVPDYGSHHHHHH |
| 54 (The CDRs are marked in bold, SEQ ID Nos: 55-57) | CB10801 | MQVQLQESGGGSVQAGNSLRLSCTYSGRTF STRAMGWFRQAPGKERELVAGIGWNGATQY YADSVKGRFTISRDSASNTVALQMNSLEPE DTAVYYCAAHGREYVTPSYNNYDYWGQGTQ VTVSSAAAYPYDVPDYGSHHHHHH |
| 58 (The CDRs are marked in bold, SEQ ID Nos: 59-61) | CB101001 | MQVQLQESGGGLTQAGDSLRLSCAASGRSF VRYTTGWFRQAPGKEREFVASISWSRGSTY YADSVKGRFTISKDNAENTVYLQMNSPEPE DTAVYYCAGNSRGATTFAQYYDDWGQGTQV TVSSAAAYPYDVPDYGSHHHHHH |
| 62 (The CDRs are marked in bold, SEQ ID Nos: 63-65) | CB101101 | MQVQLQESGGGLVQAGGSLRLSCAASGRTF SLTRMGWFRQAPGKEREIVAHIMRSSDSTF YGDSVKGRFTISRDNAKNTVYLQMNRLNPE DTAVYYCAAAQWAGYDYWGQGTQVTVSSAA AYPYDVPDYQSHHHHHH |
| 66 (The CDRs are marked in bold, SEQ ID Nos: 67-69) | CB101201 | MQVQLQESGGGLVPAGGSLRLSCAASGRTF TSSTMAWFRQVPGKEREFVAAISPRGLSQD YGHSVKGRETISRDNAENTVYLQMNSLKSE DTALYYCAATSGSYSSSRNDYYYWGQGTQV TVSSAAAYPYDVPDYGSHHHHHH |
| 70 (The CDRs are marked in bold, SEQ ID Nos: 71-73) | CB101301 | MQVQLQESGGGLVQPGGSLRLSCAASGFTL SNYRMAWFRQGLGKEREFVAHIMRNSDTTW YTESVKGRFTISRDNSKNTVYLQMNSLKPE DTAVYYCAASNAGTFDYWGQGTQVTVSSAA AYPYDVPDYGSHHHHHH |
| 74 (The CDRs are marked in bold, SEQ ID Nos: 75-77) | CB101401 | MQVQLQESGGGLVQPGGSLRLSCASSGANI RLYGMAWYRQPPGEERELVASITVGGSITY AESVKARFTISRDNARDMVFLQMNSLKPED TAVYYCNAMNPWYYWAWGQGTQVTVSSAAA YPYDVPDYGSHHHHHH |
| 78 (The CDRs are marked in bold, SEQ ID Nos: 79-81) | CB101601 | MQVQLQESGGGLVQAGGSLRLSCAASGGTL SSYDMGWFRQAPGKGRDFVAGIDWSGGSTN YERSVKGRFTITRDNAKNTVLLQMNSLKPE DTAVYYCAAARANSDLGIYDYWGQGTQVTV SSAAAYPYDVPDYGSHHHHHH |
| 82 (The CDRs are marked in bold, SEQ ID Nos: 83-85) | CB101701 | MQVQLQESGGGLVEAGGSLGLACTTSGIIF SRNDMGWFRQAPGEQRTAVATITRSSSTNY AGSVKGRFTISRDNAENTVYLQMSNLKPED TAVYYCATIPTATQPYVYWGQGTQVTVSSA AAYPYDVPDYGSHHHHHH |
| 86 (The CDRs are marked in bold, SEQ ID Nos: 87-89) | CB101801 | MQVQLQESGGGLVQTGGSLRLSCAASGRSF SSYSMGWFRQGPGKGREWVADINESGTTTN YWDPVKGRFIISRDNAQNMVYLQMNSLKPE DTAVYYCAAGPRTRWTREPDAYDYWGQGTQ VTVSSAAAYPYDVPDYGSHHHHHH |

TABLE 2B-continued

Amino acid sequences of anti-CBD Nanobodies

| SEQ ID NO: | Nanobody name | Amino Acid Sequence |
|---|---|---|
| 90 (The CDRs are marked in bold, SEQ ID Nos: 91, 80, 93) | CB102001 | MQVQLQESGGGLVQAGGSLRLSCVASGRTF STYDMGWFRQAPGKGREFVAGIDWSGGSTN YVNFVKGRFTISRDNAKNTMYLQMNSLKPE DTAVYYCAAAVGDSEMATYDYWGQGTQVTV SSAAAYPYDVPDYGSHHHHHH |
| 94 (The CDRs are marked in bold, SEQ ID Nos: 95-97) | CB102901 | MQVQLQESGGGLVQVGGSLRLSCVASEPTF RPNRMGWFRQAPGKERELVAHIMWSSGSTW YGDSVKGRFTISRDNAKNTVILQMNSLNPE DTAVYYCAAQRAGYDYWGQGTQVTVSSAA AYPYDVPDYGSHHHHHH |
| 98 (The CDRs are marked in bold, SEQ ID Nos: 99-101) | CB103001 | MQVQLQESGGGLVQAGGSLRLSCAASGRSL SSYSMGWIRQAPGKERDFVTAIRWSGGSTY YADSVKGRFTISRDIAKNAVYLQMNSLKTE DTAVYYCAARLGGRSWDAGDYQYWGQGTQV TVSSAAAYPYDVPDYGSHHHHHH |
| 102 (The CDRs are marked in bold, SEQ ID Nos: 103-105) | CB103101 | MQVQLQESGGGSVQSGGSLFLSCAASGFVF ETSPMTWVRQAPGQGVRWVGSITTDGRRAD YEDAVKGRFTISRDNVKNMLYLEMNNLKPE DTAMYFCRESRDLNAVTRGTQVTVSSAAAY PYDVPDYGSHHHHHH |
| 106 (The CDRs are marked in bold, SEQ ID Nos: 107-109) | CB103301 | MQVQLQESGGGLVQTGDSLRLSCAVSGRTG SINRMGWFRQAPGKEREIVSHIFWSNVGTW SAESVKGRFIISRDNAKNTVYLQMNSLKPE DTAVYSCAAATGSAYNYWVPSRGDPGHVSS AAAYPYDVPDYGSHHHHHH |
| 110 (The CDRs are marked in bold, SEQ ID Nos: 111-113) | CB20401 | MQVQLQESGGGQVQAGDSLRLSCVTSGMSF STSAMGWYRQASGKQREWVAIIREDSTTNY SSFAKGRFTISRDNTNKTVYLLMNSLEPDD TAVYYCRTYTGGYWGQGTQVTVSSAAAYPY DVPDYGSHHHHHH |
| 114 (The CDRs are marked in bold, SEQ ID Nos: 115-117) | CB20601 | MQVQLQESGGGLVQAGGSLRLSCAASGRTF SSYAMGWFRQAPGKEREFVAGISWSGRSTY YADSVKGRFTISRDDAKNTVYLQMNSLKPE DTAVYYCAAPDTAAQFTTPLYEYAYWGQGT QVTVSSAAAYPYDVPDYGSHHHHHH |
| 118 (The CDRs are marked in bold, SEQ ID Nos: 119-121) | CB201001 | MQVQLQESGGGLVQAGDSLRLACASSSRTF STYTMGWFRQTPGRERDFVAAISPSGATAD YADSVKGRFTISRDNAKNTLYLQMDSLKPE DTAVYYCAARYLSWSRMNHEYPYWGQGTQV TVSSAAAYPYDVPDYGSHHHHHH |
| 122 (The CDRs are marked in bold, SEQ ID Nos: 123-125) | CB201201 | MQVQLQESGGGLVQAGDSLRLSCAASERTF SSYVMGWFRQAPRKEREFVAAMTWSGSSRI YYADSVKGRFTISRDNAKNTAYLQMNSLKP EDTAVYYCAAKDAYGGISFRPNTYHSWGQG TQVTVSSAAAYPYDVPDYGSHHHHHH |
| 126 (The CDRs are marked in bold, SEQ ID Nos: 127-129) | CB201301 | MQVQLQESGGGLVQPGGSLRLSCAALGNIV NINNMGWYRQAPGGQRELVATITRGAIKNY ADSVKGRFTIFRGNANTVYLQMNSLKPEDT AVYYCVADSSWGQGTQVTVSSAAAYPYDVP DYGSHHHHHH |
| 130 (The CDRs are marked in bold, SEQ ID Nos: 131-133) | CB201401 | MQVQLQESGGGVVQAGGFLRLSCAASGLIF DDTAIGWFRQAPGKEREFVAAVSPSGVSTD YTDSVKGRFTISRDNAKKTVFLQMSRLKPE DTAVYYCAARLRHYSNDQHEYDSWGQGTQV TVSSAAAYPYDVPDYGSHHHHHH |
| 134 (The CDRs are marked in bold, SEQ ID Nos: 135-137) | CB201501 | MQVQLQESGGGLVQAGGSLRLSCAASGIVF SITTMGWYRQAPGKQRELVATIASGVRADY ADSVKGRFTISRDNGKNTVYLQMNSLKPED TAVYYCNANRFSLGNYWGQGTQVTVSSAAA YPYDVPDYGSHHHHHH |

TABLE 2B-continued

Amino acid sequences of anti-CBD Nanobodies

| SEQ ID NO: | Nanobody name | Amino Acid Sequence |
|---|---|---|
| 138 (The CDRs are marked in bold, SEQ ID Nos: 139-141) | CB201601 | MQVQLQESGGGLVQTGDSLRLSCAASGGTF SAYTMGWFRQAPGKEREFVAAISRSGSSTH YANSVKGHFTISRDNAKKTVYLQMNSLKPE DTARYYCAGERTGHFTDLYYEYDYWGQGTQ VTVSSAAAYPYDVPDYGSHHHHHH |
| 142 (The CDRs are marked in bold, SEQ ID Nos: 143-145) | CB201701 | MQVQLQESGGGLVQAGGSLRLSCAAPGSNF RINTMGWYRQAPGKQRELVATIANSGRINS ANSVKGRFTIFRGNANTVYLQMNSLKPEDT AVYYCNADVVESSNYQTLNYWGQGTQVTVS SAAAYPYDVPDYGSHHHHHH |
| 146 (The CDRs are marked in bold, SEQ ID Nos: 147-149) | CB201801 | MQVQLQESGGGLVQAGGSLRLSCVASRASG SIFGAQTMAWYRQASGERRELVATITSSGS TNYADSVKGRFTISRDNAKSTMFLQMNNLK PEDTAVYYCNVGFRSRYSYDSSVWGEGTQV TVSSAAAYPYDVPDYGSHHHHHH |
| 150 (The CDRs are marked in bold, SEQ ID Nos: 151-153) | CB201901 | MQVQLQESGGGLVQAGGSLRLSCAASGRTF STSNMGWFRQAPGKEREFVGAISPSGRSTD YASSVEGRFTISRDNPKNTMYLQMNSLKPE DTAVYYCAARRSPSYTRVGDEYDYWGQGTQ VTVSSAAAYPYDVPDYGSHHHHHH |
| 154 (The CDRs are marked in bold, SEQ ID Nos: 15, 156-157) | CB202201 | MQVQLQESGGGLVQAGDSLRLSCAASGRSF SIYTMGWFRQAPGKEREFVSLIMRSGGIIY ADFVKGRFTISRDNAKNLVYLQMNSLKPED TAVYYCAAGGSTNSRAYNYYKLSLAYDYWG QGTQVTVSSAAAYPYDVPDYGSHHHHHH |
| 158 (The CDRs are marked in bold, SEQ ID Nos: 159-161) | CB202501 | MQVQLQESGGGLVQAGDSLRLSCAASGGTF STYTMGWFRQAPGKEREFVAAISRTGRGTD YADSVKGRFTISRDNVKNTVSLQMNSLKPE DTAVYYCAERSSVHYSGIAADYDYWSQGTQ VTVSSAAAYPYDVPDYGSHHHHHH |
| 162 (The CDRs are marked in bold, SEQ ID Nos: 163-165) | CB202901 | MQVQLQESGGGLVQPGGSLRLSCAASGRNL SRSAMGWFRQNPGEEREFVAAIDWWGDSTY YGDSVTGRFTISRDNAKNTLYLQMNSLKPE DTAVYYCAAGLRPFDGSWERRYDYWGQGTQ VTVSSAAAYPYDVPDYGSHHHHHH |

TABLE 3A

Amino acid sequences of anti-V-ATPase subunit Nanobodies

| SEQ ID NO: | Nanobody name | Amino Acid Sequence |
|---|---|---|
| 166 (The CDRs are marked in bold, SEQ ID Nos: 167-169) | VAT0101A | QVQLQESGGGLVQAGGSLRLSCAASGSTF SGYIMSWFRQPPGKERELVAAITYVGSTY VEDSVKGRFTISRDNAKNTVSLQMNSLKP EDTAVYYCRAREGEQLDFWGQGTQVTVSS AAAYPYDVPDYGSHHHHHH |
| 170 (The CDRs are marked in bold, SEQ ID Nos: 171,168-169) | VAT0101B | QVQLQESGGGLVQAGGSLRLSCAASGSTL SGYIMSWFRQPPGKERELVAAITYVGSTY VEDSVKGRFTISRDNAKNTVSLQMNSLKP EDTAVYYCRAREGEQLDFWGQGTQVTVSS AAAYPYDVPDYGSHHHHHH |
| 172 (The CDRs are marked in bold, SEQ ID Nos: 167-169) | VAT0101C | QVQLQESGGGLVQSGDSLRLSCAASGSTF SGYIMSWFRQPPGKERELVAAITYVGSTY VEDSVKGRFTISRDNAKNTVSLQMNSLKP EDTAVYYCRAREGEQLDFWGQGTQVTVSS AAAYPYDVPDYGSHHHHHH |

TABLE 3A-continued

Amino acid sequences of anti-V-ATPase subunit Nanobodies

| SEQ ID NO: | Nanobody name | Amino Acid Sequence |
|---|---|---|
| 173 (The CDRs are marked in bold, SEQ ID Nos: 174, 168-169) | VAT0101D | QVQLQESGGGLVQPGGSLRLSCVASGSTF SGYIMSWFRQPPGKERELVAAITYVGSTY VEDSVKGRFTISRDNAKNTVSLQMNSLKP EDTAVYYCRAREGEQLDFWGQGTQVTVSS AAAYPYDVPDYGSHHHHHH |
| 175 (The CDRs are marked in bold, SEQ ID Nos: 167-169) | VAT0101E | QVQLQESGGGLVQAGDSLRLSCAASGSTF SGYIMSWFRQPPGKERELVAAITYVGSTY VEDSVKGRFTISRDNAKNTVSLQMNSLKP EDTAVYYCRAREGEQLDFWGQGTQVTVSS AAAYPYDVPDYGSHHHHHH |
| 176 (The CDRs are marked in bold, SEQ ID Nos: 167-169) | VAT0101F | QVQLQESGGGTVQAGGSLRLSCAASGSTF SGYIMSWFRQPPGKERELVAAITYVGSTY VEDSVKGRFTISRDNAKNTVSLQMNSLKP EDTAVYYCRAREGEQLDFWGQGTQVTVSS AAAYPYDVPDYGSHHHHHH |
| 177 (The CDRs are marked in bold, SEQ ID Nos: 167, 178, 169) | VAT0101G | QVQLQESGGGLVQAGGSLRLSCAASGSTF SGYIMSWFRQPPGKERELVAAITYVGSTW YQDSVKGRFTISRDNAKNTVSLQMNSLKP EDTAVYYCRAREGEQLDFWGQGTQVTVSS AAAYPYDVPDYGSHHHHHH |
| 179 (The CDRs are marked in bold, SEQ ID Nos: 180-182) | VAT0201 | QVQLQESGGGTVQPGGSLKLSCAASGNLN YINVWSWYRQAPGKQRERVAGIATGGGRI SYSESVKGRFIISRDDATNTVSLQMSGLT PEDTAVYYCNAFGSDPDFSDYKHDYWGQG TQVTVSSAAAYPYDVPDYGSHHHHHH |

TABLE 3B

Amino acid sequences of anti-V-ATPase subunit Nanobodies

| SEQ ID NO: | Nanobody name | Amino Acid Sequence |
|---|---|---|
| 183 (The CDRs are marked in bold, SEQ ID Nos: 167-169) | VAT101H01 | QVQLQESGGGLVQTGGSLRLSCAASGST FSGYIMSWFRQPPGKERELVAAITYVGS TYVEDSVKGRFTISRDNAKNTVSLQMNS LKPEDTAVYYCRAREGEQLDFWGQGTQV TVSSAAAYPYDVPDYGSHHHHHH |
| 185 (The CDRs are marked in bold, SEQ ID Nos: 167-169) | VAT101I01 | QVQLQESGGGLVQAGGSLRLSCAASGST FSGYIMSWFRQPPGKERELVAAITYVGS TYVEDSVKGRFTISRDNVKNTVSLQMNS LKPEDTAVYYCRAREGEQLDFWGQGTQV TVSSAAAYPYDVPDYGSHHHHHH |
| 186 (The CDRs are marked in bold, SEQ ID Nos: 187-189) | VAT10301 | QVQLQESGGGLVQPGGSLRLSCAASGTI FSAKALGWHRQAPGKQREVVAGITSGGS TNYADSVKGRFTISRDNAKNTVYLQMNS VKFEDTAVYYCVLYDLIKDRTYWGQGTQ VTVSSAAAYPYDVPDYGSHHHHHH |
| 190 (The CDRs are marked in bold, SEQ ID Nos: 191-193) | VAT10401 | QVQLQESGGGLVQPGGSLRLSCATSTSI FSINVMDWYRQAPGKQRELVAGITSGDN TNYADSVKGRFTISRDNANNTVWLQMNS LKPEDTAVYYCRGRVYNGGWYDYWGQGT QVTVSSAAAYPYDVPDYGSHHHHHH |

TABLE 4

| | | |
|---|---|---|
| Amino acid sequences of anti-trehalase Nanobodies | | |
| SEQ ID NO: | Nanobody name | Amino Acid Sequence |
| 587 (The CDRs are marked in bold, SEQ ID Nos: 588-590) | TRH1a | QVQLQESGGGLVQAGGSLRLSCATSGRAF TNYHMGWFRQTPGKEREFVALISWSGDST RYADSVKGRFTISRDNAKRTVALQMDSLK PEDSAVYYCASRLVGQSQYEVWGQGTQVT VSSAAAYPYDVPDYGSHHHHHH |
| 591 (The CDRs are marked in bold, SEQ ID Nos: 588-589 and 592) | TRH1b | QVQLQESGGGLVQAGGSLRLSCAASGRAF TNYHMGWFRQTPGKEREFVALISWSGDST RYADSVKGRFTISRDNAKRTVALQMDSLK PEDSAVYYCASRLVGQSQYEIWGQGTQVT VSSAAAYPYDVPDYGSHHHHHH |
| 593 (The CDRs are marked in bold, SEQ ID Nos: 588-590) | TRH1c | QVQLQESGGGLVQAGGSLRLSCAASGRAF TNYHMGWFRQTPGKEREFVALISWSGDST RYADSVKGRFTISRDNAKRTVALQMDSLK PEDSAVYYCASRLVGQSQYEVWGQGTQVT VSSAAAYPYDVPDYGSHHHHHH |
| 594 (The CDRs are marked in bold, SEQ ID Nos: 595, 589 and 592) | TRH1d | QVQLQESGGGLVQAGGSLRLSCAASTRAF TNYHMGWFRQTPGKEREFVALISWSGDST RYADSVKGRFTISRDNAKRTVALQMDSLK PEDSAVYYCASRLVGQSQYEIWGQGTQVT VSSAAAYPYDVPDYGSHHHHHH |
| 596 (The CDRs are marked in bold, SEQ ID Nos: 588-590) | TRH1e | QVQLQESGGGLVQTGGSLRLSCAASGRAF TNYHMGWFRQTPGKEREFVALISWSGDST RYADSVKGRFTISRDNAKRTVALQMDSLK PEDSAVYYCASRLVGQSQYEVWGQGTQVT VSSAAAYPYDVPDYGSHHHHHH |
| 194 (The CDRs are marked in bold, SEQ ID Nos: 195-197) | TRH2a | QVQLQESGGGLVQAGGSLRLACAASERTF SSYVMGWFRQGPGKEREFVAAISWSGGAR YYADSVKGRFTISRDNAKNTVYLQMSSLK PEDTAVYVCAARRTYSPRTLEYDFWGQGT QVTVSSAAAYPYDVPDYGSHHHHHH |
| 198 (The CDRs are marked in bold, SEQ ID Nos: 199, 196-197) ' | TRH2b | QVQLQESGGGLVQAGGSLRLSCAASGDTF STYVMGWFRQGPGKEREFVAAISWSGGAR YYADSVKGRFTISRDNAKNTVYLQMSSLK PEDTAVYVCAARRTYSPRTLEYDFWGQGT QVTVSSAAAYPYDVPDYGSHHHHHH |
| 200 (The CDRs are marked in bold, SEQ ID Nos: 201-203) | TRH3a | QVQLQESGGGLVQPGGSLRLSCAASGFTF SDYVMSWVRQAPGKGFEWVSIINTDGIGS RYADSVMGRFTISRDNEKKMMYLQMNSLK PEDTAMYYCARGNAALTVIRGRPWGQGTQ VTVSSAAAYPYDVPDYGSHHHHHH |
| 204 (The CDRs are marked in bold, SEQ ID Nos: 201, 205-206) | TRH3b | QVQLQESGGGLVQPGGSLRLSCAASGFTF SDYVMSWVRQAPGKGFEWVSI INTDGNGS RYADSVMGRFTISRDNDKKMMYLQMNSLK PEDTAMYYCAKGNAALSLIRGRPWGQGTQ VTVSSAAAYPYDVPDYGSHHHHHH |
| 207 (The CDRs are marked in bold, SEQ ID Nos: 208-210) | TRH5a | QVQLQESGGGLVQPGGSLRLSCAASGRTF STYAMGWFRQAHGKEREFVAAISWGRGNT YYGDSLKGRFTISRDNAKNTVYLQMDSLK PEDTAVYYCAADPGRAYVSGNYYSAATYD YWGQGTQVTVSSAAAYPYDVPDYGSHHHH HH |
| 211 (The CDRs are marked in bold, SEQ ID Nos: 212, 209-210) | TRH5b | QVQLQESGGGLVQAGGSLRLSCAASGRTF SSYAMGWFRRFPGKEREFVAAISWGRGNT YYGDSLKGRFTISRDNAKNTVYLQMDSLK PEDTAVYYCAADPGRAYVSGNYYSAATYD YWGQGTQVTVSSAAAYPYDVPDYGSHHHH HH |
| 213 (The CDRs are marked in bold, SEQ ID Nos: 208-210) | TRH5c | QVQLQESGGGLVQAGGSLRLSCAASGRTF STYAMGWFRQAHGKEREFVAAISWGRGNT YYGDSLKGRFTISRDNAKNTVYLQMDSLK PEDTAVYYCAADPGRAYVSGNYYSAATYD YWGQGTQVTVSSAAAYPYDVPDYGSHHHH HH |

TABLE 4-continued

Amino acid sequences of anti-trehalase Nanobodies

| SEQ ID NO: | Nanobody name | Amino Acid Sequence |
|---|---|---|
| 214 (The CDRs are marked in bold, SEQ ID Nos: 215-217) | TRH6 | QVQLQESGGGLVQAGGSLRLSCAASGGSF STIPMGWFRQAPEMERGFVAAISYRGTYT YYTNSVKGRFTISRDNAKNTVYLQMNSLK PEDTAVYYCAAGSPGISAYWGDLSNWKNW**GQGTQVTVSSAAAYPYDVPDYGSHHHHHH |
| 218 (The CDRs are marked in bold, SEQ ID Nos: 219-221) | TRH7 | QVQLQESGGGVVQAGGSLRLSCVASGRSF SSHAMGWFRQATGKEREFVATISWNSGST FYADSLRGRFTISRDNAKNTLYLQMNSLT AEDTAVYYCAAASGRGITASAFRYDVWGQ GTQVTVSSAAAYPYDVPDYGSHHHHHH |
| 222 (The CDRs are marked in bold, SEQ ID Nos: 223-225) | TRH8 | QVQLQESGGGLVQAGDSLRLSCAASGRTF SSYTMGWFRQAPGKEREFVAAIRWSGSIT YYSDSVKGRFTISRDNAKNTVYLQMNSLK PEDTAVYYCAADPGRIFGSGSYYGNRNTY DY**WGQGTQVTVSSAAAYPYDVPDYGSHHH HHH |
| 226 (The CDRs are marked in bold, SEQ ID Nos: 227-229) | TRH9a | QVQLQESGGGLVQAGGSLRLSCAVSERTF RTYTMAWFRQAPGKEREFVAAIRWNGDST YYADSVKGRFTISRDNAKNTMYLQMNSLK PEDTAVYNCAARAPSGGYYYPNALSEYNY**WGQGTQVTVSSAAAYPYDVPDYGSHHHHH H |
| 230 (The CDRs are marked in bold, SEQ ID Nos: 231,228,232) | TRH9b | QVQLQESGGGLVQPGGSLRLSCAASERTF RTYTMGWFRQAPGKEREFVAAIRWNGDST YYADSVKGRFTISRDNAKNTMYLQMNSLK PEDTAVYSCAARAYSIGYYYPNALSEYNY**WGQGTQVTVSSAAAYPYDVPDYGSHHHHH H |
| 233 (The CDRs are marked in bold, SEQ ID Nos: 234-236) | TRH11 | QVQLQESGGGLVQAGDSLRLSCAASGVTI SRYTMGWFRQAPGKEREFVGLIRWSNGNT YYTDSVKGRFTISRDNAKNTVYLQMNSLK PEDTAVYYCATLRSGYVGSAYSQQAYDYW**GQGTQVTVSSAAAYPYDVPDYGSHHHHHH |
| 237 (The CDRs are marked in bold, SEQ ID Nos: 238-240) | TRH12 | QVQLQESGGGLVQAGGSLRLSCAASTSTV SDYHMGWFRQGPGKEREFVAAISWSGDST DYADSVKARFTISRDNAKKTMSLQMNSLK PEDTAAYYCAARRVFKATWDY**WGQGTQVT VSSAAAYPYDVPDYGSHHHHHH |
| 241 (The CDRs are marked in bold, SEQ ID Nos: 242-244) | TRH13 | QVQLQESGGGLVQAGGSLRLTCAATVRIF SSYTMGWFRQSPGKEREFVGAITWSGGNT YYADSVKGRFTISRDNAKNTVYLQMNSLK SEDTAVYYCAADPGRSYVLSRYYDQASYD Y**WGQGTQVTVSSAAAYPYDVPDYGSHHHH HH |
| 245 (The CDRs are marked in bold, SEQ ID Nos: 246-248) | TRH14 | QVQLQESGGGLVQAGDSLRLSCAASGRPF SSYTMGWFRQAPGKEREFVAAISWSGGTT YYTDSVQGRFTISRDNAKNTVYLQMNRLK PEDTAVYYCATDVGRIYGGGSLYSSAFSY DY**WGQGTQVTVSSAAAYPYDVPDYGSHHH HHH |
| 249 (The CDRs are marked in bold, SEQ ID Nos: 250-252) | TRH17 | QVQLQESGGGLVQAGASLRLSCAASGGTF SDYVMGWFRQPPGKEREFVASINYGGDKI SYADSLEGRFTILRDNTKDTTSLQMNTLK PDDTAVYYCAAKWGYKTGPTYSY**WGQGTQ VTVSSAAAYPYDVPDYGSHHHHHH |
| 253 (The CDRs are marked in bold, SEQ ID Nos: 254-256) | TRH18 | QVQLQESGGGLVQAGGSLRLSCAASGRTF SNVAMGWFRQAPGKEREFAAAISGSGGTT YYAASVKGRFTISRDNGKKMVYLQMNSLK PEDTAVYYCSTYDGR**RGQGTQVTVSSAAA YPYDVPDYGSHHHHHH |

TABLE 4-continued

Amino acid sequences of anti-trehalase Nanobodies

| SEQ ID NO: | Nanobody name | Amino Acid Sequence |
|---|---|---|
| 257 (The CDRs are marked in bold, SEQ ID Nos: 258-260) | TRH20 | QVQLQESGGGLVQAGGSLRLSCAASGLTF SRNAIAWFRQAPGKEREFVAAISWNAITT AYGDSVKGRFTIFRGNTKNTVYLQMNSLK PEDTAVYYCAARYSSGSYYYARTYEYDYW GQGTQVTVSSAAAYPYDVPDYGSHHHHHH |

TABLE 5

Amino acid sequences of anti-cytochrome p450 Nanobodies

| SEQ ID NO: | Nanobody name | Amino Acid Sequence |
|---|---|---|
| 261 (The CDRs are marked in bold, SEQ ID Nos: 262-264) | P45001A | QVQLQESGGGLVQTGGSLRLSCAASGRTS RSYAMGWFRQAPGKERELVADIAWSDGRI YYSDSVKGRFTISRDNAKNTVYLEIDSLK PGDTAVYYCASRARGTVLYNYWGQGTQVT VSSAAAYPYDVPDYGSHHHHHH |
| 265 (The CDRs are marked in bold, SEQ ID Nos: 262-263, 266) | P45001B | QVQLQESGGGLVQPGGSLRLSCAASGRTS RSYAMGWFRQAPGKEREHVADIAWSDGRI YYSDSVKDRFTISRDNAKNTVYLEIDSLK PGDTAVYYCASRARGTVSYNYWGQGTQVT VSSAAAYPYDVPDYGSHHHHHH |
| 267 (The CDRs are marked in bold, SEQ ID Nos: 262-264) | P45001C | QVQLQESGGGLVQAGGSLRLSCAASGRTS RSYAMGWFRQAPGKERELVADIAWSDGRI YYSDSVKGRFTISRDNAKNTVYLEIDSLK PGDTAVYYCASRARGTVLYNYWGQGTQVT VSSAAAYPYDVPDYGSHHHHHH |
| 268 (The CDRs are marked in bold, SEQ ID Nos: 262-263, 266) ' | P45001D | QVQLQESGGGLVQAGGSLTLSCAASGRTS RSYAMGWFRQAPGKERELVADIAWSDGRI YYSDSVKGRFTISRDNAKNTVYLEIDSLK PGDTAVYYCASRARGTVSYNYWGQGTQVT VSSAAAYPYDVPDYGSHHHHHH |
| 269 (The CDRs are marked in bold, SEQ ID Nos: 262, 270, 264) | P45001E | QVQLQESGGGLVQAGDSLRLSCAASGRTS RSYAMGWFRQAPGKERELVADISWSDGRI YYSDSVKGRFTISRDNAKNTVYLEIDSLK PGDTAVYYCASRARGSVLYNYWGQGTQVT VSSAAAYPYDVPDYGSHHHHHH |
| 271 (The CDRs are marked in bold, SEQ ID Nos: 262-263, 266) | P45001F | QVQLQESGGGSVQAGGSLRLSCAASGRTS RSYAMGWFRQAPGKERELVADIAWSDGRI YYSDSVKGRFTISRDNAKNTVYLEIDSLK PGDTAVYYCASRARGTVSYNYWGQGTQVT VSSAAAYPYDVPDYGSHHHHHH |
| 272 (The CDRs are marked in bold, SEQ ID Nos: 262-263, 266) | P45001G | QVQLQESGGGLVQAGGSLRLSCAASGRTS RSYAMGWFRQAPGKERELVADIAWSDGRI YYSDSVKGRFTISRDNAKNTVYLEIDSLK PGDTAVYYCASRARGTVSYNYWGQGTQVT VSSAAAYPYDVPDYGSHHHHHH |
| 273 (The CDRs are marked in bold, SEQ ID Nos: 274-276) | P45002A | QVQLQESGGGLVQAGGSLRLSCVYSGNVF SINLMGWYRQAPGKQRELLAGINRGGRTN YTDVVKGRFTISRENAKNTIYLQMNGLKP EDTGVYYCAASRDPYTGYWGQGTQVTVSS AAAYPYDVPDYGSHHHHHH |
| 277 (The CDRs are marked in bold, SEQ ID Nos: 274-276) | P45002B | QVQLQESGGGLVQAGGSLRLSCVYSGNVF SINLMGWYRQAPGKQRELLAGINRGGRTN YTDVVKGRFTISKENAKNTIYLQMNSLKP EDTGVYYCAASRDPYTGYWGQGTQVTVSS AAAYPYDVPDYGSHHHHHH |
| 278 (The CDRs are marked in bold, SEQ ID Nos: 274-276) | P45002C | QVQLQESGGGLVQAGGSLRLSCVYSGNVF SINLMGWYRQAPGKQRELLAGINRGGRTN YTDVVKGRFTISRENAKNTIYLQMNSLKP EDTGVYYCAASRDPYTGYWGQGTQVTVSS AAAYPYDVPDYGSHHHHHH |

TABLE 5-continued

Amino acid sequences of anti-cytochrome p450 Nanobodies

| SEQ ID NO: | Nanobody name | Amino Acid Sequence |
|---|---|---|
| 279 (The CDRs are marked in bold, SEQ ID Nos: 280, 275-276) ' | P45002D | QVQLQESGGGLVQPGGSLRLSCVASGSVD SINLMGWYRQAPGKQRELLAGINRGGRTN YTDVVKGRFTISRENAKNTIYLQMNSLKP EDTGVYYCAASRDPYTGYWGQGTQVTVSS AAAYPYDVPDYGSHHHHHH |
| 281 (The CDRs are marked in bold, SEQ ID Nos: 282, 275-276) | P45002E | QVQLQESGGGLVPSGGSLRLSCVYSGNVF SINLMGWYRQAPGKQRELLAGINRGGRTN YTDWKGRFTISRENAKNTIYLQMNGLKPE DTGVYYCAASRDPYTGYWGQGTQVTVSSA AAYPYDVPDYGSHHHHHH |
| 283 (The CDRs are marked in bold, SEQ ID Nos: 282, 275-276) | P45002F | QVQLQESGGGLVQAGGSLRLSCVYSGNVF SINLMGWYRQAPGKQRELLAGITRGGRTN YTDVVKGRFTISRESAKNTIYLQMNSLKP EDTGVYYCAASRDPYTGYWGQGTQVTVSS AAAYPYDVPDYGSHHHHHH |
| 284 (The CDRs are marked in bold, SEQ ID Nos: 282, 275, 285) | P45002G | QVQLQESGGGLVQAGGSLRLSCVYSGNVF SINLMGWYRQAPGKQRELLAGITRGGRTN YTDVVKGRFTISRENAKNTIYLQMNSLKP EDTGVYYCAASRDPYTGYWGQGTQVTVSS AAAYPYDVPDYGSHHHHHH |
| 286 (The CDRs are marked in bold, SEQ ID Nos: 287, 220, 289) | P45003A | QVQLQESGGGLVQAGDSLRLSCVASKRSF SSHAMGWFRQAPGKAREFVATISWNSGST FYSDSSRGRFTISRDNGKNTLYLQMNSLK PEDTAVYYCAAASGRGITASDFRYDAWGQ GTQVTVSSAAAYPYDVPDYGSHHHHHH |
| 290 (The CDRs are marked in bold, SEQ ID Nos: 291,220, 289)' | P45003B | QVQLQESGGGVVQAGGSLRLSCVGSGRTF SSHAMGWFRQAPGKEREFVATISWNSGST FYADSVRGRFTISRDNAKNTLYLQMNSLK AEDTAVYYCAAASGRGITASDFRYDAWGQ GTQVTVSSAAAYPYDVPDYGSHHHHHH |
| 292 (The CDRs are marked in bold, SEQ ID Nos: 293-294,289) | P45003C | QVQLQESGGGSVQAGGSLRLSCVASGRSF SRHAMAWFRQAPGKEREFVATISWNAGST YYADSVKGRFTISRDNAKNTVTLQMNSLK PEDTAVYYCAAASGRGITASDFRYDAWGQ GTQVTVSSAAAYPYDVPDYGSHHHHHH |
| 295 (The CDRs are marked in bold, SEQ ID Nos: 296-298) | P45004 | QVQLQESGGGLVQAGGSLRLSCAASGRTF SRINMGWFRQAPGKEREFVAVISWNSIAD YADSVKARFTISRDNAKNTVYLQMNSLKP EDTAVYYCAASAPFRSKNPTLYLYWGRGT QVTVSSAAAYPYDVPDYGSHHHHHH |
| 299 (The CDRs are marked in bold, SEQ ID Nos: 300-302) | P45005 | QVQLQESGGGLVQSGDSLRLSCSASGRTF NPVAMAWFRXAPGKEREFVGTITWGIGST HYAVPVKGRFTISKENAKNTVYLQMNRLQ PEDTAVYYCAARTSLLRRADEIPSVANYD SWGQGTQVTVSSAAAYPYDVPDYGSHHHH HH |
| 303 (The CDRs are marked in bold, SEQ ID Nos: 304-306) | P45006 | QVXLQESGGGLVQAGDSLRLSCAASGRTF SMYTMGWFRQAPGKEREFVAKISTSGRYT DYVDSVRGRFTLSRDNVKNTIYLQMNSLK PDDTAVYYCAARLPRPDTWSQGKTDYWGQ GTQVTVSSAAAYPYDVPDYGSHHHHHH |
| 307 (The CDRs are marked in bold, SEQ ID Nos: 308-310) | P45007 | QVQLQESGGGLVQAGGSLRLSCAASGRTF SNNPMGWFRXAPGKEREFVATKTGGNSGI TVYSNSVKGRFTISRDLAKNTVYLQMDGL KLEDTAIYYCAASGTPLALRSEKNYDYWG QGTQVTVSSAAAYPYDVPDYGSHHHHHH |
| 311 (The CDRs are marked in bold, SEQ ID Nos: 312-314) | P45008 | QVXLQESGGGLVQPGGSLRLSCAASGSIF NINTMGWYRQAPGNQRELVAAISSDGRPN HRDSVKGRFTISRDNAKNTVYLQMNSLKP EDTAVYYCNTVPASRAGGYWGQGTQVTVS SAAAYPYDVPDYGSHHHHHH |

TABLE 5-continued

Amino acid sequences of anti-cytochrome p450 Nanobodies

| SEQ ID NO: | Nanobody name | Amino Acid Sequence |
|---|---|---|
| 315 (The CDRs are marked in bold, SEQ ID Nos: 316-318) | P45009 | QVQLQESGGGLAQAGDSLRLSCVASGRTI DNGAMGWFRQAPGKERESVAAINWSGSST YYADSVKGRFAISRDNVKHEVYLQMNRLR REDTAVYYCAAAKSIGTYSSSSAYDYWGQ GTQVTVSSAAAYPYDVPDYGSHHHHHH |

TABLE 6

Amino acid sequences of anti-chitin deacetylase Nanobodies

| SEQ ID NO: | Nanobody name | Amino Acid Sequence |
|---|---|---|
| 319 (The CDRs are marked in bold, SEQ ID Nos: 320-322) | CDA1a | QVQLQESGGGLVQAGGSLRLSCAASGRTF NTYAMGWFRQAPGKEREFVAAMNRDGSTV LYADSVKGRFAISKDNAKNTGYLQMNSLK PEDTAIYYCAANARYSDYTDGQSFVSWGQ GTQVTVSSAAAYPYDVPDYGSHHHHHH |
| 323 (The CDRs are marked in bold, SEQ ID Nos: 320,324-325) | CDA1b | QVQLQESGGGLVQAGGSLRLSCQASGRTF NTYAMGWFRQAPGKEREFVAAMNRDGSTI LYGDSVKGRFAISRDNAKNTGYLQMNSLK PEDTAIYYCAANARYSDYTHGQSFVSWGQ GTQVTVSSAAAYPYDVPDYGSHHHHHH |
| 326 (The CDRs are marked in bold, SEQ ID Nos: 327,321, 328) | CDA1c | QVQLQESGGGLVQAGGSLRLSCQASGRTF DAYAMGWFRQAPGKEREFVAAMNRDGSTV LYADSVKGRFAISKDNAKNTGYLQMNSLK PEDTAIYYCAANARYSDYTDGQSFISWGQ GTQVTVSSAAAYPYDVPDYGSHHHHHH |
| 329 (The CDRs are marked in bold, SEQ ID Nos: 320-322) | CDA1d | QVQLQESGGGLVQAGGSLRLSCQASGRTF NTYAMGWFRQAPGKEREFVAAMNRDGSTV LYADSVKGRFAISKDNAKNTGYLQMNSLK PEDTAIYYCAANARYSDYTDGQSFVSWGQ GTQVTVSSAAAYPYDVPDYGSHHHHHH |
| 331 (The CDRs are marked in bold, SEQ ID Nos: 320-321, 332) | CDA1e | QVQLQESGGGLVQAGGSLRLSCVASGRTF NTYAMGWFRQAPGKEREFVAAMNRDGSTV LYADYVKGRFAISKDNAKNTGYLQMNSLK PEDTAIYYCAANARYSDYTDEQSFVSWGQ GTQVTVSSAAAYPYDVPDYGSHHHHHH |
| 333 (The CDRs are marked in bold, SEQ ID Nos: 320-322) | CDA1f | QVQLQESGGGLVQAGGSLRLSCQASGRTF NTYAMGWFRQAPGKEREFVAAMNRDGSTV LYADSVKGRFAISKDNAKSTGYLQMNSLK PEDTAIYYCAANARYSDYTDGQSFVSWGQ GTQVTVSSAAAYPYDVPDYGSHHHHHH |
| 334 (The CDRs are marked in bold, SEQ ID Nos: 208, 336-337) | CDA1g | QVQLQESGGGLVQAGGSLRLSCKASGRTF STYAVGWFRQAPGKPREFVAAMNSRGSTI NYADSVKGRFAISRDNAKNTGYLQMDSLK PEDTAIYYCAADARYSDYTDGQSFKSWGQ GTQVTVSSAAAYPYDVPDYGSHHHHHH |
| 338 (The CDRs are marked in bold, SEQ ID Nos: 320, 324, 339) | CDA1h | QVQLQESGGGLVQAGGSLRLSCQASGRTF NTYAMGWFRQAPGKEREFVAAMNRDGSTI LYADSVKGRFAISKDNAKNTGYLQMNSLK PEDTAIYYCAANARYSDYTNGHSFVSWGQ GTQVTVSSAAAYPYDVPDYGSHHHHHH |
| 340 (The CDRs are marked in bold, SEQ ID Nos: 320-322) | CDA1i | QVQLQESGGGLVQPGGSLRLSCQASGRTF NTYAMGWFRQAPGKEREFVAAMNRDGSTV LYADSVKGRFAISKDNARNTGYLQMNSLK PEDTAIYYCAANARYSDYTDGQSFVSWGQ GTQVTVSSAAAYPYDVPDYGSHHHHHH |
| 341 (The CDRs are marked in bold, SEQ ID Nos: 320-322) | CDA1j | QVQLQESGGGLVQAGGSLRLSCQASGRTF NTYAMGWFRQAPGKEREFVAAMNRDGSTV LYRDSVKGRFAISKDNARNTGYLQMNNLK PEDTAIYYCAANARYSDYTDGQSFVSWGQ GTQVTVSSAAAYPYDVPDYGSHHHHHH |

TABLE 6-continued

Amino acid sequences of anti-chitin deacetylase Nanobodies

| SEQ ID NO: | Nanobody name | Amino Acid Sequence |
|---|---|---|
| 342 (The CDRs are marked in bold, SEQ ID Nos: 343-345) | CDA1k | QVQLQESGGGLVQAGGSLRLSCQASERSF STYAMGWFRQAPGKEREFVAAMNRNGNTI NYLDSVKGRFAISRDNAKSTGYLQMNSLK PEDTATYYCSANARLSDYINPQSFVSWGQ GTQVTVSSAAAYPYDVPDYGSHHHHHH |
| 346 (The CDRs are marked in bold, SEQ ID Nos: 347-349) | CDA2a | QVQLQESGGGLVQAGGSLRLSCAASGRAF SSYGMAWFRQAPGKEREFVAAINSNGRST YYADTVKGRFTISRDDGRNTLYLQMNSLK PEDTAVYYCAADRQSMKGYEYGYWGQGTQ VTVSSAAAYPYDVPDYGSHHHHHH |
| 350 (The CDRs are marked in bold, SEQ ID Nos: 351-353) | CDA2b | QVQLQESGGGLVQAGGSLRLSCAASGRAF SRYGMAWFRQAPGKEREFVAAITSNGRST YYADTVKGRFTISRDNGRNTLYLQMNTLK PEDTAVYYCAADRKSMTGYEYGYWGQGTQ VTVSSAAAYPYDVPDYGSHHHHHH |
| 354 (The CDRs are marked in bold, SEQ ID Nos: 351-353) | CDA2c | QVQLQESGGGLVQPGGSLRLSCAASGRAF SRYGMAWFRQAPGKEREFVAAITSNGRST YYADTVKGRFTISRDNGRNTLYLQMNTLK PEDTAVYYCAADRKSMTGYEYGYWGQGTQ VTVSSAAAYPYDVPDYGSHHHHHH |
| 355 (The CDRs are marked in bold, SEQ ID Nos: 351,347, 356) | CDA2d | QVQLQESGGGLVQAGGSLRLSCAASGRAF SRYGMAWFRQAPGKEREFVGAINSNGRST YYADTVKGRFTISRDNDRNTLYLQMNSLK PEDTAVYYCAADRQSMTRYEYGYWGQGTQ VTVSSAAAYPYDVPDYGSHHHHHH |
| 357 (The CDRs are marked in bold, SEQ ID Nos: 358-360) | CDA3a | QVQLQESGGGLVQPGGSLRLSCAASGFTF SNYAMGWFRQAPGKERDFVAAVSGIARRT YYADSVKGRSTISRDNGRNTLYLQMNNLK PEDTAVYYCARATSRMTSVTTLNDYGYWG QGTPVTVSSAAAYPYDVPDYGSHHHHHH |
| 361 (The CDRs are marked in bold, SEQ ID Nos: 358-359, 362) | CDA3b | QVQLQESGGGLVQPGESLRLSCAASGFTF SNYAMGWFRQAPGKERDFVAAVSGIARRT YYADSVKGRSTISRDNGRNTVYLQMNSLK PEDTAVYYCARATSRMTSVTTLDDYGYWG QGTQVTVSSAAAYPYDVPDYGSHHHHHH |
| 363 (The CDRs are marked in bold, SEQ ID Nos: 358-360) | CDA3c | QVQLQESGGGLVQPGGSLRLSCAASGFTF SNYAMGWFRQAPGKERDFVAAVSGIARRT YYADSVKGRSTISRDNGRNTVYLQMNSLK PEDTAVYYCARATSRMTSVTTLNDYGYWG QGTQVTVSSAAAYPYDVPDYGSHHHHHH |
| 364 (The CDRs are marked in bold, SEQ ID Nos: 365, 359, 366) | CDA3d | QVQLQESGGGLVQPGGSLRLSCAASGFTF SSYAMGWFRQAPGKEREFVAAVSGIARRT YYADSVKGRSTISRDNGRNTVYLQMNSLK PEDTAVYYCARATSRMTSVTTLNDYAYWG QGTQVTVSSAAAYPYDVPDYGSHHHHHH |
| 367 (The CDRs are marked in bold, SEQ ID Nos: 368-370) | CDA4a | QVQLQESGGGSVQSGGSLTLSCSASGSLF SINAMGWYRQAPRKQHELVATMMDGGSTS YADSVKGRFTISRDNDKKTVYLQMNSLKP EDTGVYYCVADRLGSGRYAYGIDYWGQGT QVTVSSAAAYPYDVPDYGSHHHHHH |
| 371 (The CDRs are marked in bold, SEQ ID Nos: 372, 369-370) | CDA4b | QVQLQESGGGLVQPGGSLRLACAASGSIF SINAMGWYRQAPRKQRELVATMMDGGSTS YADSVKGRFTISRDNDKKTVYLQMNSLKP EDTGVYYCVADRLGSGRYAYGIDYWGQGT QVTVSSAAAYPYDVPDYGSHHHHHH |
| 373 (The CDRs are marked in bold, SEQ ID Nos: 374, 369, 375) | CDA4c | QVQLQESGGGLVQAGGSLRLSCAASGSIV SINGMGWYRQAPRKQRELVATMMDGGSTS YADSVKGRFTISRDNDKKTVYLQMNSLKP EDTGVYYCAADRLGSGRYAYAIDYWGQGT QVTVSSAAAYPYDVPDYGSHHHHHH |

TABLE 6-continued

Amino acid sequences of anti-chitin deacetylase Nanobodies

| SEQ ID NO: | Nanobody name | Amino Acid Sequence |
|---|---|---|
| 376 (The CDRs are marked in bold, SEQ ID Nos: 377-379) | CDA5 | QVQLQESGGGLVQPGGSLRLSCTASGRTV SNYGMAWFRQVAGKERAFVAAINNRGDSK YYAESVKGRFTIARDNAKNTVYLQMNVLK PEDTAVYYCAADRRSLVRYEYNYWGQGTQ VTVSSAAAYPYDVPDYGSHHHHHH |
| 380 (The CDRs are marked in bold, SEQ ID Nos: 381-383) | CDA6a | QVQLQESGGGLVQAGGSLRLSCAASGRTF SRYTMGWFRQAPGKEREFVAAIRWSSGNT YYTDAVKGRFTISRDNTENTVYLQMNSLK PEDTAVYYCVADDGLSYASSSYLYWGQGT QVTVSSAAAYPYDVPDYGSHHHHHH |
| 384 (The CDRs are marked in bold, SEQ ID Nos: 385, 382-383) | CDA6b | QVQLQESGGGLVQPGGSLRLSCAASGFTF SRYTMGWFRQAPGKEREFVAAIRWSSGNT YYTDAVKGRFTISRDNTENTVYLQMNSLK PEDTAVYYCVADDGLSYASSSYLYWGQGT QVTVSSAAAYPYDVPDYGSHHHHHH |
| 386 (The CDRs are marked in bold, SEQ ID Nos: 387-389) | CDA7a | QVQLQESGGGLVQAGGSLRLSCVASGRTF GNYGLAWFRQPPGKEREFVAAINNRGGNT YYADSVKGRFTISRDNAANTLYLQMSSLK PEDTAVYYCAADRTSLHSYRYTYWGQGTQ VTVSSAAAYPYDVPDYGSHHHHHH |
| 390 (The CDRs are marked in bold, SEQ ID Nos: 387, 391, 389) | CDA7b | QVQLQESGGGLVQAGGSLRLSCVASGRTF GNYGLAWFRQPPGKEREFVAAISNRGGNT YYADSVKGRFTISRDNAANTLYLQMSSLK PEDTAVYYCAADRTSLHSYRYTYWGQGTQ VTVSSAAAYPYDVPDYGSHHHHHH |
| 392 (The CDRs are marked in bold, SEQ ID Nos: 387, 391, 389) | CDA7c | QVQLQESGGGLVQAGDSPKLSCVASGRTF GNYGLAWFRQPPGKEREFVAAISNRGGNT YYADSVKGRFTISRDNAANTLYLQMSSLK PEDTAVYYCAADRTSLHSYRYTYWGQGTQ VTVSSAAAYPYDVPDYGSHHHHHH |
| 393 (The CDRs are marked in bold, SEQ ID Nos: 394-396) | CDA8 | QVQLQESGGGLVQAGGSLRLSCAASERTF STYNMAWFRQAPGKERESVSRINWNGGFT GYADSVKGRFTISRDNAKKAMYLQMNSLK SEDTAVYYCAACGSAYPCRPEEYTYWGQG TQVTVSSAAAYPYDVPDYGSHHHHHH |
| 397 (The CDRs are marked in bold, SEQ ID Nos: 398-400) | CDA10 | QVQLQESGGGLVQTGESLRLSCAASGRTL SSYTMGWFRQAPGKEREIVAASSWSGGRT YYADSVKGRFTMSRNNAENTVYLQMNSLN PEDTAVYYCAADSSRAPRTYNYWGQGTQV TVSSAAAYPYDVPDYGSHHHHHH |
| 401 (The CDRs are marked in bold, SEQ ID Nos: 402-404) | CDA12 | QVQLQESGGGLVQAGGSLRLSCAASGRTF STYNMSWFRQGPGKERIFVATISWSGRVT DYADSVRGRFTISRDNAKKMVYLQMNSLK PEDTAVYYCAADSNSRRSRDYDYWGQGTQ VTVSSAAAYPYDVPDYGSHHHHHH |
| 405 (The CDRs are marked in bold, SEQ ID Nos: 406-408) | CDA14 | QVQLQESGGGLVQPGGSLRLSCAASGTTR RINSMRWYRQTPGNERDLVAGITEGGFTA YVDSVKGRFTISRDNAKNTVYLQMNSLKP EDTAVYYCYAAYLGAAYWGQGTQVTVSSA AAYPYDVPDYGSHHHHHH |

TABLE 7

| SEQ ID NO: | Nanobody name | Amino Acid Sequence |
|---|---|---|
| | | Amino acid sequences of anti-chitin synthase Nanobodies |
| 411 (The CDRs are marked in bold, SEQ ID Nos: 412-414) | CHS1a | QVQLQESGGGLVQAGGSLRLSCSASTSIAS INAVGWYRQAPGKQRELVAVIVNGSTTRYA DSVKGRFTISGDNAENTVPLLMSSLKPEDT AIYYCGARDLSGTYWGQGTQVTVSSAAAYP YDVPDYGSHHHHHH |
| 415 (The CDRs are marked in bold, SEQ ID Nos: 412-414) | CHS1b | QVQLQESGGGLVQPGGSLRLSCSASTSIAS INAVGWYRQAPGKQRELVAVIVNGSTTRYA DSVKGRFTISGDNAKNTVPLQMSSLKPEDT AIYYCGARDLSGTYWGQGTQVTVSSAAAYP YDVPDYGSHHHHHH |
| 416 (The CDRs are marked in bold, SEQ ID Nos: 412-414) | CHS1c | QVQLQESGGGLVQAGGSLRLSCSASTSIAS INAVGWYRQAPGKQRELVAVIVNGSTTRYA DSVKGRFTISGDNAKNTVPLQMSSLKPEDT AIYYCGARDLSGTYWGQGTQVTVSSAAAYP YDVPDYGSHHHHHH |
| 417 (The CDRs are marked in bold, SEQ ID Nos: 418-420) | CHS2a | QVQLQESGGGLVQAGGSLRLSCAASRGTFS RYVMGWFRQGPGKEREFVAGISWSGISTYY ADFVKGRFTISRDNAKNTVYLQMNSLKPED TAVYYCAADPGRGYDYWGQGTQVTVSSAAA YPYDVPDYGSHHHHHH |
| 421 (The CDRs are marked in bold, SEQ ID Nos: 422-424) | CHS2b | QVQLQESGGGLVQAGGSLRLSCAASGRSFS RSVMGWFRQAPGKEREFVAATSWSGGGTYY ADSVKGRFTISRDNAQNTVYLQMNSLKPED TAVYYCAADVGRGYHYWGQGTQVTVSSAAA YPYDVPDYGSHHHHHH |
| 425 (The CDRs are marked in bold, SEQ ID Nos: 426-428) | CHS3a | QVQLQESGGGLVQAGGSLRLSCVASGGTFS GLTMGWFRQAPQKEREFVAAISWTGRSTYY ADSVKGRFTISRDNVKNMVYLQMNSLKPED TGVYFCAADWASGTPYWGQGTQVTVSSAAA YPYDVPDYGSHHHHHH |
| 429 (The CDRs are marked in bold, SEQ ID Nos: 426-427 and 430) | CHS3b | QVQLQESGGGLVQAGTSLRLSCAASGGTFS GLTMGWFRQAPQKEREFVAAISWTGRSTYY ADSVKGRFTISRDNVKNMVYLQMVALNPED TAVYYCAADWASATPYWGQGTQVTVSSAAA YPYDVPDYGSHHHHHH |
| 431 (The CDRs are marked in bold, SEQ ID Nos: 432-434) | CHS4 | QVQLQESGGGLVQSGESLTLACVISGITLE RYTVGWFHQAPGKNPEGVSCIGKSNDETFY TDSVKGRFTISSDNAKNTVYLQMNSLTPSD AGVYYCAAAKAPVTAYDCSLYLYTWRSTYR GQGTQVTVSSAAAYPYDVPDYGSHHHHHH |
| 435 (The CDRs are marked in bold, SEQ ID Nos: 436, 140 and 437) | CHS5 | QVQLQESGGGLVQAGGSLTLSCAASARTFS TYALAWFRQTPGKGREFVGAISRSGSSTRY ADSVKGRFAISRDNAQRAIYLQMNSLKPED TAVYYCAAGSRSYYNIPYYDYWGQGTQVTV SSAAAYPYDVPDYGSHHHHHH |
| 438 (The CDRs are marked in bold, SEQ ID Nos: 439-441) | CHS6 | QVQLQESGGGLVQAGASLRLSCAASVRTFS SYAVGWFRQAPGKEREFVAGITWSGGSKYY RDAVKGRFTISRDNAKNAVYLQMNSLKPED TAVYSCAATSARYTSGALYYRDRQYNYWGQ GTQVTVSSAAAYPYDVPDYGSHHHHHH |
| 442 (The CDRs are marked in bold, SEQ ID Nos: 443-445) | CHS7 | QVQLQESGGGLVQAGGSLRLSCAASTRTFG NYAMGWFRQAPGKEREFVAAINRRGTTTYY ADSVKDRFTISTDYAKNTVYLEMISLKPED TAVYYCAVDRSTGWQPSTSRYDYASWGQGT QVTVSSAAAYPYDVPDYGSHHHHHH |
| 446 (The CDRs are marked in bold, SEQ ID Nos: 447-449) | CHS8 | QVQLQESGGGLVQAGSSLRLSCAASGRTFR YHAMGWFRQAPGKEREFVAGISTSGGMTYY PDSVKGRFTISRDNAKNTLYLQMNSLKPGD TAVYYCAKFHGDKGYGSSWYYDYWGQGTQV TVSSAAAYPYDVPDYGSHHHHHH |

TABLE 7-continued

Amino acid sequences of anti-chitin
synthase Nanobodies

| SEQ ID NO: | Nanobody name | Amino Acid Sequence |
|---|---|---|
| 450 (The CDRs are marked in bold, SEQ ID Nos: 356 and 451-452) | CHS9 | QVQLQESGGGLVQPGGSLRLSCAASGFTFS SYAMSWVRQAPGKGLERISIINSGGGSTSY ADSVKGRFTVSRDNNKNTLYLQMNSLQPED TAVYYCGVRRNWGLGTHSGEYVYWGRGTQV TVSSAAAYPYDVPDYGSHHHHHH |
| 453 (The CDRs are marked in bold, SEQ ID Nos: 454-456) | CHS10 | QVQLQESGGGLVQAGGSLRLSCAASGFTFD DYAIGWFRQAPGKVREGVSTIKSSDGSTYY ADSVKGRFTISLDNAKRTVSLQMNNLKPED TAVYYCAAGARRWPYDYIYWGRGTQVTVSS AAAYPYDVPDYGSHHHHHH |
| 457 (The CDRs are marked in bold, SEQ ID Nos: 458-460) | CHS11 | QVQLQESGGGVVQAGASLRLSCAASERIFL NYNMAWVRQAPGKEREFVAAITWSGSNIDY ADTVKGRFTISRDNAKNTVYLQMDSLKPED TAVYYCAADPSYWKIRTTLNGLDKWGQGTQ VTVSSAAAYPYDVPDYGSHHHHHH |
| 461 (The CDRs are marked in bold, SEQ ID Nos: 462-464) | CHS12 | QVQLQESGGGFVQAGDSLRLSCAASGRTFS RFPMGWFRQAPGKEREFVAAISWSGGSTLI TDSVKDRFTISRDNAKNTMYLQMNSLKPED TAVYYCAARRDSTTSYVTWGQGTQVTVSSA AAYPYDVPDYGSHHHHHH |
| 465 (The CDRs are marked in bold, SEQ ID Nos: 466-468) | CHS13 | QVQLQESGGGLVQAGGSLRLSCTVSGGTFT TYTMAWFRQAPGKEREFVAQISWSGGITAY LDSVKGRFTISRDNAKNTVYLQMNSLKPED TAVYYCARRGRKYEDDYWGQGTQVTVSSAA AYPYDVPDYGSHHHHHH |
| 469 (The CDRs are marked in bold, SEQ ID Nos: 470-472) | CHS14 | QVQLQESGGGLVQAGGSLRLSCAASGRTFS SYIMGWFRQAPGKVREFVASISWSGGFTYY ADSVKGRST1SRDNAKNTLYLQMNSLKSED TAVYYCAADPGQGYKYWGQGTQVTVSSAAA YPYDVPDYGSHHHHHH |
| 473 (The CDRs are marked in bold, SEQ ID Nos: 474-476) | CHS15 | QVQLQESGGGLVQAGGSLRLSCVASGRSFR SYTMGWLRQAPGKEREFVAAISMSGVVTYY ADSVKGRFTISRDNAAKTLYLQMNSLKPED TAVYYCAARPDRTGKADYSGQGTQVTVSSA AAYPYDVPDYGSHHHHHH |
| 477 (The CDRs are marked in bold, SEQ ID Nos: 478-480) | CHS16 | QVQLQESGGGLVQPGGSLRLSCAASGGTFS RSIMGWFRQAPGKERERVAAISWSGSLTFY ADSVKGRFTISRDNAKNSVYLQMDSLKPED TAVYYCAADKLGGTWDSWGPGTQVTVSSAA AYPYDVPDYGSHHHHHH |
| 481 (The CDRs are marked in bold, SEQ ID Nos: 482, 479 and 483) | CHS18 | QVQLQESGGGLVQAGGSLRLSCTASGRTFS SYSMAWFRQASGKEREIVAAVSRFGKFKYY ADSVKGRFTISRDNAKNTLYLQMNSLKPED TAVYYCAKTDGSSWYLDYWGQGTQVTVSSA AAYPYDVPDYGSHHHHHH |
| 484 (The CDRs are marked in bold, SEQ ID Nos: 485-487) | CHS19 | QVQLQESGGGLVQAGDSLRLSCTASGRTFS SYVMGWFRQAPGKEREFVAAISRSGGNTYF GDSAEARFTISRDNTKNTVYLQMSSLRPDD TAVYYCARYRLVAGSTSRYTYDQWGQGTQV TVSSAAAYPYDVPDYGSHHHHHH |
| 488 (The CDRs are marked in bold, SEQ ID Nos: 489-491) | CHS20 | QVQLQESGGGLVQAGDSLRLTCAHSGRPFS SSAMGWFRQAPGKEREFVAAISRGGLSKYY ADSVKGRFTIFRDNAKNTVYLQMNSLKPED TAIYYCAGSLRDRPTKDEYVVWGQGTQVTV SSAAAYPYDVPDYGSHHHHHH |
| 492 (The CDRs are marked in bold, SEQ ID Nos: 493-495) | CHS21 | QVQLQESGGGSVQAGDSLKLSCVASGRSRY ALGWFRQAPGKAREFVGAARGGAGNTYYHE SVKGRFTISRDNDKLTVYLQMNDLKPEDTA VYTCAAGKDFGTAVSWTSWGQGTQVTVSSA AAYPYDVPDYGSHHHHHH |

TABLE 7-continued

Amino acid sequences of anti-chitin
synthase Nanobodies

| SEQ ID NO: | Nanobody name | Amino Acid Sequence |
|---|---|---|
| 496 (The CDRs are marked in bold, SEQ ID Nos: 426 and 497-498) | CHS22 | QVQLQESGGGLVQAGGSLRLSCAASGGTFS GLTMGWFRQAPGKERDFVAAISWNGRFTY YKDSVKGRFAISRDNAKSTVYLQMTSLKPE DTAVYYCGADVLSGRGYRYWGQGTQVTV SSAAAYPYDVPDYGSHHHHHH |
| 499 (The CDRs are marked in bold, SEQ ID Nos: 500-502) | CHS23 | QVQLQESGGGLVQAGGSLRLSCAVSGRAFS TYGMGWFRQAPRKEREFITAINRNGDRTWY ADSVTGRFTISRDNDKNMVYLQMDSLKTED TGIYYCHTRRFGYDYWGQGTQVTVSSAAAY PYDVPDYGSHHHHHH |
| 503 (The CDRs are marked in bold, SEQ ID Nos: 504-506) | CHS24 | QVQLQESGGGWVQPGGSLRLSCTISGLSRY YAMGWFRQVPGKERESVATISLRGGRTYYA DSVEGRFTISRDNAKNTMYLQMNSLKPEDT AVYYCVADTTWGAPRSRYHYWGQGTQVTVS SAAAYPYDVPDYGSHHHHHH |
| 507 (The CDRs are marked in bold, SEQ ID Nos: 508-510) | CHS26 | QVQLQESGGGLVQPGGSLRLSCAASGFTFR SYAMSWVRQAPGQGLEWVSAINSGGGSTTY ADSVKGRFTISRDNAKNTLYLQMNSLKPED TAVYYCAKMGSSSRGNRYLEVWGQGTQVTV SSAAAYPYDVPDYGSHHHHHH |

TABLE 8

Amino acid sequences of anti-NPC1 sterol
transporter Nanobodies

| SEQ ID NO: | Nanobody name | Amino Acid Sequence |
|---|---|---|
| 511 (The CDRs are marked in bold, SEQ ID Nos: 512-514) | NPC1a | QVQLQESGGGLVQAGDSLRLSCEASARTFI AYAVGWFRQAPGKEREFVAAISWNGGMTDY ADFVKGRFAISRDNAKIVSLQMNNLKPEDT ALYYCTAGPARRSYSYRDGYDYWGQGTQVT VSSAAAYPYDVPDYGSHHHHHH |
| 515 (The CDRs are marked in bold, SEQ ID Nos: 512-514) | NPC1b | QVQLQESGGGLVQTGGSLRLSCEASARTFI AYAVGWFRQAPGKEREFVAAISWNGGMTDY ADFVKGRFAISRDSAKTVSLQMNNLKPEDT ALYYCTAGPARRSYSYRDGYDYWGQGTQVT VSSAAAYPYDVPDYGSHHHHHH |
| 516 (The CDRs are marked in bold, SEQ ID Nos: 517 and 513-514) | NPC1c | QVQLQESGGGLVQVGGSLRISCVASGRTGS YYAMGWFRQAPGKEREFVAAISWNGGMTDY ADFVKGRFAISRDNAKTVSLQMNNLKPEDT ALYYCTAGPARRSYSYRDGYDYWGQGTQVT VSSAAAYPYDVPDYGSHHHHHH |
| 518 (The CDRs are marked in bold, SEQ ID Nos: 512-514) | NPC1d | QVQLQESGGGLVQPGRSLRLSCEASARTFI AYAVGWFRQAPGKEREFVAAISWNGGMTDY ADFVKGRFAISRDNAKTVSLQMNNLKPEDT ALYYCTAGPARRSYSYRDGYDYWGQGTQVT VSSAAAYPYDVPDYGSHHHHHH |
| 519 (The CDRs are marked in bold, SEQ ID Nos: 512-514) | NPC1e | QVQLQESGGGLVQSGGSLTLSCAASARTFI AYAVGWFRQAPGKEREFVAAISWNGGMTDY ADFVKGRFAISRDNAKTVSLQMNNLKPEDT ALYYCTAGPARRSYSYRDGYDYWGQGTQVT VSSAAAYPYDVPDYGSHHHHHH |
| 520 (The CDRs are marked in bold, SEQ ID Nos: 521-523) | NPC2a | QVQLQESGGGLVQAGGSLRLSCAASGSIFS TNAMGWYRQAPDKQREFLAVITPRGRTAYA DSAKGRFTISRDNAMNSVYLQMNSLKFEDT AVYYCYAGRYRSYDARFATDIWGQGTQVTV SSAAAYPYDVPDYGSHHHHHH |

TABLE 8-continued

| | | |
|---|---|---|
| Amino acid sequences of anti-NPC1 sterol transporter Nanobodies | | |
| SEQ ID NO: | Nanobody name | Amino Acid Sequence |
| 524 (The CDRs are marked in bold, SEQ ID Nos: 521-523) | NPC2b | QVQLQESGGGLVQPGGSLRLSCAASGSIFS TNAMGWYRQAPDKQREFLAVITPRGRTAYA DSAKGRFTISRDNAMNSVYLQMNSLKFEDT AVYYCYAGRYRSYDARFATDIWGQGTQVTV SSAAAYPYDVPDYGSHHHHHH |
| 525 (The CDRs are marked in bold, SEQ ID Nos: 521-522 and 526) | NPC2c | QVQLQESGGGLVQAGGSLRLSCAASGSIFS TNAMGWYRQAPDKQREFLAVITPRGRTAYA DSAKGRFTISRDNAMNSVYLQMNSLKFEDT AVYYCYAGRYRSFDARFATDIWGQGTQVTV SSAAAYPYDVPDYGSHHHHHH |
| 527 (The CDRs are marked in bold, SEQ ID Nos: 521-522 and 526) | NPC2d | QVQLQESGGGLVRAGGSLRLSCAASGSIFS TNAMGWYRQAPDKQREFLAVITPRGRTAYA DSAKGRFTISRDNAMNSVYLQMNSLKFEDT AVYYCYAGRYRSFDARFATDIWGQGTQVTV SSAAAYPYDVPDYGSHHHHHH |
| 528 (The CDRs are marked in bold, SEQ ID Nos: 521-522 and 526) | NPC2e | QVQLQESGGGLVQAGGSLRLSCAASGSIFS TNAMGWYRQAPDKQREFLAVITPRGRTAYA DSAKGRFTISRDNAMNSVYLQMNSLKFEDT AVYYCYAGRYRSFDARFATDIWSQGTQVTV SSAAAYPYDVPDYGSHHHHHH |
| 529 (The CDRs are marked in bold, SEQ ID Nos: 521-522 and 526) | NPC2f | QVQLQESGGGLVQAGGSLRLSCAASGSIFS TNAMGWYRQAPDKQREFLAVITPRGRTAYA DSAKGRFTISRDNAVNSVYLQMNSLKFEDT AVYYCYAGRYRSFDARFATDIWGQGTQVTV SSAAAYPYDVPDYGSHHHHHH |
| 530 (The CDRs are marked in bold, SEQ ID Nos: 531-533) | NPC3a | QVQLQESGGGLVHPGGSLRLSCVASGAFLT GATVGWYRQAPGKLRELVAAIITGGTTTYA DSVKGRFSISRDYTKRALILQMDSLRPDDT AVYFCSIRGFYRQTQFREIWGQGTQVTVSS AAAYPYDVPDYGSHHHHHH |
| 534 (The CDRs are marked in bold, SEQ ID Nos: 531-533) | NPC3b | QVQLQESGGGLVQPGESLRLSCVASGAFLT GATVGWYRQAPGKLRELVAAIITGGTTTYA DSVKGRFSISRDYTKRALILQMDSLRPDDT AVYFCSIRGFYRQTQFREIWGQGTQVTVSS AAAYPYDVPDYGSHHHHHH |
| 535 (The CDRs are marked in bold, SEQ ID Nos: 531-533) | NPC3c | QVQLQESGGGLVQAGGSLRLSCVASGAFLT GATVGWYRQAPGKLRELVAAIITGGTTTYA DSVKGRFSISRDYTKRALILQMDSLRPDDT AVYFCSIRGFYRQTQFREIWGQGTQVTVSS AAAYPYDVPDYGSHHHHHH |
| 536 (The CDRs are marked in bold, SEQ ID Nos: 531-533) | NPC3d | QVQLQESGGGEVQAGGSLRLSCVASGAFLT GATVGWYRQAPGKLRELVAAIITGGTTTYA DSVKGRFS1SRDYTKRALILQMDSLRPDDT AVYFCSIRGFYRQTQFREIWGQGTQVTVSS AAAYPYDVPDYGSHHHHHH |
| 537 (The CDRs are marked in bold, SEQ ID Nos: 531-533) | NPC3e | QVQLQESGGGEVQAGGSLRLSCVASGAFLT GATVGWYRQTPGNLRELVAAIITGGTTTYA DSVKGRFSISRDYTKRALILQMDSLRPDDT AVYFCSIRGFYRQTQFREIWGQGTQVTVSS AAAYPYDVPDYGSHHHHHH |
| 538 (The CDRs are marked in bold, SEQ ID Nos: 539-541) | NPC4a | QVQLQESGGGLVQTGGSLRLSCAASGRTFS NYVMGWFRQAPGKERELIGAINRSSTRLYY ADSVKGRFSISRDNAKSTVYLQMNSLKPED TAVYYCAADLVSILGKGYRDVDYWGQGTQV TVSSAAAYPYDVPDYGSHHHHHH |
| 542 (The CDRs are marked in bold, SEQ ID Nos: 539-541) | NPC4b | QVQLQESGGGSVQAGGSLRLSCAASGRTFS NYVMGWFRQAPGKERELIGAINRSSTRLYY ADSVKGRFSISRDNAKSTVYLQMNSLKPED TAVYYCAADLVSILGKGYRDVDYWGQGTQV TVSSAAAYPYDVPDYGSHHHHHH |

TABLE 8-continued

| Amino acid sequences of anti-NPC1 sterol transporter Nanobodies | | |
| --- | --- | --- |
| SEQ ID NO: | Nanobody name | Amino Acid Sequence |
| 543 (The CDRs are marked in bold, SEQ ID Nos: 485 and 540-541) | NPC4c | QVQLQESGGGLVQAGGSLRLSCAASGRTFS SYVMGWFRQAPGKERELIGAINRSSTRLYY ADSVKGRFSISRDNAKSTVYLQMNSLKPED TAVYYCAADLVSILGKGYRDVDYWGQGTQV TVSSAAAYPYDVPDYGSHHHHHH |
| 544 (The CDRs are marked in bold, SEQ ID Nos: 545 and 540-541) | NPC4d | QVQLQESGGGLVQPGGSLRVSCAASGFSFS NYVMGWFRQAPGKERELIGAINRSSTRLYY ADSVKGRFSISRDNAKSTVYLQMNSLKPED TAVYYCAADLVSILGKGYRDVDYWGQGT QVTVSSAAAYPYDVPDYGSHHHHHH |
| 546 (The CDRs are marked in bold, SEQ ID Nos: 547-549) | NPC5a | QVQLQESGGGLVQAGGSLRLSCVASGRTFS PYTMGWFRRAPGKEREFVAAISWGAGVKSY ADSVKGRFTISRDNAENTVYLQMNMLKPDD TALYYCAAKRPISGSYSNERDYAYWGQGTQ VTVSSAAAYPYDVPDYGSHHHHHH |
| 550 (The CDRs are marked in bold, SEQ ID Nos: 547-549) | NPC5b | QVQLQESGGGLVQPGGSLRLSCVASGRTFS PYTMGWFRRAPGKEREFVAAISWGAGVKSY ADSVKGRFTISRDNAENTVYLQMNMLKPDD TALYYCAAKRPISGSYSNERDYAYWGQGTQ VTVSSAAAYPYDVPDYGSHHHHHH |
| 551 (The CDRs are marked in bold, SEQ ID Nos: 552-554) | NPC6 | QVQLQESGGGLVQTGESLRLSCAGTNFLSS RFEMGWYRQIPGKQRELVARIFRDGNTDYV DSVKGRFTISRDTAKNTIDLQMNNLKPEDT AGYFCHVHILGRDYWGQGTQVTVSSAAAYP YDVPDYGSHHHHHH |
| 555 (The CDRs are marked in bold, SEQ ID Nos: 556-558) | NPC7a | QVQLQESGGGLVQAGDSLRISCKASGRTFS SYPIGWFRQAPGKEREFVAAISRSGGRTYY ADSVKGRLTISRDNAKNTVYLQMNSLKLED TAVYYCAAKTTMGLPVGGTYEYDYWGQGTQ VTVSSAAAYPYDVPDYGSHHHHHH |
| 559 (The CDRs are marked in bold, SEQ ID Nos: 556-558) | NPC7b | QVQLQESGGGLVQAGDSLRISCKASGRTFS SYPIGWFRQAPGKEREFVAAISRSGGRTYY ADSVKGRFTISRDNAKNTVYLQMNSLKLED TAVYYCAAKTTMGLPVGGTYEYDYWGQGTQ VTVSSAAAYPYDVPDYGSHHHHHH |
| 560 (The CDRs are marked in bold, SEQ ID Nos: 561-563) | NPC8 | QVQLQESGGGLVQPGGSLRLSCAASGFTLD DYAIGWFRQAPGKERSFVAAIDSNGSNTYY ADSLKGRFTIARDNAKSMVFLRMNNLEPED TAVYYCAAGQNFWTFTTTPPPYWGQGTQVT VSSAAAYPYDVPDYGSHHHHHH |
| 564 (The CDRs are marked in bold, SEQ ID Nos: 565-567) | NPC9 | QVQLQESGGGLVQAGDSLRISCKASGRTFS NYPIGWFRQAPGKEREFVAAISRSGGGTRY ADSVKGRFTISRDNAKNTVYLQMNSLKRDD TAVYYCAAYFGNLGGGVGRSSDYDYWGQGT QVTVSSAAAYPYDVPDYGSHHHHHH |
| 568 (The CDRs are marked in bold, SEQ ID Nos: 569-571) | NPC10 | QVQLQESGGGSVQAGESLTLSCAASNVLVS KFTVAWFRQAPGKQRELVADIARAGFTSYA DFVRGRFSISRDNAQNTVTLQMNSLTPEDT AVYYCNCHVLGRDYWGQGTQVTVSSAAAYP YDVPDYGSHHHHHH |
| 572 (The CDRs are marked in bold, SEQ ID Nos: 573-575) | NPC11 | QVQLQESGGGSVQPGGSLRLSCAASIRTFS TYAFAWYRQAPGKQRELVAGISSGSRTNYA DSVKGRFTISRDNAKKTVYLQMNNLQPEDT AVYYCTKGRTNIDYWGQGTQVTVSSAAAYP YDVPDYGSHHHHHH |
| 576 (The CDRs are marked in bold, SEQ ID Nos: 485 and 577-578) | NPC12 | QVQLQESGGGVVQPGGSLRLSCAASGRTFS SYVMGWFRQAPGKEREFVATISTGGGTTYY ADSVKGRFTISRDNAKNTVYLQMNGLKPED TAVYYCAAKMATGTASIRTYEYAYWGQGTQ VTVSSAAAYPYDVPDYGSHHHHHH |

TABLE 8-continued

| SEQ ID NO: | Nanobody name | Amino Acid Sequence |
|---|---|---|
| | | Amino acid sequences of anti-NPC1 sterol transporter Nanobodies |
| 579 (The CDRs are marked in bold, SEQ ID Nos: 580-582) | NPC13 | QVQLQESGGGLVQPGGSLRLSCAASGFTFS RYAMGWFRQTPGKEREFVAAILWGGVIADS VKGRFTISRDNAKNTVDLQMFSLKPEDTAV YYCARRRGGLNNHLGSVGNYDYWGQGTQVT VSSAAAYPYDVPDYGSHHHHHH |
| 583 (The CDRs are marked in bold, SEQ ID Nos: 584-586) | NPC14 | QVQLQESGGGSVQPGGSLRLSCEIIGATVS SSSMAWYRQAPGLQRELVAGITTPSNPHYA ASVRGRFTISRDGARNLNYLQIDSAKPEDT AVYYCHAAIRGSIYRGQGTQVTVSSAAAYP YDVPDYGSHHHHHH |

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first, indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Protein Target Preparation for Immunization—

DNA sequences of the targets proteins from *Helicoverpa armigera* (see Table 1 hereinabove) were optimized and synthesized. The synthesized sequences were cloned with His tag into a pET-28a or pET-30a vector and expressed in *E. coli.* strain BL21 Star (DE3). A single colony was inoculated into LB medium containing kanamycin; and the culture was incubated at 37° C. at 200 rpm and then induced with Isopropyl β-D-1-thiogalactopyranoside (IPTG). SDS-PAGE analysis was used to monitor protein expression. Following, BL21 Star (DE3) stored in glycerol was inoculated into TB medium containing kanamycin and cultured at 37° C. When the OD600 reached 1.2, cell culture was induced with IPTG at 15° C. for 16 hours. Cells were harvested by centrifugation and pellets were resuspended with lysis buffer (20 mM NaPi pH7.4, 500 mM NaCl, 20 mM Imidazole, Protease Inhibitor cocktail—cOmplete™, EDTA-free Protease Inhibitor Cocktail—Roche cat #4693132001) followed by sonication and centrifugation. The precipitate was dissolved using urea; and the denatured supernatant was kept for future purification. Following, the protein was purified from the supernatant using a Ni-NTA column (GE-Healthcare, Cat No. 17-5318-02): The column was washed with 10 bed volumes of wash buffer (20 mM NaPi pH7.4, 500 mM NaCl, 50 mM Imidazole) and the protein was eluted with elution buffer (20 mM NaPi pH7.4, 500 mM NaCl, 500 mM Imidazole). Following the elution, the fractions were placed in MEGA tubes with membrane cutoff of 3.5 kDa (Tivan Biotech MEGA3-50) and dialyzed in 1 L PBS pH7.4 at 4° C. overnight, followed by a second round of dialysis under the same conditions. Some of the target proteins (e.g. the V-ATPase subunit C target protein) were also refolded and sterilized by 0.22 μm filter prior to storing in aliquots. The concentration was determined using a -Nano-drop. The protein purity and molecular weight were determined by a standard SDS-PAGE.

Immunization—

A llama was subcutaneously injected on days 0, 7, 14, 21, 28 and 35, each time with about 125 or 150 μg target protein in combination with a Gerbu adjuvant P (Gerbu Biotech, #3111-0025). On day 40, about 100 ml anti-coagulated blood was collected from the llama for lymphocyte preparation.

Construction of a VHH Library—

A VHH library was constructed from the llama lymphocytes to screen for the presence of antigen-specific nanobodies. To this end, total RNA from peripheral blood lymphocytes was used as a template for first strand cDNA synthesis with an oligo(dT) primer. Using this cDNA, the VHH encoding sequences were amplified by PCR, digested with PstI (#ER0611 from Thermofischer) and NotI (#11037668001 from Sigma), and cloned into the PstI & NotI sites of the phagemid vector pMECS. The VHH library comprised about $10^8$ independent transformants, with about 80-92% of transformants harboring the vector with the right insert size.

Isolation and Sequencing of Specific Target Nanobodies—

The library was panned for 3 rounds on solid-phase coated with the target antigen (100 μg/ml in 100 mM NaHCO3 pH 8.2). The enrichment for antigen-specific phages was assessed following each round of panning by comparing the number of phagemid particles eluted from antigen-coated wells with the number of phagemid particles eluted from negative control (uncoated blocked) wells. These experiments indicated that the phage population was enriched for antigen-specific phages by the 3rd round. The antigen used for panning & ELISA screening was the same as the one used for immunization, using uncoated blocked wells as a negative control. The amino acid sequences of the generated nanobodies are shown in Table 2A-6 hereinabove.

Nanobodies Expression and Purification—

The nanobodies DNA sequence were optimized and synthesized by GenScript. The synthesized sequences were cloned with His tag into a pET-28b+ vector for protein expression in *E. coli.* Following, *E. coli* SHuffle T7 was transformed with the recombinant plasmids. A single colony was inoculated into LB medium containing kanamycin; and the culture was incubated at 37° C. at 220 rpm and then induced with 1M IPTG. SDS-PAGE analysis were used to monitor expression. Following, SHuffle T7 stored in glycerol was inoculated into TB medium containing kanamycin and cultured at 37° C. When the OD600 reached about 1.2, cell culture was induced with 1M IPTG at 30° C. for 20-22 hours. Cells were harvested by centrifugation and cell pellets were resuspended with lysis buffer (20 mM NaPi pH7.5, 500 mM NaCl, 20 mM imidazole) followed by sonication and centrifugation. The precipitate was dissolved using urea and the denatured supernatant was kept for future purification. The nanobodies were purified with a Ni-NTA column: The column was washed with 10 bed volumes of Wash Buffer (20 mM NaPi pH7.5, 500 mM NaCl, 50 mM imidazole) and the protein was eluted with elution buffer (20 mM NaPi pH7.5, 500 mM NaCl, 500 mM imidazole). Following, the elution fractions were dialyzed at 4° C. for overnight with dialyzed buffer (PBS pH 7.4). The concentration was determined by Nanodrop. Protein purity and molecular weight were determined by standard SDS-PAGE.

Binding of the Generated Nanobodies to the Target Protein—

Maxisorb 96-wells plates were coated with 10 μg/ml of the target protein by an overnight incubation at 4° C. The coated plates were washed with PBS and blocked for 1 hour at 37° C. in blocking buffer containing PBS+0.5% tween+ 1% BSA, followed by 1 hour incubation at room temperature with 2 μg/ml of the tested nanobody. Following washes with PBS, the plates were incubation with MonoRab™ Rabbit Anti-Camelid VHH Antibody-HRP (Genscript, Cat no. A01860) in blocking buffer. Finally, the plates were washed with PBS, incubated for 30 minutes with TMB solution followed by addition of $H_2SO_4$ and absorbance was read at 450 nm.

Stability Assays—

The stability of the generated nanobodies was tested in "field-like conditions" by incubating them in natural sunlight, natural UV radiation and high summer out door/filed temperatures. In addition, stability to enzymatic proteolytic activity and high pH was evaluated by incubation of the nanobodies with lumen juices harvested from *H. armigera* $4^{th}$ in start larvae guts [see e.g. Purcell, John P., John T. Greenplate, and R. Douglas Sammons. *Insect Biochemistry and Molecular Biology* 22.1 (1992): 41-47; Pang, A. S., & Gringorten, J. L. (1998). *FEMS microbiology letters,* 167(2), 281-285; and Ma, Gang, et al. *Insect biochemistry and molecular biology* 35.7 (2005): 729-739]. Specifically, Maxisorb 96-wells plates were coated with 2 μg/ml of the tested nanobody by an overnight incubation at 4° C. The coated plates were washed with PBS and blocked for 1 hour at 37° C. in blocking buffer containing PBS+0.5% tween+1% BSA and washed with PBS. The coated plates were incubated with PBS in "field-like condition" for 1-3 hours or in presence of lumen gut juices for 1 hour at room temperature. Following incubation, plates were washed with PBS and incubated with MonoRab™ Rabbit Anti-Camelid VHH Antibody-HRP in blocking buffer. Finally, the plates were washed with PBS, incubated for 30 min with TMB solution followed by addition of $H_2SO_4$ and absorbance was read at 450 nm.

Insect Culture—

Cotton bollworms were collected from cotton fields in Israel and reared in the laboratory at 24° C. with 70% relative humidity on 10 hours day/14 hours night photoperiod. The collected larvae were kept on an artificial diet with Ward's diet powder Stonefly *Heliothis* Diet (Product No. 38-0600, Ward's Natural Science, Rochester, NY) supplemented with Vitamin mixture (Nicotinic acid 40 μM, Calcium pantothenate 5 μM, Riboflavin 5 μM, Thiamine hydrochloride 4 μM, Pyridoxine hydrochloride 5 μM, Folic acid 2.5 μM, D-biotin 4 μM and Cyanocobalamin 5 nM), Sorbic acid 0.2%, Methyl paraben 0.4%, Ascorbic acid 0.25%, Brewer Yeast 1%, white vinegar 4% and Linseed oil 0.5%.

Feeding Bioassays—

0.5 gr of *Heliothis* artificial diet was added into each well of 24 wells plates and overlaid with 100 μl suspension of the tested nanobody in a concentration of 0.4 mg/ml or PBS as a negative control. To each well, one 24-48 hours old larva was added in 12 replications. The plates were coated with polyofin sealing foil (HJ-BIOANALITIC, Cat No. 900371) and incubated in the laboratory at 24° C. with 70% relative humidity in the dark. Each study for each nanobody was repeated 3-5 times. Following 7 days of incubation, the larvae were moved to larger petri dishes with a diameter of 5 cm with the same artificial food with no addition of the nanobody. The body length and weight of each larva was measured following 7 and 14 days of incubation and then followed by observation on the pupation and adult emerged timing.

Cotton Growth—

Cotton cultivar Akalpi (Inter-specific hybrid (ISH) between *G. hirsutum* and *G. barbadense;* 1432 Intercott Hazera) was grown under a control temperature regime of 25/18° C. day/night. Temperatures were monitored and maintained by the SAS automation system. In addition, fertigation was provided with Sheffer7-7-7 plus calcium; keeping a leaching fraction of 30%. Pest control was conducted exclusively mechanically by using sticky-colored traps. Cropping cycle duration was between six to eight weeks. Following this period, plants were transferred to the laboratory serving as a plant model for the bioassay experiments.

Leaf Bioassays—

1 ml sterilized agar was added to each well of 12 wells plates and a 2 cm Ø cotton leave disc was deposited over the agar in each well. Each leave disc was overlaid with 50 μl suspension of the tested nanobody in a concentration of 0.4, 1, 2 or 4 mg/ml, or PBS as a negative control. To each well, one 24-48 hours old larva was added in 12 replicates. The plates were sealed with polyofin sealing foil (HJ-BIO-ANALITIC, Cat No. 900371) and incubated in the laboratory at 24° C. and 70% relative humidity. Following 4 days of incubation, the larvae were moved to new plates with fresh cotton discs, treated with the same nanobody concentration or PBS, and on day 7 the larvae were moved once again to bigger wells (6 wells plates), with an addition of agar and fresh 2.8 cm Ø cotton leave discs treated with 100 μl of the same nanobody at the same concentration. The larvae mortality was evaluated on days 4, 7 and 10. Each study for each nanobody was repeated 2-3 times.

Immunofluorescence—

Purified anti-CBD nanobody referred to herein as "CB20901" at a concentration of 1 mg/ml was conjugated to fluorescently-labeled Cy3 (ab188287-Cy3 Fast Conjugation kit Cambridge, UK) following manufacturer instructions. The feeding bioassay was carried as described hereinabove. Specifically, 12 larvae were fed with 100 μl Cy3-fluorescently-labeled nanobody and 12 larvae served as control and fed with 100 μl of PBS. Following 36 hours of incubation treated larvae were transferred to clean freshly prepared *Heliothis* artificial diet for another 12 hours, in order to eliminate false-positive fluorescent signals, following which the first imaging session took place. In the next step, larvae were returned to nanobody/PBS-food until they were six days old followed by 12 hours feeding on food without the nanobody, and finally a second imaging session of live larvae and extracted gut was carried. For valid imaging comparisons, set up was kept as fallow: Nikon Eclipse 80i microscope, NIS-element software, Camara DS-Ri2, lent 1×_zoom_2.0×_exposure 10 ms_gain_7.6× (for food imaging), lent 1×_zoom 1.4×_exposure 200 ms_gain_2.0× (for 48 hours old larvae) and lent 1×_zoom1.4×_exposure 400 ms_gain_6.2× (for 6 days old live larvae and extracted gut).

Example 1

Anti-Chitin Binding Domain Nanobodies

Several nanobodies were generated against the *Helicoverpa armigera* chitin binding domains (CBD) antigen, referred to herein as Ha-PMP5B1 and Ha-PMP5B2 (see Tables 2A-B hereinabove). The Ha-PMP5B1 protein contains 506 amino acid with five different CBDs from *Heli-*

Figure 2:
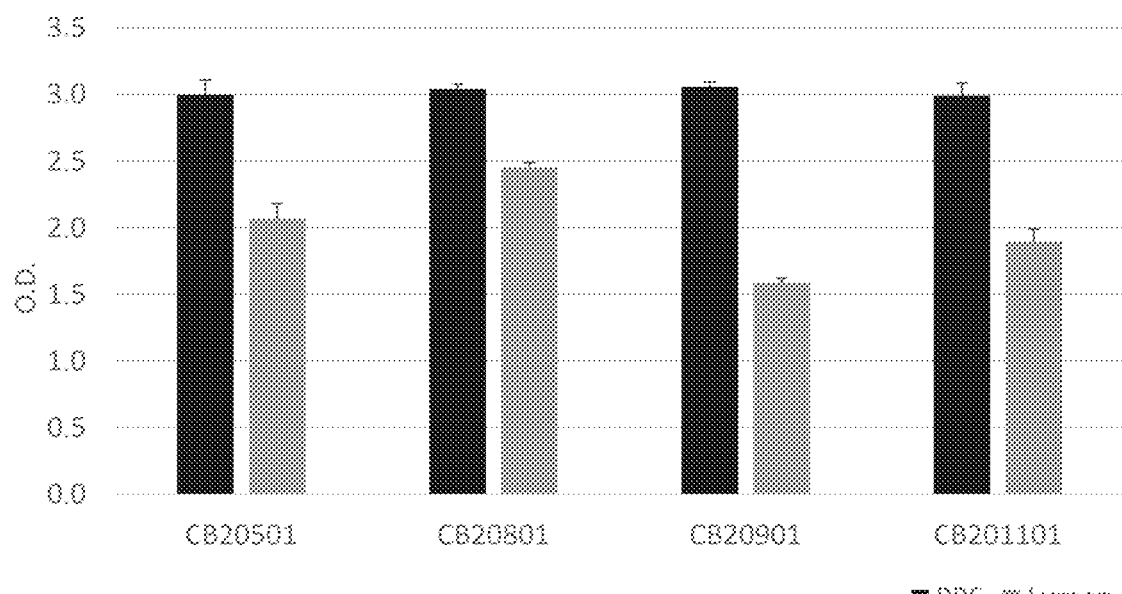
FIG. 2 is a graph demonstrating stability of the generated anti-CBD nanobodies CB20501, CB20801, CB20901 and CB201101 following 1 hour incubation with larvae gut juice harvested from *H. armigera* larvae guts as compared to PBS control, as determined by ELISA. Each experiment was performed three times; data is presented as average ±SE.
Figure 3:
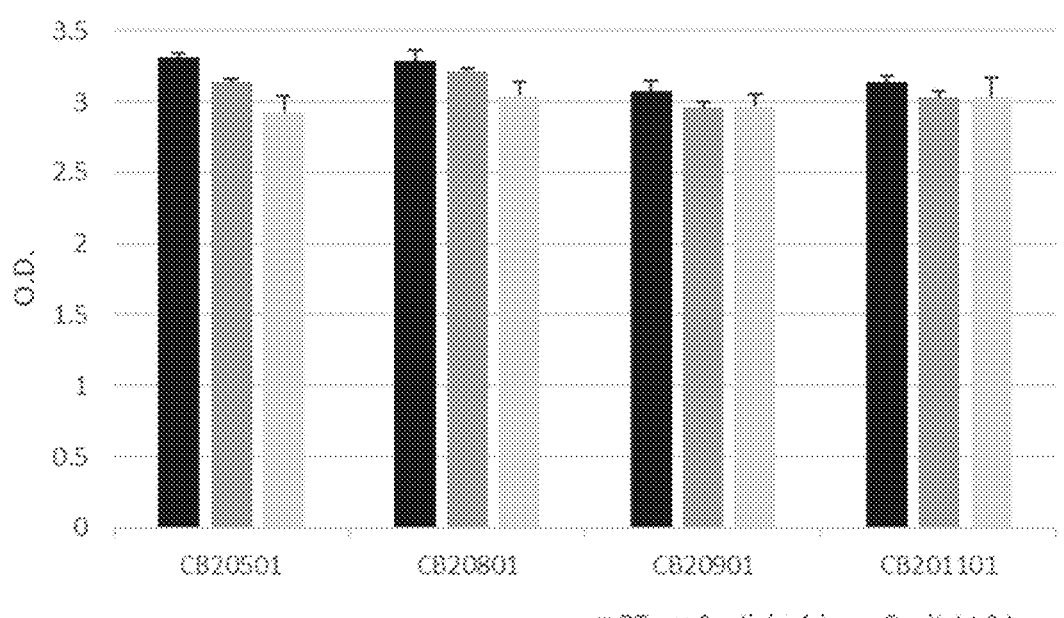
FIG. 3 is a graph demonstrating stability of the generated anti-CBD nanobodies CB20501, CB20801, CB20901 and CB201101 following 1-3 hours incubation in field like conditions as compared to room temperature (RT) control, as determined by ELISA. Each treatment included 5 repetitions; data is presented as average ±SE.

*coverpa armigera* and the Ha-PMP5B2 protein is a partial protein of Ha-PMP5B1 and contains 192 amino acid with two CBDs. ELISA assays using plates coated with the target antigen verified that the generated nanobodies bind the target CBD antigen (FIG. 1). As specific embodiments disclose administration of the nanobodies to *Helicoverpa armigera* larvae by oral delivery, thereby the nanobodies are absorbed into the larvae gut lumen (which has a high pH and contains a high content of proteolytic enzymes) until reaching the target site in the peritrophic membrane of the larvae gut; the stability of the anti-CBD nanobodies in the lumen was studied. ELISA assays using plates coated with the generated anti-CBD nanobodies and incubated for 1 hour in the presence of lumen juices harvested from *Helicoverpa armigera* demonstrated that 40-70% of the nanobodies remained intact following an hour of incubation (FIG. 2), thus indicating the survival ability of the generated anti-CBD nanobodies in lumen conditions. In addition, stability of the generated anti-CBD nanobodies was also tested under conditions that mimic field conditions by incubation outside in the open air with natural solar radiation and at high external temperatures of 30° C. for 1-3 hours. The results demonstrated that following 3 hours of incubation in filed like condition of 30° C., 60-70% humidity and a UV index of 4-5, only a slight decrease in the nanobodies content was observed compared to control (FIG. 3).

Figure 4A:
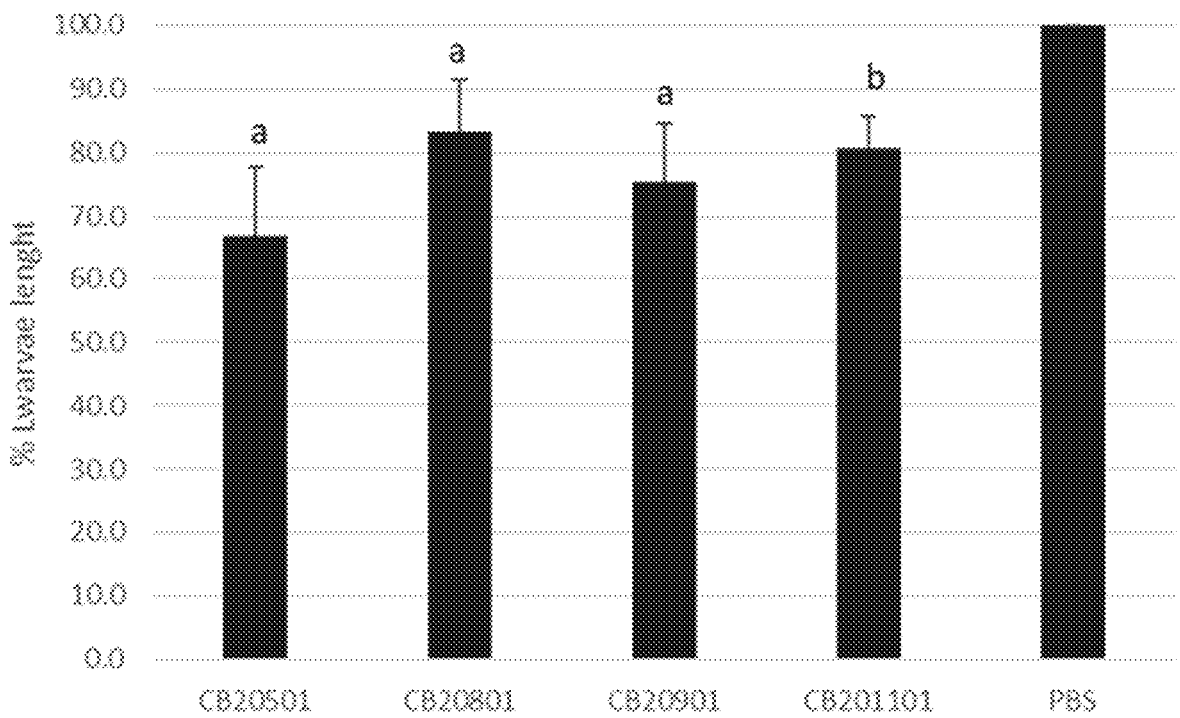
FIGS. 4A-C demonstrate the effect of the anti-CBD nanobodies CB20501, CB20801, CB20901 and CB20110 on *H. armigera* body length (FIG. 4A), weight (FIG. 4B) and mortality (FIG. 4C) following feeding with single dose of 40 μg of the indicated nanobody. The measurements were taken on day 7 and on day 7 or 14 for mortality. Each experiment included 12 larvae and had 3-5 repetitions with error bars indicating the standard error deviations. Shown the percentage of length of the larvae fed with the indicated nanobody relative to the length of the PBS fed larvae control (FIG. 4A), percentages of weight of the larvae fed with the indicated nanobody relative to the weight of the PBS fed larvae control (FIG. 4B) and the percentages of dead larvae following 7 and 14 days (FIG. 4C). Statistically significant differences are indicated by a ($P>0.05$) and b ($P>0.01$).
Figure 4B:
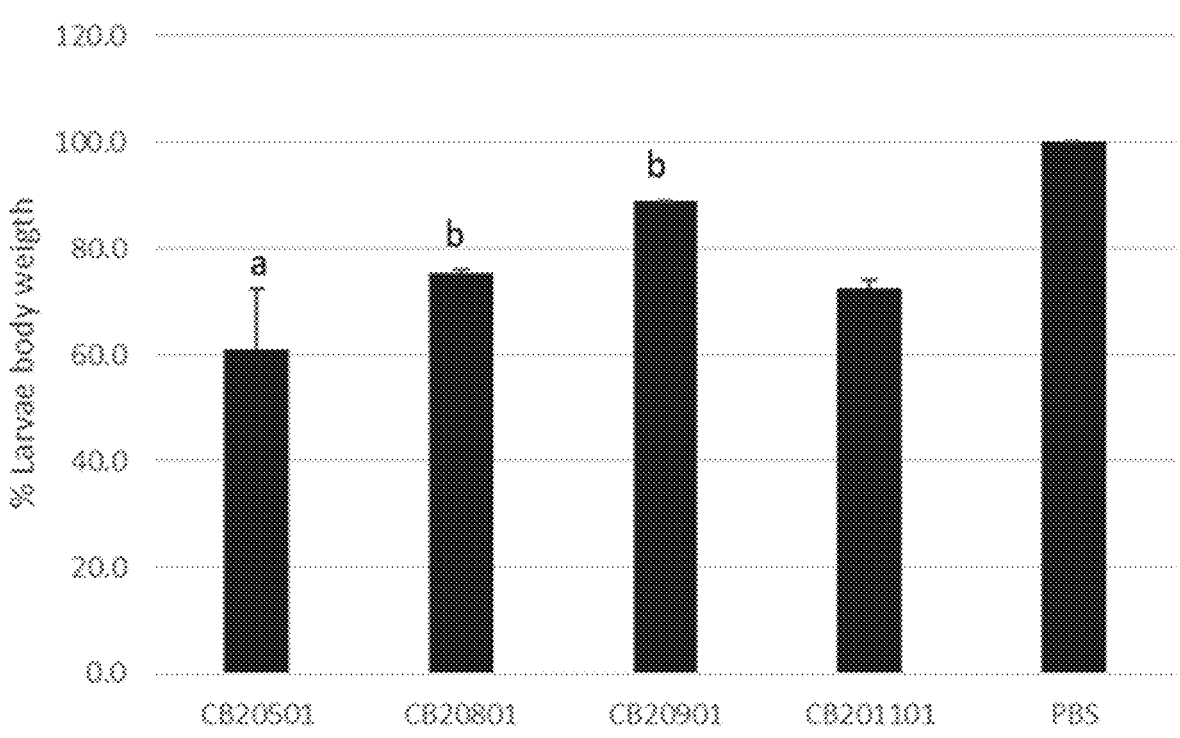
Figure 4C:
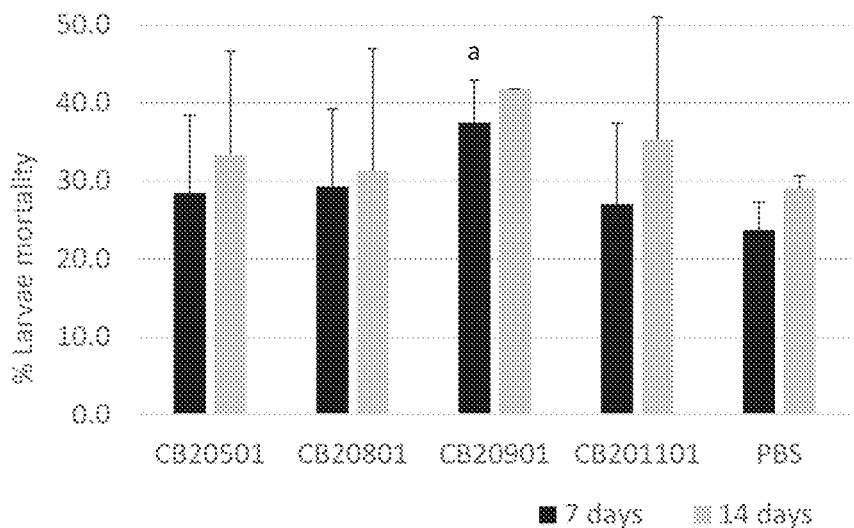

To assess the insecticidal activity of the generated nanobodies, young *Helicoverpa armigera* larvae at the age of no more than 48 hours were grown on artificial food supplemented with a single dose of the anti-CBD generated nanobodies. Observations were carried out through all of the insect's life cycle, including weight and length measurements of the larvae on day 7 and 14 and later on observation on the number of individuals transformed from pupa to adults. The results demonstrated that larvae fed 7 days with several anti-CBD nanobodies demonstrated loss in their length (FIG. 4A) and/or weight loss (FIG. 4B) and/or an increase in mortality (FIG. 4C), depending on the nanobody tested.

Figure 5A:
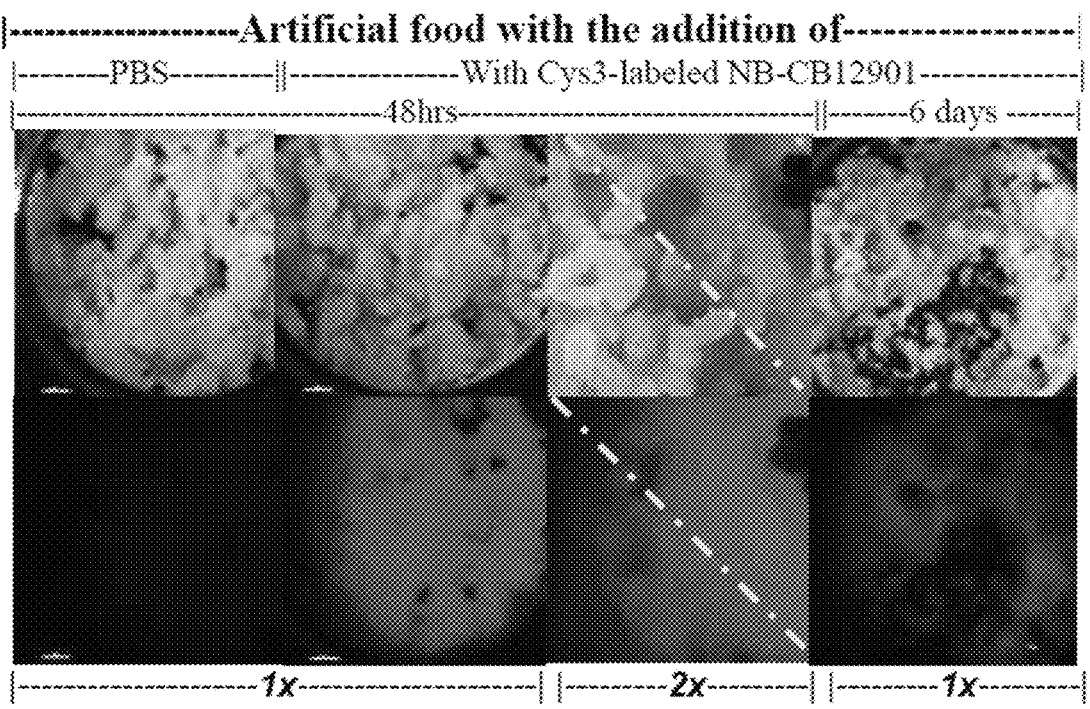
FIGS. 5A-C demonstrate presence of the generated anti-CBD nanobody CB20901 in insect gut following incubation with artificial food containing a fluorescently Cy3 labeled CB20901.
Figure 5B:
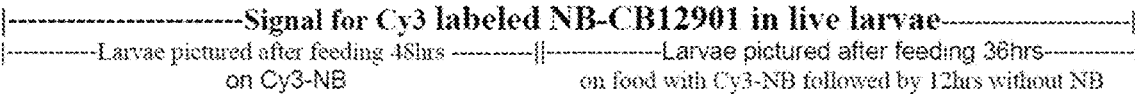
Figure 5B:
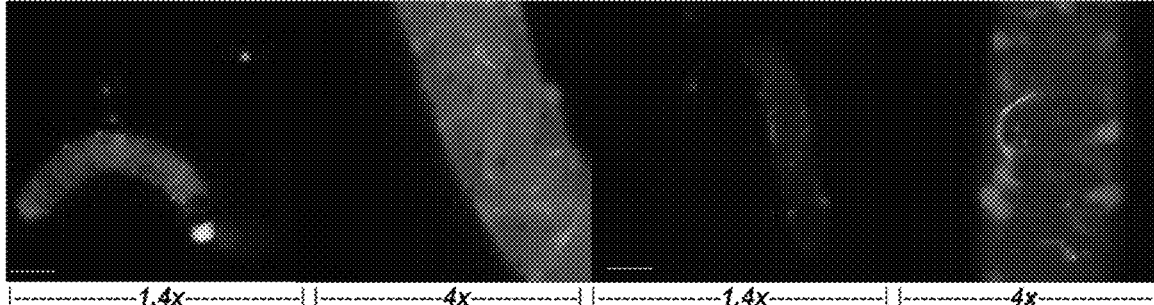
Figure 5C:
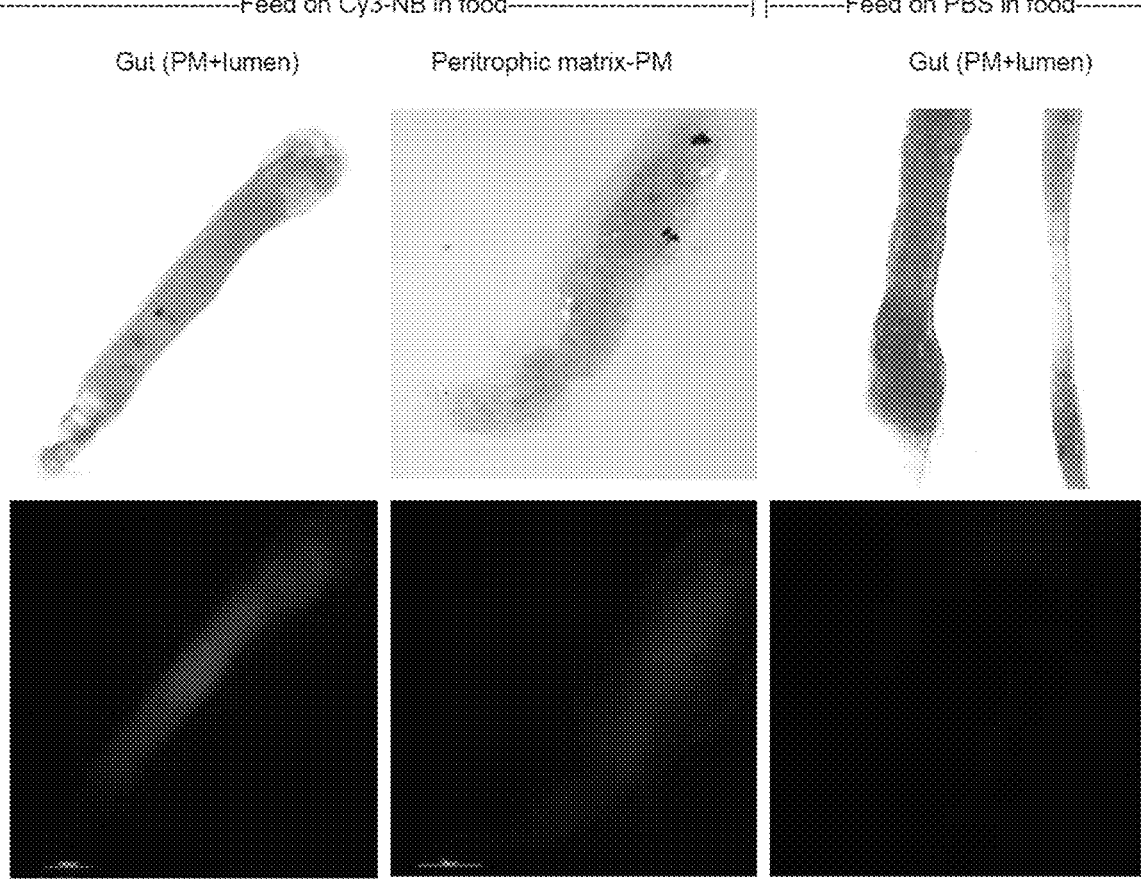

In order to track the nanobodies trajectory in larvae gut, *Helicoverpa armigera* larvae were grown on artificial food supplemented with a fluorescently-labeled Cy3 anti-CBD nanobody CB12901. As shown in FIG. 5A, the labeled nanobody was stable in the food for at least a week. In addition, a decrease in the fluorescence signal was observed between the food and larvae feces following feeding, suggesting uptake of the labeled nanobody by larvae gut (FIG. 5A). Moreover, the labeled nanobody was detected in larvae 12 hours following transfer of the larvae to food not containing the nanobody, indicating that the labeled nanobody is retained in larvae gut (FIG. 5B). Furthermore, the ability of the labeled nanobody to reach the peritrophic matrix was confirmed following 6 days of feeding: at this timing positive signal was observed from all gut and specifically from peritrophic matrix following separation between the peritrophic matrix and the lumen gut (FIG. 5C).

Example 2

Anti-V-ATPase Subunit C Nanobodies

Figure 6:
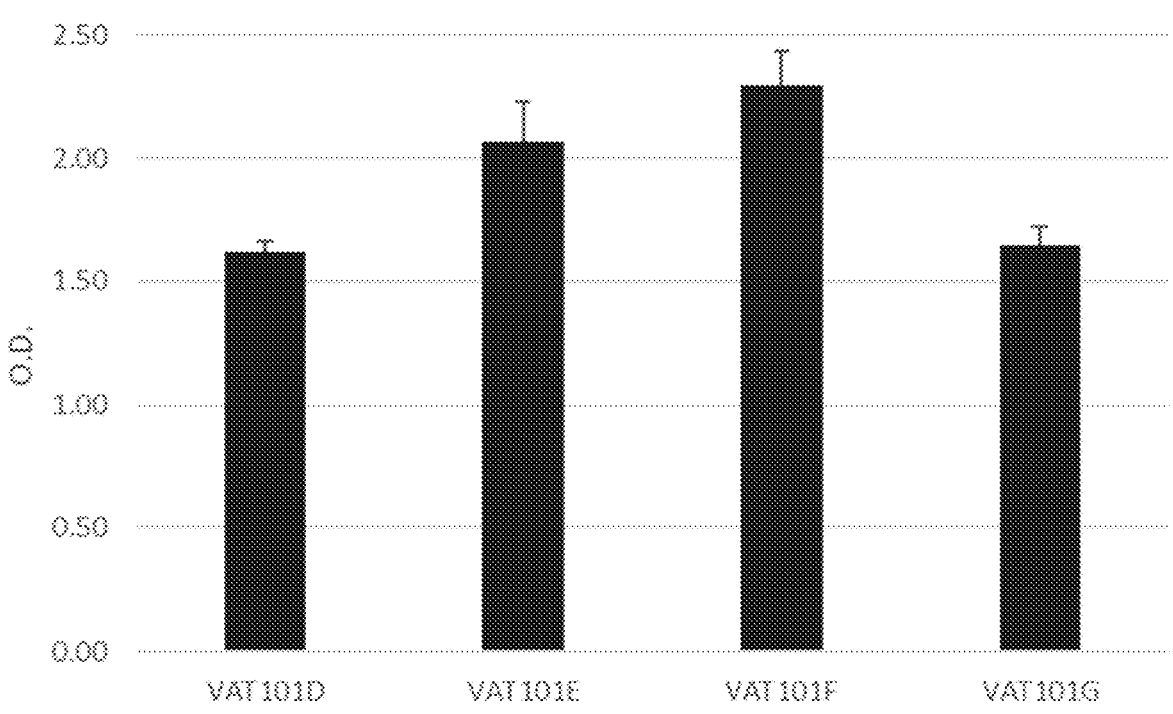
FIG. 6 is a graph demonstrating specific binding of the generated anti-ATPase V subunit c (referred to herein as "VAT") nanobodies referred to herein as VAT0101A, VAT0101B, VAT0101C, VAT0101D, VAT0101E, VAT0101F, and VAT0101G to the target VAT antigen, as determined by ELISA. Each experiment was performed five times; data is presented as average ±SE.
Figure 7:
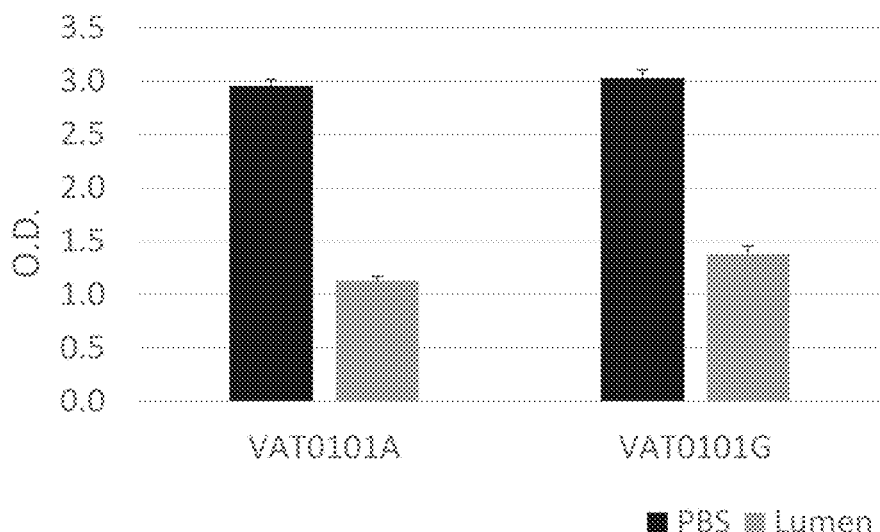
FIG. 7 is a graph demonstrating stability of the generated anti-VAT nanobodies VAT0101A and VAT0101G following 1 hour incubation with larvae gut juice harvested from *H. armigera* larvae guts as compared to PBS control, as determined by ELISA. Each experiment was performed three times; data is presented as average ±SE.
Figure 8:
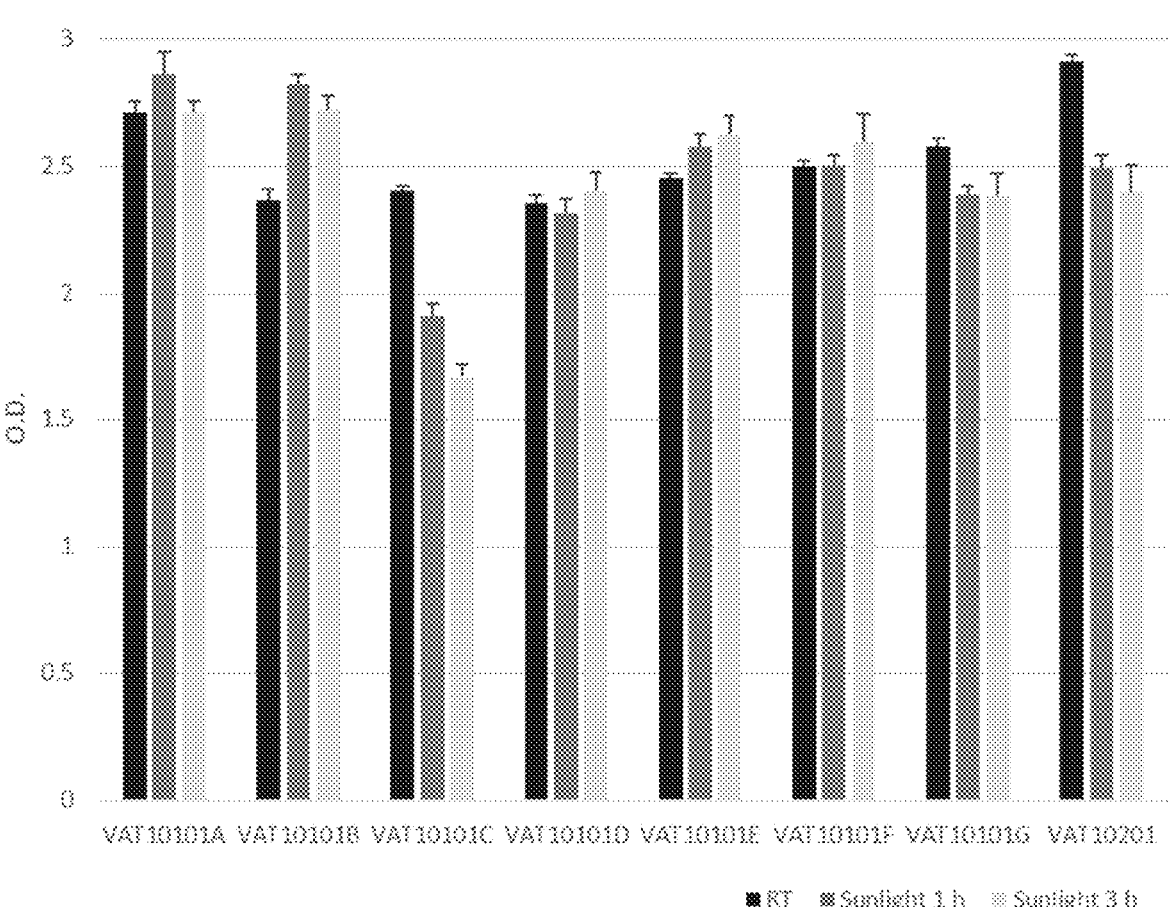
FIG. 8 is a graph demonstrating stability of the generated anti-VAT nanobodies VAT0101A, VAT0101B, VAT0101C, VAT0101D, VAT0101E, VAT0101F, and VAT0101G following 1-3 hours incubation in field like conditions as compared to room temperature (RT) control, as determined by ELISA. Each treatment included three repetitions; data is presented as average ±SE.

Several nanobodies were generated against the *Helicoverpa armigera* V-ATPases Subunit C (referred to herein as "VAT") antigen (see Tables 3A-B hereinabove). ELISA assays using plates coated with the target antigen verified that the generated nanobodies bind the target VAT antigen (FIG. 6). Following, the stability of the anti-VAT nanobodies in lumen conditions and in field like conditions was studied (FIGS. 7-8). The results indicated that 40-70% of the nanobodies remained intact following an hour of incubation in the presence of lumen juices, thus indicating the survival ability of the generated anti-VAT nanobodies in lumen conditions. In addition, the results demonstrated that following 3 hours of incubation in filed like condition of 30° C., 60-70% humidity and a UV index of 4-5, only a slight decrease in the nanobodies content was observed compared to control.

Figure 9A:
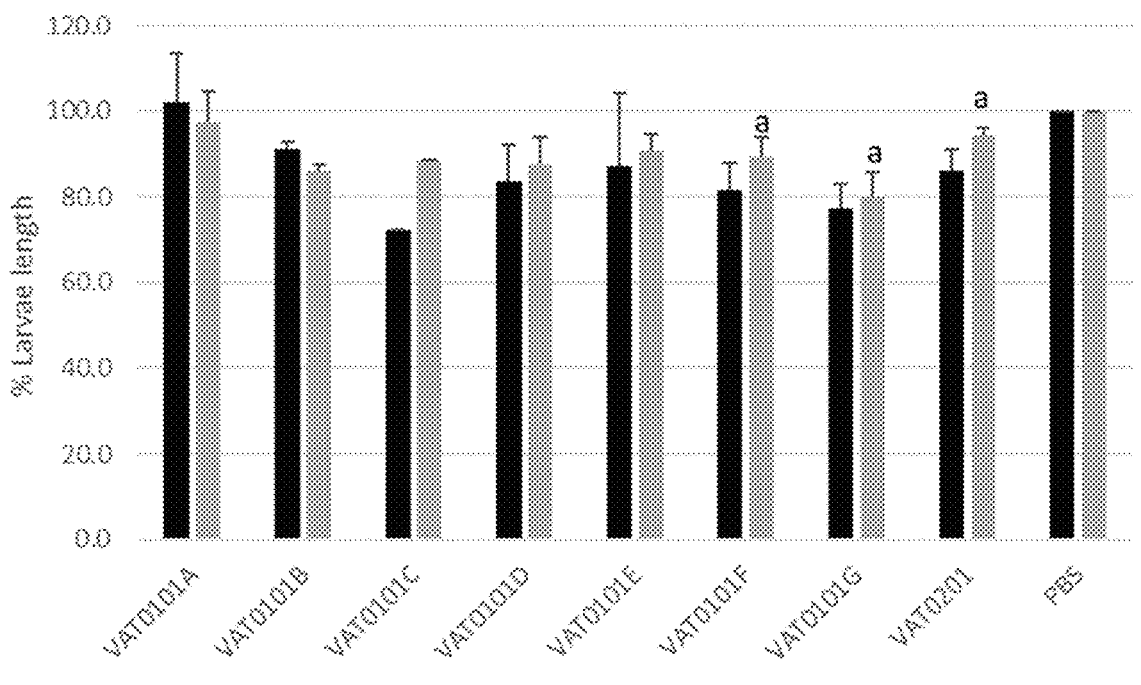
FIGS. 9A-C demonstrate the effect of the anti-VAT nanobodies VAT0101A, VAT0101B, VAT0101C, VAT0101D, VAT0101E, VAT0101F, VAT0101G and VAT0201 on *H. armigera* body length (FIG. 9A), weight (FIG. 9B) and mortality (FIG. 9C) following feeding with single dose of 40 μg of the indicated nanobody. The measurements were taken on day 7 or 14, as indicated. Each experiment included 12 larvae and had 3-5 repetitions with error bars indicating the standard error deviations. Shown the percentage of length of the larvae fed with the indicated nanobody relative to the length of the PBS fed larvae control (FIG. 9A), percentages of weight of the larvae fed with the indicated nanobody relative to the weight of the PBS fed larvae control (FIG. 9B) and the percentages of dead larvae following 7 and 14 days (FIG. 9C). Statistically significant differences are indicated by a (P>0.05) and b (P>0.01).
Figure 9B:
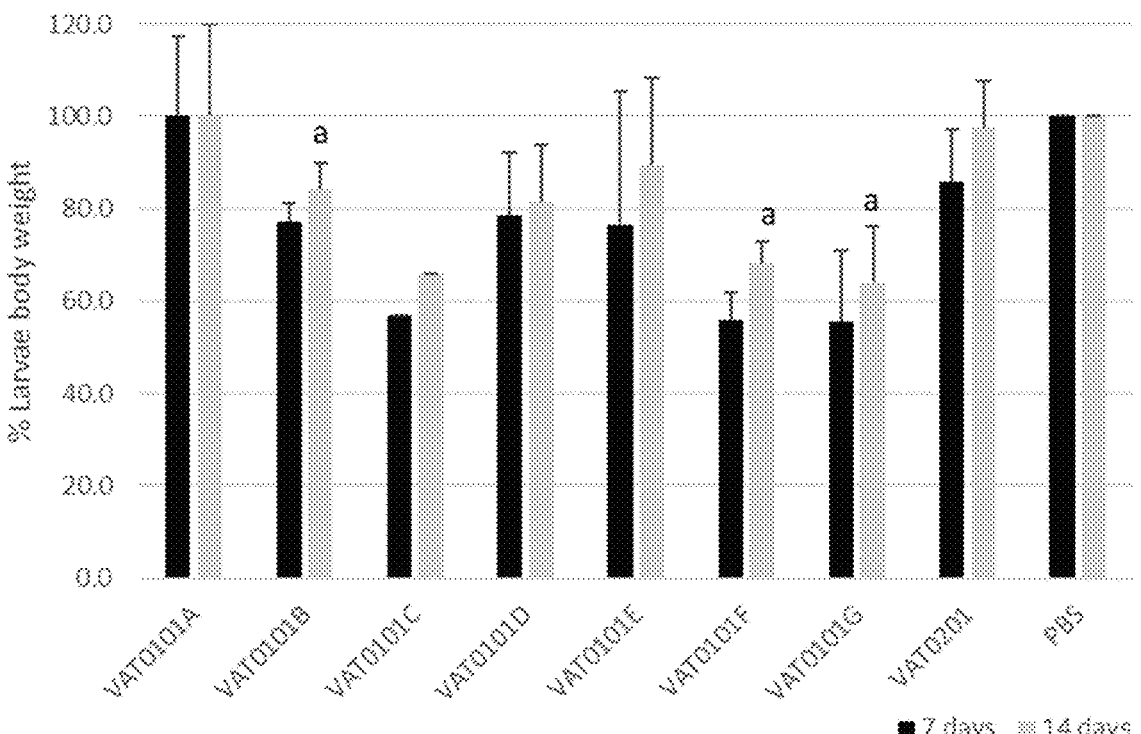
Figure 9C:
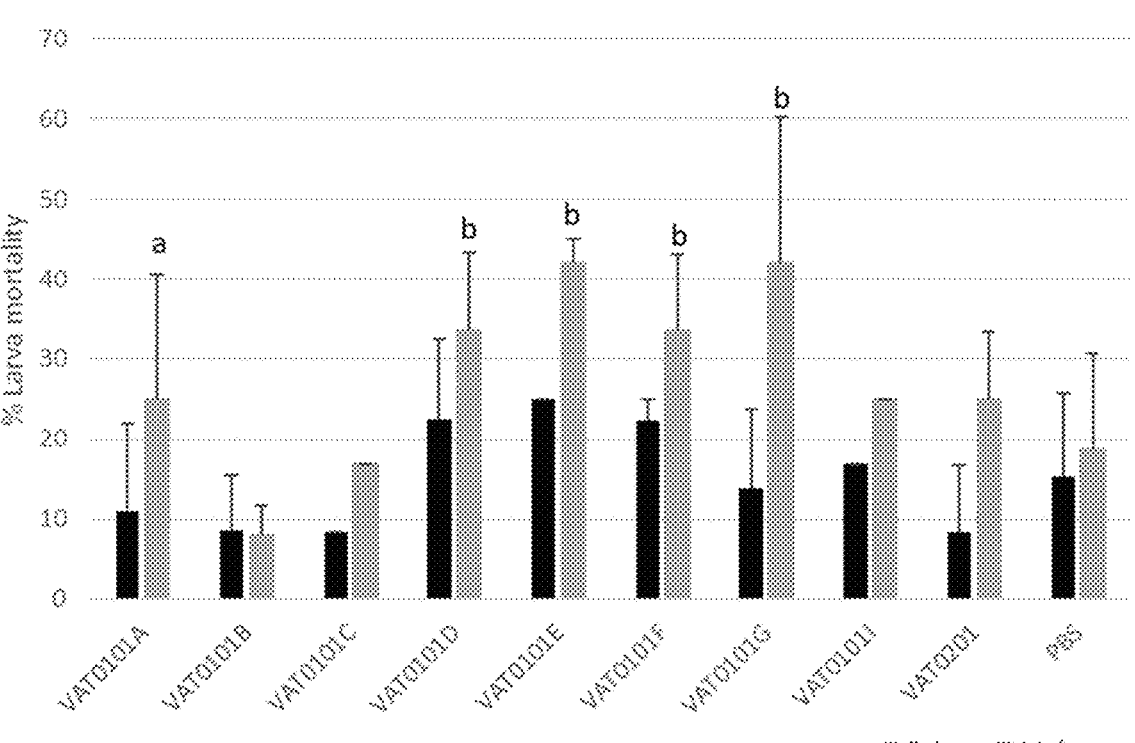

To assess the insecticidal activity of the generated nanobodies, young *Helicoverpa armigera* larvae at the age of no more than 48 hours were grown on artificial food supplemented with a single dose of the anti-VAT generated nanobodies. Observations were carried out through all of the insect's life cycle, including weight and length measurements of the larvae on day 7 and 14 and later on observation on the number of individuals transformed from pupa to adults. The results show that larvae fed 7 days with the generated anti-VAT nanobodies demonstrated loss in their length (FIG. 9A) and/or weight loss and/or an increase in mortality (FIG. 9C), depending on the nanobody tested.

In addition, the percentage of larvae that survived and completed a full life cycle from larvae to pupa stage and then turned to adult moths was determined. As shown in Table 9 hereinbelow, the larvae treated for 7 days with anti-VAT nanobodies had lower percentages of larvae, which completed a full life cycle to become adult moths. Importantly, though the larvae were exposed to the anti-VAT nanobodies only at the first 7 days out of 25-30 days of the experiment, the results showed that they had a long-term stable effect on the *Helicoverpa armigera* and influenced them also later development stages of pupation and adultness.

TABLE 9

Percentages of larvae, which completed a full life cycle to adult moths

|  | % adult moths |
| --- | --- |
| VAT0101A | 58 |
| VAT0101B | 42 |
| VAT0101C | 33 |
| VAT0101D | 16 |
| VAT0101E | 33 |
| VAT0101F | 42 |
| VAT0101G | 58 |
| VAT0202 | 58 |
| PBS | 67 |

Example 3

Anti-Trehalase Nanobodies

Figure 10:
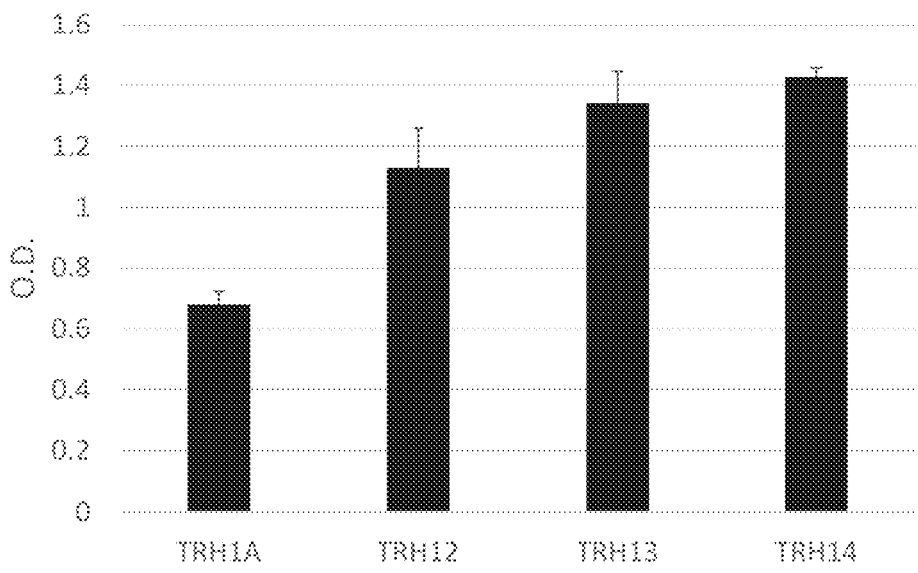
FIG. 10 is a graph demonstrating specific binding of the generated anti-trehalase (referred to herein as "TRH") nanobodies, referred to herein as TRH1A, TRH12, TRH13 and TRH14, to the target TRH antigen, as determined by ELISA. Each experiment was performed five times; data is presented as average ±SE.
Figure 11A:
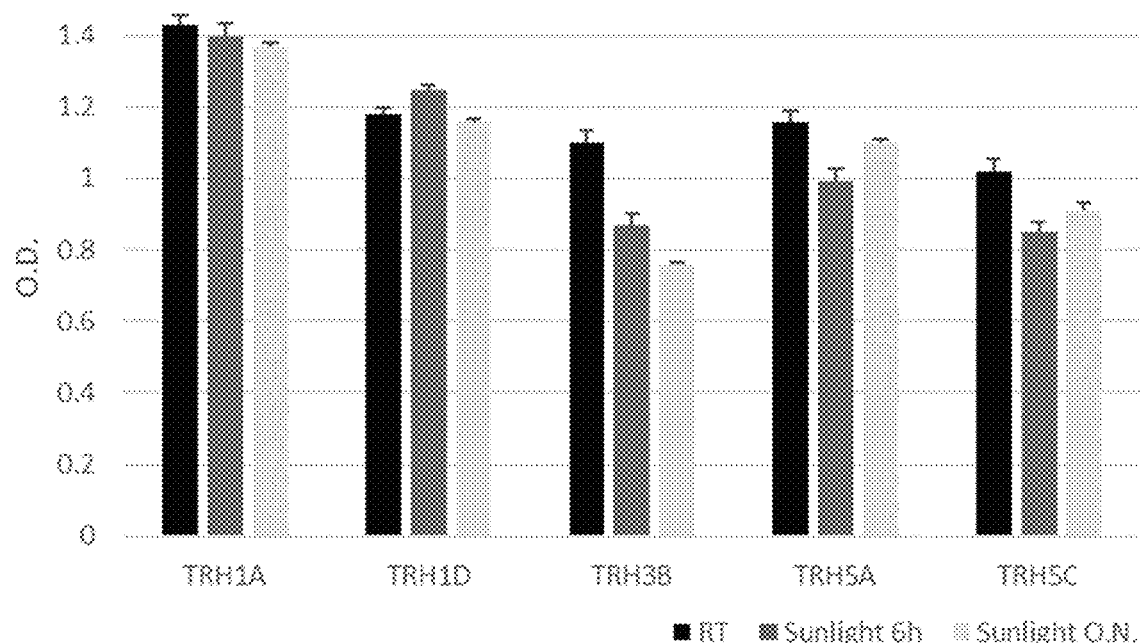
FIGS. 11A-B are graphs demonstrating stability of the generated anti-TRH nanobodies referred to herein as TRH1A, TRH1D, TRH3B, TRH5A and TRH5C, following 6 hours or overnight incubation in field-like conditions (FIG. 11A), and following 6 hours or overnight incubation at 50° C.
Figure 11B:
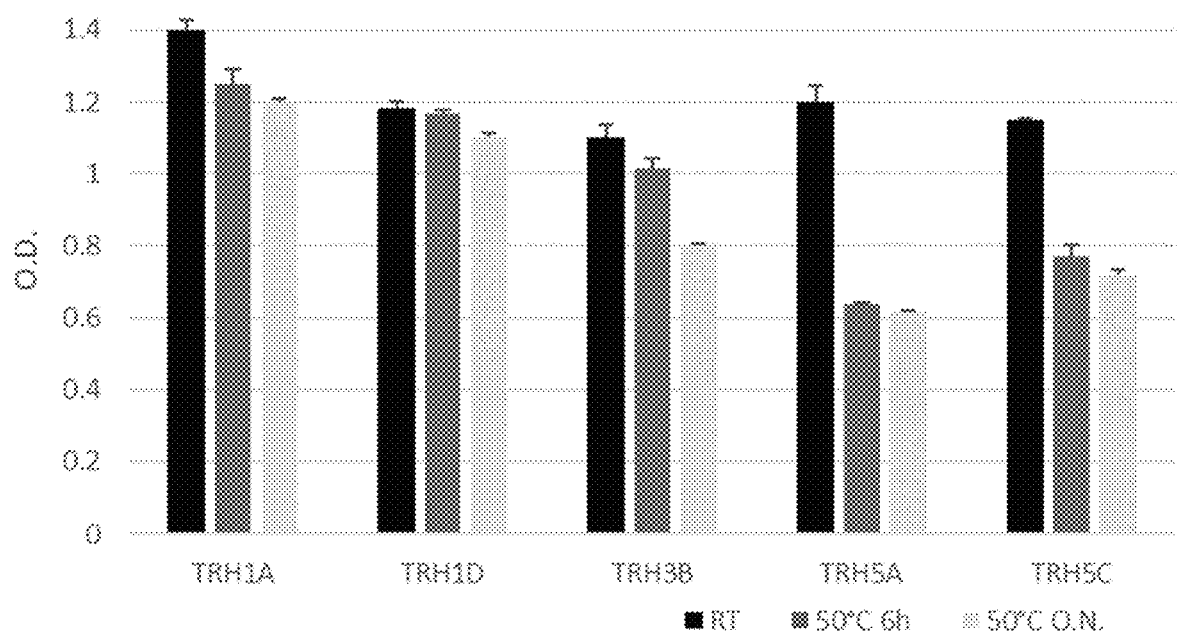

Several nanobodies were generated against the *Helicoverpa armigera* trehalase (referred to herein as "TRH") antigen (see Table 4 hereinabove). ELISA assays using plates coated with the target antigen verified that the generated nanobodies bind the target trehalase antigen (FIG. 10). Following, the stability of the anti-TRH nanobodies in field-like conditions and in high temperature of 50° C. was studied (FIGS. 11A-B). The results demonstrated that overnight incubation in field like conditions of 30° C., 60-70% humidity and a UV index of 4-5 had no effect or induced only a slight decrease in the nanobodies content compared to control. Similar results were demonstrated following an overnight incubation at 50° C.

Figure 12A:
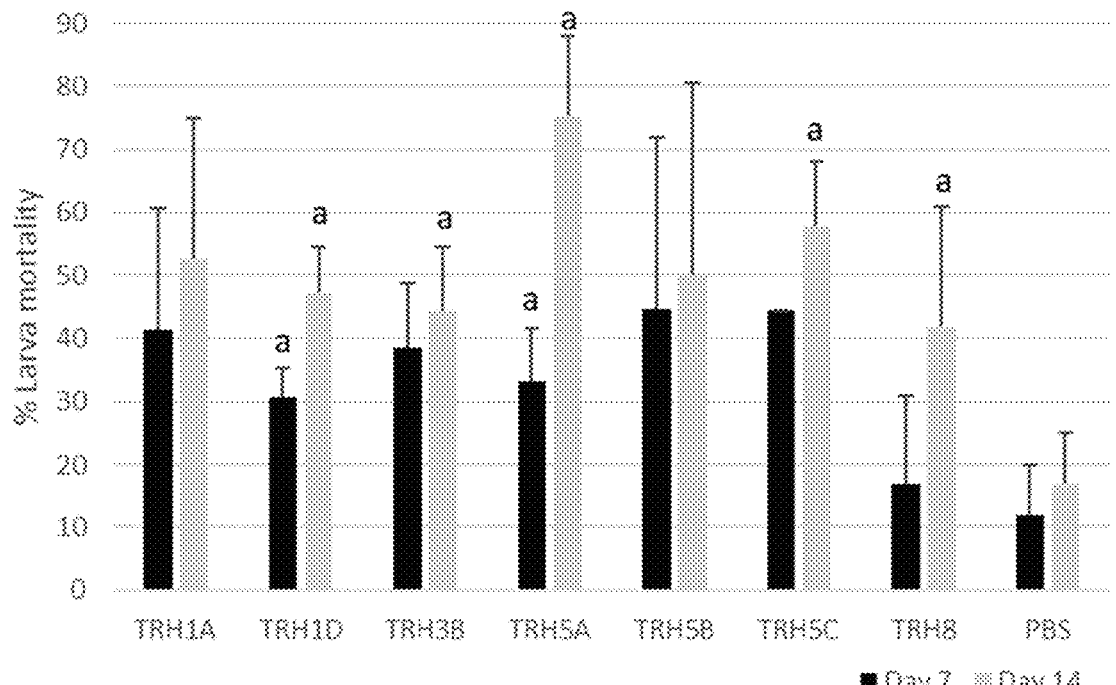
FIG. 12A demonstrates the effect of the anti-TRH nanobodies TRH1A, TRH1D, TRH3B, TRH5A, TRH5B, TRH5C and TRH8 on mortality of *H. armigera* fed with artificial food containing the indicated nanobody at a final concentration of 0.4 mg/ml on days 0 and 7. The measurements were taken on days 7 and 14, as indicated. Each experiment included 12 larvae and had 3 repetitions, with error bars indicating the standard error. Statistically significant differences are indicated by a (P>0.05).
Figure 12B:
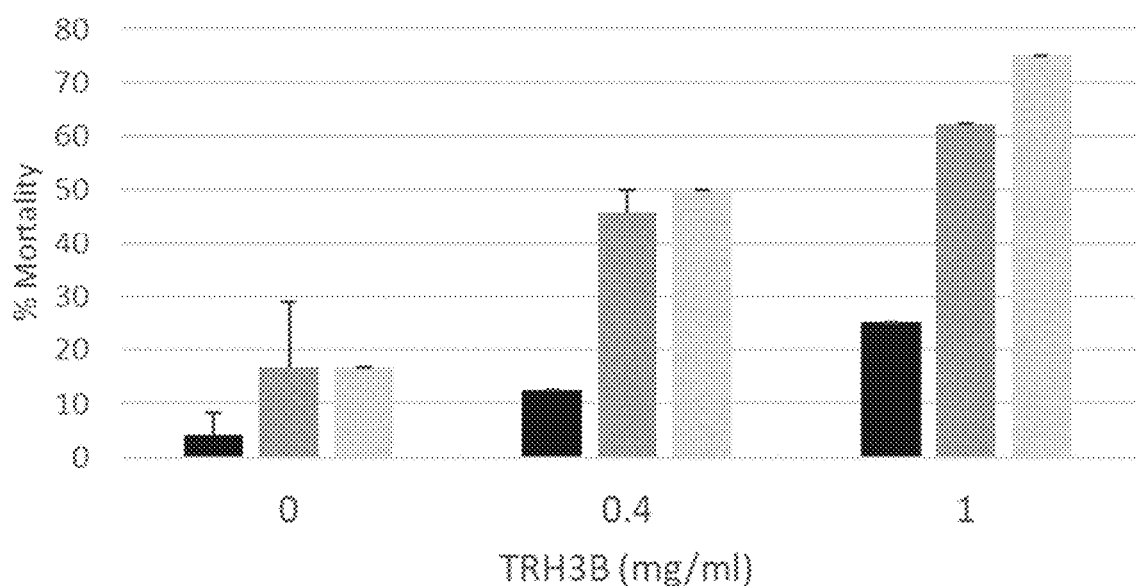
FIG. 12B demonstrates the effect of the anti-TRH3B nanobody on mortality of *H. armigera* fed with cotton leave discs applied with nanobody concentrations of 0.4 or 1 mg/ml, on day 0. Larvae were moved on days 4 and 7 to fresh leave discs treated with similar concentration of the indicated nanobody. The mortality measurements were taken on days 4, 7 and 10, as indicated. Each experiment included 12 larvae and had 2 repetitions with error bars indicating the standard error.

To assess the insecticidal activity of the generated nano-bodies, young *Helicoverpa armigera* larvae at the age of no more than 48 hours were grown on artificial food supple-mented with anti-TRH generated nanobodies; and mortality rate was measured on days 7 and 14. Results showed a significant increase in larvae mortality following treatment with the generated anti-TRH nanobodies (FIG. 12A). Fol-lowing, young *Helicoverpa armigera* larvae at the age of no more than 48 hours were grown on cotton leave discs supplemented with the generated anti-TRH nanobodies administrated on days 0, 4 and 7, and mortality rate was measured on days 4, 7 and 10. Results showed a significant dose dependent increase in larvae mortality following treat-ment with the anti-TRH nanobodies (FIG. 12B).

In addition, observations were carried out through all of the insect's life cycle, including weight, length measure-ments of the larvae and later on observation on the number of individuals transformed from pupa to adults. In addition, the percentage of larvae that survive and complete a full cycle from larvae to pupa stage and then to adult moths was determined.

Example 4

Anti-Cytochrome P450 Monooxygenase Nanobodies

Figure 13:
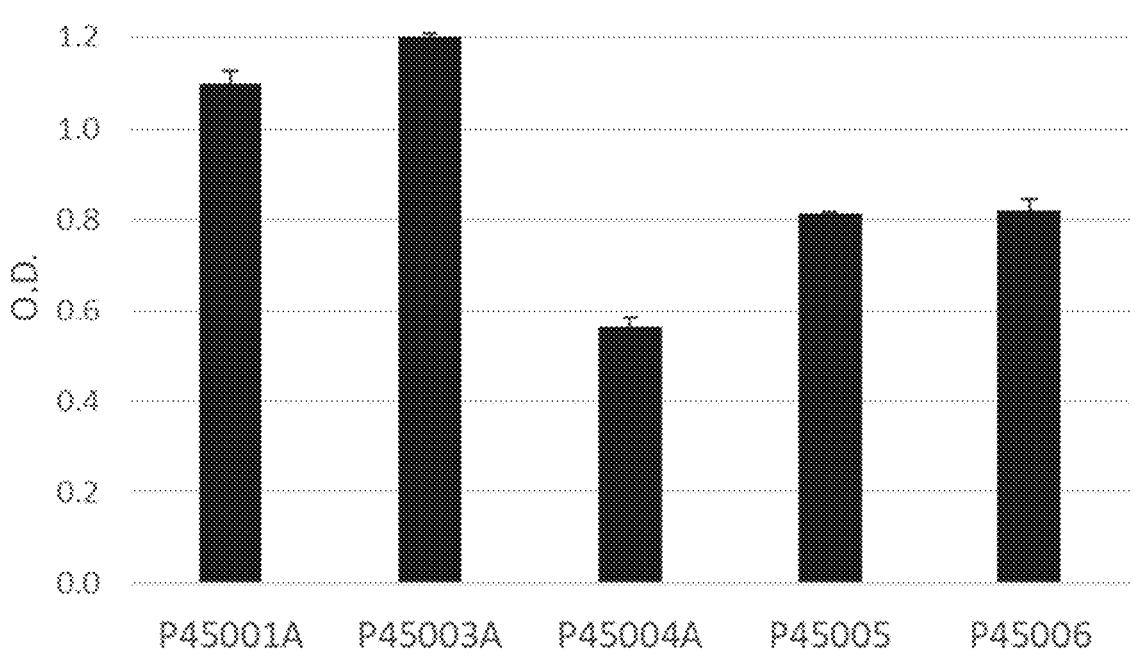
FIG. 13 is a graph demonstrating specific binding of the generated anti-cytochrome p450 monooxygenase (referred to herein as "P450") nanobodies, referred to herein as P45001A, P45003A, P45004, P45005 and P45006, to the target P450 antigen, as determined by ELISA. Each experiment was performed five times; data is presented as average ±SE.

Several nanobodies were generated against the *Helicov-erpa armigera* cytochrome p450 monooxygenase (referred to herein as "P450") antigen (see Table 5 hereinabove). ELISA assays using plates coated with the target antigen verified that the generated nanobodies bind the target P450 antigen (FIG. 13). Following, the stability of the anti-P450 nanobodies in lumen conditions and in field like conditions is studied.

Figure 14:
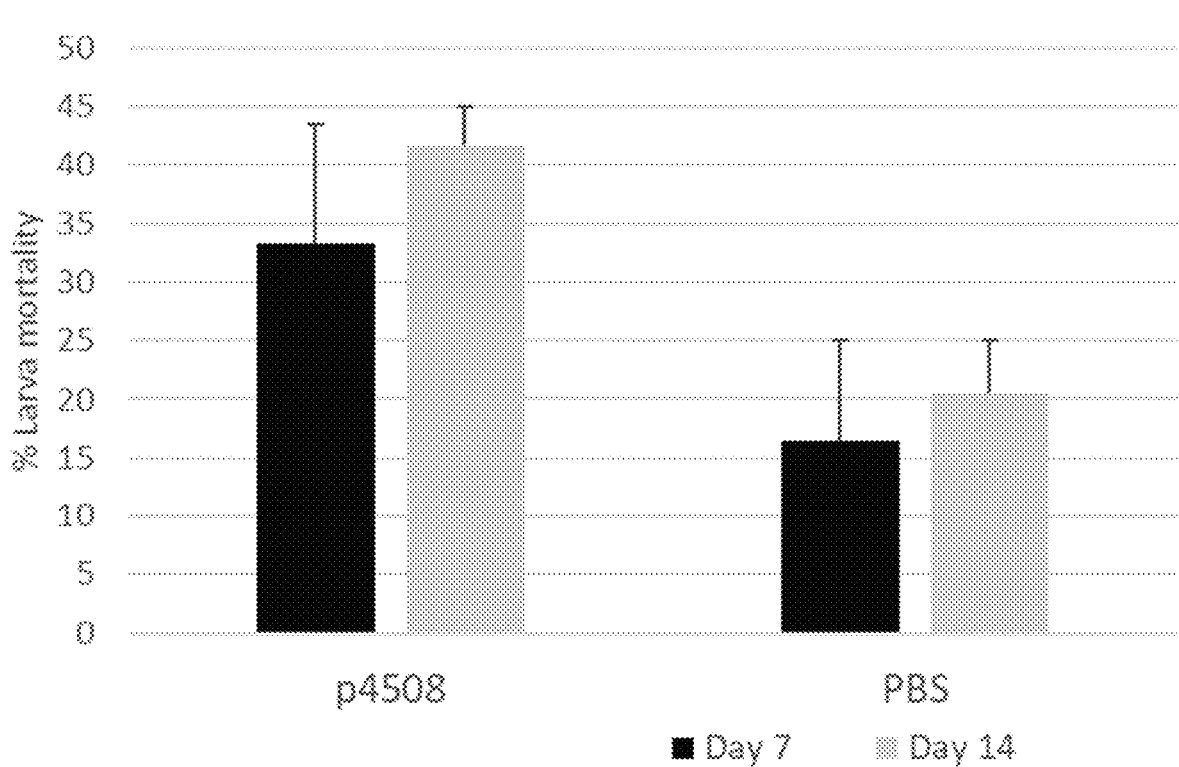
FIG. 14 demonstrates the effect of the generated anti-P450 nanobody referred to herein as P45008 on mortality of *H. armigera* fed with an artificial diet containing the indicated nanobody at a final concentration of 0.4 mg/ml on days 0 and 7. The measurements were taken on days 7 and 14, as indicated. Each experiment included 12 larvae and had 3 repetitions with error bars indicating the standard error.

To assess the insecticidal activity of the generated nano-bodies, young *Helicoverpa armigera* larvae at the age of no more than 48 hours were grown on artificial food supple-mented with the anti-P450 generated nanobodies; and mor-tality rate was measured on days 7 and 14. Results showed a significant increase in larvae mortality following treatment with the anti-P450 nanobodies (FIG. 14).

In addition, observations were carried out through all of the insect's life cycle, including weight and length measure-ments of the larvae on day 7 and 14 and later on observation on the number of individuals transformed from pupa to adults. In addition, the percentage of larvae that survive and complete a full life cycle from larvae to pupa stage and then to adult moths was determined.

Example 5

Anti-Chitin Deacetylase Nanobodies

Figure 15:
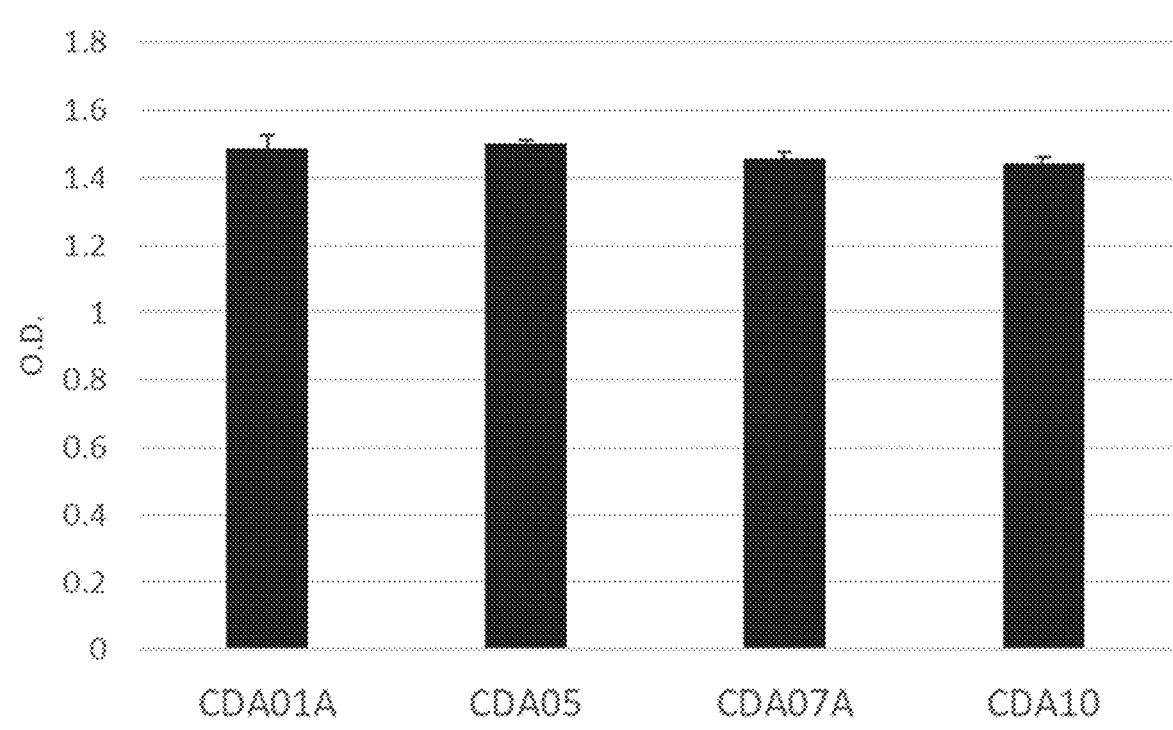
FIG. 15 is a graph demonstrating specific binding of the generated anti-chitin deacetylase (referred to herein as "CDA") nanobodies, referred to herein as CDA01A, CDA05, CDA07A and CDA10, to the target CDA antigen, as determined by ELISA. Each experiment was performed five times; data is presented as average ±SE.
Figure 16A:
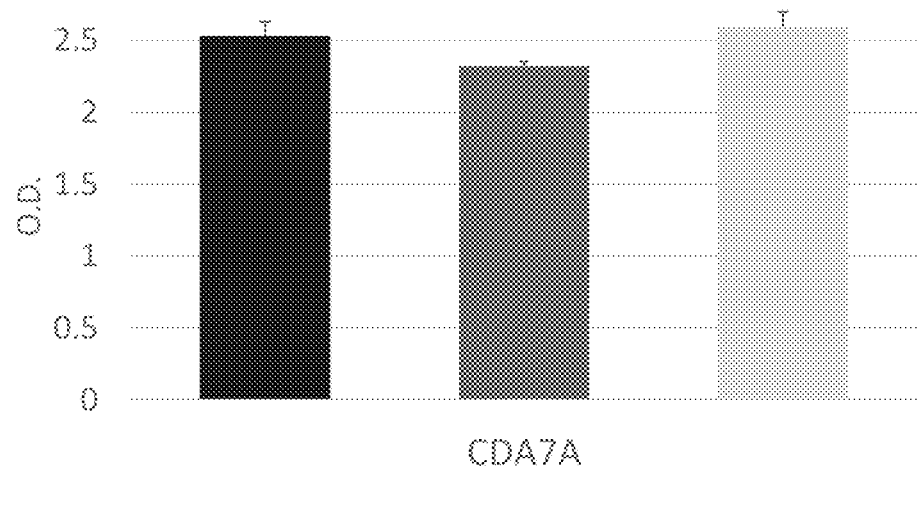
FIGS. 16A-B are graphs demonstrating stability of the generated CDA7A nanobody following 6 hours or overnight incubation in field-like conditions (FIG. 16A), and following 6 hours or overnight incubation at 50° C.
Figure 16B:
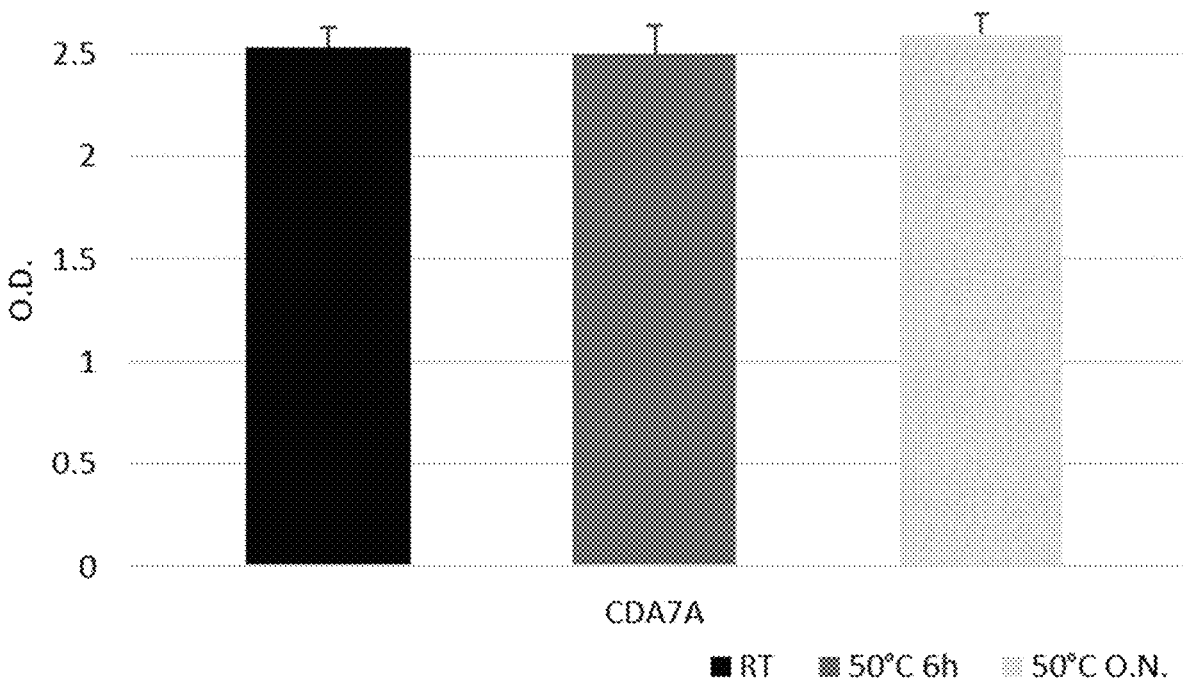

Several nanobodies were generated against the *Helicov-erpa armigera* chitin deacetylase (referred to herein as "CDA") antigen (see Table 6 hereinabove). ELISA assays using plates coated with the target antigen verified that the generated nanobodies bind the target CDA antigen (FIG. 15). Following, the stability of the anti-CDA nanobodies in field like conditions and in high temperature of 50° C. was studied (FIGS. 16A-B). The results demonstrated that over-night incubation in field-like conditions of 30° C., 60-70% humidity and a UV index of 4-5, resulted in no change in the nanobodies content compared to control. Similar results were demonstrated following an overnight incubation at 50° C.

Figure 17A:
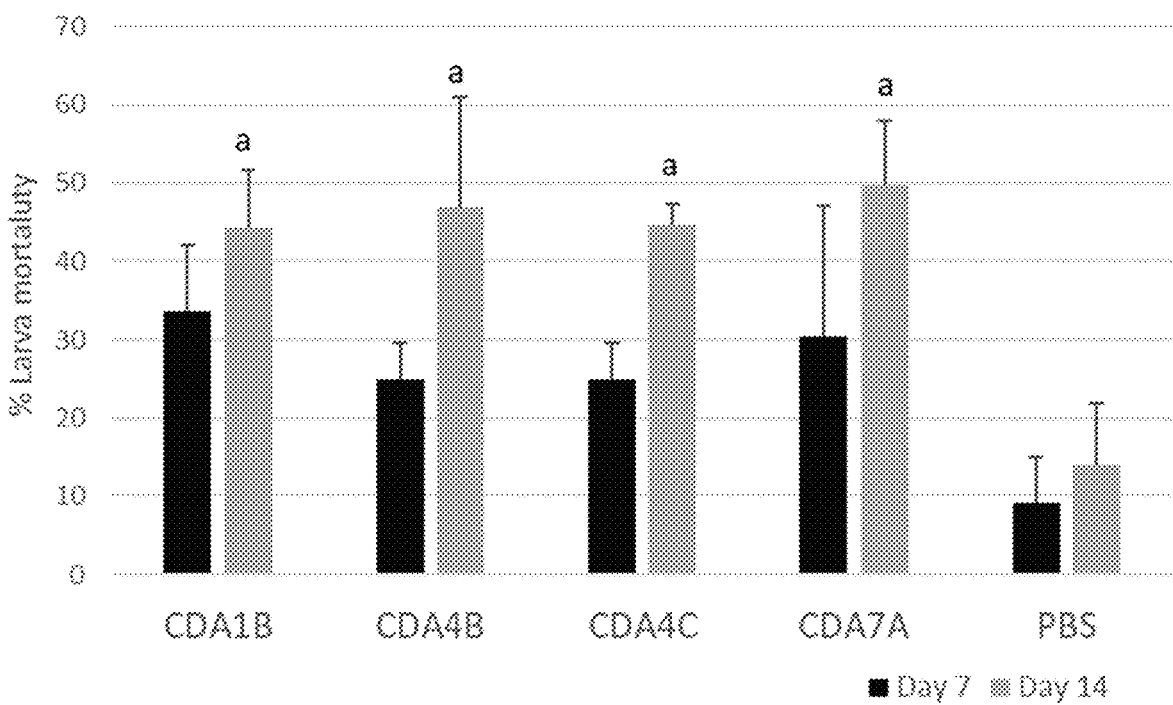
FIG. 17A demonstrates the effect of the anti-CDA nanobodies referred to herein as CDA1B, CDA4B, CDA4C and CDA7A on mortality of *H. armigera* fed with an artificial diet containing the indicated nanobody at a final concentration of 0.4 mg/ml on days 0 and 7. The measurements were taken on day 7 and 14, as indicated. Each experiment included 12 larvae and had 3 repetitions with error bars indicating the standard error. Statistically significant differences are indicated by a (P>0.05).
Figure 17B:
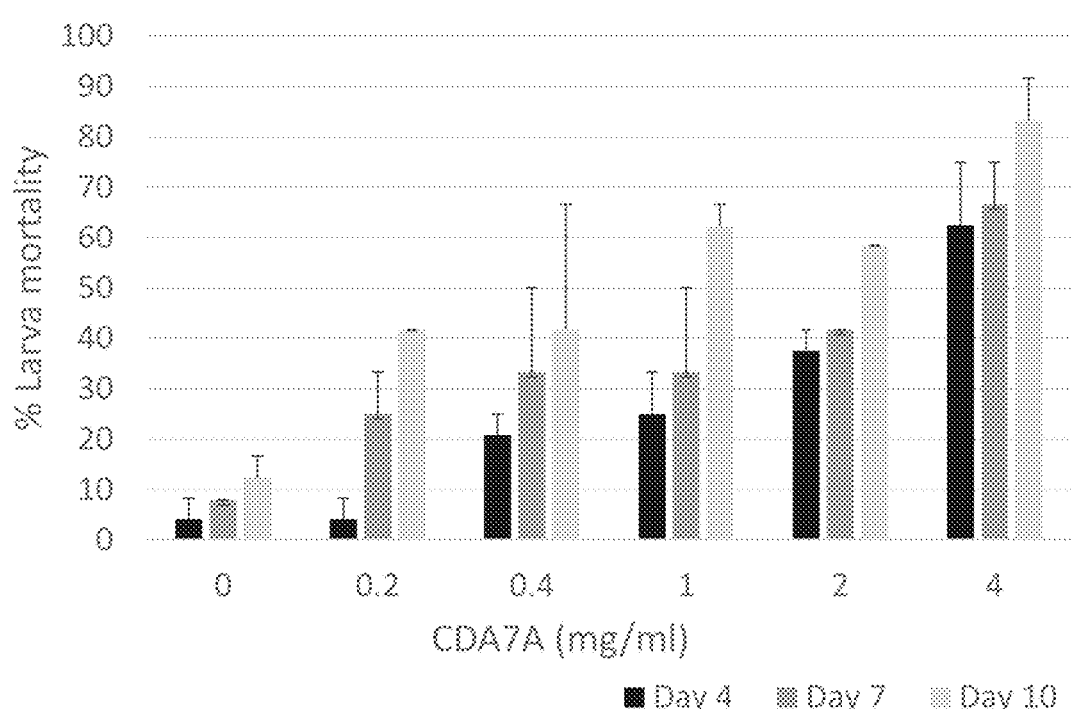
FIG. 17B demonstrates the effect of the CDA7A nanobody on mortality of *H. armigera* fed with cotton leave discs applied with increasing nanobody concentrations (0.2, 0.4, 1, 2 or 4 mg/ml, as indicated) on day 0. Larvae were moved on days 4 and 7 to fresh leave discs treated with similar concentrations of the indicated nanobody. The mortality measurements were taken on day 4, 7 and 10, as indicated. Each experiment included 12 larvae and had 2 repetitions with error bars indicating the standard error.

To assess the insecticidal activity of the generated nano-bodies, young *Helicoverpa armigera* larvae at the age of no more than 48 hours were grown on artificial food supple-mented with the generated anti-CDA nanobodies; and mor-tality rate was measured on days 7 and 14. Results showed a significant increase in larvae mortality following treatment with the anti-CDA nanobodies (FIG. 17A). Following, young *Helicoverpa armigera* larvae at the age of no more than 48 hours were grown on cotton leave discs supple-mented with the anti-CDA nanobodies, administrated on days 0, 4 and 7, and mortality rate was measured on days 4, 7 and 10. Results showed a significant dose dependent increase in larvae mortality following treatment with the anti-CDA nanobodies (FIG. 17B).

In addition, observations were carried out through all of the insect's life cycle, including weight and length measure-ments of the larvae on day 7 and 14 and later on observation on the number of individuals transformed from pupa to adults. In addition, the percentage of larvae that survive and complete a full life cycle from larvae to pupa stage and then to adult moths was determined.

Example 6

Anti-Chitin Synthase Nanobodies

Figure 18:
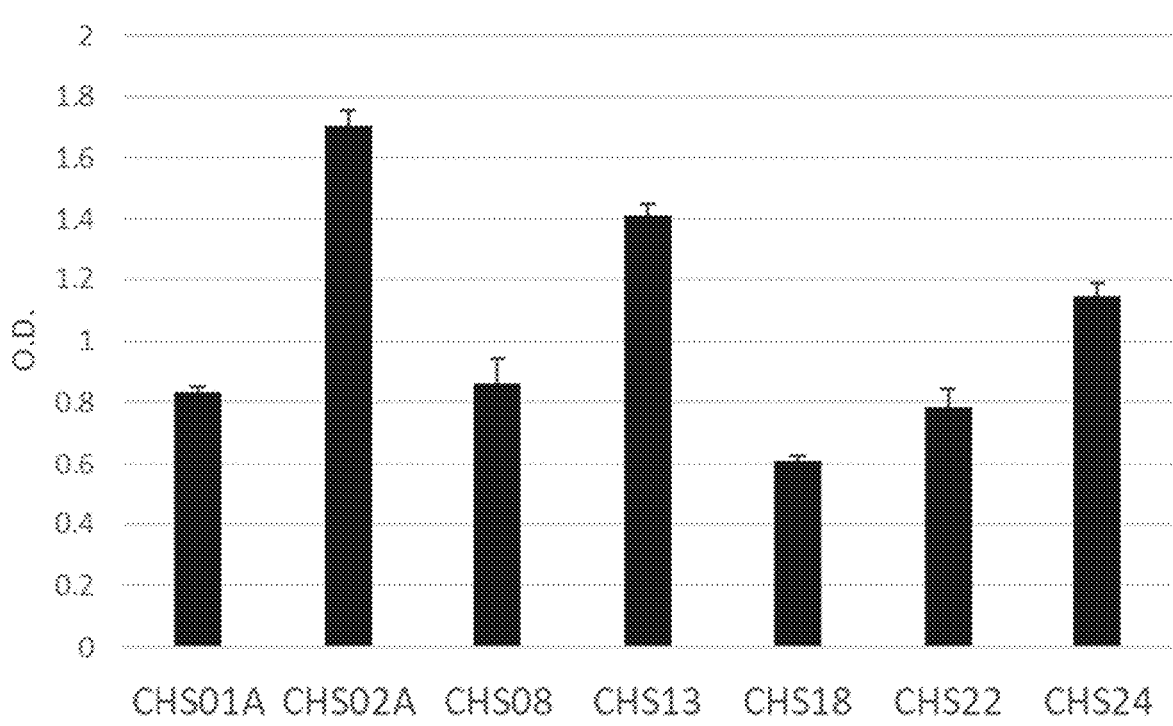
FIG. 18 is a graph demonstrating specific binding of the generated anti-chitin synthase (referred to herein as "CHS") nanobodies, referred to herein as CHS01A, CHS02A, CHS08, CHS13, CHS18, CHS22 and CHS24, to the target CHS antigen, as determined by ELISA. Each experiment was performed five times; data is presented as average ±SE.
Figure 19A:
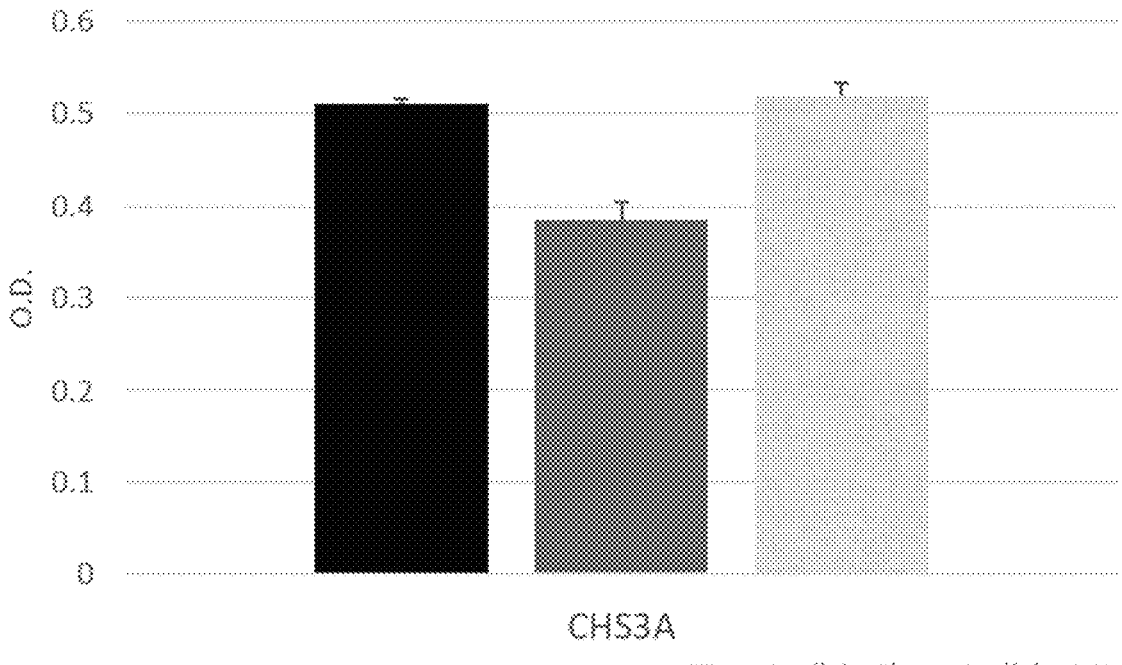
FIGS. 19A-B are graphs demonstrating stability of the generated anti-CHS nanobody referred to herein as CHS3A following 6 hours or overnight incubation in field-like conditions (FIG. 19A), and following 6 hours or overnight incubation at 50° C.
Figure 19B:
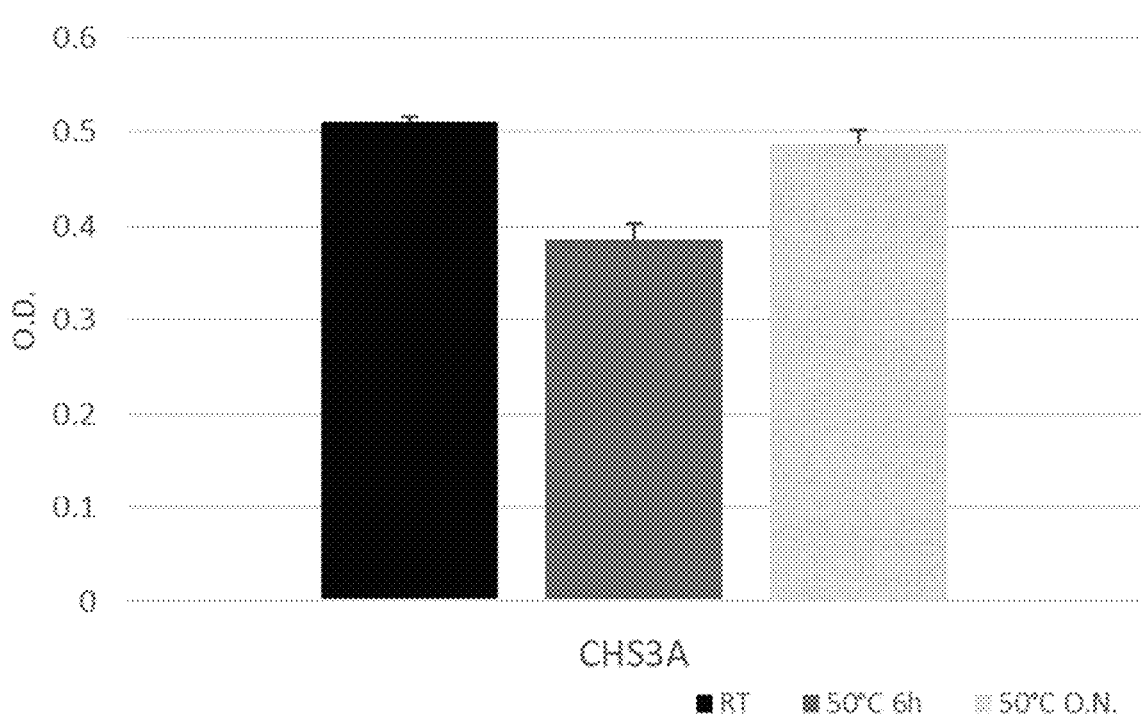

Several nanobodies were generated against the *Helicov-erpa armigera* chitin synthase (referred to herein as "CHS) antigen (see Table 7 hereinabove). ELISA assays using plates coated with the target antigen verified that the gen-erated nanobodies bind the target CHS antigen (FIG. 18). Following, the stability of the anti-CHS nanobodies in field-like conditions and in high temperature of 50° C. was studied (FIGS. 19A-B). The results demonstrated that over-night incubation in field-like conditions of 30° C., 60-70% humidity and a UV index of 4-5, generated only a slight decrease in the nanobodies content compared to control. Similar results were demonstrated following an overnight incubation at 50° C.

Figure 20A:
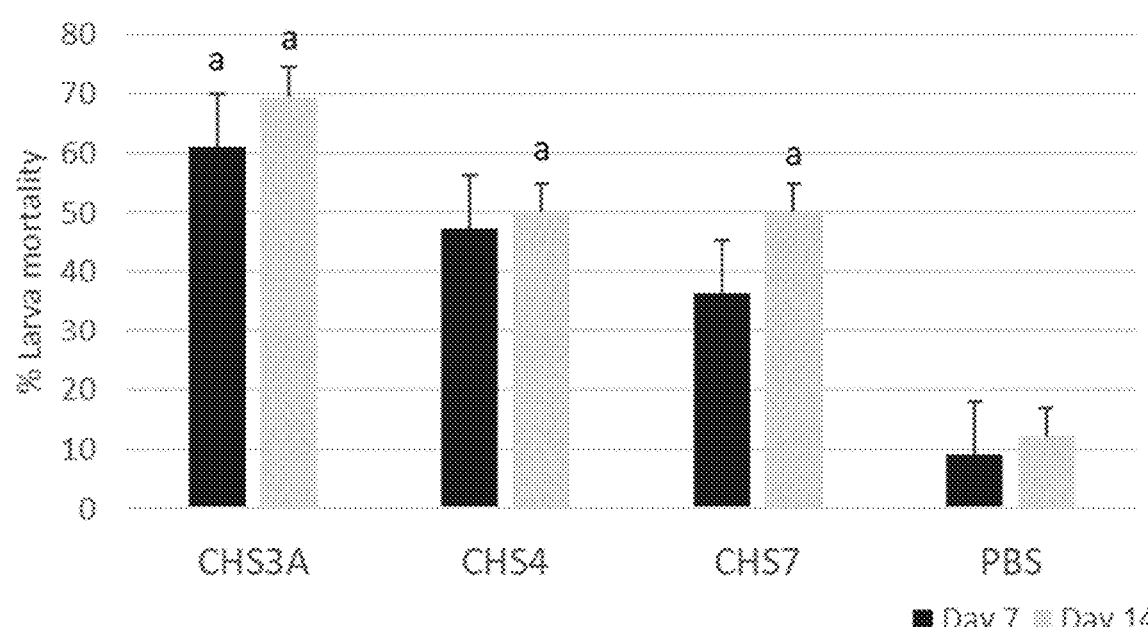
FIG. 20A demonstrates the effect of the generated anti-CHS nanobodies referred to herein as CHS3A, CHS4, and CHS7 on mortality of *H. armigera* fed with an artificial diet containing the indicated nanobody at a final concentration of 0.4 mg/ml on day 0 and 7. The measurements were taken on day 7 and 14, as indicated. Each experiment included 12 larvae and had 3 repetitions with error bars indicating the standard error. Statistically significant differences are indicated by a (P>0.05).
Figure 20B:
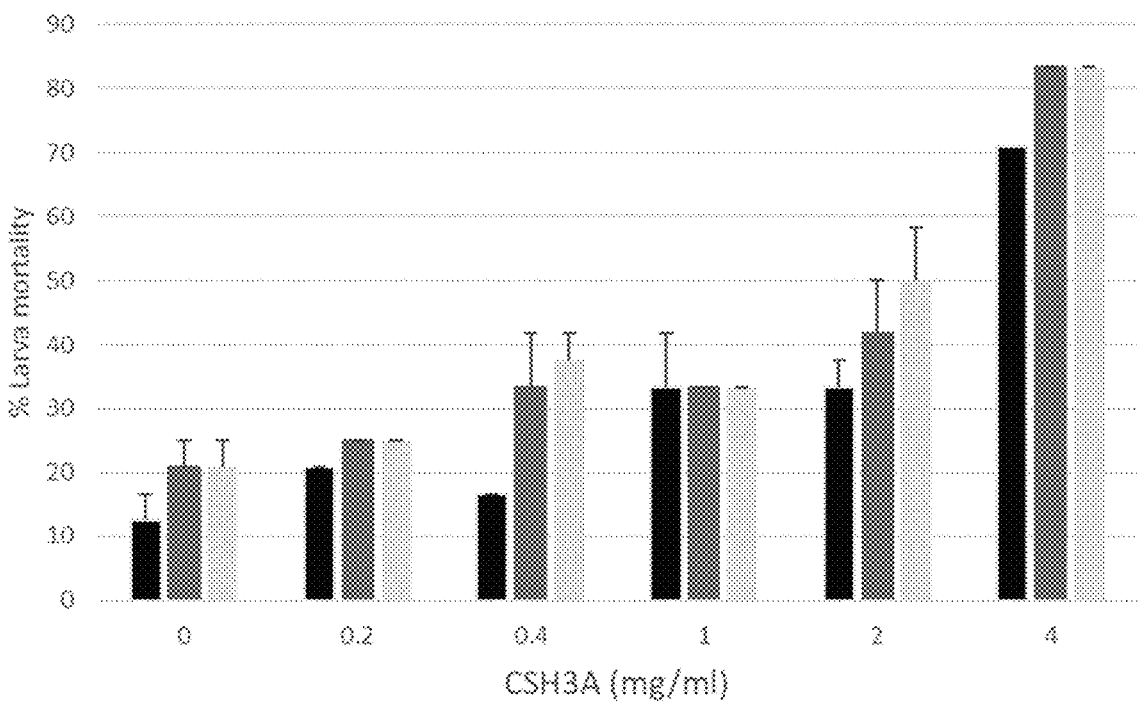
FIG. 20B demonstrates the effect of the CHS3A nanobody on mortality of *H. armigera* fed with cotton leave discs applied with increasing nanobody concentration (0.2, 0.4, 1, 2 and 4 mg/ml, as indicated) on day 0. Larvae were moved on days 4 and 7 to fresh leave discs treated with similar concentrations of the indicated nanobody. The mortality measurements were taken on days 4, 7 and 10, as indicated. Each experiment included 12 larvae and had 3 repetitions with error bars indicating the standard error. Statistically significant differences are indicated by a ($P>0.05$).

To assess the insecticidal activity of the generated nano-bodies, young *Helicoverpa armigera* larvae at the age of no more than 48 hours were grown on artificial food supple-mented with the generated anti-CHS nanobodies; and mor-tality rate was measured on days 7 and 14. Results showed a significant increase in larvae mortality following treatment with the anti-CHS nanobodies (FIG. 20A). Following, young *Helicoverpa armigera* larvae at the age of no more than 48 hours were grown on cotton leave discs supple-mented with the anti-CHS nanobodies, administrated on days 0, 4 and 7, and mortality rate was measured on days 4, 7 and 10. Results showed a significant dose dependent increase in larvae mortality following treatment with the anti-CHS nanobodies (FIG. 20B).

In addition, observations were carried out through all of the insect's life cycle, including weight and length measure-ments of the larvae on day 7 and 14 and later on observation on the number of individuals transformed from pupa to adults. In addition, the percentage of larvae that survive and complete a full life cycle from larvae to pupa stage and then to adult moths was determined.

Example 7

Anti-NPC1 Sterol Transporter Nanobodies

Figure 21:
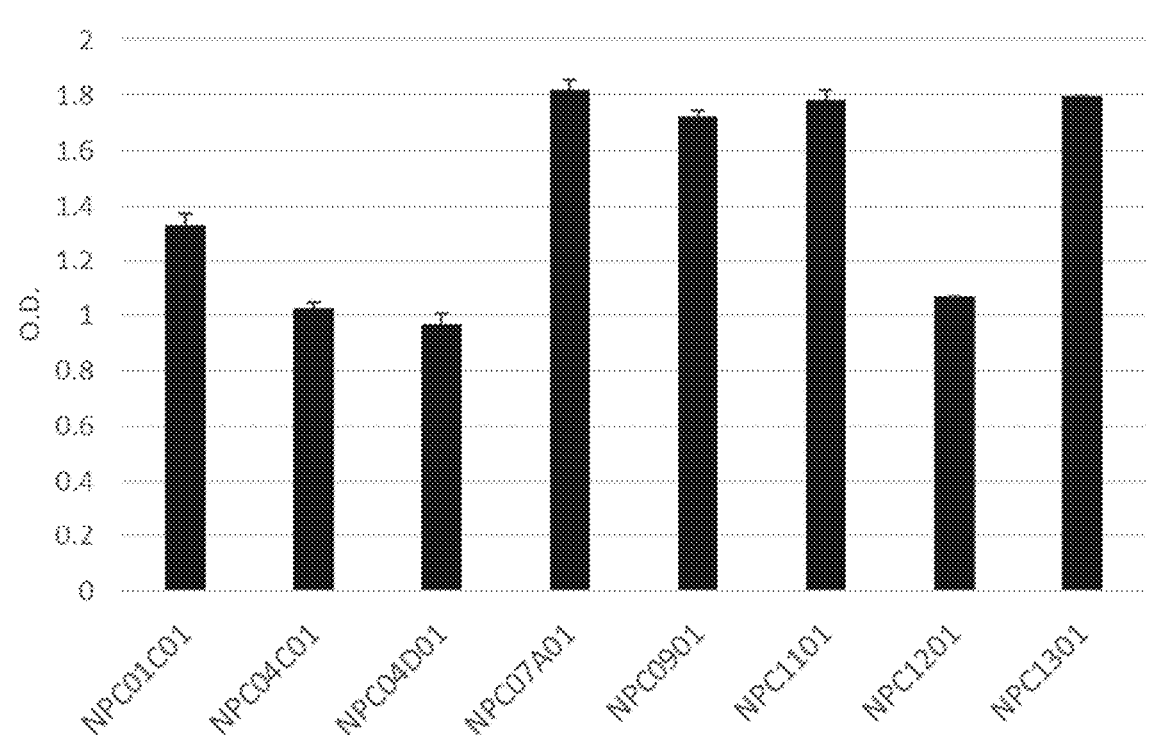
FIG. 21 is a graph demonstrating specific binding of the generated anti-NPC1 sterol transporter (referred to herein as "NPC") nanobodies, referred to herein as NPC01C01, NPC04C01, NPC04D01, NPC07A01, NPC0901, NPC01101 and NPC01201, to the target NPC antigen, as determined by ELISA. Each experiment was performed five times; data is presented as average ±SE.

Several nanobodies were generated against the *Helicov-erpa armigera* NPC1 sterol transporter (referred to herein as "NPC1") antigen (see Table 8 hereinabove). ELISA assays using plates coated with the target antigen verified that the generated nanobodies bind the target NPC1 antigen (FIG. 21). Following, the stability of the anti-NPC1 sterol trans- porter nanobodies in lumen conditions and in field like conditions is studied.

Figure 22:
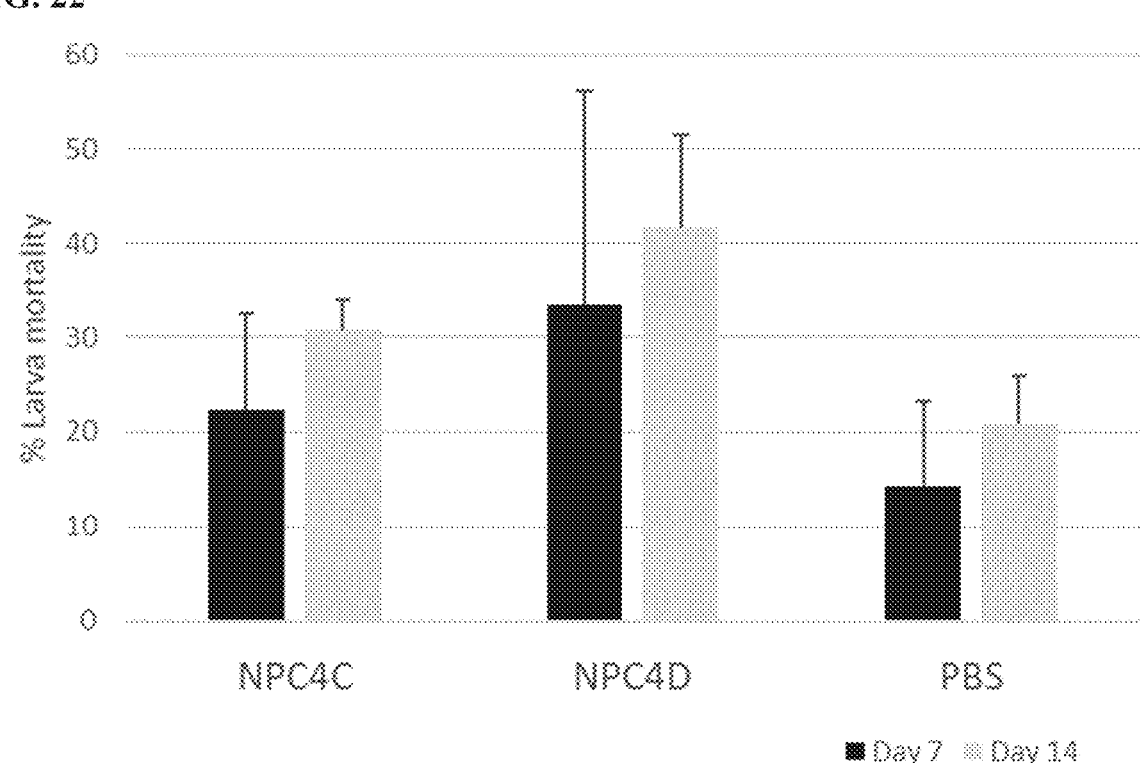
FIG. 22 demonstrates the effect of the generated anti-NPC nanobodies referred to herein as NPC4C and NPC4D on mortality of *H. armigera* fed with an artificial diet containing the indicted nanobody at a final concentration of 0.4 mg/ml on days 0 and 7. The measurements were taken on days 7 or 14, as indicated. Each experiment included 12 larvae and had 3 repetitions with error bars indicating the standard error.

To assess the insecticidal activity of the generated nano- bodies, young *Helicoverpa armigera* larvae at the age of no more than 48 hours were grown on artificial food supple- mented with the generated anti-NPC1 nanobodies; and mor- tality rate was measured on days 7 and 14. Results showed a significant increase in larvae mortality following treatment with the anti-NPC1 nanobodies (FIG. 22).

In addition, observations were carried out through all of the insect's life cycle, including weight and length measure- ments of the larvae on day 7 and 14 and later on observation on the number of individuals transformed from pupa to adults. In addition, the percentage of larvae that survive and complete a full life cycle from larvae to pupa stage and then to adult moths was determined.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications men- tioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as neces- sarily limiting. In addition, any priority document(s) of this application is/are hereby incorporated herein by reference in its/their entirety.

---

What is claimed is:

1. A VHH antibody which specifically binds to an insect chitin deacetylase comprising complementarity determining regions (CDRs) as set forth in SEQ ID NOs: 351, 347 and 356 arranged in a sequential order from N to C on said nanobody, wherein binding of said nanobody to said insect chitin deacetylase confers an insect control activity to said VHH antibody.

2. A composition comprising a VHH antibody which specifically binds to an insect chitin deacetylase comprising complementarity determining regions (CDRs) as set forth in SEQ ID NOs: 351, 347 and 356 arranged in a sequential order from N to C on said nanobody;

and a toxin moiety having an insect control activity.

3. The composition of claim 2, wherein binding of said VHH antibody to said insect chitin deacetylase confers an insect control activity to said VHH antibody.

4. The VHH antibody of claim 1, wherein said VHH antibody downregulates activity of said insect chitin deacetylase.

5. The VHH antibody of claim 1, being formulated for delivery by spraying, irrigation and/or fumigation.

6. A polynucleotide encoding the VHH antibody of claim 1.

7. A nucleic acid construct comprising the polynucleotide of claim 6 and a cis-acting regulatory element for directing expression of said polynucleotide.

8. A transformed host cell comprising the VHH antibody of claim 1.

9. A method of producing an insect control VHH antibody, the method comprising expressing in a host cell the polynucleotide of claim 6.

10. The method of claim 9, comprising isolating the VHH antibody.

11. A method of insect control, the method comprising contacting the insect with the nanobody of claim 1, a polynucleotide or a nucleic acid construct encoding same or a host cell expressing same.

12. The nanobody of claim 1, wherein said VHH antibody is formulated as a liquid formulation.

13. The nanobody of claim 1, wherein said VHH antibody is formulated as a dry formulation.

14. A plant comprising the VHH antibody of claim 1 or a polynucleotide or a nucleic acid construct encoding same.

15. The plant of claim 14, being a transgenic plant.

16. A commodity product comprising the VHH antibody of claim 1.

17. The VHH antibody of claim 1, wherein said insect is selected from the group consisting of moth, stinkbug, hopper, beetle, aphid and honeybee.

18. The VHH antibody of claim 1, wherein said insect is a moth.

19. The VHH antibody of claim 1, being a synthetic recombinant VHH antibody.

20. The VHH antibody of claim 1, wherein said insect chitin deacetylase is a *Helicoverpa armigera* chitin deacetylase.

21. The nucleic acid construct of claim 7, wherein said cis-acting regulatory element is heterologous to said polynucleotide.

* * * * *